US007405209B2

(12) United States Patent
Marquis, Jr. et al.

(10) Patent No.: US 7,405,209 B2
(45) Date of Patent: *Jul. 29, 2008

(54) PROTEASE INHIBITORS

(75) Inventors: Robert Wells Marquis, Jr., Wayne, PA (US); Yu Ru, Wayne, PA (US); Daniel Frank Veber, Ambler, PA (US); Maxwell David Cummings, Strafford, PA (US); Scott Kevin Thompson, Phoenixville, PA (US); Dennis Shinji Yamashita, Wayne, PA (US)

(73) Assignees: SmithKline Beecham Corporation, Philadelphia, PA (US); SmithKline Beecham p.l.c., Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/152,745

(22) Filed: Jun. 14, 2005

(65) Prior Publication Data

US 2005/0256104 A1    Nov. 17, 2005

Related U.S. Application Data

(63) Continuation of application No. 10/404,716, filed on Apr. 1, 2003, now abandoned, which is a continuation of application No. 09/881,334, filed on Jun. 14, 2001, now abandoned, which is a continuation-in-part of application No. 09/593,845, filed on Jun. 14, 2000, now abandoned, which is a continuation-in-part of application No. PCT/US99/30730, filed on Dec. 21, 1999.

(60) Provisional application No. 60/113,636, filed on Dec. 23, 1998, provisional application No. 60/164,581, filed on Nov. 10, 1999.

(51) Int. Cl.
*A61P 19/00* (2006.01)
*A61K 31/55* (2006.01)
*A61K 31/00* (2006.01)
*C07D 223/08* (2006.01)
*C07D 403/00* (2006.01)
*C07D 405/00* (2006.01)
*C07D 409/00* (2006.01)

(52) U.S. Cl. .............................. 514/211.03; 514/217.03; 514/217.04; 514/217.05; 514/217.06; 514/217.07; 514/217.08; 514/217.09; 514/217.1; 514/217.11; 540/525; 540/596; 540/597; 540/598; 540/599; 540/601; 540/602; 540/603; 540/604

(58) Field of Classification Search ............ 514/211.03, 514/217.03, 217.04, 217.05, 217.06, 217.07, 514/217.08, 217.09, 217.1, 217.11; 540/525, 540/596, 597, 598, 599, 601, 602, 603, 604
See application file for complete search history.

(56) References Cited

U.S. PATENT DOCUMENTS

| 4,038,247 | A |  | 7/1977 | Muller et al. ............... 260/45.9 |
| 4,447,419 | A |  | 5/1984 | Quadro ....................... 424/177 |
| 4,518,528 | A |  | 5/1985 | Rasnick ................ 260/112.5 R |
| 4,638,010 | A |  | 1/1987 | Weller, III et al. .......... 514/423 |
| 4,749,792 | A |  | 6/1988 | Natarajan et al. ............ 546/312 |
| 4,994,471 | A |  | 2/1991 | Lalinde et al. .............. 514/326 |
| 5,057,525 | A |  | 10/1991 | Van Daele ................... 514/318 |
| 5,142,056 | A |  | 8/1992 | Kempe et al. ............... 546/265 |
| 5,206,251 | A |  | 4/1993 | Khanna et al. .............. 514/315 |
| 5,216,168 | A |  | 6/1993 | Khanna et al. .............. 546/242 |
| 5,374,637 | A |  | 12/1994 | Van Daele ................... 514/320 |
| 5,395,824 | A |  | 3/1995 | Higuchi et al. ................ 514/19 |
| 5,422,359 | A |  | 6/1995 | Ando et al. .................. 514/365 |
| 5,424,325 | A |  | 6/1995 | Ando et al. .................. 514/357 |
| 5,501,969 | A |  | 3/1996 | Hastings et al. ........... 435/240.2 |
| 5,523,313 | A |  | 6/1996 | Nunami et al. .............. 514/365 |
| 5,585,387 | A |  | 12/1996 | Lu et al. ...................... 514/327 |
| 5,668,128 | A |  | 9/1997 | Tsubotani et al. ............ 514/183 |
| 5,830,850 | A |  | 11/1998 | Gelb et al. ...................... 514/2 |
| 5,861,298 | A |  | 1/1999 | Adams et al. ................ 435/226 |
| 5,902,882 | A |  | 5/1999 | Matzinger et al. ........... 540/604 |
| 5,948,669 | A |  | 9/1999 | Feild et al. ................... 435/226 |
| 5,998,470 | A |  | 12/1999 | Halbert et al. ............... 514/482 |
| 6,057,362 | A |  | 5/2000 | Yamashita et al. .......... 514/468 |
| 6,232,342 | B1 |  | 5/2001 | Carr et al. ................... 514/524 |
| 6,274,336 | B1 |  | 8/2001 | Abdel-Meguid et al. ...... 435/23 |
| 6,284,777 | B1 |  | 9/2001 | Halbert et al. ............... 514/332 |
| 6,331,542 | B1 |  | 12/2001 | Carr et al. ................. 514/237.8 |
| 2006/0052365 | A1 | * | 3/2006 | Bondinell et al. ....... 514/217.04 |
| 2006/0194787 | A1 | * | 8/2006 | Cummings et al. ..... 514/212.08 |

FOREIGN PATENT DOCUMENTS

EP            0 237 082 A        9/1987

(Continued)

OTHER PUBLICATIONS

Bossard, et al., (1996), J. of Bio. Chem;, vol. 271, No. 21, pp. 12517-12524.

(Continued)

*Primary Examiner*—Brenda L Coleman
(74) *Attorney, Agent, or Firm*—Linda E Hall; Stephen A Venetianer; Charles M Kinzig

(57) ABSTRACT

The present invention provides 4-amino-azepan-3-one protease inhibitors and pharmaceutically acceptable salts, hydrates and solvates thereof which inhibit proteases, including cathepsin K, pharmaceutical compositions of such compounds, novel intermediates of such compounds, and methods for treating diseases of excessive bone loss or cartilage or matrix degradation, including osteoporosis; gingival disease including gingivitis and periodontitis; arthritis, more specifically, osteoarthritis and rheumatoid arthritis; Paget's disease; hypercalcemia of malignancy; and metabolic bone disease, comprising inhibiting said bone loss or excessive cartilage or matrix degradation by administering to a patient in need thereof a compound of the present invention.

16 Claims, No Drawings

FOREIGN PATENT DOCUMENTS

| | | |
|---|---|---|
| EP | 0 504 938 A2 | 3/1992 |
| EP | 0 525 420 A1 | 2/1993 |
| EP | 0 543 310 | 5/1993 |
| EP | 0 603 873 A1 | 6/1994 |
| EP | 0 611 756 A2 | 8/1994 |
| EP | 0 623 592 | 11/1994 |
| WO | WO 92/04371 | 3/1992 |
| WO | WO 94/00095 | 1/1994 |
| WO | WO 94/04172 | 3/1994 |
| WO | WO 94/23033 | 10/1994 |
| WO | WO 95/05192 | 2/1995 |
| WO | WO 94/24182 A | 9/1995 |
| WO | WO 96/13523 | 5/1996 |
| WO | WO 96/40737 | 12/1996 |
| WO | WO 97/16433 | 5/1997 |
| WO | WO 97/47642 | 12/1997 |
| WO | WO 97/47643 | 12/1997 |
| WO | WO97/49668 | 12/1997 |
| WO | WO 98/05336 | 2/1998 |
| WO | WO 98/08802 | 3/1998 |
| WO | WO 98/48799 | 11/1998 |
| WO | WO 98/49152 | 11/1998 |
| WO | WO 98/50342 | 11/1998 |
| WO | WO 99/11637 | 3/1999 |
| WO | WO 99/53039 | 10/1999 |
| WO | WO 99/59526 | 11/1999 |
| WO | WO 99/59570 | 11/1999 |
| WO | WO 99/64399 | 12/1999 |
| WO | WO 99/66925 | 12/1999 |
| WO | WO 00/09653 | 2/2000 |
| WO | WO 00/29408 | 5/2000 |
| WO | WO 00/38687 | 7/2000 |
| WO | WO 00/39115 | 7/2000 |
| WO | WO 00/49011 | 8/2000 |
| WO | WO 00/54769 | 9/2000 |
| WO | WO 00/58296 | 10/2000 |
| WO | WO 01/34153 | 5/2001 |
| WO | WO 01/34154 | 5/2001 |
| WO | WO 01/34155 | 5/2001 |
| WO | WO 01/34156 | 5/2001 |
| WO | WO 01/34157 | 5/2001 |
| WO | WO 01/34158 | 5/2001 |
| WO | WO 01/34159 | 5/2001 |
| WO | WO 01/34160 | 5/2001 |
| WO | WO 01/34565 | 5/2001 |
| WO | WO 01/34566 | 5/2001 |
| WO | WO 01/34599 | 5/2001 |
| WO | WO 01/70232 | 9/2001 |
| WO | WO 02/17924 | 3/2002 |
| WO | WO 02/092563 | 11/2002 |
| WO | WO 03/053331 | 7/2003 |

OTHER PUBLICATIONS

Bromme, et al., (1996), Biochemical Journal, vol. 315, pp. 85-89, especially abstract, Figure 1.
Velasco, et al., (1994), J. of Bio. Chem; vol. 269, No. 43, pp. 27136-27142, especially the abstract.
Magrath, et al., (1992), J. of Med. Chem; vol. 35, No. 23, pp. 4279-4283, especially p. 4281, col. 1, structures 1-4 and 7.
Graybill, et al., (1992), Bioorganic & Medicinal Chemistry Letters; vol. 2, No. 11, pp. 1375-1380, especially p. 1377, Scheme I.
Palmer, et al., (1995), J. of Med. Chem; vol. 38, No. 17, pp. 3193-3196.
Danheiser, (1995), Genetic Engineering News; vol. 15, No. 17, pp. 1-1 and 35-36.
Rasnick, (1996), Perspectives in Drug Discovery & Design; vol. 6, pp. 48-63.
Potempa, et al., "Host and *Porphyromonas gingivalis* proteinases in periodontitis: A biochemical model of infection and tissue destruction", (1994), Perspectives in Drug Discovery and Design, vol. 2, pp. 445-458.
Drake, et al., "Cathepsin K, but Not Cathepsins B, L, or S, Is Abundantly Expressed in Human Osteoclasts", (1996), J. of Biological Chemistry, 271(21), pp. 12511-12516.
Bromme, et al., "Human Cathepsin 02, a Matrix Protein-degrading Cysteine Protease Expressed in Osteoclasts", (1996), J. of Biological Chemistry, 271(4), pp. 2126-2132.
Delaisse, et al., "In Vivo and In Vitro Evidence for the Involvement of Cysteine Proteinases in Bone Resorption", (1984), Biochemical and Biophysical Research Communications, 125(2), pp. 441-447.
Delaisse, et al., "Inhibition of bone resorption in culture by inhibitors of thiol proteinases", (1980), Biochem. J., 192, pp. 365-368.
Lerner, et al., "Human Cystatin C, a Cysteine Proteinase Inhibitor, Inhibits Bone Resporption In Vitro Stimulated by Parathyroid Hormone and Parathyroid Hormone-Related Peptide of Malignancy", (1992), J. of Bone and Mineral Research, 7(4), pp. 433-439.
Hill, et al., "Inhibition of Bone Resorption by Selective Inactivators of Cysteine Proteinases", (1994), J. of Cellular Biochemistry, 56, pp. 118-130.
Delaise, et al., "The Effects of Inhibitors of Cysteine-Proteinases and Collagenase on the Resorptive Activity of Isolated Osteoclasts", Bone, 8. pp. 305-313, 1987.
Borg, et al, "Synthesis of 1,2,4-Oxadiazole-, 1,3,4-Oxadiazole-, and 1,2,4-Triazole-Derived Dipeptidomietics", J. Org. Chem., 60, pp. 3112-3120, 1995.
Boden, et al, "Total Synthesis of Lissoclinamide 5, a Cytotoxic Cyclic Peptide from the Tunicate *Lissoclinum patella*", (1994), Tetrahedron. Ltrs., 35(44), pp. 8271-8274.
Everts, et al., "Degradation of Collagen in the Bone-Resorbing Compartment Underlying the Osteoclast Involves Both Cysteine-Proteinases and Matrix Metalloproteinases", (1992), Journal of Cellular Physiology, 150, pp. 221-231.
Shi, et al., "Molecular cloning of human cathepsin O, a novel endoproteinase and homologue of rabbit OC2", (1995), FEBS Ltrs., 357, pp. 129-134.
Inaoka, et al., "Molecular Cloning of Human cDNA for Cathepsin K: Novel Cysteine Proteinase Predominantly Expressed in Bone", (1995), Biochemical and Biophysical Research Communications, 206(1), pp. 89-96.
Elmore, et al., "A New Method for Determining the Absolute Molarity of Solutions of Trypsin and Chymotrypsin . . . ", (1968), Biochem J., 107, pp. 103-107.
Barker, et al., "The Reaction of an α-Aza-Amino Acid Derivative with Chymotrypsin and Its Use as a Ligand . . . ", (1974), Biochem J., 139, 555-563.
Gray, et al., "$N^\alpha$-Ethyloxycarbonyl-α-Azaornithine Phen . . . ", (1977), Tetrahedron, 33, p. 837-840.
Tezuka, et al., "Molecular Cloning of a Possible Cysteine Proteinase Predominantly Expressed in Osteoclasts", (1994), J. Biolog. Chem., 269(2), pp. 1106-1109.
Gupton, et al., "Reaction of Azapeptides with Chymotrypsin-like Enzymes", (1984), J. Biol. Chem., 259:7, pp. 4279-4287.
Powers, et al., "Reaction of Azapeptides with Human Leukocyte Elastase and Pricine Pancreatic Elastase", (1984), J. Biol. Chem., 259:7, pp. 4288-4294.
McConnell, et al., "New Leupeptin Analogues: Synthesis and Inhibition Data", J. Med. Chem. 33, pp. 86-93, 1990.
Umezawa, "Structures and Activities of Protease Inhibitors of Microbial Origin", Meth. Enzymol., pp. 678-695, 1976.
Barrett, et al., "L-*trans*-Epoxysuccinyl-leucylamido(4-guanidino)butane(E-64) and its analogues . . . ", (1982), Biochem. J., 201, p. 189-198.
Han et al., Azatides: "Solution and Liquid Phase Syntheses of a New Peptidomimetic", (1986), J. Amer. Chem. Soc., 118:11, p. 2539-2544.
Grinde, "Selective Inhibition of Lysomal Protein Degradation By the Thiol Proteinase . . . " (1982), Biochem. J. Biophys. Acta., 701, pp. 328-333.

Baggio, et al., "From Poor Substrates to Good Inhibitors: Design of Inhibitors for Serine and Thiol Proteases", (1996), Biochem., 35:11, pp. 3351-3353.

Calabretta, et al., "Peptidyl and azapeptidyl methylketones as substrate analog inhibitors of papain and cathepsin B", (1995), Eur. J. Med. Chem., 30, pp. 931-941.

McConnell, et al., "Inhibition Studies of Some Serine and Thiol Proteinases by New Leupeptin Analogues", (1993), J. Med. Chem, 36, pp. 1084-1089.

Kawada, et al., "Polymer Compositions", (1971), Chemical Abstracts, vol. 83, DN 83: 180329; JP 50058142 (1975).

Castelhano, et al., "Synthesis, Chemistry and Absolute Configuration of Novel Transglutaminase Inhibitors Containing a 3-Halo-4,5-dihydroisoxazole", (1988), Bioorg. Chem., vol. 16, No. 3, pp. 335-340.

Greenlee, et al., "Azapeptides: A New Class of Angiotensin-Converting Enzyme Inhibitors", (1984), Biochem. & Biophys. Research Communications, 122:2, pp. 791-797.

Auger, et al., "Solid-State 13C NMR Study of a Transglutaminase-Inhibitor Adduct", (1993), Biochemistry, vol. 32, No. 15, pp. 3930-3934.

Database WPIDS on STN, Derwent Publications LTD., (Columbus, Ohio), AN 85-029005, JP 59225172 A (Yamanouchi Pharm Co. LTD), Abstract, (1984).

Thompson, et al., "Design of potent and selective human cathepsin K Inhibitors that span the active site", (1997), Proc. Natl. Acad. Sci. USA, 94, pp. 14249-14254.

Yamashita, et al., "Structure and Design of Potent and Selective Cathepsin K Inhibitors", (1997), J. Amer. Chem. Soc., 119, pp. 11351-11352.

Afridi, et al., "Heterocyclic Rearrangements. Part XIV. Attempts to Activate Ring-opening-Ring-closure Rearrangements with Carbon as the Central Atom", (1976), J.C.S. Perkin Trans I, vol. 3, pp. 315-320.

Kosary, et al., "Synthesis of pyridylthiazoles as antisecretory agents", (1989), Pharmazie, 44:3, pp. 191-193.

Sridevi, et al., "Some reactions and rearrangements of isoxazol-3-carbonyl azides and hydrazides", (1990), Indian J. of Chem., 29B:2, pp. 182-183.

Tanner, et al., "Total Synthesis of Balanol, Part 1. Enantioselective Synthesis of the Hexahydroazepine Ring via Chiral Epoxides and Axiridines", (1995), Tetrahedron, vol. 51, No. 21, pp. 6061-6070.

Winkler, "Molecular Molding Studies of "Flap Up" Mannosyl Cation Mimics", (1996), J. Med.Chem., 39, pp. 4332-4334.

Veber et al., "The Role of Conformational Constraint in Improved Oral Bioavailability of Cathepsin K Inhibitors", (2000), Peptides, pp. 113-114 (XP009028910).

* cited by examiner

PROTEASE INHIBITORS

This application is a continuation of U.S. Ser. No. 10/404,716 filed Apr. 1, 2003 now abandoned; which is a continuation of U.S. Ser. No. 09/881,334 filed Jun. 14, 2001 now abandoned; which is a continuation-in-part of U.S. Ser. No. 09/593,845, filed Jun. 14, 2000 now abandoned; which is a continuation-in-part of Application No. PCT/US99/30730 filed 21 Dec. 1999; which claims the benefit of priority of Provisional Application No. 60/113,636, filed Dec. 23, 1998 and Provisional Application No. 60/164,581 filed Nov. 10, 1999.

FIELD OF THE INVENTION

This invention relates in general to 4-amino-azepan-3-one protease inhibitors, particularly such inhibitors of cysteine and serine proteases, more particularly compounds which inhibit cysteine proteases, even more particularly compounds which inhibit-cysteine proteases of the papain superfamily, yet more particularly compounds which inhibit cysteine proteases of the cathepsin family, most particularly compounds which inhibit cathepsin K. Such compounds are particularly useful for treating diseases in which cysteine proteases are implicated, especially diseases of excessive bone or cartilage loss, e.g., osteoporosis, periodontitis, and arthritis.

BACKGROUND OF THE INVENTION

Cathepsins are a family of enzymes, which are part of papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem.* 271, 12517-12524; Drake, F. H., et al., (1996) *J. Biol. Chem.* 271, 12511-12516; Bromme, D., et al., (1996) *J. Biol. Chem.* 271, 2126-2132.

Cathepsin K has been variously denoted as cathepsin O or cathepsin O2 in the literature. The designation cathepsin K is considered to be the more appropriate one.

Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by pneumocystis carinii, *trypsanoma cruzi, trypsanoma brucei brucei,* and Crithidia fusiculata; as well as in schistosomiasis, malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from P. gingivallis, called gingipains, have been implicated in the pathogenesis of gingivitis. Potempa, J., et al. (1994) *Perspectives in Drug Discovery and Design,* 2, 445-458.

Cathepsin K is believed to play a causative role in diseases of excessive bone or cartilage loss. Bone is composed of a protein matrix in which spindle- or plate-shaped crystals of hydroxyapatite are incorporated. Type I collagen represents the major structural protein of bone comprising approximately 90% of the protein matrix. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodelling at discrete foci throughout life. These foci, or remodelling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive mhembrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

Several published studies have demonstrated that inhibitors of cysteine proteases are effective at inhibiting osteoclast-mediated bone resorption, and indicate an essential role for a cysteine proteases in bone resorption. For example, Delaisse, et al., *Biochem. J.,* 1980, 192, 365, disclose a series of protease inhibitors in a mouse bone organ culture system and suggest that inhibitors of cysteine proteases (e.g., leupeptin, Z-Phe-Ala-$CHN_2$) prevent bone resorption, while serine protease inhibitors were ineffective. Delaisse, et al., *Biochem. Biophys. Res. Commun.,* 1984, 125, 441, disclose that E-64 and leupeptin are also effective at preventing bone resorption in vivo, as measured by acute changes in serum calcium in rats on calcium deficient diets. Lerner, et al., *J. Bone Min. Res.,* 1992, 7, 433, disclose that cystatin, an endogenous cysteine protease inhibitor, inhibits PTH stimulated bone resorption in mouse calvariae. Other studies, such as by Delaisse, et al., *Bone,* 1987, 8, 305, Hill, et al., *J. Cell. Biochem.,* 1994, 56, 118, and Everts, et al., *J. Cell. Physiol.,* 1992, 150, 221, also report a correlation between inhibition of cysteine protease activity and bone resorption. Tezuka, et al., *J. Biol. Chem.,* 1994, 269, 1106, Inaoka, et al., *Biochem. Biophys. Res. Commun.,* 1995, 206, 89 and Shi, et al., *FEBS Lett.,* 1995, 357, 129 disclose that under normal conditions cathepsin K, a cysteine protease, is abundantly expressed in osteoclasts and may be the major cysteine protease present in these cells.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

Several cysteine protease inhibitors are known. Palmer, (1995) *J. Med. Chem.,* 38, 3193, disclose certain vinyl sulfones which irreversibly inhibit cysteine proteases, such as the cathepsins B, L, S, O2 and cruzain. Other classes of compounds, such as aldehydes, nitriles, α-ketocarbonyl compounds, halomethyl ketones, diazomethyl ketones, (acyloxy) methyl ketones, ketomethylsulfonium salts and epoxy succinyl compounds have also been reported to inhibit cysteine proteases. See Palmer, id, and references cited therein.

U.S. Pat. No. 4,518,528 discloses peptidyl fluoromethyl ketones as irreversible inhibitors of cysteine protease. Published International Patent Application No. WO 94/04172, and European Patent Application Nos. EP 0 525 420 A1, EP 0 603 873 A1, and EP 0 611 756 A2 describe alkoxymethyl and mercaptomethyl ketones which inhibit the cysteine proteases cathepsins B, H and L. International Patent Application No. PCT/US94/08868 and and European Patent Application No. EP 0 623 592 A1 describe alkoxymethyl and mercaptomethyl ketones which inhibit the cysteine protease IL-1βconvertase. Alkoxymethyl and mercaptomethyl ketones have also been described as inhibitors of the serine protease kininogenase (International Patent Application No. PCT/GB91/01479).

Azapeptides which are designed to deliver the azaamino acid to the active site of serine proteases, and which possess a good leaving group, are disclosed by Elmore et al., *Biochem. J.,* 1968, 107, 103, Garker et al., *Biochem. J.,* 1974, 139, 555, Gray et al., *Tetrahedron,* 1977, 33, 837, Gupton et al., *J. Biol. Chem.,* 1984, 259, 4279, Powers et al., *J. Biol. Chem.,* 1984, 259, 4288, and are known to inhibit serine proteases. In addition, *J. Med. Chem.,* 1992, 35, 4279, discloses certain azapeptide esters as cysteine protease inhibitors.

Antipain and leupeptin are described as reversible inhibitors of cysteine protease in McConnell et al., *J. Med. Chem.,* 33, 86; and also have been disclosed as inhibitors of serine protease in Umezawa et al., 45 *Meth. Enzymol.* 678. E64 and its synthetic analogs are also well-known cysteine protease inhibitors (Barrett, *Biochem. J.,* 201, 189, and Grinde, *Biochem. Biophys. Acta,* 701, 328).

1,3-diamido-propanones have been described as analgesic agents in U.S. Pat. Nos. 4,749,792 and 4,638,010.

Thus, a structurally diverse variety of protease inhibitors have been identified. However, these known inhibitors are not considered suitable for use as therapeutic agents in animals, especially humans, because they suffer from various shortcomings. These shortcomings include lack of selectivity, cytotoxicity, poor solubility, and overly rapid plasma clearance. A need therefore exists for methods of treating diseases caused by pathological levels of proteases, particularly cysteine proteases, more particularly cathepsins, most particularly cathepsin K, and for novel inhibitor compounds useful in such methods.

We have now discovered a novel class of 4-amino-azepan-3-one compounds which are protease inhibitors, most particularly of cathepsin K.

SUMMARY OF THE INVENTION

An object of the present invention is to provide 4-amino-azepan-3-one carbonyl protease inhibitors, particularly such inhibitors of cysteine and serine proteases, more particularly such compounds which inhibit cysteine proteases, even more particularly such compounds which inhibit cysteine proteases of the papain superfamily, yet more particularly such compounds which inhibit cysteine proteases of the cathepsin family, most particularly such compounds which inhibit cathepsin K, and which are useful for treating diseases which may be therapeutically modified by altering the activity of such proteases.

Accordingly, in the first aspect, this invention provides a compound according to Formula I.

In another aspect, this invention provides a pharmaceutical composition comprising a compound according to Formula I and a pharmaceutically acceptable carrier, diluent or excipient.

In yet another aspect, this invention provides intermediates useful in the preparation of the compounds of Formula I.

In still another aspect, this invention provides a method of treating diseases in which the disease pathology may be therapeutically modified by inhibiting proteases, particularly cysteine and serine proteases, more particularly cysteine proteases, even more particularly cysteine proteases of the papain superfamily, yet more particularly cysteine proteases of the cathepsin family, most particularly cathepsin K.

In a particular aspect, the compounds of this invention are especially useful for treating diseases characterized by bone loss, such as osteoporosis and gingival diseases, such as gingivitis and periodontitis, or by excessive cartilage or matrix degradation, such as osteoarthritis and rheumatoid arthritis.

DETAILED DESCRIPTION OF THE INVENTION

The present invention provides compounds of Formula I:

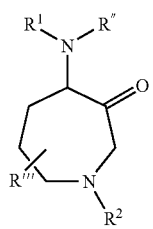

wherein:
$R^1$ is selected from the group consisting of:

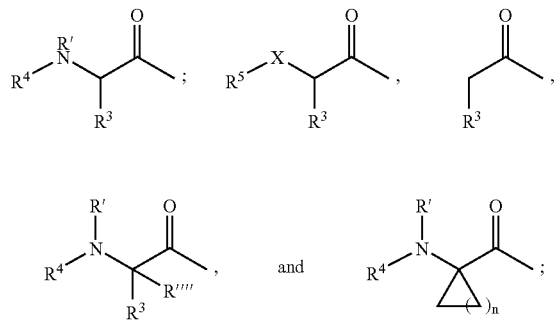

$R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9C$ (O)—, R⁹C(S)—, R⁹SO₂—, R⁹OC(O)—, R⁹R¹¹NC(O)—, R⁹R¹¹NC(S)—, R⁹(R¹¹)NSO₂—

[structure: pyridyl-phenyl-CH₂-C(O)]

[structure: pyridyl-phenyl-CH₂ and NR⁶R⁷—C(R⁸)—Z]

and R⁹SO₂R¹¹NC(O)—;

R³ is selected from the group consisting of: H, C₁₋₆alkyl, C₃₋₆cycloalkyl-C₀₋₆alkyl, C₂₋₆alkenyl, C₂₋₆alkynyl, HetC₀₋₆alkyl and ArC₀₋₆alkyl;

R³ and R' may be connected to form a pyrrolidine, piperidine or morpholine ring;

R⁴ is selected from the group consisting of: H, C₁₋₆alkyl, C₃₋₆cycloalkyl-C₀₋₆alkyl, Ar—C₀₋₆alkyl, Het-C₀₋₆alkyl, R⁵C(O)—, R⁵C(S)—, R⁵SO₂—, R⁵OC(O)—, R⁵R¹²NC(O)—, and R⁵R¹²NC(S)—;

R⁵ is selected from the group consisting of: H, C₁₋₆alkyl, C₂₋₆alkenyl, C₂₋₆alkynyl, C₃₋₆cycloalkyl-C₀₋₆alkyl, Ar—C₀₋₆ alkyl and Het-C₀₋₆alkyl;

R⁶ is selected from the group consisting of: H, C₁₋₆alkyl, Ar—C₀₋₆alkyl, and Het-C₀₋₆alkyl;

R⁷ is selected from the group consisting of: H, C₁₋₆alkyl, C₃₋₆cycloalkyl-C₀₋₆alkyl, Ar—C₀₋₆alkyl, Het-C₀₋₆alkyl, R¹⁰C(O)—, R¹⁰C(S)—, R¹⁰S)₂—, R¹⁰OC(O)—, R¹⁰R¹³NC(O)—, and R¹⁰R¹³NC(S)—;

R⁸ is selected from the group consisting of: H, C₁₋₆alkyl, C₂₋₆alkenyl, C₂₋₆alkynyl, HetC₀₋₆alkyl and ArC₀₋₆alkyl;

R⁹ is selected from the group consisting of: C₁₋₆alkyl, C₃₋₆cycloalkyl-C₀₋₆alkyl, Ar—C₀₋₆alkyl and Het-C₀₋₆alkyl;

R¹⁰ is selected from the group consisting of: C₁₋₆alkyl, C₃₋₆cycloalkyl-C₀₋₆alkyl, Ar—C₀₋₆alkyl and Het-C₀₋₆alkyl;

R¹¹ is selected from the group consisting of: H, C₁₋₆alkyl, Ar—C₀₋₆alkyl, and Het-C₀₋₆alkyl;

R¹² is selected from the group consisting of: H, C₁₋₆alkyl, Ar—C₀₋₆alkyl, and Het-C₀₋₆alkyl;

R¹³ is selected from the group consisting of: H, C₁₋₆alkyl, Ar—C₀₋₆alkyl, and Het-C₀₋₆alkyl;

R' is selected from the group consisting of: H, C₁₋₆alkyl, Ar—C₀₋₆alkyl, and Het-C₀₋₆alkyl;

R" is selected from the group consisting of: H, C₁₋₆alkyl, Ar—C₀₋₆alkyl, or Het-C₀₋₆alkyl;

R''' is selected from the group consisting of: H, C₁₋₆alkyl, C₃₋₆cycloalkyl-C₀₋₆alkyl, Ar—C₀₋₆alkyl, and Het-C₀₋₆alkyl;

R'''' is selected from the group consisting of: C₁₋₆alkyl, C₃₋₆cycloalkyl-C₀₋₆alkyl C₂₋₆alkenyl, C₂₋₆alkynyl, HetC₀₋₆alkyl and ArC₀₋₆alkyl;

X is selected from the group consisting of: CH₂, S, and O;

Z is selected from the group consisting of: C(O) and CH₂;

n is an integer from 1 to 5;

and pharmaceutically acceptable salts, hydrates and solvates thereof.

In compounds of Formula I, when R¹ is

[structure: R⁴—N(R')—C(R³)—C(O)—]:

R³ is selected from the group consisting of: H, C₁₋₆alkyl, C₃₋₆cycloalkyl-C₀₋₆alkyl, C₂₋₆alkenyl, C₂₋₆alkynyl, Het-C₀₋₆alkyl and Ar—C₀₋₆alkyl;

R³ is preferably selected from the group consisting of: H, C₃₋₆cycloalkyl-C₀₋₆alkyl, C₂₋₆alkenyl, Ar—C₀₋₆alkyl, and C₁₋₆alkyl;

R³ is more preferably selected from the group consisting of:

H, methyl, ethyl, n-propyl, prop-2-yl, n-butyl, isobutyl, but-2-yl, cyclopropylmethyl, cyclohexylmethyl, 2-methanesulfinyl-ethyl, 1-hydroxyethyl, toluyl, naphthalen-2-ylmethyl, benzyloxymethyl, and hydroxymethyl.

R³ is even more preferably selected from the group consisting of: toluyl, isobutyl and cyclohexylmethyl.

R³ is most preferably isobutyl.

R⁴ is selected from the group consisting of: H, C₁₋₆alkyl, C₃₋₆cycloalkyl-C₀₋₆alkyl, Ar—C₀₋₆alkyl, Het-C₀₋₆alkyl, R⁵C(O)—, R⁵C(S)—, R⁵SO₂—, R⁵OC(O)—, R⁵R¹³NC(O)—, and R⁵R¹³NC(S)—.

R⁴ is preferably selected from the group consisting of: R⁵OC(O)—, R⁵C(O)— and R⁵SO₂—.

R⁴ is most preferably R⁵C(O)—.

In some embodiments, R⁴ is preferably methanesulfonyl.

R⁵ is selected from the group consisting of: H, C₁₋₆alkyl, C₂₋₆alkenyl, C₂₋₆alkynyl, C₃₋₆cycloalkyl-C₀₋₆alkyl, Ar—C₀₋₆ alkyl or Het-C₀₋₆alkyl.

Preferably R⁵ is selected from the group consisting of: C₁₋₆alkyl, Ar—C₀₋₆alkyl and Het-C₀₋₆alkyl.

More preferably, and especially when R⁴ is R⁵C(O)—, R⁵ is selected from the group consisting of:

methyl, especially halogenated methyl, more especially trifluoromethyl , especially C₁₋₆alkoxy substituted methyl, more especially phenoxy-methyl, 4-fluoro-phenoxy-methyl, especially heterocycle substituted methyl, more especially 2-thiophenyl-methyl;

ethyl, especially piperidin-1-yl-ethyl;

butyl, especially aryl substituted butyl, more especially 4-(4-methoxy)phenyl-butyl;

isopentyl;

cyclohexyl;

pentanonyl, especially 4-pentanonyl;

butenyl, especially aryl substituted butenyl, more especially 4,4-bis(4-methoxyphenyl)-but-3-enyl;

acetyl;

phenyl, especially phenyl substituted with one or more halogens, more especially 3,4-dichlorophenyl and 4-fluorophenyl, especially phenyl substituted with one or more aryloxy or C₁₋₆alkoxy groups, more especially 3,4-dimethoxy-phenyl, 3-benzyloxy-4-methoxy-phenyl, especially phenyl substituted with one or more C₁₋₆alkyl sulfonyl groups, more especially 4-methanesulfonyl-phenyl;

benzyl;

naphthalenyl, especially naphthylen-2-yl;

benzo[1,3]dioxolyl, especially benzo[1,3]dioxol-5-yl;

furanyl, especially furan-2-yl, especially substituted furanyl, such as 5-nitro-furan-2-yl, 5-(4-nitrophenyl)-furan-2-yl, 5-(3-trifluoromethyl-phenyl)-furan-2-yl, more especially halogen substituted furanyl, even more especially 5-bromofuran-2-yl, more especially aryl substituted furanyl, even more especially 5-(4-chloro-phenyl)-furan-2-yl, more especially $C_{1-6}$alkyl substituted furanyl, even more especially 3-methyl-furan-2-yl, 4-methyl-furan-2-yl, 2,5-dimethyl-furan-2-yl, and 2,4-dimethyl-furan-3-yl;

tetrahydrofuranyl, tetrahydrofuran-2-yl;

benzofuranyl, especially benzofuran-2-yl, and substituted benzofuranyl, more especially 5-(2-piperazin-4-carboxylic acid tert-butyl ester-ethoxy)benzofuran-2-yl, 5-(2-morpholino-4-yl-ethoxy)-benzofuran-2-yl, 5-(2-piperazin-1-yl-ethoxy)benzofuran-2-yl, 5-(2-cyclohexyl-ethoxy)-benzofuran-2-yl; especially $C_{1-6}$alkoxy substituted benzofuranyl, more especially 7-methoxy-benzofuran-2-yl, 5-methoxy-benzofuran-2-yl, 5,6-dimethoxy-benzofuran-2-yl, especially halogen substituted benzofuranyl, more especially 5-fluoro-benzofuran-2-yl, 5,6-difluoro-benzofuran-2-yl, especially $C_{1-6}$alkyl substituted benzofuranyl, most especially 3-methyl-benzofuran-2-yl, 3,5-dimethyl-benzofuran-2-yl, and 3-ethyl-benzofuran-2-yl; also 5-fluoro-3-methyl-benzofuran-2-yl, 6-fluoro-3-methyl-benzofuran-2-yl, 5-methoxy-3-methyl-benzofuran-2-yl, 4-methoxy-3-methyl-benzofuran-2-yl, and 6-methoxy-3-methyl-benzofuran-2-yl;

naphtho[2,1-b]-furanyl, especially naphtho[2,1-b]-furan-2-yl, alkyl substituted naphtho[2,1-b]-furanyl, especially 1-methyl-naphtho[2,1-b]-furan-2-yl;

benzo[b]thiophenyl, especially benzo[b]thiophen-2-yl; especially $C_{1-6}$alkoxy substituted benzo[b]thiophenyl, more especially 5,6-dimethoxy-benzo[b]thiophen-2-yl;

quinolinyl, especially quinolin-2-yl, quinolin-3-yl, quinolin-4-yl, quinolin-6-yl, and quinolin-8-yl;

quinoxalinyl, especially quinoxalin-2-yl;

1,8 naphthyridinyl, especially 1,8 naphthyridin-2-yl;

indolyl, especially indol-2-yl, especially indol-6-yl, indol-5-yl, especially $C_{1-6}$alkyl substituted indolyl, more especially N-methyl-indol-2-yl;

pyridinyl, especially pyridin-2-yl, pyridin-3-yl, pyridin-5-yl, especially $C_{1-6}$alkyl substituted pyridinyl, more especially 2-methyl-pyridin-5-yl, and oxy-pyridinyl, especially 1-oxy-pyridin-2-yl and 1-oxy-pyridin-3-yl;

furo[3,2-b]-pyridinyl, especially furo[3,2-b]-pyridin-2-yl, $C_{1-6}$alkyl substituted furo[3,2-b]-pyridinyl, especially 3-methyl-furo[3,2-b]-pyridin-2-yl;

thiophenyl, especially thiophen-3-yl, also thiophen-2-yl, especially $C_{1-6}$alkyl substituted thiophenyl, more especially 5-methyl-thiophen-2-yl and 5-methyl-thiophen-3-yl, especially halogen substituted thiophenyl, more especially 4,5-dibromo-thiophen-2-yl;

thieno[3,2-b]thiophene, especially thieno[3,2-b]thiophene-2-yl, more especially $C_{1-6}$alkyl substituted thieno[3,2-b]thiophene-2-yl, more especially 5-tert-butyl-3-methyl-thieno[3,2-b]thiophene-2-yl;

isoxazolyl, especially isoxazol-4-yl, especially $C_{1-6}$alkyl substituted isoxazolyl, more especially 3,5-dimethyl-isoxazol-4-yl;

oxazolyl, especially oxazol-4-yl, more especially 5-methyl-2-phenyl oxazol-4-yl, 2-phenyl-5-trifluoromethyl-oxazol-4-yl; and 1H-benzoimidazolyl, especially 1H-benzoimidazol-5-yl.

When $R^4$ is $R^5SO_2$, $R^5$ is preferably pyridin-2-yl or 1-oxo-pyridin-2-yl.

R' is selected from the group consisting of: H, $C_{1-6}$alkyl, Ar—$C_{0-6}$alkyl, and Het-$C_{0-6}$alkyl.

Preferably R' is selected from the group consisting of: H and naphthalen-2-yl-methyl.

Most preferably R' is H.

R" is selected from the group consisting of: H, $C_{1-6}$alkyl, Ar—$C_{0-6}$alkyl, and Het-$C_{0-6}$alkyl.

Most preferably R" is H.

R''' is selected from the group consisting of: H, $C_{1-6}$alkyl, $C_{3-6}$cycloalkyl-$C_{0-6}$alkyl, and Het-$C_{0-6}$alkyl.

R''' is preferably selected from the group consisting of: H and $C_{1-6}$alkyl.

R''' is more preferably selected from the group consisting of: H, methyl and 6,6-dimethyl.

R''' is still more preferably selected from the group consisting of: H and 6,6-dimethyl.

Most preferably R''' is H.

In compounds of Formula I, when $R^1$ is

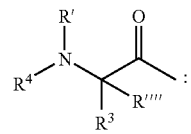

$R^3$ is selected from the group consisting of $C_{1-6}$alkyl, $C_{3-6}$cycloalkyl-$C_{0-6}$alkyl, $C_{2-6}$alkenyl, $C_{2-6}$alkynyl, Het-$C_{0-6}$alkyl and Ar—$C_{0-6}$alkyl.

$R^3$ is preferably $C_{1-6}$alkyl.

$R^3$ is more preferably selected from the group consisting of methyl, ethyl, n-propyl, n-butyl, isobutyl, t-butyl, cyclohexylmethyl, and toluyl.

R'''' is selected from the group consisting of: $C_{1-6}$alkyl, $C_{3-6}$cycloalkyl-$C_{0-6}$alkyl, $C_{2-6}$alkenyl, $C_{2-6}$alkynyl, Het$C_{0-6}$alkyl and Ar$C_{0-6}$alkyl;

R'''' is preferably $C_{1-6}$alkyl;

R'''' is more preferably selected from the group consisting of methyl, ethyl, n-propyl, n-butyl, isobutyl and t-butyl.

R'''' is most preferably methyl.

In such compounds, R', R", R''', $R^4$, and $R^5$ are as described above wherein $R^1$ is

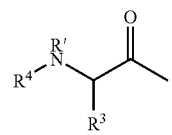

In compounds of Formula I, when $R^1$ is

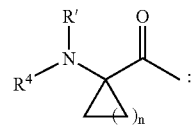

n is preferably an integer of from 1 to 5; and
R', R", R''', $R^4$, and $R^5$ are as described above wherein
$R^1$ is

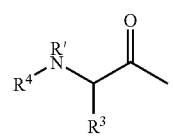

n is most preferably 3.

The ring may be unsubstituted or substituted with one or more of $C_{1-6}$alkyl, $C_{3-6}$cycloalkyl-$C_{0-6}$alkyl, $C_{2-6}$alkenyl, $C_{2-6}$alkynyl, Het$C_{0-6}$alkyl, Ar$C_{0-6}$alkyl, or halogen.

The ring is preferably unsubstituted.

In compounds of Formula I, $R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9C(O)$—, $R^9C(S)$—, $R^9SO_2$—, $R^9OC(O)$—, $R^9R^{11}NC(O)$—, $R^9R^{11}NC(S)$—, $R^9R^{11}NSO_2$—,

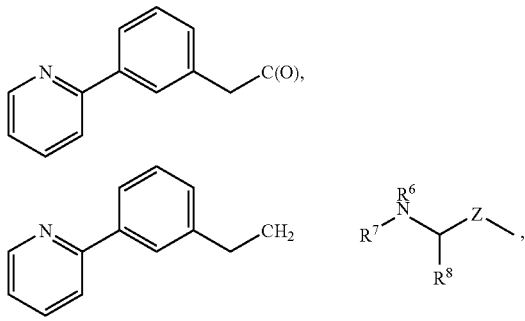

and $R^9SO_2R^{11}NC(O)$—.

More preferably $R^2$ is selected from the group consisting of: Ar—$C_{0-6}$alkyl, $R^9C(O)$—, $R^9SO_2$, $R^9R^{11}NC(O)$—, and

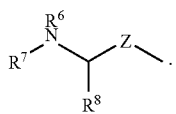

Even more preferably, $R^2$ is selected from the group consisting of: Ar—$C_{0-6}$alkyl, $R^9C(O)$—, and $R^9SO_2$.

Most preferably $R^2$ is $R^9SO_2$.

In such embodiments:

$R^6$ is selected from the group consisting of: H, $C_{1-6}$alkyl, Ar—$C_{0-6}$alkyl, or Het-$C_{0-6}$alkyl, preferably H.

$R^7$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^{10}C(O)$—, $R^{10}C(S)$—, $R^{10}SO_2$—, $R^{10}OC(O)$—, $R^{10}R^{14}NC(O)$—, $R^{10}R^{14}NC(S)$—, $R^7$ is preferably $R^{10}OC(O)$.

$R^8$ is selected from the group consisting of: H, $C_{1-6}$alkyl, $C_{2-6}$alkenyl, $C_{2-6}$alkynyl, Het$C_{0-6}$alkyl and Ar$C_{0-6}$alkyl; preferably $C_{1-6}$alkyl, more preferably isobutyl.

$R^9$ is selected from the group consisting of: $C_{1-6}$alkyl, $C_{3-6}$cycloalkyl-$C_{0-6}$alkyl; Ar—$C_{0-6}$alkyl, and Het-$C_{0-6}$alkyl:

$R^9$ is preferably selected from the group consisting of: $C_{1-6}$alkyl, Ar—$C_{0-6}$alkyl, and Het-$C_{0-6}$alkyl.

More preferably, $R^9$ is selected from the group consisting of:

methyl;

ethyl, especially $C_{1-6}$alkyl-substituted ethyl, more especially 2-cyclohexyl-ethyl;

propyl;

butyl, especially $C_{1-6}$butyl, more especially 3-methylbutyl;

tert-butyl, particularly when $R^2$ is $R^9OC(O)$;

isopentyl;

phenyl, especially halogen substituted phenyl, more especially 3,4-dichlorophenyl, 4-bromophenyl, 2-fluorophenyl, 3-fluorophenyl, 4-fluorophenyl, 2-chlorophenyl, 3-chlorophenyl, 4-chlorophenyl, especially $C_{1-6}$alkoxy phenyl, more especially 3-methoxyphenyl, 4-methoxyphenyl, 3,4-dimethoxyphenyl, especially cyanophenyl, more especially 2-cyanophenyl; especially $C_{1-6}$alkyl substituted phenyl, more especially 4-ethyl-phenyl, 2-methyl phenyl, 4-methyl phenyl, especially $C_{1-6}$alkyl sulfonyl substituted phenyl, more especially 4-methanesulfonyl phenyl, and 2-methanesulfonyl phenyl;

toluyl, especially Het-substituted toluyl, more especially 3-(pyridin-2-yl)toluyl;

naphthylene, especially naphthyl-2-ene;

benzoic acid, especially 2-benzoic acid;

benzo[1,3]dioxolyl, especially benzo[1,3]dioxol-5-yl;

benzo[1,2,5]oxadiazolyl, especially benzo[1,2,5]oxadiazol-4-yl;

pyridinyl, especially pyridin-2-yl, pyridin-3-yl, especially 1-oxy-pyridinyl, more especially 1-oxy-pyridin-2-yl, 1-oxy-pyridin-3-yl; especially $C_{1-6}$alkylpyridinyl, more especially 3-methyl-pyridin-2-yl, 6-methyl-pyridin-2-yl;

thiophenyl, especially thiophenyl-2-yl;

thiazolyl, especially thiazol-2-yl;

1H-imidazolyl, especially 1H-imidazol-2-yl, 1H-imidazol-4-yl, more especially $C_{1-6}$alkyl substituted imidazolyl, even more especially 1-methyl-1H-imidazol-2-yl, 1-methyl-1H-imidazol-4-yl, and 1,2-dimethyl-1H-imidazol-4-yl;

triazolyl, especially 1H-[1,2,4]triazolyl, more especially 1H-[1,2,4]triazol-3-yl, especially $C_{1-6}$alkyl substituted 1H-[1,2,4]triazolyl, more especially 5-methyl-1H-[1,2,4]triazol-3-yl; and isoxazolyl, especially isoxazol-4-yl, especially $C_{1-6}$alkyl-substituted isoxazolyl, more especially 3,5-dimethyl-isoxazol-4-yl.

When $R^2$ is $R^9SO_2$, $R^9$ is most preferably selected from the group consisting of: pyridin-2-yl and 1-oxy-pyridin-2-yl.

When $R^2$ is $R^9SO_2R^{11}NC(O)$—, $R^9$ is preferably Ar—$C_{0-6}$alkyl, more preferably Ar, most preferably substituted phenyl such as 2-methyl phenyl, 4-methyl phenyl, 2-chloro phenyl, and 4-fluoro phenyl.

When $R^2$ is $R^9C(O)$—, $R^9$ is preferably selected from the group consisting of $C_{1-6}$alkyl, $C_{3-6}$cycloalkyl-$C_{0-6}$alkyl, and Het-$C_{0-6}$alkyl, more preferably 1-oxy-pyridin-2-yl, cyclohexyl ethyl, and 3-methyl butyl.

$R^{11}$ is selected from the group consisting of: H, $C_{1-6}$alkyl, Ar—$C_{0-6}$alkyl, and Het-$C_{0-6}$alkyl.

When $R^2$ is $R^9SO_2R^{11}NC(O)$—, $R^{11}$ is preferably H.

When $R^2$ is Ar—$C_{0-6}$alkyl, $R^2$ is preferably phenyl, especially substituted phenyl, more especially halogen substituted phenyl, even more especially 2-fluorobenzyl.

When $R^2$ is $C_{1-6}$alkyl, $R^2$ is preferably selected from 1-propyl, 1-butyl, and 1-pentyl.

When $R^2$ is Het-$C_{0-6}$alkyl, Het-$C_{0-6}$alkyl is preferably Het-methyl, and Het in Het-methyl is preferably selected from the group consisting of:

pyridinyl, especially pyridin-2-yl, especially $C_{1-6}$alkylpyridinyl, more especially 6-methyl-pyridin-2-yl;

thiophenyl, especially thiophene-2-yl, more especially thiophen-2-yl or benzo[b]thiophen-2-yl;

thiazolyl, especially thiazol-4-yl such as 1-(2-morpholin-4-yl-thiazol-4-yl), and 1-(isothiazol-3-yl);

1H-imidazolyl, especially 1H-imidazol-2-yl, 1H-imidazol-4-yl, especially $C_{1-6}$alkyl substituted imidazolyl, more especially 1-methyl-1H-imidazol-2yl;

triazolyl, especially 3H-[1,2,3]triazolyl, more especially 3H-[1,2,3]triazol-4-yl, especially $C_{1-6}$alkyl substituted 3H-[1,2,3]triazolyl, more especially 3-phenyl-3H-[1,2,3]triazolyl -4-yl;

quinolinyl, especially quinolin-2-yl, quinolin-2-yl;

furanyl, especially furan-2-yl, especially substituted furanyl, such as 5-ethyl-furan-2-yl;

thieno[3,2-b]thiophene, especially thieno[3,2-b]thiophene-2-yl, especially $C_{1-6}$alkyl substituted thieno[3,2-b]thiophenyl, especially 3,4-dimethyl-thieno[3,2-b]thiophene-2-yl.

$R^2$ is also preferably:
H;
toluyl;
aryl substituted ethyl, especially 2-phenyl ethyl, 2-[3-(pyridin-2-yl)phenyl]ethyl.

Compounds of Formula I where R" and R'" are both H are preferred.

More preferred are compounds of Formula I wherein:
$R^1$ is

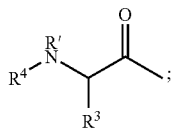

$R^2$ is selected from the group consisting of: Ar—$C_{0-6}$alkyl, $R^9C(O)$—, $R^9SO_2$, $R^9R^{11}NC(O)$—, and

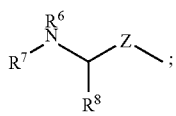

$R^3$ is selected from the group consisting of: H, $C_{1-6}$alkyl, $C_{3-6}$cycloalkyl-$C_{0-6}$alkyl and Ar—$C_{0-6}$alkyl;
$R^4$ is selected from the group consisting of: $R^5OC(O)$—, $R^5C(O)$— and $R^5SO_2$—;
$R^5$ is selected from the group consisting of: $C_{1-6}$alkyl, Ar—$C_{0-6}$alkyl and Het—$C_{0-6}$alkyl;
$R^6$ is H;
$R^7$ is $R^{10}OC(O)$;
$R^8$ is $C_{1-6}$alkyl;
$R^9$ is selected from the group consisting of: $C_{1-6}$alkyl, Ar—$C_{0-6}$alkyl and Het—$C_{0-6}$alkyl;
$R^{10}$ is selected from the group consisting of: $C_{1-6}$alkyl, Ar—$C_{0-6}$alkyl and Het—$C_{0-6}$alkyl;
R' is H;
R" is H;
R'" is H; and
Z is selected from the group consisting of: C(O) and $CH_2$.

Even more preferred are such compounds of Formula I wherein $R^2$ is selected from the group consisting of: Ar—$C_{0-6}$alkyl, $R^9C(O)$—, $R^9SO_2$.

Yet more preferred are compounds of Formula I wherein:
$R^1$ is

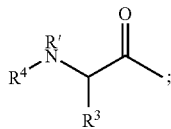

$R^2$ is selected from the group consisting of: Ar—$C_{0-6}$alkyl, $R^9C(O)$— and $R^9SO_2$;
$R^3$ is selected from the group consisting of: H, methyl, ethyl, n-propyl, prop-2-yl. n-butyl, isobutyl, but-2-yl, cyclopropylmethyl, cyclohexylmethyl, 2-methanesulfinyl-ethyl, 1-hydroxyethyl, toluyl, naphthalen-2-ylmethyl, benzyloxymethyl, and hydroxymethyl;
$R^4$ is $R^5C(O)$—;
$R^5$ is selected from the group consisting of:
methyl, especially halogenated methyl, more especially trifluoromethyl, especially $C_{1-6}$alkoxy substituted methyl, more especially phenoxy-methyl, 4-fluoro-phenoxy-methyl, especially heterocycle substituted methyl, more especially 2-thiophenyl-methyl
ethyl, especially piperndin-1-yl-ethyl;
butyl, especially aryl substituted butyl, more especially 4-(4-methoxy)phenyl-butyl;
isopentyl;
cyclohexyl;
pentanonyl, especially 4-pentanonyl;
butenyl, especially aryl substituted butenyl, more especially 4,4-bis(4-methoxyphenyl)-but-3-enyl;
acetyl;
phenyl, especially phenyl substituted with one or more halogens, more especially 3,4-dichlorophenyl and 4-fluorophenyl, especially phenyl substituted with one or more aryloxy or $C_{1-6}$alkoxy groups, more especially 3,4-dimethoxy-phenyl, 3-benzyloxy-4-methoxy-phenyl, especially phenyl substituted with one or more $C_{1-6}$alkyl sulfonyl groups, more especially 4-methanesulfonyl-phenyl;
benzyl;
naphthalenyl, especially naphthylen-2-yl;
benzo[1,3]dioxolyl, especially benzo[1,3]dioxol-5-yl;
furanyl, especially furan-2-yl, especially substituted furanyl, such as 5-nitro-furan-2-yl, 5-(4-nitrophenyl)-furan-2-yl, 5-(3-trifluoromethyl-phenyl)-furan-2-yl, more especially halogen substituted furanyl, even more especially 5-bromo-furan-2-yl, more especially aryl substituted furanyl, even more especially 5-(4-chloro-phenyl)-furan-2-yl, more especially $C_{1-6}$alkyl substituted furanyl, even more especially 3-methyl-furan-2-yl, 4-methyl-furan-2-yl, 2,5-dimethyl-furan-2-yl, and 2,4-dimethyl-furan-3-yl;
tetrahydrofuranyl, especially tetrahydrofuran-2-yl;
benzofuranyl, especially benzofuran-2-yl, and substituted benzofuranyl, more especially 5-(2-piperazin-4-carboxylic acid tert-butyl ester-ethoxy)benzofuran-2-yl, 5-(2-morpholino-4-yl-ethoxy)-benzofuran-2-yl, 5-(2-piperazin-1-yl-ethoxy)benzofuran-2-yl, 5-(2-cyclohexyl-ethoxy)-benzofuran-2-yl; especially $C_{1-6}$alkoxy substituted benzofuranyl, more especially 7-methoxy-benzofuran-2-yl, 5-methoxy-benzofuran-2-yl, 5,6-dimethoxy-benzofuran-2-yl, especially halogen substituted benzofuranyl, more especially 5-fluoro-benzofuran-2-yl, 5,6-difluoro-benzofuran-2-yl, especially $C_{1-6}$alkyl substituted benzofuranyl, most especially 3-methyl-benzofuran-2-yl, 3,5-dimethyl-benzofuran-2-yl, and 3-ethyl-benzofuran-2-yl; also 5-fluoro-3-methyl-benzofuran-2-yl, 6-fluoro-3-methyl-benzofuran-2-yl, 5-methoxy-3-methyl-benzofuran-2-yl, 4-methoxy-3-methyl-benzofuran-2-yl, and 6-methoxy-3-methyl-benzofuran-2-yl;
naphtho[2,1-b]-furanyl, especially naphtho[2,1-b]-furan-2-yl, alkyl substituted naphtho[2,1-b]-furanyl, especially 1-methyl-naphtho[2,1-b]-furan-2-yl;
benzo[b]thiophenyl, especially benzo[b]thiophen-2-yl; especially $C_{1-6}$alkoxy substituted benzo[b]thiophenyl, more especially 5,6-dimethox-y-benzo[b]thiophen-2-yl;
quinolinyl, especially quinolin-2-yl, quinolin-3-yl, quinolin-4-yl, quinolin-6-yl, and quinolin-8-yl;
quinoxalinyl, especially quinoxalin-2-yl;
1,8 naphthyridinyl, especially 1,8 naphthyridin-2-yl;

indolyl, especially indol-2-yl, especially indol-6-yl, indol-5-yl, especially $C_{1-6}$alkyl substituted indolyl, more especially N-methyl-indol-2-yl;

pyridinyl, especially pyridin-2-yl, pyridin-3-yl, pyridin-5-yl, especially $C_{1-6}$alkyl substituted pyridinyl, more especially 2-methyl-pyridin-5-yl, and oxy-pyridinyl, especially 1-oxy-pyridin-2-yl and 1-oxy-pyridin-3-yl;

furo[3,2-b]-pyridinyl, especially furo[3,2-b]-pyridin-2-yl, $C_{1-6}$alkyl substituted furo[3,2-b]-pyridinyl, especially 3-methyl-furo[3,2-b]-pyridin-2-yl;

thiophenyl, especially thiophen-3-yl, also thiophen-2-yl, especially $C_{1-6}$alkyl substituted thiophenyl, more especially 5-methyl-thiophen-2-yl and 5-methyl-thiophen-3-yl, especially halogen substituted thiophenyl, more especially 4,5-dibromo-thiophen-2-yl;

thieno[3,2-b]thiophene, especially thieno[3,2-b]thiophene-2-yl, more especially $C_{1-6}$alkyl substituted thieno[3,2-b]thiophene-2-yl, more especially 5-tert-butyl-3-methyl-thieno[3,2-b]thiophene-2-yl;

isoxazolyl, especially isoxazol-4-yl, especially $C_{1-6}$alkyl substituted isoxazolyl, more especially 3,5-dimethyl-isoxazol-4-yl;

oxazolyl, especially oxazol-4-yl, more especially 5-methyl-2-phenyl oxazol-4-yl, 2-phenyl-5-trifluoromethyl-oxazol-4-yl; and 1H-benzoimidazolyl, especially 1H-benzoimidazol-5-yl.

$R^9$ is selected from the group consisting of:

methyl;

ethyl, especially $C_{1-6}$alkyl-substituted ethyl, more especially 2-cyclohexyl-ethyl;

propyl;

butyl, especially $C_{1-6}$butyl, more especially 3-methylbutyl;

tert-butyl, particularly when $R^2$ is $R^9OC(O)$;

isopentyl;

phenyl, especially halogen substituted phenyl, more especially 3,4-dichlorophenyl, 4-bromophenyl, 2-fluorophenyl, 3-fluorophenyl, 4-fluorophenyl, 2-chlorophenyl, 3-chlorophenyl, 4-chlorophenyl, especially $C_{1-6}$alkoxy phenyl, more especially 3-methoxyphenyl, 4-methoxyphenyl, 3,4-dimethoxyphenyl, especially cyanophenyl, more especially 2-cyanophenyl; especially $C_{1-6}$alkyl substituted phenyl, more especially 4-ethyl-phenyl, 2-methyl phenyl, 4-methyl phenyl, especially $C_{1-6}$alkyl sulfonyl substituted phenyl, more especially 4-methanesulfonyl phenyl, and 2-methanesulfonyl phenyl;

toluyl, especially Het-substituted toluyl, more especially 3-(pyridin-2-yl)toluyl;

naphthylene, especially naphthyl-2-ene;

benzoic acid, especially 2-benzoic acid;

benzo[1,3]dioxolyl, especially benzo[1,3]dioxol-5-yl;

benzo[1,2,5]oxadiazolyl, especially benzo[1,2,5]oxadiazol-4-yl;

pyridinyl, especially pyridin-2-yl, pyridin-3-yl, especially 1-oxy-pyridinyl, more especially 1-oxy-pyridin-2-yl, 1-oxy-pyridin-3-yl; especially $C_{1-6}$alkylpyridinyl, more especially 3-methyl-pyridin-2-yl, 6-methyl-pyridin-2-yl;

thiophenyl, especially thiophenyl-2-yl;

thiazolyl, especially thiazol-2-yl;

1H-imidazolyl, especially 1H-imidazol-2-yl, 1H-imidazol-4-yl, more especially $C_{1-6}$alkyl substituted imidazolyl, even more especially 1-methyl-1H-imidazol-2-yl, 1-methyl-1H-imidazol-4-yl, and 1,2-dimethyl-1H-imidazol-4-yl;

triazolyl, especially 1H-[1,2,4]triazolyl, more especially 1H-[1,2,4]triazol-3-yl, especially $C_{1-6}$alkyl substituted 1H-[1,2,4]triazolyl, more especially 5-methyl-1H-[1,2,4]triazol-3-yl; and isoxazolyl, especially isoxazol-4-yl, especially $C_{1-6}$alkyl substituted isoxazolyl, more especially 3,5-dimethyl-isoxazol-4-yl.

R' is H;

R" is H; and

R''' is H.

Most preferred are compounds of Formula I wherein:

$R^1$ is

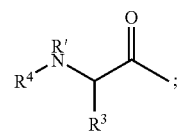

$R^2$ is $R^9SO_2$;

$R^3$ is isobutyl;

$R^4$ is $R^5C(O)$;

$R^5$ is selected from the group consisting of: 3-methyl-benzofuran-2-yl, thieno[3,2-b]thiophen-2-yl, 5-methoxy-benzofuran-2-yl, quinoxalin-2-yl, and quinblin-2-yl, preferably 3-methyl-benzofuran-2-yl;

$R^9$ is selected from the group consisting of: pyridin-2-yl and 1-oxy-pyridin-2-yl, preferably 1-oxy-pyridin-2-yl.

R' is H; and

R''' is H;

An embodiment of the present invention provides compounds of Formula I:

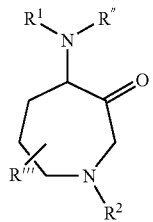

wherein:

$R^1$ is selected from the group consisting of:

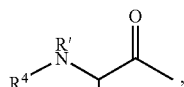

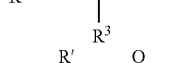

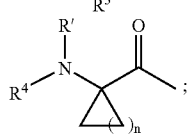

$R^2$ is selected from the group consisting of: $C_{1-6}$alkyl, Ar—$C_{0-6}$alkyl, Het-$C_{0-6}$alkyl, $R^9C(O)$—, $R^9SO_2$—, $R^9R^{11}NC(O)$—, and $R^9SO_2R^{11}NC(O)$—;

$R^3$ is selected from the group consisting of: $C_{1-6}$alkyl, $C_{3-6}$cycloalkyl-$C_{0-6}$alkyl, $C_{2-6}$alkenyl, $C_{2-6}$alkynyl, Het-$C_{0-6}$alkyl and Ar—$C_{0-6}$alkyl;

$R^3$ and R' may be connected to form a pyrrolidine, piperidine or morpholine ring;

$R^4$ is $R^5C(H)$—;

$R^5$ is selected from the group consisting of: $C_{1-6}$alkyl and Het-$C_{0-6}$alkyl;

$R^9$ is selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

$R^{11}$ is H;

R' is H;

R" is H;

R'" is selected from the group consisting of: H and $C_{1-6}$alkyl;

R"" is selected from the group consisting of: $C_{1-6}$alkyl, $C_{3-6}$cycloalkyl-$C_{0-6}$alkyl $C_{2-6}$alkenyl, $C_{2-6}$alkynyl, Het$C_{0-6}$alkyl and Ar$C_{0-6}$alkyl; and n is an integer from 1 to 5;

and pharmaceutically acceptable salts, hydrates and solvates thereof.

In such embodiment, when $R^1$ is

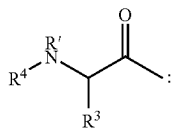

$R^3$ is preferably $C_{1-6}$alkyl;

$R^3$ is more preferably selected from the group consisting of: 1-methyl-propyl and isobutyl.

$R^3$ is most preferably isobutyl.

$R^4$ is $R^5C(O)$—.

$R^5$ is selected from the groupconsisting of: $C_{1-6}$alkyl and Het-$C_{0-6}$alkyl;

More preferably, $R^5$ is selected from the group consisting of:

ethyl, especially piperidin-1-yl-ethyl;

benzo[1,3]dioxolyl, especially benzo[1,3]dioxol-5-yl;

furanyl, especially furan-2-yl, especially substituted furanyl, such as 5-(3-trifluoromethyl-phenyl)-furan-2-yl, more especially $C_{1-6}$alkyl substituted furanyl, even more especially 3-methyl-furan-2-yl, 4-methyl-furan-2-yl, 2,5-dimethyl-furan-2-yl, and 2,4-dimethyl-furan-3-yl;

benzofuranyl, especially benzofuran-2-yl, especially $C_{1-6}$alkoxy substituted benzofuranyl, more especially 5-methoxy-benzofuran-2-yl, especially halogen substituted benzofuranyl, more especially 5-fluoro-benzofuran-2-yl, especially $C_{1-6}$alkyl substituted benzofuranyl, most especially 3-methyl-benzofuran-2-yl, 3,5-dimethyl-benzofuran-2-yl, and 3-ethyl-benzofuran-2-yl; also 5-fluoro-3-methyl-benzofuran-2-yl, 6-fluoro-3-methyl-benzofuran-2-yl, 5-methoxy-3-methyl-benzofuran-2-yl, 4-methoxy-3-methyl-benzofuran-2-yl, and 6-methoxy-3-methyl-benzofuran-2-yl;

naphtho[2,1-b]-furanyl, especially naphtho[2,1-b]-furan-2-yl, $C_{1-6}$alkyl substituted naphtho[2,1-b]-furanyl, especially 1-methyl-naphtho[2,1-b]-furan-2-yl;

benzo[b]thiophenyl, especially benzo[b]thiophen-2-yl;

quinolinyl, especially quinolin-2-yl;

quinoxalinyl, especially quinoxalin-2-yl;

pyridinyl, especially pyridin-2-yl, pyridin-3-yl, pyridin-5-yl, and oxy-pyridinyl, especially 1-oxy-pyridin-2-yl and 1-oxy-pyridin-3-yl;

furo[3,2-b]-pyridinyl, especially furo[3,2-b]-pyridin-2-yl, $C_{1-6}$alkyl substituted furo[3,2-b]-pyridin-2-yl, especially 3-methyl-furo[3,2-b]-pyridin-2-yl;

thiophenyl, especially thiophen-3-yl, and thiophen-2-yl, $C_{1-6}$alkyl substituted thiophenyl, especially 5-methyl-thiophen-2-yl and 5-methyl-thiophen-3-yl; and thieno[3,2-b]thiophene, especially thieno[3,2-b]thiophene-2-yl; and 1H-benzoimidazolyl, especially 1H-benzoimidazol-5-yl.

In such embodiment, when $R^1$ is

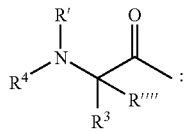

$R^3$ is selected from the group consisting of: $C_{1-6}$alkyl, $C_{3-6}$cycloalkyl-$C_{0-6}$alkyl, $C_{2-6}$alkenyl, $C_{2-6}$alkynyl, Het-$C_{0-6}$alkyl and Ar—$C_{0-6}$alkyl.

$R^3$ is preferably $C_{1-6}$alkyl, $C_{3-6}$cycloalkyl-$C_{0-6}$alkyl, and Ar—$C_{0-6}$alkyl.

$R^3$ is more preferably selected from the group consisting of methyl, ethyl, n-propyl, n-butyl, isobutyl, t-butyl, cyclohexylmethyl, and toluyl.

R"" is selected from the group consisting of: $C_{1-6}$alkyl, $C_{3-6}$cycloalkyl-$C_{0-6}$alkyl, $C_{2-6}$alkenyl, $C_{2-6}$alkynyl, Het$C_{0-6}$alkyl and Ar$C_{0-6}$alkyl;

R"" is preferably $C_{1-6}$alkyl;

R"" is more preferably selected from the group consisting of methyl, ethyl, n-propyl, n-butyl, isobutyl and t-butyl.

In such compounds, R', R", R'", $R^4$, and $R^5$ are as described above wherein $R^1$ is

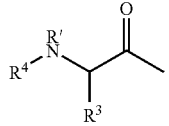

In compounds of Formula I, when $R^1$ is

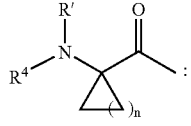

n is an integer of from 1 to 5; preferably 3; and

R', R", R'", $R^4$, and $R^5$ are as described above wherein $R^1$ is

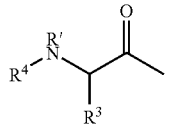

The cyclic ring may be unsubstituted or substituted with one or more of $C_{1-6}$alkyl, $C_{3-6}$cycloalkyl-$C_{0-6}$alkyl, $C_{2-6}$alkenyl, $C_{2-6}$alkynyl, Het$C_{0-6}$alkyl, Ar$C_{0-6}$alkyl, or halogen.

The cyclic ring is preferably unsubstituted.

In such embodiment, $R^2$ is selected from the group consisting of:

$C_{1-6}$alkyl, Ar—$C_{0-6}$alkyl, Het-$C_{0-6}$alkyl, $R^9C(O)$—, $R^9SO_2$—, $R^9R^{11}NC(O)$—, and $R^9SO_2R^{11}NC(O)$—.

More preferably $R^2$ is selected from the group consisting of: Ar—$C_{0-6}$alkyl, $R^9C(O)$—, $R^9SO_2$, and $R^9R^{11}NC(O)$—.

Even more preferably, $R^2$ is selected from the group consisting of: Ar—$C_{0-6}$alkyl, $R^9C(O)$—, and $R^9SO_2$.

Most preferably $R^2$ is $R^9SO_2$.

In such embodiments:

$R^9$ is selected from the group consisting of: $C_{1-6}$alkyl, $C_{3-6}$cycloalkyl-$C_{0-6}$alkyl, Ar—$C_{0-6}$alkyl, and Het-$C_{0-6}$alkyl.

$R^9$ is preferably selected from the group consisting of: $C_{1-6}$alkyl, Ar—$C_{0-6}$alkyl, and Het-$C_{0-6}$alkyl.

More preferably, $R^9$ is selected from the group consisting of:

ethyl, especially $C_{1-6}$alkyl-substituted ethyl, more especially 2-cyclohexyl-ethyl;

propyl;

butyl, especially 3-methylbutyl;

phenyl, especially halogen substituted phenyl, more especially 2-fluorophenyl, 3-fluorophenyl, 4-fluorophenyl, 2-chlorophenyl, 3-chlorophenyl, 4-chlorophenyl; especially $C_{1-6}$alkyl substituted phenyl, more especially 4-ethyl-phenyl, 2-methyl phenyl, 4-methyl phenyl, especially $C_{1-6}$alkyl sulfonyl substituted phenyl, more especially 4-methanesulfonyl phenyl, and 2-methanesulfonyl phenyl;

pyridinyl, especially pyridin-2-yl, pyridin-3-yl, especially 1-oxy-pyridinyl, more especially 1-oxy-pyridin-2-yl, and 1-oxy-pyridin-3-yl;

1H-imidazolyl, especially 1H-imidazol-2-yl, 1H-imidazol-4-yl, $C_{1-6}$alkyl substituted imidazolyl, especially 1-methyl-1H-imidazol-2-yl, 1-methyl-1H-imidazol-4-yl, and 1,2-dimethyl-1H-imidazol-4-yl;

triazolyl, especially 1H-[1,2,4]triazolyl, especially 1H-[1,2,4]triazol-3-yl, $C_{1-6}$alkyl substituted 1H-[1,2,4]triazolyl, especially 5-methyl-1H-[1,2,4]triaiol-3-yl;

isoxazolyl, especially isoxazol-4-yl, $C_{1-6}$alkyl substituted isoxazolyl, especially 3,5-dimethyl-isoxazol-4-yl.

When $R^2$ is $R^9SO_2$, $R^9$ is most preferably selected from the group consisting of: pyridin-2-yl and 1-oxy-pyridin-2-yl.

When $R^2$ is $R^9SO_2R^{11}NC(O)$—, $R^9$ is preferably Ar—$C_{0-6}$alkyl, more preferably Ar, most preferably substituted phenyl such as 2-methyl phenyl, 4-methyl phenyl, 2-chloro phenyl, 4-fluoro phenyl.

When $R^2$ is $R^9C(O)$—, $R^9$ is preferably selected from the group consisting of $C_{1-6}$alkyl, $C_{3-6}$cycloalkyl-$C_{0-6}$alkyl, and Het-$C_{0-6}$alkyl, more preferably 1-oxy-pyridin-2-yl, cyclohexyl ethyl, and 3-methyl butyl.

When $R^2$ is $R^9SO_2R^{11}NC(O)$—, $R^{11}$ is selected from the group consisting of: $C_{1-6}$alkyl, Ar—$C_{0-6}$alkyl and Het-$C_{0-6}$alkyl. Preferably in such embodiment, $R^{11}$ is H.

When $R^2$ is Ar—$CO_{0-6}$alkyl, $R^2$ is preferably phenyl, especially substituted phenyl, more especially halogen substituted phenyl, even more especially 2-fluorobenzyl.

When $R^2$ is $C_{1-6}$alkyl, $R^2$ is preferably selected from 1-propyl, 1-butyl, and 1-pentyl.

When $R^2$ is Het-$C_{0-6}$alkyl, Het-$C_{0-6}$alkyl is preferably Het-methyl, and Het in Het-methyl is preferably selected from the group consisting of:

pyridinyl, especially pyridin-2-yl, $C_{1-6}$alkylpyridinyl, especially 6-methyl-pyridin-2-yl;

thiophenyl, especially thiophene-2-yl and benzo[b]thiophen-2-yl;

thiazolyl, especially thiazol-4-yl such as 1-(2-morpholin-4-yl-thiazol-4-yl), and 1-(isothiazol-3-yl);

1H-imidazolyl, especially 1H-imidazol-2-yl, 1H-imidazol-4-yl, $C_{1-6}$alkyl substituted imidazolyl, especially 1-methyl-1H-imidazol-2yl;

triazolyl, especially 3H-[1,2,3]triazolyl, more especially 3H-[1,2,3]triazol-4-yl, especially $C_{1-6}$alkyl substituted 3H-[1,2,3]triazolyl, more especially 3-phenyl-3H-[1,2,3]triazolyl -4-yl;

quinolinyl, especially quinolin-2-yl, quinolin-2-yl;

furanyl, especially furan-2-yl, especially substituted furanyl, such as 5-ethyl-furan-2-yl;

thieno[3,2-b]thiophene, especially thieno[3,2-b]thiophene-2-yl, $C_{1-6}$alkyl substituted thieno[3,2-b]thiophene-2-yl, especially 3,4-dimethyl-thieno[3,2-b]thiophene-2-yl.

Compounds of Formula I selected from the following group are particularly preferred embodiments of the present invention:

| Example No. | Chemical Name |
|---|---|
| 1 | {(S)-1-[1-((S)-2-Benzyloxycarbonylamino-4-methyl-pentanoyl)-3-oxo-azepan-4-ylcarbamoyl}carbamic acid benzyl ester |
| 2 | Naphthylene-2-carboxylic acid[(S)-1-(1-benzyl-3-oxo-azepan-4-ylcarbamoyl)-3-methyl-butyl]amide |
| 3 | Benzo[1,3]dioxole-5-carboxylic acid [(S)-1-(1-benzyl-3-oxo-azepan-4-ylcarbamoyl)-3-methyl-butyl]amide |
| 4 | Benzofuran-2-carboxylic acid [(S)-1-(1-benzyl-3-oxo-azepan-4-ylcarbamoyl)-3-methyl-butyl]amide |
| 5 | Benzo[b]thiophene-2-carboxylic acid [(S)-1-(1-benzyl-3-oxo-azepan-4-ylcarbamoyl)-3-methyl-butyl]amide |
| 6 | Naphthylene-2-sulphonyl [(S)-1-(1-benzyl-3-oxo-azepan-4-ylcarbamoyl)-3-methyl-butyl]-amide |
| 7 | Quinoline-2-carboxylic acid[(S)-1-(1-benzyl-3-oxo-azepan-4-ylcarbamoyl)-3-methyl-butyl]amide |
| 8 | 3,4-dichlorobenzoic acid [(S)-1-(1-benzyl-3-oxo-azepan-4-ylcarbamoyl)-3-methyl-butyl]amide |
| 9 | 4-{(S)-Methyl-2-[(quinoline-2-carbonyl)-amino]pentanoylamino}-3-oxo-1-[2-(3-pyridin-2-yl-phenyl)-acetyl]azepanium |
| 10 | 1-((S)-2-Benzyloxycarbonylamino-4-methyl-pentyl)-4-{(S)-4-methyl-2-[(2-quinoiline-2-carbonyl)-amino]-pentanoylamino)-3-oxo-azepanium |
| 11 | 1-Benzoyl-4-((S)-2-(benzo[1,3]dioxole-carbonylamino)-4-methyl-pentanoylamino)-3-oxo-azepanium |
| 12 | 1-Benzoyl-4-((S)-2-(4-fluoro-benzoylamino)-4-methyl-pentanoylamino)-3-oxo-azepanium |
| 13 | 3-Oxo-4-((S)-4-methyl-2-{[5-(2-morpholino-4-yl-ethoxy)-benzofuran-2-carbonyl]amino}-pentanoylamino)-1-(4-methyl-pentanoyl)-azepanium |
| 14 | 5-(2-Morpholin-4-yl-ethoxy)-benzofuran-2-carboxylic acid [(S)-1-(1-benzenesulfonyl-3-oxo-azepan-4-ylcarbamoyl)-3-methyl-butyl]amide |
| 15 | 4-((S)-4-Methyl-2-{[5-(2-morpholino-4-yl-ethoxy)-benzofuran-2-carbonyl]amino}-pentanoylamino)-3-oxo-azepane-1-carboxylic acid phenylamide |
| 16 | 5-(2-Morpholino-4-yl-ethoxy)-benzofuran-2-carboxylic acid ((S)-3-methyl-1-{3-oxo-1-[2-(3-pyridin-2-yl-phenyl)acetyl]-azepan-4-ylcarbamoyl}-butyl)amide |
| 17 | 5-(2-Morpholino-4-yl-ethoxy)-benzofuran-2-carboxylic acid [(S)-1-(1-benzoyl-3-oxo-azepan-4-ylcarbamoyl)-3-methyl-butyl]amide |
| 18 | 5-(2-Pyrrolidin-1-yl-ethoxy)-benzofuran-2-carboxylic acid [(S)-1-(1-benzenesulfonyl-3-oxo-azepan-4-ylcarbamoyl)-3-methyl-butyl]amide |
| 19 | 5-(2-Piperidin-1-yl-ethoxy)-benzofuran-2-carboxylic acid [(S)-1-(1-benzenesulfonyl-3-oxo-azepan-4-ylcarbamoyl)-3-methyl-butyl]amide |
| 20 | 5-(2-Morpholino-4-yl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide |
| 21 | Naphthlene-2-carboxylic acid ((S)-3-methyl-1-{3-oxo-1-[2-(3-pyridin-2-yl-phenyl)ethyl]-azepan-4-ylcarbamoyl}-butyl)amide |
| 22 | 1H_Indole-2-carboxylic acid ((S)-3-methyl-1-{3-oxo-1-[2-(3-pyridin-2-yl-phenyl)ethyl]-azepan-4-ylcarbamoyl}-butyl)amide |
| 23 | 1H-Indole-2-carboxylic acid [(S)-1-(1-benzenesulfonyl-3-oxo-azepan-4-ylcarbamoyl)-3-methyl-butyl]amide |
| 24 | Benzofuran-2-carboxylic acid [(S)-1-(1-benzenesulfonyl-3-oxo-azepan-4-ylcarbamoyl)-3-methyl-butyl]amide |
| 25 | Benzofuran-2-carboxylic acid [(S)-3-methyl-1-{3-oxo-1-[2-(3-pyridin-2-yl-phenyl)ethyl]-azepan-4-ylcarbamoyl}-butyl)amide |
| 26 | 5-(2-Morpholino-4-yl-ethoxy)-benzofuran-2-carboxylic acid [(S)-3-methyl-1-(3-oxo-1-phenethyl-azepan-4-ylcarbamoyl]-butyl}amide |

-continued

| Example No. | Chemical Name |
|---|---|
| 27 | Naphthylene-2-carboxylic acid [(S)-3-methyl-1-(3-oxo-1-phenethyl-azepan-4-ylcarbamoyl)-butyl]-amide |
| 28 | Benzofuran-2-carboxylic acid {(S)-3-methyl-1-[3-oxo-1-(pyridine-2-sulfonyl)-azepan-4-ylcarbamoyl]-butyl}-amide |
| 29 | Naphthylene-2-carboxylic acid {(S)-3-methyl-1-[3-oxo-1-(pyridine-2-sulfonyl)-azepan-4-ylcarbamoyl]-butyl}-amide |
| 30 | 5-(2-Morpholino-4-yl-ethoxy)-benzofuran-2-carboxylic acid {(S)-3-methyl-1-[3-oxo-1-(pyridine-2-sulfonyl)-azepan-4-ylcarbamoyl]-butyl}-amide |
| 31 | 4-((S)-4-Methyl-2-{[(5-(2-morpholino-4-yl-ethoxy)-benzofuran-2-carbonyl]-amino}-pentanoylamino)-3-oxo-azepane-1-carboxylic acid tert-butyl ester |
| 32 | 4-((S)-4-Methyl-2-{[(5-(2-morpholino-4-yl-ethoxy)-benzofuran-2-carboxylic acid [(S)-3-methyl-1-(3-oxo-azepan-4-ylcarbamoyl)-butyl]amide |
| 33 | 4-Methyl-pentanoic acid {3-oxo-1-[2-(3-pyridin-2-yl-phenyl-acetyl]-azepan-4-yl}-amide |
| 34 | ((S)-3-Methyl-1-{3-oxo-1-[2-(3-pyridin-2-yl-phenyl)-acetyl]-azepan-4-ylcarbamoyl}-butyl)-naphthylene-2-methyl-carbamic acid cert-butyl ester |
| 35 | (S)-4-Methyl-2-[(naphthylen-2-ylmethyl)-amino]-pentenoic acid [3-oxo-1-[2-(3-pyridin-2-yl-phenyl)-acetyl]-azepan-4-yl]-amide |
| 36 | 4-[2-(2-{(S)-3-Methyl-1-[3-oxo-1-(pyidine-2-sulfonyl)-azepan-4-ylcarbamoyl]-butylcarbamoyl}-benzofuran-5-yloxy)-ethyl]-piperazine-1-carboxylic acid tert-butyl ester |
| 37 | 5-(2-Piperizin-1-yl-ethoxy)-benzofuran-2-carboxylic acid {(S)-3-methyl-1-[3-oxo-1-(pyridine-2-sulfonyl)-azepan-4-ylcarbamoyl]-3-butyl}-amide |
| 38 | 5-(2-Cyclohexyl-ethoxy)-benzofuran-2-carboxylic acid {(S)-3-methyl-1-[3-oxo-1-(pyridine-2-sulfonyl)-azepan-4-ylcarbamoyl]-butyl}amide |
| 39 | 5-(2-Cyclohexyl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide |
| 40 | 4-[2-(2-{(S)-3-Methyl-1-[3-oxo-1-(3-pyridin-2-yl-phenyl)-ethyl][azepan-4-ylcarbamoyl]-butylcarbamoyl}-benzofuran-5-yloxy)-ethyl]-piperazine-1-carboxylic acid tert-butyl ester |
| 41 | 5-(2-piperizin-1-yl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide |
| 42 | (S)-4-Methyl-2-(methyl-naphthalen-2-ylmethyl-amino)pentanoic acid [3-oxo-1-(pyridine-2-sulphonyl)-azepan-4-yl]-amide |
| 43 | (S)-4-Methyl-2-(methyl-naphthalen-2-ylmethyl-amino)pentanoic acid {3-oxo-1-[2-(3-pyridin-2-yl-phenyl)-acetyl]-azepan-4-yl}-amide |
| 44 | 5-(2-Morpholino-4-yl-ethoxy)-benzofuran-2-carboxylic acid methyl ((S)-3-methyl-1-{3-oxo-1-[2-(3-pyridin-2-yl-phenyl)acetyl]-azepan-4-ylcarbamoyl}-butyl)amide |
| 45 | Benzofuran-2-carboxylic acid methyl {(S)-3-methyl-1-[3-oxo-1-(pyridine-2-sulfonyl)-azepan-4-ylcarbamoyl)-3-methyl-butyl]-amide |
| 46 | 2,2,2-Trifluoro-N-((S)-3-methyl-1-{3-oxo-1-[2-(3-pyridin-2-yl-phenyl)-acetyl]-azepan-4-ylcarbamoyl}-butyl)-N-naphthylen-2-ylmethyl-acetamide |
| 47 | 4-[(S)-(Methanesulphonyl-naphthylen-2-ylmethyl-amino)-4-methyl-pentanoylamino]-3-oxo-azepane-1-carboxylic acid benzyl ester |
| 48 | Quinoline-2-carboxylic acid {(S)-3-methyl-1-[3-oxo-1-(pyridine-2-sulfonyl)-azepan-4-ylcarbamoyl]-butyl}amide |
| 49 | Quinoline-8-carboxylic acid {(S)-3-methyl-1-[3-oxo-1-(pyridine-2-sulfonyl)-azepan-4-ylcarbamoyl]-butyl}amide |
| 50 | Quinoline-6-carboxylic acid {(S)-3-methyl-1-[3-oxo-1-(pyridine-2-sulfonyl)-azepan-4-ylcarbamoyl]-butyl}amide |
| 51 | Quinoline-4-carboxylic acid {(S)-3-methyl-1-[3-oxo-1-(pyridine-2-sulfonyl)-azepan-4-ylcarbamoyl]-butyl}amide |
| 52 | Quinoline-3-carboxylic acid {(S)-3-methyl-1-[3-oxo-1-(pyridine-2-sulfonyl)-azepan-4-ylcarbamoyl]-butyl}amide |
| 53 | Isoquinoline-3-carboxylic acid {(S)-3-methyl-1-[3-oxo-1-(pyridine-2-sulfonyl)-azepan-4-ylcarbamoyl]-butyl}amide |
| 54 | Isoquinoline-1-carboxylic acid {(S)-3-methyl-1-[3-oxo-1-(pyridine-2-sulfonyl)-azepan-4-ylcarbamoyl]-butyl}amide |
| 55 | Quinoxaline-2-carboxylic acid {(S)-3-methyl-1-[3-oxo-1-(pyridine-2-sulfonyl)-azepan-4-ylcarbamoyl]-butyl}amide |
| 56 | Benzo[b]thiophene-2-carboxylic acid {(S)-3-methyl-1-[3-oxo-1-(pyridine-2-sulfonyl)-azepan-4-ylcarbamoyl]-butyl}amide |
| 57 | 1,8-Naphthyridine-2-carboxylic acid {(S)-3-methyl-1-[3-oxo-1-(pyridine-2-sulfonyl)-azepan-4-ylcarbamoyl]-butyl}amide |
| 58 | 1H-Indole-2-carboxylic acid {(S)-3-methyl-1-[3-oxo-1-(pyridine-2-sulfonyl)-azepan-4-ylcarbamoyl]-butyl}amide |
| 59 | 5-Methoxy-benzofuran-2-carboxylic acid {(S)-3-methyl-1-[3-oxo-1-(pyridine-2-sulfonyl)-azepan-4-ylcarbamoyl]-butyl}amide |
| 60 | 5-Bromo-furan-2-carboxylic acid {(S)-3-methyl-1-[3-oxo-1-(pyridine-2-sulfonyl)-azepan-4-ylcarbamoyl]-butyl}amide |
| 61 | Furan-2-carboxylic acid {(S)-3-methyl-1-[3-oxo-1-(pyridine-2-sulfonyl)-azepan-4-ylcarbamoyl]-butyl}amide |
| 62 | 5-Nitro-furan-2-carboxylic acid {(S)-3-methyl-1-[3-oxo-1-(pyridine-2-sulfonyl)-azepan-4-ylcarbamoyl]-butyl}amide |
| 63 | 5-(4-Nitro-phenyl)-furan-2-carboxylic acid {(S)-3-methyl-1-[3-oxo-1-(pyridine-2-sulfonyl)-azepan-4-ylcarbamoyl]-butyl}amide |
| 64 | 5-(3-Trifluoromethyl-phenyl)-furan-2-carboxylic acid {(S)-3-methyl-1-[3-oxo-1-(pyridine-2-sulfonyl)-azepan-4-ylcarbamoyl]-butyl}amide |
| 65 | Tetrahydro-furan-2-carboxylic acid {(S)-3-methyl-1-[3-oxo-1-(pyridine-2-sulfonyl)-azepan-4-ylcarbamoyl]-butyl}amide |
| 66 | (S)-4-Methyl-2-(2-phenoxy-acetylamino)-pentanoic acid [3-oxo-(pyridine-2-sulfonyl)-azepan-4-yl]-amide |
| 67 | (S)-2-[2-(4-Fluoro-phenoxy)-acetylamino]-4-methyl-pentanoic acid [3-oxo-(pyridine-2-sulfonyl)-azepan-4-yl]-amide |
| 68 | Benzofuran-2-carboxylic acid {(S)-3-methyl-1-[3-oxo-1-(pyridine-2-carbonyl)-azepan-4-ylcarbamoyl]-3-butyl}-amide |
| 69 | Benzofuran-2-carboxylic acid {(S)-3-methyl-1-[3-oxo-1-(1-oxy-pyridine-2-carbonyl)-azepan-4-ylcarbamoyl]-butyl}amide |
| 70 | 4-((S)-2-tert-Butylcarbonylamino-4-methyl-pentanoylamino)-3-oxo-azepane-1-carboxylic acid benzyl ester |
| 71 | 5,6-Dimethoxy-benzofuran-2-carboxylic acid {(S)-3-methyl-1-[3-oxo-1-(1-methyl-1H-imidazole-4-sulfonyl)-azepan-4-ylcarbamoyl]-butyl}amide |
| 72 | Benzofuran-2-carboxylic acid {(S)-3-methyl-1-[1-(5-methyl-1H-[1,2,4]triazole-3-sulfonyl)-3-oxo-azepan-4-ylcarbamoyl]-butyl}amide |
| 73 | Benzofuran-2-carboxylic acid {(S)-3-methyl-1-[1-(1-methyl-1H-imidazole-3-sulfonyl)-3-oxo-azepan-4-ylcarbamoyl]-butyl}amide |
| 74 | Benzofuran-2-carboxylic acid {(S)-3-methyl-1-[1-(1H-imidazole-2-sulfonyl)-3-oxo-azepan-4-ylcarbamoyl]-butyl}amide |
| 75 | Benzofuran-2-carboxylic acid {(S)-3-methyl-1-[3-oxo-1-(thiazole-2-sulfonyl)-azepan-4-ylcarbamoyl]-butyl}amide |
| 76 | Benzofuran-2-carboxylic acid {(S)-3-methyl-1-[1-(1-methyl-1H-imidazole-4-sulfonyl)-3-oxo-azepan-4-ylcarbamoyl]-butyl}amide |
| 77 | 5-(4-Oxy-morpholino-4-yl-ethoxy)-benzofuran-2-carboxylic acid {(S)-3-methyl-1-[3-oxo-1-(pyridine-2-sulfonyl)-azepan-4-ylcarbamoyl]-butyl}amide |
| 78 | Benzofuran-2-carboxylic acid {(S)-3-methyl-1-[3-oxo-1-(pyridine-3-sulfonyl)-azepan-4-ylcarbamoyl]-butyl}amide |
| 79 | Benzofuran-2-carboxylic acid {(S)-3-methyl-1-[3-oxo-1-(1-oxy-pyridine-3-sulfonyl)-azepan-4-ylcarbamoyl]-butyl}amide |
| 80 | Quinoline-3-carboxylic acid {(S)-1-(3,4-dichloro-benzene-sulfonyl)-3-oxo-azepan-4-ylcarbamoyl))-3-methyl-butyl}-amide |
| 81 | 5-Hydroxy-benzofuran-2-carboxylic acid {(S)-3-methyl-1-[1-(1-methyl-1H-imidazole-4-sulfonyl)-3-oxo-azepan-4-ylcarbamoyl]-butyl}amide |
| 82 | Benzofuran-2-carboxylic acid {(S)-3-methyl-1-[3-oxo-1-(1-oxy-pyridine-2-sulfonyl)-azepan-4-ylcarbamoyl))-3-methyl-butyl}-amide |
| 83 | 2-(4-{(S)-2-{(Benzofuran-2-carbonyl)-amino}-4-methyl-pentanoylamino}-3-oxo-azepane-1-sulfonyl)-benzoic acid |
| 84 | 3-(4-{(S)-2-{(Benzofuran-2-carbonyl)-amino}-4-methyl-pentanoylamino}-3-oxo-azepane-1-sulfonyl)-benzoic acid |
| 85 | Benzo[b]thiophene-2-carboxylic acid {(S)-3-methyl-1-[3-oxo-1-(1-oxy-pyridine-2-sulfonyl)-azepan-4-ylcarbamoyl]-butyl}amide |
| 86 | 5-Bromo-furan-2-carboxylic acid {(S)-3-methyl-1-[3-oxo-1-(1-oxy-pyridine-2-sulfonyl)-azepan-4-ylcarbamoyl]-butyl}amide |
| 87 | 5,6-Dimethoxy-benzofuran-2-carboxylic acid {(S)-3-methyl-1-[3-oxo-1-(1-oxy-pyridine-2-sulfonyl)-azepan-4-ylcarbamoyl]-butyl}amide |
| 88 | 1-Oxy-pyridine-2-carboxylic acid {(S)-3-methyl-1-[3-oxo-1-(pyridine-2-sulfonyl)-azepan-4-ylcarbamoyl]-butyl}amide |

| Example No. | Chemical Name |
|---|---|
| 89 | (S)-4-Methyl-2-(pyridine-2-sulfonylamino)-pentanoic acid [3-oxo-1-(pyridine-2-sulfonyl)-azepan-4-yl]-amide |
| 90 | (S)-2-(3-Benzyl-ureido)-4-methyl-pentanoic acid [3-oxo-1-(pyridine-2-sulfonyl)-azepan-4-yl]-amide |
| 91 | (S)-4-Methyl-2-(3-phenyl-uriedo)-pentanoic acid [3-oxo-1-(pyridine-2-sulfonyl)-azepan-4-yl]-amide |
| 92 | Benzofuran-2-carboxylic acid {(S)-1-[6,6-dimethyl-3-oxo-1(pyridine-sulphonyl)-azepan-4-ylcarbamoyl]-3-methyl-butyl}-amide |
| 93 | 5-Methoxy-benzofuran-2-carboxylic acid {(S)-3-methyl-1-[3-oxo-1-(1-oxy-pyridine-2-sulfonyl)-azepan-4-ylcarbamoyl]-butyl}amide |
| 94 | Thieno[3,2-b]thiophene-2-carboxylic acid {(S)-3-methyl-1-[3-oxo-1-(1-oxy-pyridine-2-sulfonyl)-azepan-4-ylcarbamoyl]-butyl}amide |
| 95 | Quinoxaline-2-carboxylic acid {(S)-3-methyl-1-[3-oxo-1-(1-oxy-pyridine-2-sulfonyl)-azepan-4-ylcarbamoyl]-butyl}amide |
| 96 | Quinoline-2-carboxylic acid {(S)-3-methyl-1-[3-oxo-1-(1-oxy-pyridine-2-sulfonyl)-azepan-4-ylcarbamoyl]-butyl}amide |
| 97 | Thiophene-3-carboxylic acid {(S)-3-methyl-1-[3-oxo-1-(1-oxy-pyridine-2-sulfonyl)-azepan-4-ylcarbamoyl]-butyl}amide |
| 98 | 1H-Indole-5-carboxylic acid {(S)-3-methyl-1-[3-oxo-1-(1-oxy-pyridine-2-sulfonyl)-azepan-4-ylcarbamoyl]-butyl}amide |
| 99 | Benzo[1,3]dioxole-5-carboxylic acid {(S)-3-methyl-1-[3-oxo-1-(1-oxy-pyridine-2-sulfonyl)-azepan-4-ylcarbamoyl]-butyl}amide |
| 100 | Furan-2-carboxylic acid {(S)-3-methyl-1-[3-oxo-1-(1-oxy-pyridine-2-sulfonyl)-azepan-4-ylcarbamoyl]-butyl}amide |
| 101 | (S)-4-Methyl-2-(2-thiophen-2-yl-acetylamino)-pentanoic acid [3-oxo-1-(1-oxy-pyridine-2-sulfonyl)-azepan-4-yl]-amide |
| 102 | 1H-Indole-6-carboxylic acid {(S)-3-methyl-1-[3-oxo-1-(1-oxy-pyridine-2-sulfonyl)-azepan-4-ylcarbamoyl]-butyl}amide |
| 103 | 4-Fluoro-{(S)-3-methyl-1-[3-oxo-1-(1-oxy-pyridine-2-sulphonyl)-azepan-4-carbamoyl]-butyl}-benzamide |
| 104 | 5-(2-Morpholin-4-yl-ethoxy)-benzofuran-2-carboxylic acid {(S)-3-methyl-1-[3-oxo-(1-oxy-pyridine2-sulphonyl)-azepan-4-ylcarbamoyl]--buty}-amide |
| 105 | Thiophene-2-carboxylic acid {(S)-3-methyl-1-[3-oxo-1-(1-oxy-pyridine-2-sulfonyl)-azepan-4-ylcarbamoyl]-butyl}amide |
| 106 | 3-Methyl-benzofuran-2-carboxylic acid {(S)-3-methyl-1-[3-oxo-1-(1-oxy-pyridine-2-sulfonyl)-azepan-4-ylcarbamoyl]-butyl}amide |
| 107 | 6-Methyl-N-{(S)-3-methyl-1-[3-oxo-1-(1-oxy-pyridine-2-sulfonyl)-azepan-4-ylcarbamoyl]-butyl}-nicotinamide |
| 108 | (S)-4-Methyl-2-(2-thiophen-yl-acetylamino)-pentanoic acid-[3-oxo-1-(pyridine-2-sulfonyl)-azepan-4-yl]-butyl}amide |
| 109 | 1H-Indole-6-carboxylic acid {(S)-3-methyl-1-[3-oxo-1-(pyridine-2-sulfonyl)-azepan-4-ylcarbamoyl]-butyl}amide |
| 110 | Benzo[1,3]dioxole-5-carboxylic acid {(S)-3-methyl-1-[3-oxo-1-(pyridine-2-sulfonyl)-azepan-4-ylcarbamoyl]-butyl}amide |
| 111 | 3,4-Dihydro-2H-benzo[b][1,4]dioxepine-7-carboxylic acid {(S)-3-methyl-1-[3-oxo-1-(1-oxy-pyridine-2-sulfonyl)-azepan-4-ylcarbamoyl] butyl}amide |
| 112 | 5-Methyl-thiophene-2-carboxylic acid {(S)-3-methyl-1-[3-oxo-1-(1-oxy-pyridine-2-sulfonyl)-azepan-4-ylcarbamoyl]-butyl}amide |
| 113 | 4,5-Dibromo-thiophene-2-carboxylic acid {(S)-3-methyl-1-[3-oxo-1-(1-oxy-pyridine-2-sulfonyl)-azepan-4-ylcarbamoyl]-butyl}amide |
| 114 | 3,5-Dimethyl-isoxazole-4-carboxylic acid {(S)-3-methyl-1-[3-oxo-1-(1-oxy-pyridine-2-sulfonyl)-azepan-4-ylcarbamoyl]-butyl}amide |
| 115 | (S)-2-(2-Benzyloxy-acetylamino)-4-methyl-pentanoic acid[1-(4-methoxy-benzenesulfonyl)-3-oxo-azepan-4-yl]-amide |
| 116 | 5-(3-Trifluoromethyl-phenyl)-furan-2-carboxylic acid {(S)-3-methyl-1-[3-oxo-1-(1-oxy-pyridine-2-sulfonyl)-azepan-4-ylcarbamoyl]-butyl}amide |
| 117 | 5-Methyl-2-phenyl-oxazole-4-carboxylic acid {(S)-3-methyl-1-[3-oxo-1-(1-oxy-pyridine-2-sulfonyl)-azepan-4-ylcarbamoyl]-butyl}amide |
| 118 | Benzofuran-2-carboxylic acid {(S)-1-[1-(3,4-dimethoxy-benzenesulfonyl)-3-oxo-azepan-4-ylcarbamoyl]-butyl}-amide |
| 119 | Benzofuran-2-carboxylic acid {(S)-1-[1-(4-bromo-benzenesulfonyl)-3-oxo-azepan-4-ylcarbamoyl]-3-methyl-butyl}-amide |
| 120 | Benzofuran-2-carboxylic acid {(S)-1-[1-(benzo[1,2,5]oxadiazole-4-sulfonyl)-3-oxo-azepan-4-ylcarbamoyl]-3-methyl-butyl}-amide |
| 121 | Benzofuran-2-carboxylic acid {(S)-1-[1-(3,5-dimethyl-oxazole-4-sulfonyl)-3-oxo-azepan-4-ylcarbamoyl]-3-methyl-butyl}-amide |
| 122 | 3-Methyl-benzofuran-2-carboxylic acid {(S)-3-methyl-1-[3-oxo-1-(pyridine-2-sulfonyl)-azepan-4-ylcarbamoyl]-butyl}amide |
| 123 | Thieno[3,2-b]thiophene-2-carboxylic acid {(S)-3-methyl-1-[3-oxo-1-(pyridine-2-sulfonyl)-azepan-4-ylcarbamoyl]-butyl}amide |
| 124 | 5-tert-Butyl-3-methyl-thieno[3,2-b]thiophene-2-carboxylic acid {(S)-3-methyl-1-[3-oxo-1-(pyridine-2-sulfonyl)-azepan-4-ylcarbamoyl]-butyl}amide |
| 125 | 5-Methyl-2-phenyl-oxazole-4-carboxylic acid {(S)-3-methyl-1-[3-oxo-1-(pyridine-2-sulfonyl)-azepan-4-ylcarbamoyl]-butyl}amide |
| 126 | 2-Phenyl-5-trifluoromethyl-oxazole-4-carboxylic acid {(S)-3-methyl-1-[3-oxo-1-(pyridine-2-sulfonyl)-azepan-4-ylcarbamoyl]-butyl}amide |
| 127 | Quinoline-2-carboxylic acid [(S)-1-(1-methanesulfonyl-3-oxo-azepan-4-ylcarbamoyl)-3-methyl-butyl]-amide |
| 128 | 1-Methyl-1H-indole-2-carboxylic acid [(S)-1-(1-methanesulfonyl-3-oxo-azepan-4-ylcarbamoyl)-3-methyl-butyl]-amide |
| 129 | Furan-2-carboxylic acid {[(S)-1-(1-methanesulfonyl-3-oxo-azepan-4-ylcarbamoyl)-3-methyl-butylcarbamoyl]-methyl}-amide |
| 130 | 5-Methoxy-benzofuran-2-carboxylic acid [(S)-1-(1-methanesulfonyl-3-oxo-azepan-4-ylcarbamoyl)-3-methyl-butyl]-amide |
| 131 | Quinoxaline-2-carboxylic acid [(S)-1-(1-methanesulfonyl-3-oxo-azepan-4-ylcarbamoyl)-3-methyl-butyl]-amide |
| 132 | 5-(4-Chloro-phenyl)-furan-2-carboxylic acid {(S)-3-methyl-1-[3-oxo-1-(pyridine-2-sulfonyl)-azepan-4-ylcarbamoyl]-butyl}amide |
| 133 | (S)-2-[2-(4-Methoxy-phenyl)-acetylamino)-4-methyl-pentanoic acid (1-methanesulfonyl-3-oxo-azepan-4-yl)-amide |
| 134 | Quinoline-2-carboxylic acid {[(S)-1-[1-(2-cyano-benzenesulfonyl)-3-oxo-azepan-4-ylcarbamoyl]-3-methyl-butyl}-amide |
| 135 | 1-Methyl-1H-indole-2-carboxylic acid {[(S)-1-[1-(2-cyano-benzenesulfonyl)-3-oxo-azepan-4-ylcarbamoyl]-3-methyl-butyl}-amide |
| 136 | Furan-2-carboxylic acid ({(S)-1-[1-(2-cyano-benzenesulfonyl)-3-oxo-azepan-4-ylcarbamoyl]-3-methyl-butylcarbamoyl}-methyl)-amide |
| 137 | 5-Methoxy-benzofuran-2-carboxylic acid {[(S)-1-[1-(2-cyano-benzenesulfonyl)-3-oxo-azepan-4-ylcarbamoyl]-3-methyl-butyl}-amide |
| 138 | Quinoxaline-2-carboxylic acid {[(S)-1-[1-(2-cyano-benzenesulfonyl)-3-oxo-azepan-4-ylcarbamoyl]-3-methyl-butyl}-amide |
| 139 | (S)-2-[2-(4-Methoxy-phenyl)-acetylamino)-4-methyl-pentanoic acid [1-(2-cyano-benzenesulfonyl)-3-oxo-azepan-4-yl]-amide |
| 140 | Quinoline-2-carboxylic acid {[(S)-1-[1-(4-methoxy-benzenesulfonyl)-3-oxo-azepan-4-ylcarbamoyl]-3-methyl-butyl}-amide |
| 141 | 1-Methyl-1H-indole-2-carboxylic acid {[(S)-1-[1-(4-methoxy-benzenesulfonyl)-3-oxo-azepan-4-ylcarbamoyl]-3-methyl-butyl}-amide |
| 142 | Furan-2-carboxylic acid ({(S)-1-[1-(4-methoxy-benzenesulfonyl)-3-oxo-azepan-4-ylcarbamoyl]-3-methyl-butylcarbamoyl}-methyl)-amide |
| 143 | 5-Methoxy-benzofuran-2-carboxylic acid {[(S)-1-[1-(4-methoxy-benzenesulfonyl)-3-oxo-azepan-4-ylcarbamoyl]-3-methyl-butyl}-amide |
| 144 | Quinoxaline-2-carboxylic acid {[(S)-1-[1-(4-methoxy-benzenesulfonyl)-3-oxo-azepan-4-ylcarbamoyl]-3-methyl-butyl}-amide |
| 145 | (S)-2-[2-(4-Methoxy-phenyl)-acetylamino)-4-methyl-pentanoic acid [1-(4-methoxy-benzenesulfonyl)-3-oxo-azepan-4-yl]-amide |
| 146 | 1-Methyl-1H-indole-2-carboxylic acid {[(S)-1-[1-(4-fluoro-benzenesulfonyl)-3-oxo-azepan-4-ylcarbamoyl]-3-methyl-butyl}-amide |
| 147 | Furan-2-carboxylic acid ({(S)-1-[1-(4-fluoro-benzenesulfonyl)-3-oxo-azepan-4-ylcarbamoyl]-3-methyl-butylcarbamoyl}-methyl)-amide |
| 148 | 5-Methoxy-benzofuran-2-carboxylic acid {[(S)-1-[1-(4-fluoro-benzenesulfonyl)-3-oxo-azepan-4-ylcarbamoyl]-3-methyl-butyl}-amide |
| 149 | Quinoxaline-2-carboxylic acid {[(S)-1-[1-(4-fluoro-benzenesulfonyl)-3-oxo-azepan-4-ylcarbamoyl]-3-methyl-butyl}-amide |
| 150 | (S)-2-[2-(4-Methoxy-phenyl)-acetylamino)-4-methyl-pentanoic acid [1-(4-fluoro-benzenesulfonyl)-3-oxo-azepan-4-yl]-amide |

| Example No. | Chemical Name |
|---|---|
| 151 | Benzofuran-2-carboxylic acid-{(S)-1-[1-(3-chloro-benzenesulphonyl)-3-oxo-azepan-4-ylcarbamoyl]-3-methyl-butyl}-amide |
| 152 | 5-Methoxy-benzofuran-2-carboxylic acid-{(S)-1-[1-(3-chloro-benzenesulphonyl)-3-oxo-azepan-4-ylcarbamoyl]-3-methyl-butyl}-amide |
| 153 | 7-Methoxy-benzofuran-2-carboxylic acid-{(S)-1-[1-(3-chloro-benzenesulphonyl)-3-oxo-azepan-4-ylcarbamoyl]-3-methyl-butyl}-amide |
| 154 | 5,6-Dimethoxy-benzofuran-2-carboxylic acid-{(S)-1-[1-(3-chloro-benzenesulphonyl)-3-oxo-azepan-4-ylcarbamoyl]-3-methyl-butyl}-amide |
| 155 | 3-Methyl-benzofuran-2-carboxylic acid-{(S)-1-[1-(3-chloro-benzenesulphonyl)-3-oxo-azepan-4-ylcarbamoyl]-3-methyl-butyl}-amide |
| 156 | Benzo[b]thiophene-2-carboxylic acid-{(S)-1-[1-(3-chloro-benzenesulphonyl)-3-oxo-azepan-4-ylcarbamoyl]-3-methyl-butyl}-amide |
| 157 | 1-Methyl-1H-indole-2-carboxylic acid-{(S)-1-[1-(3-chloro-benzenesulphonyl)-3-oxo-azepan-4-ylcarbamoyl]-3-methyl-butyl}-amide |
| 158 | Quinoxaline-2-carboxylic acid-{(S)-1-[1-(3-chloro-benzenesulphonyl)-3-oxo-azepan-4-ylcarbamoyl]-3-methyl-butyl}-amide |
| 159 | Benzofuran-2-carboxylic acid-{(S)-1-[1-(2-fluoro-benzenesulphonyl)-3-oxo-azepan-4-ylcarbamoyl]-3-methyl-butyl}-amide |
| 160 | 5-Methoxy-benzofuran-2-carboxylic acid-{(S)-1-[1-(2-fluoro-benzenesulphonyl)-3-oxo-azepan-4-ylcarbamoyl]-3-methyl-butyl}-amide |
| 161 | 7-Methoxy-benzofuran-2-carboxylic acid-{(S)-1-[1-(2-fluoro-benzenesulphonyl)-3-oxo-azepan-4-ylcarbamoyl]-3-methyl-butyl}-amide |
| 162 | 5,6-Dimethoxy-benzofuran-2-carboxylic acid-{(S)-1-[1-(2-fluoro-benzenesulphonyl)-3-oxo-azepan-4-ylcarbamoyl]-3-methyl-butyl}-amide |
| 163 | 5-Methyl-benzofuran-2-carboxylic acid-{(S)-1-[1-(2-fluoro-benzenesulphonyl)-3-oxo-azepan-4-ylcarbamoyl]-3-methyl-butyl}-amide |
| 164 | Benzo[b]thiophene-2-carboxylic acid-{(S)-1-[1-(2-fluoro-benzenesulphonyl)-3-oxo-azepan-4-ylcarbamoyl]-3-methyl-butyl }-amide |
| 165 | 1-Methyl-1H-indole-2-carboxylic acid-{(S)-1-[1-(2-fluoro-benzenesulphonyl)-3-oxo-azepan-4-ylcarbamoyl]-3-methyl-butyl}-amide |
| 166 | (S)-4-Methyl-2-(1-oxy-pyridine-2-sulfonylamino)-pentanoic acid [3-oxo-1-(pyridine-2-sulfonyl)-azepan-4-yl]-amide |
| 167 | Quinoxaline-2-carboxylic acid-{(S)-1-[1-(2-fluoro-benzenesulphonyl)-3-oxo-azepan-4-ylcarbamoyl]-3-methyl-butyl}-amide |
| 168 | 5-Methoxy-benzofuran-2-carboxylic acid-{(S)-3-methyl-1-[3-oxo-1-(thiophene-2-sulfonyl)-azepan-4-ylcarbamoyl]-butyl}-amide |
| 169 | 7-Methoxy-benzofuran-2-carboxylic acid-{(S)-3-methyl-1-[3-oxo-1-(thiophene-2-sulfonyl)-azepan-4-ylcarbamoyl]-butyl}-amide |
| 170 | 5,6-Dimethoxy-benzofuran-2-carboxylic acid-{(S)-3-methyl-1-[3-oxo-1-(thiophene-2-sulfonyl)-azepan-4-ylcarbamoyl]-butyl}-amide |
| 171 | 3-Methyl-benzofuran-2-carboxylic acid-{(S)-3-methyl-1-[3-oxo-1-(thiophene-2-sulfonyl)-azepan-4-ylcarbamoyl]-butyl}-amide |
| 172 | Benzo[b]thiophene-2-carboxylic acid-{(S)-3-methyl-1-[3-oxo-1-(thiophene-2-sulfonyl)-azepan-4-ylcarbamoyl]-butyl}-amide |
| 173 | 1-Methyl-1-H-indole-2-carboxylic acid-{(S)-3-methyl-1-[3-oxo-1-(thiophene-2-sulfonyl)-azepan-4-ylcarbamoyl]-butyl}-amide |
| 174 | Quinoxaline-2-carboxylic acid-{(S)-3-methyl-1-[3-oxo-1-(thiophene-2-sulfonyl)-azepan-4-ylcarbamoyl]-butyl}-amide |
| 175 | Benzofuran-2-carboxylic acid-{(S)-1-[1-(4-chloro-benzenesulphonyl)-3-oxo-azepan-4-ylcarbamoyl]-3-methyl-butyl}-amide |
| 176 | 5-Methoxy-benzofuran-2-carboxylic acid-{(S)-1-[1-(4-chloro-benzenesulphonyl)-3-oxo-azepan-4-ylcarbamoyl]-3-methyl-butyl}-amide |
| 177 | 7-Methoxy-benzofuran-2-carboxylic acid-{(S)-1-[1-(4-chloro-benzenesulphonyl)-3-oxo-azepan-4-ylcarbamoyl]-3-methyl-butyl}-amide |
| 178 | 5,6-Dimethoxy-benzofuran-2-carboxylic acid-{(S)-1-[1-(4-chloro-benzenesulphonyl)-3-oxo-azepan-4-ylcarbamoyl]-3-methyl-butyl}-amide |
| 179 | 3-Methyl-benzofuran-2-carboxylic acid-{(S)-1-[1-(4-chloro-benzenesulphonyl)-3-oxo-azepan-4-ylcarbamoyl]-3-methyl-butyl}-amide |
| 180 | Benzo[b]thiophene-2-carboxylic acid-{(S)-1-[1-(4-chloro-benzenesulphonyl)-3-oxo-azepan-4-ylcarbamoyl]-3-methyl-butyl}-amide |
| 181 | 1-Methyl-1H-indole-2-carboxylic acid-{(S)-1-[1-(4-chloro-benzenesulphonyl)-3-oxo-azepan-4-ylcarbamoyl]-3-methyl-butyl}-amide |
| 182 | Quinoxaline-2-carboxylic acid-{(S)-1-[1-(4-chloro-benzenesulphonyl)-3-oxo-azepan-4-ylcarbamoyl]-3-methyl-butyl}-amide |
| 183 | Benzofuran-2-carboxylic acid-{(S)-1-[1-(3-methoxy-benzenesulphonyl)-3-oxo-azepan-4-ylcarbamoyl]-3-methyl-butyl}-amide |
| 184 | 5-Methoxy-benzofuran-2-carboxylic acid-{(S)-1-[1-(3-methoxy-benzenesulphonyl)-3-oxo-azepan-4-ylcarbamoyl]-3-methyl-butyl}-amide |
| 185 | 7-Methoxy-benzofuran-2-carboxylic acid-{(S)-1-[1-(3-methoxy-benzenesulphonyl)-3-oxo-azepan-4-ylcarbamoyl]-3-methyl-butyl}-amide |
| 186 | 5,6-Dimethoxy-benzofuran-2-carboxylic acid-{(S)-1-[1-(3-methoxy-benzenesulphonyl)-3-oxo-azepan-4-ylcarbamoyl]-3-methyl-butyl}-amide |
| 187 | 3-Methyl-benzofuran-2-carboxylic acid-{(S)-1-[1-(3-methoxy-benzenesulphonyl)-3-oxo-azepan-4-ylcarbamoyl]-3-methyl-butyl}-amide |
| 188 | Benzo[b]thiophene-2-carboxylic acid-{(S)-1-[1-(3-methoxy-benzenesulphonyl)-3-oxo-azepan-4-ylcarbamoyl]-3-methyl-butyl}-amide |
| 189 | 1-Methyl-1H-indole-2-carboxylic acid-{(S)-1-[1-(3-methoxy-benzenesulphonyl)-3-oxo-azepan-4-ylcarbamoyl]-3-methyl-butyl}-amide |
| 190 | Quinoxaline-2-carboxylic acid-{(s)-1-[-(3-methoxy-benzenesulphonyl)-3-oxo-azepan-4-ylcarbamoyl]-3-methyl-butyl}-amide |
| 191 | Benzofuran-2-carboxylic acid-{(S)-3-methyl-1-[3-oxo-1-(thiophene-2-sulfonyl)-azepan-4-ylcarbamoyl]-butyl}-amide |
| 192 | Benzofuran-2-carboxylic acid {(S)-3-methyl-1-[(2,2',4-trideuterio)-3-oxo-1-(pyridine-2-sulfonyl)-azepan-4-ylcarbamoyl]-butyl}amide |
| 193 | Benzofuran-2-carboxylic acid {(S)-2-methyl-1-[3-oxo-1-(pyridine-2-sulfonyl)-azepan-4-ylcarbamoyl]-butyl}-amide |
| 194 | Benzofuran-2-carboxylic acid {(S)-1-[3-oxo-1-(pyridine-2-sulfonyl)-azepan-4-ylcarbamoyl]-propyl}-amide |
| 195 | Benzofuran-2-carboxylic acid {(S)-2-cyclohexyl-1-[3-oxo-1-(pyridine-2-sulfonyl)-azepan-4-ylcarbamoyl]-ethyl}-amide |
| 196 | Benzofuran-2-carboxylic acid {(S)-1-[3-oxo-1-(pyridine-2-sulfonyl)-azepan-4-ylcarbamoyl]-ethyl}-amide |
| 197 | Benzofuran-2-carboxylic acid {(S)-3-methanesulfinyl-1-[3-oxo-1-(pyridine-2-sulfonyl)-azepan-4-ylcarbamoyl]-propyl}-amide |
| 198 | Benzofuran-2-carboxylic acid {[3-oxo-1-(pyridine-2-sulfonyl)-azepan-4-ylcarbamoyl]-methyl}-amide |
| 199 | Benzofuran-2-carboxylic acid {(S)-1-[3-oxo-1-(pyridine-2-sulfonyl)-azepan-4-ylcarbamoyl]-pentyl}-amide |
| 200 | Benzofuran-2-carboxylic acid {(S)-1-[3-oxo-1-(pyridine-2-sulfonyl)-azepan-4-ylcarbamoyl]-butyl}-amide |
| 201 | Benzofuran-2-carboxylic acid {(S)-2-methyl-1-[3-oxo-1-(pyridine-2-sulfonyl)-azepan-4-ylcarbamoyl]-propyl}-amide |
| 202 | Benzofuran-2-carboxylic acid {(S)-2-hydroxy-1-[3-oxo-1-(pyridine-2-sulfonyl)-azepan-4-ylcarbamoyl]-propyl}-amide |
| 203 | Benzofuran-2-carboxylic acid {(S)-1-[3-oxo-1-(pyridine-2-sulfonyl)-azepan-4-ylcarbamoyl]-2-phenyl-ethyl}-amide |
| 204 | 1-(Benzofuran-2-carbonyl)-pyrrolidine-2-carboxylic acid [3-oxo-1-(pyridine-2-sulfonyl)-azepan-4-yl]-amide |
| 205 | 3,4-Dimethoxy-N-{(S)-1-[1-(4-methoxy-benzenesulfonyl)-3-oxo-azepan-4-ylcarbamoyl]-3-methyl-butyl)-benzamide |
| 206 | Benzo[b]thiophene-2-carboxylic acid-{(S)-1-[1-(4-imethoxy-benzenesulfonyl)-3-oxo-azepan-4-ylcarbamoyl]-3-methyl-butyl}-amide |

| Example No. | Chemical Name |
|---|---|
| 207 | Benzo[1,3]dioxole-5-carboxylic acid {(S)-1-[1-(4-fluoro-benzenesulfonyl)-3-oxo-azepan-4-ylcarbamoyl]-3methyl-butyl}-amide |
| 208 | (S)-2-(2-Benzyloxy-acetylamino)-4-methyl-pentanoic acid[1-(4-fluoro-benzenesulfonyl)-3-oxo-azepan-4-yl]-amide |
| 209 | Benzo[b]thiophene-2-carboxylic acid-{(S)-1-[1-(4-fluoro-benzenesulfonyl)-3-oxo-azepan-4-yl carbamoyl]-3-methyl-butyl}-amide |
| 210 | Benzofuran-2-carboxylic acid {(S)-1-[1-benzoyl-3-oxo-azepan-4-ylcarbamoyl]-3-methyl-butyl}-amide |
| 211 | (S)-4-Methyl-2-(quinoline-8-sulfonylamino)-pentanoic acid [3-oxo-1-(pyridine-2-sulfonyl)-azepan-4-yl]-amide |
| 212 | (S)-4-Methyl-2-(naphthylene-2-sulfonylamino)-pentanoic acid [3-oxo-1-(pyridine-2-sulfonyl)-azepan-4-yl]-amide |
| 213 | Benzofuran-2-carboxylic acid-{(S)-1-[1-(4-fluoro-benzenesulfonyl)-3-oxo-azepan-4-yl carbamoyl]-3-methyl-butyl}-amide |
| 214 | N-{(S)-1-[1-(4-Fluoro-benzenesulfonyl)-3-oxo-azepan-4-ylcarbamoyl}-3-methyl-butyl}-3,4-dimethoxy-benzamide |
| 215 | Cyclohexanecarboxylic acid {(S)-1-[1-(4-fluoro-benzenesulfonyl)-3-oxo-azepan-4-ylcarbamoyl]-3-methyl-butyl}-amide |
| 216 | (S)-2-(2-Benzyloxy-acetylamino)-4-methyl-pentanoic acid[1-(methanesulfonyl)-3-oxo-azepan-4-yl]-amide |
| 217 | Benzo[b]thiophene-2-carboxylic acid-{(S)-1-(1-methanesulfonyl-3-oxo-azepan-4-yl carbamoyl)-3-methyl-butyl}-amide |
| 218 | Benzo[1,3]dioxole-5-carboxylic acid-{(S)-1-(1-methanesulfonyl-3-oxo-azepan-4-yl carbamoyl)-3-methyl-butyl}-amide |
| 219 | Benzofuran-2-carboxylic acid-{(S)-1-(1-methanesulfonyl-3-oxo-azepan-4-yl carbamoyl)-3-methyl-butyl}-amide |
| 220 | N-[(S)-1-(1-Methanesulfonyl)-3-oxo-azepan-4-ylcarbamoyl}-3-methyl-butyl]-3,4-dimethoxy-benzamide |
| 221 | (S)-2-(2-Benzyloxy-acetylamino)-4-methyl-pentanoic acid[1-(2-cyano-benzensulfonyl)-3-oxo-azepan-4-yl]-amide |
| 222 | N-{(S)-1-[1-(2-Cyano-benzenesulfonyl)-3-oxo-azepan-4-ylcarbamoyl]-3-methyl-butyl}-4-methanesulfonyl-1-benzamide |
| 223 | Benzo[b]thiophene-2-carboxylic acid-{(S)-1-[1-(2-cyano-benzenesulfonyl)-3-oxo-azepan-4-yl carbamoyl]-3-methyl-butyl}-amide |
| 224 | Benzo[1,3]dioxole-5-carboxylic acid-{(S)-1-[1-(2-cyano-benzenesulfonyl)-3-oxo-azepan-4-ylcarbamoyl]-3-methyl-butyl}-amide |
| 225 | (S)-4-Methyl-2-[4-oxo-4-((4-phenoxy-phenyl)-butyrylamino]-pentanoic acid [3-oxo-1-(pyridine-2-sulfonyl)-azepan-4-yl]-amide |
| 226 | N-{(S)-1-[(1-(2-cyano-benzenesulfonyl)-3-oxo-azepan-4-ylcarbamoyl]-3-methyl-butyl}-3,4-dimethoxy-benzamide |
| 227 | Cyclohexanecarboxylic acid {(S)-1-[1-(4-methoxy-benzenesulfonyl)-3-oxo-azepan-4-ylcarbamoyl]-3-methyl-butyl}-amide |
| 228 | 4-Methansulfonyl-N-{(S)-1-[4-methoxy-benzenesulfonyl)-3-oxo-azepane-4-carbamoyl]-3-methyl-butyl-benzamide |
| 229 | 4-Methansulfonyl-N-{(S)-1-[4-fluoro-benzenesulfonyl)-3-oxo-azepane-4-carbamoyl]-3-methyl-butyl-benzamide |
| 230 | ({(S)-3-Methyl-1-[3-oxo-1-(pyridine-2-sulfonyl)-azepan-4-ylcarbamoyl]-butylcarbamoyl}-carbamic acid benzyl ester |
| 231 | (S)-2-[5-(4-Methoxy-phenyl)-pentanoylamnio]-4-methyl-pentanoic acid [3-oxo-1-(pyridine-2-sulfonyl)-azepan-4-yl]-amide |
| 232 | (S)-2-[2-(3-Benzyloxy-4-methoxy-phenyl)-acetylamnio]-4-methylpentanoic acid [3-oxo-1-(pyridine-2-sulfonyl)-azepan-4-yl]-amide |
| 233 | 5,6-Difluoro-benzofuran-2-carboxylic acid {(S)-3-methyl-1-[1-(pyridine-2-sulfonyl)-3-oxo-azepan-4-ylcarbamoyl]-butyl}amide |
| 234 | (S)-4-Methyl-2-(5-oxo-hexanoylamino)-pentanoic acid [3-oxo-1-(pyridine-2-sulfonyl)-azepan-4-yl]-amide |
| 235 | Benzofuran-2-carboxylic acid {(S)-3-methyl-1-[1-(6-methyl-pyridine-2-sulfonyl)-3-oxo-azepan-4-ylcarbamoyl]-butyl}amide |
| 236 | 5-Methoxy-benzofuran-2-carboxylic acid {(S)-3-methyl-1-[1-(6-methyl-pyridine-2-sulfonyl)-3-oxo-azepan-4-ylcarbamoyl]-buryl}amide |
| 237 | 3-Methyl-benzofuran-2-carboxylic acid {(S)-3-methyl-1-[1-(6-methyl-pyridine-2-sulfonyl)-3-oxo-azepan-4-ylcarbamoyl]-buryl}amide |
| 238 | 7-Methoxy-benzofuran-2-carboxylic acid {(S)-3-methyl-1-[1-(pyridine-2-sulfonyl)-3-oxo-azepan-4-ylcarbamoyl]-butyl}amide |
| 239 | 5,6-Dimethoxy-benzo[b]thiophene-2-carboxylic acid {(S)-3-methyl-1-[1-(pyridine-2-sulfonyl)-3-oxo-azepan-4-ylcarbamoyl]-butyl}amide |
| 240 | (R)-1-Benzyl-5-oxo-pyrrolidine-2-carboxylic acid {(S)-3-methyl-1-{3-oxo-(pyridine-2-sulfonyl)-azepan-4-ylcarbamoyl]-butyl}amide |
| 241 | (S)-1-Benzyl-5-oxo-pyrrolidine-2-carboxylic acid {(S)-3-methyl-1-{3-oxo-(pyridine-2-sulfonyl)-azepan-4-ylcarbamoyl]-butyl}amide |
| 242 | Benzofuran-2-carboxylic acid {(S)-2-cyclopropyl-1-[3-oxo-1-(pyridine-2-sulfonyl)-azepan-4-ylcarbamoyl]-ethyl}-amide |
| 243 | Benzofuran-2-carboxylic acid {(S)-3-methylsulfanyl-1-[3-oxo-1-(pyridine-2-sulfonyl)-azepan-4-ylcarbamoyl)-propyl}-amide |
| 244 | Benzofuran-2-carboxylic acid {(S)-2-naphthylen-2-yl-1-[3-oxo-1-(pyridine-2-sulfonyl)-azepan-4-ylcarbamoyl]-ethyl}-amide |
| 245 | Thieno[3,2-b]thiophene-2-carboxylic acid {(S)-3-methyl-1-[1-(6-methyl-pyridine-2-sulfonyl)-3-oxo-azepan-4-ylcarbamoyl]-butyl}amide |
| 246 | Thieno[3,2-b]thiophene-2-carboxylic acid {(S)-3-methyl-1-[1-(3-methyl-pyridine-2-sulfonyl)-3-oxo-azepan-4-ylcarbamoyl]-butyl}amide |
| 247 | 3-Methyl-benzofuran-2-carboxylic acid {(S)-3-methyl-1-[1-(3-methyl-pyridine-2-sulfonyl)-3-oxo-azepan-4-ylcarbamoyl]-butyl}amide |
| 248 | 5-Methoxy-benzofuran-2-carboxylic acid {(S)-3-methyl-1-[1-(3-methyl-pyridine-2-sulfonyl)-3-oxo-azepan-4-ylcarbamoyl]-butyl}amide |
| 249 | 5,6-Difluoro-benzofuran-2-carboxylic acid {(S)-3-methyl-1-[3-oxo-1-(1-oxy-pyridine-2-sulfonyl)-azepan-4-ylcarbamoyl]-butyl}amide |
| 250 | 5-(3-Trifluoromethyl-phenyl)-furan-2-carboxylic acid {(S)-2-cyclohexyl-1-{3-oxo-1-(pyridine-2-sulfonyl)-azepan-4-ylcarbamoyl]-ethyl}-amide |
| 251 | 5-(4-Chloro-phenyl)-furan-2-carboxylic acid {(S)-2-cyclohexyl-1-{3-oxo-1-(pyridine-2-sulfonyl)-azepan-4-ylcarbamoyl]-ethyl}-amide |
| 252 | Benzofuran-2-carboxylic acid {(S)-3-methyl-1-[6-methyl-3-oxo-1-(pyridine-sulphonyl)-azepan-4-ylcarbamoyl]-butyl}-amide |
| 253 | 5-(4-Chloro-phenyl)-furan-2-carboxylic acid {(S)-2-cyclohexyl-1-[3-oxo-1-(1-oxy-pyridine-2-sulfonyl)-azepan-4-ylcarbamoyl]-ethyl}-amide |
| 254 | 5-(3-Trifluoromethyl-phenyl)-furan-2-carboxylic acid{(S)-2-cyclohexyl-1-[3-oxo-1-(1-oxy-pyridine-2-sulfonyl)-azepan-4-ylcarbamoyl]-ethyl}-amide |
| 255 | 5-Fluoro-benzofuran-2-carboxylic acid {(S)-3-methyl-1-[3-oxo-1-(pyridine-2-sulfonyl)-azepan-4-ylcarbamoyl]-butyl}-amide |
| 256 | 5,6-Dimethoxy-benzofuran-2-carboxylic acid{(S)-2-cyclohexyl-1-[3-oxo-1-(1-oxy-pyridine-2-sulfonyl)-azepan-4-ylcarbamoyl]-ethyl}-amide |
| 257 | 5,5-Bis-(4-methoxy-phenyl)-pent-4-enoic acid {(S)-3-methyl-1-[3-oxo-1-(pyridine-2-sulfonyl)-azepan-4-ylcarbamoyl]}-butyl}-amide |
| 258 | Quinoline-8-carboxylic acid {(S)-2-naphthylen-2-yl-1-[3-oxo-1-(pyridine-2-sulfonyl)-azepan-4-ylcarbamoyl)-ethyl}-amide |
| 259 | Naphthylene-1-carboxylic acid {(S)-2-naphthylen-2-yl-1-[3-oxo-1-(pyridine-2-sulfonyl)-azepan-4-ylcarbamoyl]-ethyl}-amide |
| 260 | Quinoline-8-carboxylic acid {(S)-1-[3-oxo-1-(pyridine-2-sulfonyl)-azepan-4-ylcarbamoyl]-2-phenyl-ethyl}-amide |
| 261 | Naphthyridine-2-carboxylic acid {(S)-3-methyl-1-[3-oxo-1-(pyridine-2-sulfonyl)-azepan-4-ylcarbamoyl]-butyl}-amide |
| 262 | Naphthylene-1-carboxylic acid {(S)-1-[3-oxo-1-(pyridine-2-sulfonyl)-azepan-4-ylcarbamoyl]-2-phenyl-ethyl}-amide |
| 263 | 3-Methylbenzofuran-2-carboxylic acid {(S)-methyl-1-[3-oxo-1-(cyclohexyl-proprionyl)-azepan-4-ylcarbamoyl]-butyl}-amide |
| 264 | 3-Methylbenzofuran-2-carboxylic acid {(S)-3-methyl-1-[3-oxo-1-(4-methyl-pentanoyl)-azepan-4-ylcarbamoyl]-butyl}-amide |
| 265 | 3-Methylbenzofuran-2-carboxylic acid {(S)-3-methyl-1-[3-oxo-1-(1-oxy-pyridine-2-carbonyl)-azepan-4-ylcarbamoyl]-butyl}-amide |
| 266 | (S)-Acetylamino-4-methyl-pentanoic acid [3-oxo-1-(pyridine-2-sulfonyl)-azepan-4-yl]-amide |

| Example No. | Chemical Name |
|---|---|
| 267 | Quinoline-2-carboxylic acid {1-[3-oxo-1-(pyridine-2-sulfonyl)-azepan-4-ylcarbamoyl]-pentyl}-amide |
| 268 | Benzofuran-2-carboxylic acid {(S)-3-methyl-1-[3-oxo-1-(cyclohexyl-proprionyl)-azepan-4-ylcarbamoyl]-butyl}-amide |
| 269 | Benzofuran-2-carboxylic acid {(S)-3-methyl-1-[3-oxo-1-(4-methyl-pentanoyl)-azepan-4-ylcarbamoyl]-butyl}-amide |
| 270 | Quinoline-2-carboxylic acid {(S)-1-[3-oxo-1-(pyridine-2-sulfonyl)-azepan-4-ylcarbamoyl]-2-phenyl-ethyl}-amide |
| 271 | Benzofuran-2-carboxylic acid{(S)-2-benzyloxy-1-[3-oxo-1-(pyridine-2-sulfonyl)-azepane-4-ylcarbamoyl]-ethyl}-amide |
| 272 | Benzofuran-2-carboxylic acid{(S)-2-hydroxy-1-[3-oxo-1-(pyridine-2-sulfonyl)-azepane-4-ylcarbamoyl]-ethyl}-amide |
| 273 | 5-Methoxybenzofuran-2-carboxylic acid {(S)-3-methyl-1-[3-oxo-1-(thiazole-2-sulfonyl)-azepan-4-ylcarbamoyl]-butyl}amide |
| 274 | 7-Methoxybenzofuran-2-carboxylic acid {(S)-3-methyl-1-[3-oxo-1-(thiazole-2-sulfonyl)-azepan-4-ylcarbamoyl]-butyl}amide |
| 275 | 3-Methylbenzofuran-2-carboxylic acid {(S)-3-methyl-1-[3-oxo-1-(thiazole-2-sulfonyl)-azepan-4-ylcarbamoyl]-butyl}amide |
| 276 | Benzo[b]thiophene-2-carboxylic acid {(S)-3-methyl-1-[3-oxo-1-(thiazole-2-sulfonyl)-azepan-4-ylcarbamoyl]-butyl}amide |
| 277 | 1-Methyl-1H-indole-2-carboxylic acid {(S)-3-methyl-1-[3-oxo-1-(thiazole-2-sulfonyl)-azepan-4-ylcarbamoyl]-butyl}amide |
| 278 | Quinoxaline-2-carboxylic acid {(S)-3-methyl-1-[3-oxo-1-(thiazole-2-sulfonyl)-azepan-4-ylcarbamoyl]-butyl}amide |
| 279 | Quinoline-2-carboxylic acid {[(S)-1-[1-(4-fluoro-benzenesulfonyl)-3-oxo-azepan-4-ylcarbamoyl]-3-methyl-butyl}-amide |
| | The following compounds are also particularly preferred embodiments of the present invention: |
| 280 | Benzofuran-2-carboxylic acid {(S)-1-[-(3-fluoro-benzensulfonyl)-3-oxo-azepan-4-ylcarbamoyl]-3-methyl-1-butyl}-amide |
| 281 | (S)-4-methyl-2-(3-piperidin-1-yl-propanoylamino)-pentanoic acid [3-oxo-1-(pyridine-2-sulfonyl)-azepan-4-yl]-amide |
| 282 | Benzofuran-2-carboxylic acid {(S)-1-[-(4-ethyl-benzensulfonyl)-3-oxo-azepan-4-ylcarbamoyl]-3-methyl-1-butyl}-amide |
| 283 | 5-(3-Trifluoromethyl-phenyl)-furan-2-carboxylic acid ((S)-3-methyl-1-{3-oxo-1-[1-(1-oxy-pyridin-2-yl)-methanoyl]-azepan-4-ylcarbamoyl}-butyl)-amide |
| 284 | Benzo[1,3]-dioxole-5-carboxylic acid ((S)-3-methyl-1-{3-oxo-1-[1-oxy-pyridin-2-yl]-methanoyl]-azepan-4-ylcarbamoyl}-butyl)-amide |
| 285 | 5-(3-Trifluoromethyl-phenyl)-furan-2-carboxylic acid {(S)-1-[1-(3-cyclohexyl-propanoyl)-3-oxo-azepan-4-ylcarbamoyl]-3-methyl-butyl}-amide |
| 286 | Benzo[1,3]-dioxole-5-carboxylic acid {(S)-1-[1-(3-cyclohexyl-propanoyl)-3-oxo-azepan-4-ylcarbamoyl]-3-methyl-butyl}-amide |
| 287 | 5-(3-Trifluoromethyl-phenyl)-furan-2-carboxylic acid {(S)-1-[1-(4-methyl-pentanoyl)-3-oxo-azepan-4-ylcarbamoyl]-3-methyl-butyl}-amide |
| 288 | Benzo[1,3]-dioxole-5-carboxylic acid {(S)-1-[1-(4-methyl-pentanoyl)-3-oxo-azepan-4-ylcarbamoyl]-3-methyl-butyl}-amide |
| 289 | Benzofuran-2-carboxylic acid {(S)1-[3-oxo-1-(propane-1-sulfonyl)-azepan-4-ylcarbamoyl]-3-methyl-1-butyl}-amide |
| 290 | Benzofuran-2-carboxylic acid [(S)-1-[3-oxo-1-(ethanesulfonyl)-azepan-4-ylcarbamoyl]-3-methyl-1-butyl]-amide |
| 291 | 5-Fluoro-benzofuran-2-carboxylic acid {(S)-3-methyl-1-[3-oxo-1-(1-oxy-pyridine-2-sulfonyl)-azepan-4-ylcarbamoyl]-butyl}-amide |
| 292 | 5-Fluoro-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide |
| 293 | 6-Fluoro-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide |
| 294 | 3-Methyl-benzofuran-2-carboxylic acid {(R)-3-methyl-1-[3-oxo-1-(1-oxy-pyridine-2-sulfonyl)-azepan-4-ylcarbamoyl]-butyl}-amide |
| 295 | 3-Methyl-furo[3,2-b]-pyridine-2-carboxylic acid {(S)-3-methyl-1-[-3-oxo-1-(1-oxy-pyridine-2-sulfonyl)-azepan-4-ylcarbamoyl]-butyl}-amide |
| 296 | 5-Methoxy-benzofuran-2-carboxylic acid {(S)-1-[1-(3-fluoro-benzenesulfonyl)-3-oxo-azepan-4-ylcarbamoyl]-3-methyl-butyl}-amide |
| 297 | 3-Methyl-benzofuran-2-carboxylic acid {(S)-1-[1-(3-fluoro-benzenesulfonyl)-3-oxo-azepan-4-ylcarbamoyl]-3-methyl-butyl}-amide |
| 298 | Benzo[b]thiophene-2-carboxylic acid {(S)-1-[1-(3-fluoro-benzenesulfonyl)-3-oxo-azepan-4-ylcarbamoyl]-3-methyl-butyl}-amide |
| 299 | 3-methyl-furan-2-carboxylic acid {(S)-1-[1-(3-fluoro-benzenesulfonyl)-3-oxo-azepan-4-ylcarbamoyl]-3-methyl-butyl}-amide |
| 300 | Quinoline-2-carboxylic acid {(S)-1-[1-(3-fluoro-benzenesulfonyl)-3-oxo-azepan-4-ylcarbamoyl]-3-methyl-butyl}-amide |
| 301 | Thieno[3,2-b]thiophene-2-carboxylic acid {(S)-1-[1-(3-fluoro-benzenesulfonyl)-3-oxo-azepan-4-ylcarbamoyl]-3-methyl-butyl}-amide |
| 302 | Quinoxaline-2-carboxylic acid {(S)-1-[1-(3-fluoro-benzenesulfonyl)-3-oxo-azepan-4-ylcarbamoyl]-3-methyl-butyl}-amide |
| 303 | Thiophene-2-carboxylic acid {(S)-1-[1-(3-fluoro-benzenesulfonyl)-3-oxo-azepan-4-ylcarbamoyl]-3-methyl-butyl}-amide |
| 304 | 5-Methyl-thiophene-2-carboxylic acid {(S)-1-[1-(3-fluoro-benzenesulfonyl)-3-oxo-azepan-4-ylcarbamoyl]-3-methyl-butyl}-amide |
| 305 | 5-Methoxy-benzofuran-2-carboxylic acid [(S)-1-(1-ethanesulfonyl-3-oxo-azepan-4-ylcarbamoyl)-3-methyl-butyl]-amide |
| 306 | 3-Methyl-benzofuran-2-carboxylic acid [(S)-1-(1-ethanesulfonyl-3-oxo-azepan-4-ylcarbamoyl)-3-methyl-butyl]-amide |
| 307 | Benzo[b]thiophene-2-carboxylic acid [(S)-1-(1-ethanesulfonyl-3-oxo-azepan-4-ylcarbamoyl)-3-methyl-butyl]-amide |
| 308 | 3-Methyl-furan-2-carboxylic acid [(S)-1-(1-ethanesulfonyl-3-oxo-azepan-4-ylcarbamoyl)-3-methyl-butyl]-amide |
| 309 | Quinoline-2-carboxylic acid [(S)-1-(1-ethanesulfonyl-3-oxo-azepan-4-ylcarbamoyl)-3-methyl-butyl]-amide |
| 310 | Thieno[3,2-b]thiophene-2-carboxylic acid [(S)-1-(1-ethanesulfonyl-3-oxo-azepan-4-ylcarbamoyl)-3-methyl-butyl]-amide |
| 311 | Quinoxaline-2-carboxylic acid [(S)-1-(1-ethanesulfonyl-3-oxo-azepan-4-ylcarbamoyl)-3-methyl-butyl]-amide |
| 312 | Thiophene-2-carboxylic acid [(S)-1-(1-ethanesulfonyl-3-oxo-azepan-4-ylcarbamoyl)-3-methyl-butyl]-amide |
| 313 | 5-Methyl-thiophene-2-carboxylic acid [(S)-1-(1-ethanesulfonyl-3-oxo-azepan-4-ylcarbamoyl)-3-methyl-butyl]-amide |
| 314 | 5-Methoxy-benzofuran-2-carboxylic acid {(S)-1-[3-oxo-1-(propane-1-sulfonyl)-azepan-4-ylcarbamoyl]-3-methyl-1-butyl}-amide |
| 315 | 3-Methyl-benzofuran-2-carboxylic acid {(S)-1-[3-oxo-1-(propane-1-sulfonyl)-azepan-4-ylcarbamoyl]-3-methyl-1-butyl}-amide |
| 316 | Benzo[b]thiophene-2-carboxylic acid {(S)-1-[3-oxo-1-(propane-1-sulfonyl)-azepan-4-ylcarbamoyl]-3-methyl-1-butyl}-amide |
| 317 | 3-Methyl-furan-2-carboxylic acid {(S)-1-[3-oxo-1-(propane-1-sulfonyl)-azepan-4-ylcarbamoyl]-3-methyl-1-butyl}-amide |
| 318 | 2,5-Dimethyl-furan-2-carboxylic acid {(S)-1-[3-oxo-1-(propane-1-sulfonyl)-azepan-4-ylcarbamoyl]-3-methyl-1-butyl}-amide |
| 319 | Quinoline-2-carboxylic acid {(S)-1-[3-oxo-1-(propane-1-sulfonyl)-azepan-4-ylcarbamoyl]-3-methyl-1-butyl}-amide |
| 320 | Thieno[3,2-b]thiophene-2-carboxylic acid {(S)-1-[3-oxo-1-(propane-1-sulfonyl)-azepan-4-ylcarbamoyl]-3-methyl-1-butyl}-amide |
| 321 | Quinoxaline-2-carboxylic acid {(S)-1-[3-oxo-1-(propane-1-sulfonyl)-azepan-4-ylcarbamoyl]-3-methyl-1-butyl}-amide |
| 322 | Thiophene-2-carboxylic acid {(S)-1-[3-oxo-1-(propane-1-sulfonyl)-azepan-4-ylcarbamoyl]-3-methyl-1-butyl}-amide |
| 323 | 5-Methyl-thiophene-2-carboxylic acid {(S)-1-[3-oxo-1-(propane-1-sulfonyl)-azepan-4-ylcarbamoyl]-3-methyl-1-butyl}-amide |
| 324 | 5-Methoxy-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide |
| 325 | 3,5-Dimethyl-benzofuran-2-carboxylic acid {(S)-3-methyl-1-[3-oxo-1-(1-oxy-pyridine-2-sulfonyl)-azepan-4-ylcarbamoyl]-butyl}-amide |
| 326 | 3-Ethyl-benzofuran-2-carboxylic acid {(S)-3-methyl-1-[3-oxo-1-(1-oxy-pyridine-2-sulfonyl)-azepan-4-ylcarbamoyl]-butyl}-amide |
| 327 | 4-Methoxy-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide |

| Example No. | Chemical Name |
|---|---|
| 328 | 1-methyl-naphtho[2,1-b]-furan-2-carboxylic acid {(S)-3-methyl-1-[3-oxo-1-(1-oxy-pyridine-2-sulfonyl)-azepan-4-ylcarbamoyl]-butyl}-amide |
| 329 | 6-Methoxy-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide |
| 330 | 3-Methyl-benzofuran-2-carboxylic acid {1,3-dimethyl-1-[3-oxo-1-(1-oxy-pyridine-2-sulfonyl)-azepan-4-ylcarbamoyl]-butyl}-amide |
| 331 | Benzofuran-2-carboxylic acid [(S)-3-methyl-1-[3-oxo-1-quinolin-2-ylmethyl-azepan-4-ylcarbamoyl]-butyl}-amide |
| 332 | 3-Methyl-benzofuran-2-carboxylic acid [(S)-3-methyl-1-[3-oxo-1-quinolin-2-ylmethyl-azepan-4-ylcarbamoyl]-butyl}-amide |
| 333 | Benzo[b]thiophene-2-carboxylic acid [(S)-3-methyl-1-[3-oxo-1-quinolin-2-ylmethyl-azepan-4-ylcarbamoyl]-butyl}-amide |
| 334 | Benzofuran-2-carboxylic acid ((S)-3-methyl-1-{3-oxo-1-[1-toluene-2-sulfonylamino)-methanoyl]-azepan-4-ylcarbamoyl}-butyl)-amide |
| 335 | 3-Methyl-benzofuran-2-carboxylic acid ((S)-3-methyl-1-{3-oxo-1-[1-toluene-2-sulfonylamino)-methanoyl]-azepan-4-ylcarbamoyl}-butyl)-amide |
| 336 | Benzo[b]thiophene-2-carboxylic acid ((S)-3-methyl-1-{3-oxo-1-[1-toluene-2-sulfonylamino)-methanoyl]-azepan-4-ylcarbamoyl}-butyl)-amide |
| 337 | Benzofuran-2-carboxylic acid ((S)-3-methyl-1-{3-oxo-1-[2-chloro-benzenesulfonylamino)-methanoyl]-azepan-4-ylcarbamoyl}-butyl)-amide |
| 338 | 3-Methyl-benzofuran-2-carboxylic acid ((S)-3-methyl-1-{3-oxo-1-[2-chloro-benzenesulfonylamino)-methanoyl]-azepan-4-ylcarbamoyl}-butyl)-amide |
| 339 | Benzo[b]thiophene-2-carboxylic acid ((S)-3-methyl-1-{3-oxo-1-[2-chloro-benzenesulfonylamino)-methanoyl]-azepan-4-ylcarbamoyl}-butyl)-amide |
| 340 | Benzofuran-2-carboxylic acid ((S)-3-methyl-1-{3-oxo-1-[4-fluoro-benzenesulfonylamino)-methanoyl]-azepan-4-ylcarbamoyl}-butyl)-amide |
| 341 | 3-Methyl-benzofuran-2-carboxylic acid ((S)-3-methyl-1-{3-oxo-1-[4-fluoro-benzenesulfonylamino)-methanoyl]-azepan-4-ylcarbamoyl}-butyl)-amide |
| 342 | Benzo[b]thiophene-2-carboxylic acid ((S)-3-methyl-1-{3-oxo-1-[4-fluoro-benzenesulfonylamino)-methanoyl]-azepan-4-ylcarbamoyl}1-butyl)-amide |
| 343 | Benzofuran-2-carboxylic acid ((S)-3-methyl-1-{3-oxo-1-[1-toluene-4-sulfonylamino)-methanoyl]-azepan-4-ylcarbamoyl}-butyl)-amide |
| 344 | 3-Methyl-benzofuran-2-carboxylic acid ((S)-3-methyl-1-{3-oxo-1-[1-toluene-4-sulfonylamino)-methanoyl]-azepan-4-ylcarbamoyl}-butyl)-amide |
| 345 | Benzo[b]thiophene-2-carboxylic acid ((S)-3-methyl-1-{3-oxo-1-[1-toluene-4-sulfonylamino)-methanoyl]-azepan-4-ylcarbamoyl}-butyl)-amide |
| 346 | Benzofuran-2-carboxylic acid {(S)-3-methyl-1-[1-(6-methyl-pyridin-2-ylmethyl)-3-oxo-azepan-4-ylcarbamoyl]-butyl}-amide |
| 347 | 3-Methyl-benzofuran-2-carboxylic acid {(S)-3-methyl-1-[1-(6-methyl-pyridin-2-ylmethyl)-3-oxo-azepan-4-ylcarbamoyl]-butyl}-amide |
| 348 | Benzo[b]thiophene-2-carboxylic acid {(S)-3-methyl-1-[1-(6-methyl-pyridin-2-ylmethyl)-3-oxo-azepan-4-ylcarbamoyl]-butyl}-amide |
| 349 | Benzo[b]thiophene-2-carboxylic acid {(S)-1-[1-(2-fluoro-phenylcarbamoyl)-3-oxo-azepan-4-ylcarbamoyl]-3-methyl-butyl}-amide |
| 350 | 3-Methyl-benzofuran-2-carboxylic acid {(S)-1-[1-(2-fluoro-phenylcarbamoyl)-3-oxo-azepan-4-ylcarbamoyl]-3-methyl-butyl}-amide |
| 351 | 2,4-Dimethylfuran-3-carboxylic acid {(S)-1-[1-(2-fluoro-phenylcarbamoyl)-3-oxo-azepan-4-ylcarbamoyl]-3-methyl-butyl}-amide |
| 352 | Quinoxaline-2-carboxylic acid {(S)-1-[1-(2-fluoro-phenylcarbamoyl)-3-oxo-azepan-4-ylcarbamoyl]-3-methyl-butyl}-amide |
| 353 | Thieno[3,2-b]thiophene-2-carboxylic acid {(S)-1-[1-(2-fluoro-phenylcarbamoyl)-3-oxo-azepan-4-ylcarbamoyl]-3-methyl-butyl}-amide |
| 354 | Quinoline-2-carboxylic acid {(S)-1-[1-(2-fluoro-phenylcarbamoyl)-3-oxo-azepan-4-ylcarbamoyl]-3-methyl-butyl}-amide |
| 355 | 4-Methyl-thiophene-2-carboxylic acid {(S)-1-[1-(2-fluoro-phenylcarbamoyl)-3-oxo-azepan-4-ylcarbamoyl]-3-methyl-butyl}-amide |
| 356 | 5-Methoxy-benzofuran-2-carboxylic acid {(S)-1-[1-(2-fluoro-phenylcarbamoyl)-3-oxo-azepan-4-ylcarbamoyl]-3-methyl-butyl}-amide |
| 357 | 4-Methyl-furan-2-carboxylic acid {(S)-1-[1-(2-fluoro-phenylcarbamoyl)-3-oxo-azepan-4-ylcarbamoyl]-3-methyl-butyl}-amide |
| 358 | Benzofuran-2-carboxylic acid [(S)-1-(1-butyl-3-oxo-azepan-4-ylcarbamoyl)-3-methyl-butyl]-amide |
| 359 | Benzofuran-2-carboxylic acid [(S)-1-(1-propyl-3-oxo-azepan-4-ylcarbamoyl)-3-methyl-butyl]-amide |
| 360 | Benzofuran-2-carboxylic acid {(S)-1-[1-(2-fluoro-benzyl)-3-oxo-azepan-4-ylcarbamoyl]-3-methyl-butyl}-amide |
| 361 | Benzofuran-2-carboxylic acid {(S)-3-methyl-1-[1-(2-morpholin-4-yl-thiazol-4-ylmethyl)-3-oxo-azepan-4-ylcarbamoyl]-butyl}-amide |
| 362 | Benzofuran-2-carboxylic acid {(S)-1-[1-(5-ethyl-furan-2-ylmethyl)-3-oxo-azepan-4-ylcarbamoyl]-3-methyl-butyl}-amide |
| 363 | Benzofuran-2-carboxylic acid {(S)-1-[1-(3,4-dimethyl-thieno[3,2-b]thiophen-2-ylmethyl)-3-oxo-azepan-4-ylcarbamoyl]-3-methyl-butyl}-amide |
| 364 | Benzofuran-2-carboxylic acid {(S)-3-methyl-1-[3-oxo-1-(3-phenyl-3H-[1,2,3]triazol-4-ylmethyl)-azepan-4-ylcarbamoyl]-butyl}-amide |
| 365 | Benzofuran-2-carboxylic acid [(S)-1-[1-(isothiazol-3-ylmethyl-3-oxo-azepan-4-ylcarbamoyl]-3-methyl-butyl]-amide |
| 366 | Benzofuran-2-carboxylic acid [(S)-3-methyl-1-(3-oxo-1-thiophen-2-ylmethyl-azepan-4-ylcarbamoyl)-butyl]-amide |
| 367 | Benzofuran-2-carboxylic acid {(S)-1-(1-benzo[b]thiophen-2-ylmethyl-3-oxo-azepan-4-ylcarbamoyl]-3-methyl-butyl}-amide |
| 368 | Benzofuran-2-carboxylic acid [(S)-3-methyl-1-(3-oxo-1-pentyl-azepan-4-ylcarbamoyl)-butyl]-amide |
| 369 | Benzofuran-2-carboxylic acid {(S)-3-methyl-1-[1-(1-methyl-1H-imidazol-2-ylmethyl)-3-oxo-azepan-4-ylcarbamoyl]-buty}-amide |
| 370 | 1-Oxy-pyridine-2-carboxylic acid {(S)-3-methyl-1-[3-oxo-1-(pyridine-2-sulfonyl)-azepan-4-ylcarbamoyl]-butyl}-amide |
| 371 | 2-Oxy-pyridine-3-carboxylic acid {(S)-3-methyl-1-[3-oxo-1-(pyridine-2-sulfonyl)-azepan-4-ylcarbamoyl]-butyl}-amide |
| 372 | 1H-Benzoimidazole-5-carboxylic acid {(S)-3-methyl-1-[3-oxo-1-(pyridine-2-sulfonyl)-azepan-4-ylcarbamoyl]-butyl}-amide |
| 373 | 4-{(S)-2-[(1-Benzofuran-2-yl-methanoyl)-amino]-4-methyl-pentanoylamino}-1-methyl-3-oxo-1-pentyl-azepanium |
| 374 | Benzofuran-2-carboxylic acid {(S)-1-[1-(1,2-dimethyl-1H-imidazole-4-sulfonyl)-3-oxo-azepan-4-ylcarbamoyl]-3-methyl-butyl}-amide |
| 375 | Benzofuran-2-carboxylic acid {(S)-1-[1-(1-methyl-1H-imidazole-4-sulfonyl)-3-oxo-azepan-4-ylcarbamoyl]-3-methyl-butyl}-amide |
| 376 | Benzofuran-2-carboxylic acid {(S)-1-[1-(4-methanesulfonyl-benzenesulfonyl)-3-oxo-azepan-4-ylcarbamoyl]-3-methyl-butyl}-amide |
| 377 | Benzofuran-2-carboxylic acid {(S)-1-[1-(2-methanesulfonyl-benzenesulfonyl)-3-oxo-azepan-4-ylcarbamoyl]-3-methyl-butyl}-amide |
| 378 | Benzofuran-2-carboxylic acid {(S)-1-[1-(3,5-dimethyl-isoxazole-4-sulfonyl)-3-oxo-azepan-4-ylcarbamoyl]-3-methyl-butyl}-amide |
| 379 | 3-Methyl-benzofuran-2-carboxylic acid {(1S,2R)-2-methyl-1-[3-oxo-1-(pyridine-2-sulfonyl)-azepan-4-ylcarbamoyl]-butyl}-amide |
| 380 | 3-Methyl-benzofuran-2-carboxylic acid {1-[3-oxo-1-(pyridine-2-sulfonyl)-azepan-4-ylcarbamoyl]-cyclopentyl}-amide |
| 381 | Furo[3,2-b]-pyridine-2-carboxylic acid {(S)-3-methyl-1-[3-oxo-1-(1-oxy-pyridine-2-sulfonyl)-azepan-4-ylcarbamoyl]-butyl}-amide |

Specific representative compounds of the present invention are set forth in Examples 1-381

Compared to the corresponding 5 and 6 membered ring compounds, the 7 membered ring compounds of the present invention are configurationally more stable at the carbon center alpha to the ketone.

The present invention includes deuterated analogs of the inventive compounds. A representative example of such a deuterated compound is set forth in Example 192. A representative synthetic route for the deuterated compounds of the present invention is set forth in Scheme 4, below. The deuterated compounds of the present invention exhibit superior chiral stability compared to the protonated isomer.

Where possible the present invention includes quaternary salts of the inventive compounds. A representative example of such a quaternary salt is set forth in Example 373. A representative synthetic route for the quaternary salts of the present invention is set forth in Scheme 6, below.

DEFINITIONS

The present invention includes all hydrates, solvates, complexes and prodrugs of the compounds of this invention. Prodrugs are any covalently bonded compounds which release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center maybe used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984).

"Proteases" are enzymes that catalyze the cleavage of amide bonds of peptides and proteins by nucleophilic substitution at the amide bond, ultimately resulting in hydrolysis. Such proteases include: cysteine proteases, serine proteases, aspartic proteases, and metalloproteases. The compounds of the present invention are capable of binding more strongly to the enzyme than the substrate and in general are not subject to cleavage after enzyme catalyzed attack by the nucleophile. They therefore competitively prevent proteases from recognizing and hydrolyzing natural substrates and thereby act as inhibitors.

The term "amino acid" as used herein refers to the D- or L-isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. $C_{1-6}$alkyl may be optionally substituted by a moiety selected from the group consisting of: $OR^{14}$, $C(O)R^{14}$, $SR^{14}$, $S(O)R^{14}$, $NR^{14}_2$, $R^{14}NC(O)OR^5$, $CO_2R^{14}$, $CO_2NR^{14}_2$, $N(C\!\!=\!\!NH)NH_2$, Het, $C_{3-6}$cycloalkyl, and Ar; where $R^5$ is selected from the group consisting of: H, $C_{1-6}$alkyl, $C_{2-6}$alkenyl, $C_{2-6}$alkynyl, $C_{3-6}$cycloalkyl-$C_{0-6}$alkyl, Ar—$C_{0-6}$alkyl and Het-$C_{0-6}$alkyl; and $R^{14}$ is selected from the group consisting of: H, $C_{1-6}$alkyl, Ar—$C_{0-6}$alkyl, and Het-$C_{0-6}$alkyl;

"$C_{3-6}$cycloalkyl" as applied herein is meant to include substituted and unsubstituted cyclopropane, cyclobutane, cyclopentane and cyclohexane.

"$C_{2-6}$ alkenyl" as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

"$C_{2-6}$alkynyl" means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

"Halogen" means F, Cl, Br, and I.

"Ar" or "aryl" means phenyl or naphthyl, optionally substituted by one or more of Ph-$C_{0-6}$alkyl; Het-$C_{0-6}$alkyl; $C_{1-6}$alkoxy; Ph-$C_{0-6}$alkoxy; Het-$C_{0-6}$alkoxy; OH, $(CH_2)_{1-6}$NR$^{15}$R$^{16}$; $O(CH_2)_{1-6}$NR$^{15}$R$^{16}$; $C_{1-6}$alkyl, $OR^{17}$, $N(R^{17})_2$, $SR^{17}$, $CF_3$, $NO_2$, $CN$, $CO_2R^{17}$, $CON(R^{17})$, F, Cl, Br or I; where $R^{15}$ and $R^{16}$ are H, $C_{1-6}$alkyl, Ph-$C_{0-6}$alkyl, naphthyl-$C_{0-6}$alkyl or Het-$C_{0-6}$alkyl; and $R^{17}$ is phenyl, naphthyl, or $C_{1-6}$alkyl.

As used herein "Het" or "heterocyclic" represents a stable 5- to 7-membered monocyclic, a stable 7- to 10-membered bicyclic, or a stable 11- to 18-membered tricyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quatemized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{0-6}$Ar, $C_{1-6}$alkyl, $OR^{17}$, $N(R^{17})_2$, $SR^{17}$, $CF_3$, $NO_2$, $CN$, $CO_2R^{17}$, $CON(R^{17})$, F, Cl, Br and I, where $R^{17}$ is phenyl, naphthyl, or $C_{1-6}$alkyl. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridinyl, 1-oxo-pyridinyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, quinoxalinyl, isoquinolinyl, benzimidazolyl, benzopyranyl, benzoxazolyl, furanyl, benzofuranyl, thiophenyl, benzo[b]thiophenyl, thieno[3,2-b]thiophenyl, benzo[1,3]dioxolyl, 1,8 naphthyridinyl, pyranyl, tetrahydrofuranyl, tetrahydropyranyl, thienyl, benzoxazolyl, thiamorpholinyl sulfoxide, thiamorpholinyl sulfone, and oxadiazolyl, as well as triazolyl, thiadiazolyl, oxadiazolyl, isothiazolyl, imidazolyl, pyridazinyl, pyrimidinyl, triazinyl and tetrazinyl which are available by routine chemical synthesis and are stable. The term heteroatom as applied herein refers to oxygen, nitrogen and sulfur.

Here and throughout this application the term $C_0$ denotes the absence of the substituent group immediately following; for instance, in the moiety ArC$_{0-6}$alkyl, when C is 0, the substituent is Ar, e.g., phenyl. Conversely, when the moiety ArC$_{0-6}$alkyl is identified as a specific aromatic group, e.g., phenyl, it is understood that the value of C is 0.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical.

Certain reagents are abbreviated herein. m-CPBA refers to 3-chloroperoxybenzoic acid, EDC refers to N-ethyl-N'(dimethylaminopropyl)-carbodiimide, DMF refers to dimethyl formamide, DMSO refers to dimethyl sulfoxide, TEA refers to triethylamine, TFA refers to trifluoroacetic acid, and THF refers to tetrahydrofuran.

Methods of Preparation

Compounds of the general formula I may be prepared in a fashion analogous to that outlined in Schemes 1, 2 and 3. Alkylation of tert-butyl N-allylcarbamate (1) with a base such as sodium hydride and 5-bromo-1-pentene provides the diene 2. Treatment of 2 with either 2,6-diisopropylphenylimido neophylidene molybenum bis(tert-butoxide) or bis(tricyclohexylphosphine)benzylidine ruthenium (IV) dichloride olefin nietathesis catalysts developed by Grubbs provides the azepine 3. Epoxidation of 3 with standard oxidizing agents common to the art such as m-CPBA provide the epoxide 4. Nucleophilic epoxide ring opening may be effected with a reagent such as sodium azide to provide the azido alcohol (not shown) which may be reduced to the amino alcohol 5 under conditions common to the art such as 1,3-propanedithiol and triethylamine in methanol or with hydrogen gas in the presence of a catalyst such as palladium on carbon. Acylation of 5 with an acid such as Cbz-leucine in the presence of a coupling agent such as EDC followed by removal of the BOC protecting group under acidic conditions provides the amine salt 6. Coupling of 6 with Cbz-leucine may be effected with a coupling agent such as EDC to provide the intermediate alcohol (not shown) which was oxidized with an oxidant such as pyridine sulfur trioxide complex in DMSO and triethylamine to provide the ketone 7.

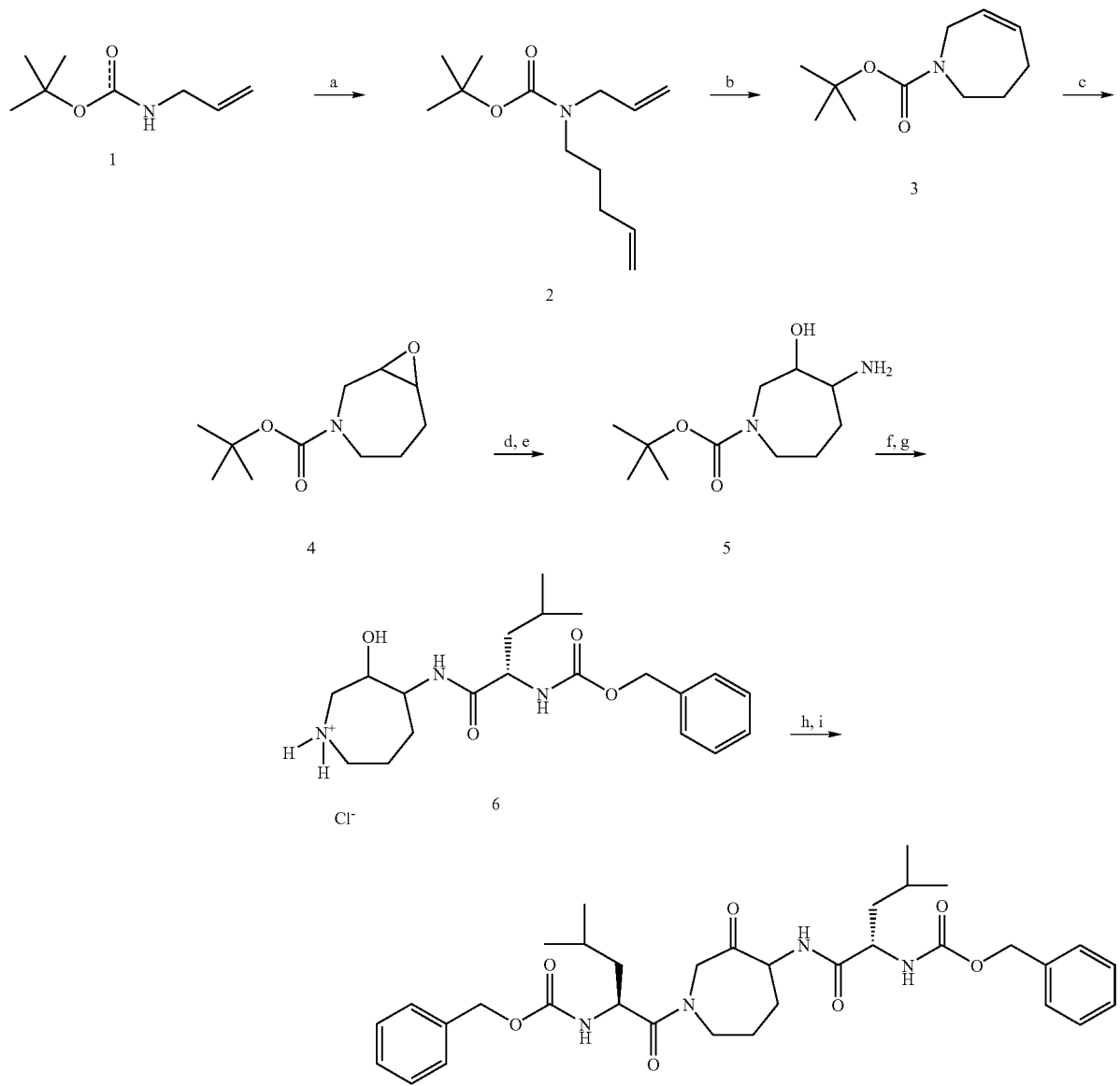

Scheme 1

Reagents and conditions: a.) NaH, 5-bromo-1-pentene, DMF; b.) 2,6-diisopropylphenylimido neophylidene molybenum bis(tert-butoxide) or bis(tricyclohexylphosphine)benzylidine ruthenium (IV) dichloride catalyst, toluene c.) m-CPBA, CH$_2$Cl$_2$; d.) NaN$_3$, CH$_3$OH, H$_2$O, NH$_4$Cl; e.) 10% Pd/C, H$_2$, f.) Cbz-leucine, EDC, CH$_2$Cl$_2$; g.) HCl, EtOAc; h.) Cbz-leucine, EDC, CH$_2$Cl$_2$; i.) pyridine sulfur trioxide complex, DMSO, TEA.

Compounds of the general formula I wherein R$^1$ and R$^2$ are amides may be prepared in the general fashion outlined in Scheme 2. Alkylation of N-Cbz allyl amine (8) with a base such as sodium hydride and 5-bromo-1-pentene provides the diene 9. Treatment of 9 with bis(tricyclohexylphosphine)benzylidine ruthenium(IV)dichloride olefin metathesis catalyst developed by Grubbs provides the azepine 10. Epoxidation of 10 with standard oxidizing agents common to the art such as m-CPBA provide the epoxide 11. Nucleophilic epoxide ring opening may be effected with a reagent such as sodium azide to provide the azido alcohol (not shown) which may be reduced to the amino alcohol 12 with a reducing agent such as propanedithiol in the presence of triethylamine. Acylation of 12 with N-Boc-leucine and a coupling agent such as EDC followed by removal of the Cbz protecting group under hydrogenolysis conditions provides the amine 13. Coupling of 13 with a carboxylic acid was effected with a coupling agent such as EDC followed by removal of the acid labile N-Boc protecting group with an acid such as HCL or TFA provides intermediate 14. Acylation of 14 may be effected with a carboxylic acid in the presence of a coupling agent common to the art such as EDC to give the intermediate alcohol (not shown) which is oxidized with an oxidant such as pyridine sulfur trioxide complex in DMSO and triethylamine to provide the ketone 15.

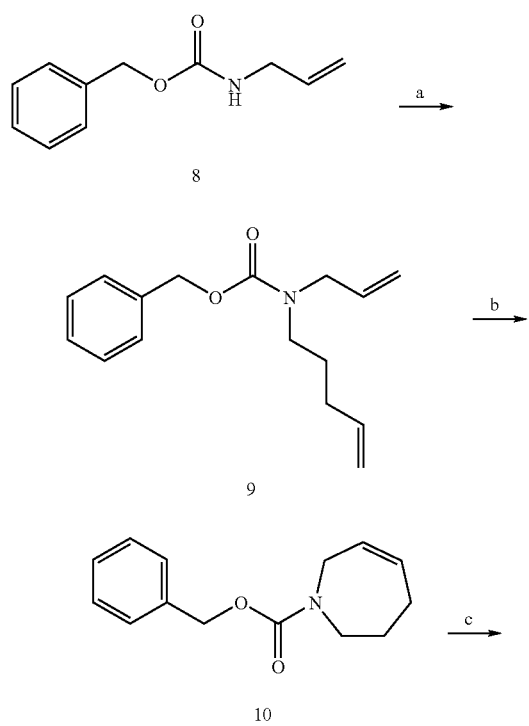

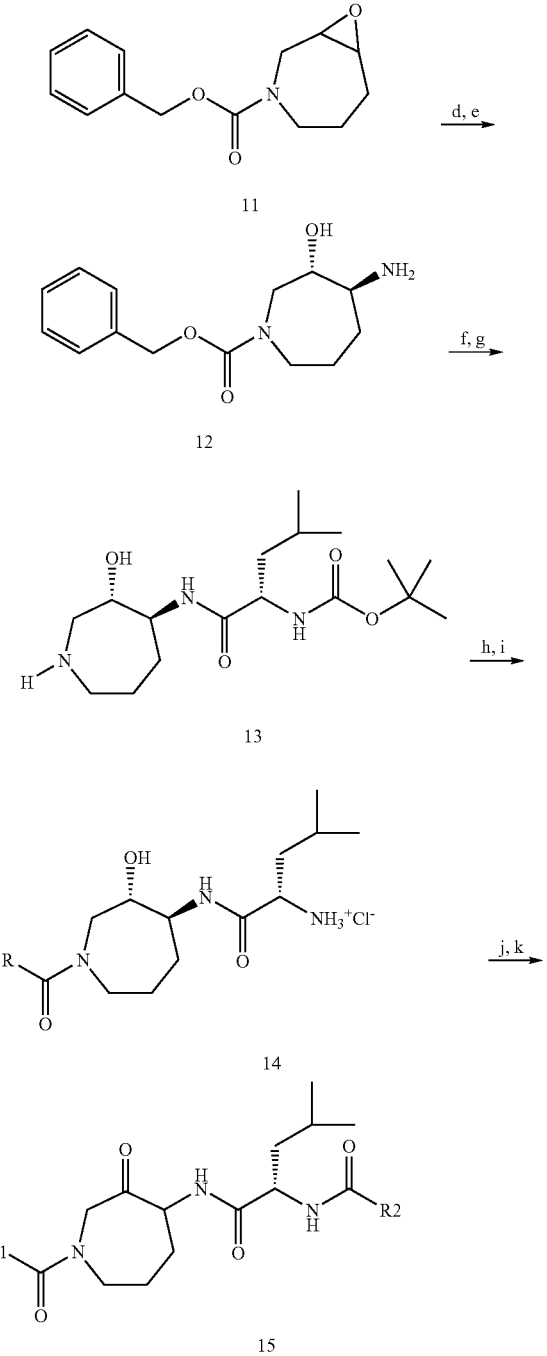

Reagents and conditions: a.) NaH, 5-bromo-1-pentene, DMF; b.) bis(tricyclohexylphosphine)benzylidine ruthenium (IV) dichloride catalyst, CH$_2$Cl$_2$; c.) m-CPBA, CH$_2$Cl$_2$; d.) NaN$_3$, CH$_3$OH, H$_2$O, NH$_4$Cl; e.) propanedithiol, CH$_3$OH, TEA; f.) Boc-leucine, EDC, CH$_2$Cl$_2$; g.) 10% Pd/C, H$_2$; h.) R$_1$CO$_2$H, EDC, CH$_2$Cl$_2$ or R$_1$COCl, CH$_2$Cl$_2$; i.) HCl/EtOAc; j.) R$_2$CO$_2$H, EDC, CH$_2$Cl$_2$; k.) pyridine sulfur trioxide complex, DMSO, TEA.

Compounds of the general formula I wherein R$^2$ is an alkyl, urea or sulphonamide group and R$^1$ is an amide may be prepared in the general fashion outlined in Scheme 3. Reductive amination of 13 may be effected by treatment with an aldehyde followed by a reducing agent such as sodium triacetoxyborohydride. Subsequent deprotection of the N-Boc group under acidic conditions provides the amine salt 16. Coupling of 16 with an acid chloride or with a carboxylic acid in the presence of a coupling agent common to the art such as EDC followed by oxidation of the intermediate alcohol (not shown) with an oxidant such as pyridine sulfur trioxide complex provides the ketone 17. Alternatively, treatment of amine 13 with an isocyanate followed by deprotection of the N-Boc group provides the amine salt 18. Acylation and oxidation provides the ketone 19. Further derivatization of amine 13 may be effected by treatment with a sulphonyl chloride followed by deprotection of the N-Boc group to provide the amine salt 20. Acylation and oxidation provides the ketone 21.

dine-2-sulfonyl)-azepan-4-ylcarbamoyl]-butyl}amide 31 and 32 may be prepared as outlined in Scheme 4. Alkylation of allyl-carbamic acid benzyl ester 22 with 5-bromo-1-pentene in the presence of a base such as sodium hydride provides the diene 23. Treatment of diene 23 with bis(tricyclohexylphosphine)benzylidine ruthenium (IV) dichloride developed by Grubbs provides the 2,3,4,7-tetrahydro-azepine-1-carboxylic acid benzyl ester 24. Epoxidation of azepine 24 may be effected with standard oxidizing agents common to the art such as m-CPBA to provide epoxide 25. Nucleophilic epoxide ring opening of 25 may be effected with a reagent such as sodium azide to provide the azido alcohol (not shown).

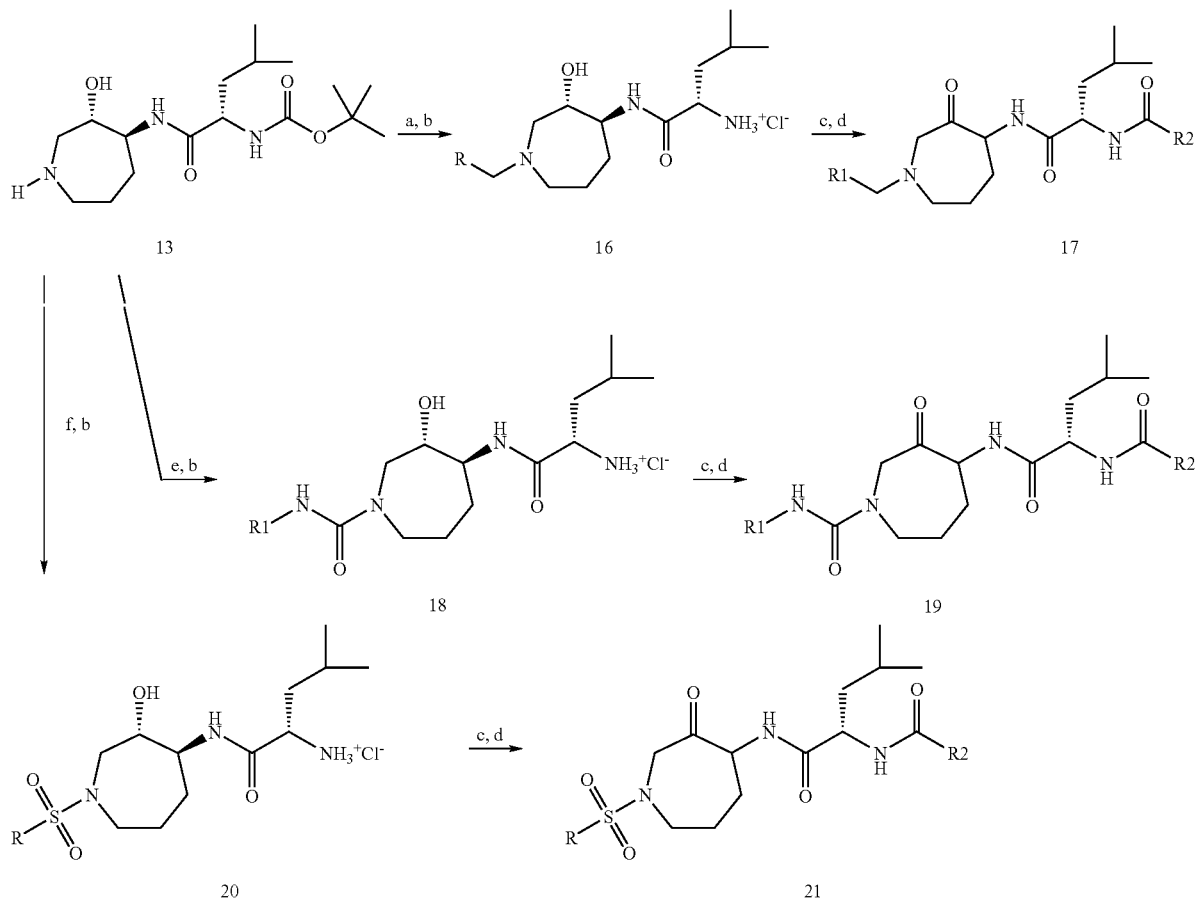

Reagents and conditions: a.) R₁CHO, NaBH(OAc)₃; b.) HCl; c.) R₂CO₂H, EDC, CH₂Cl₂; d.) pyridine sulfur trioxide complex, DMSO, TEA; e.) R₁NCO, base; f.) R₁SO₂Cl, TEA, CH₂Cl₂.

The deuterated compound of the Example 192 may be conveniently prepared according to Scheme 4. The skilled artisan will understand from Example 192 and Scheme 4 how to make any of the the deuterated compounds of the present invention.

The individual diastereomers of benzofuran-2-carboxylic acid {(S)-3-methyl-1-[(2,2',4-trideuterio)-3-oxo-1-(pyri-

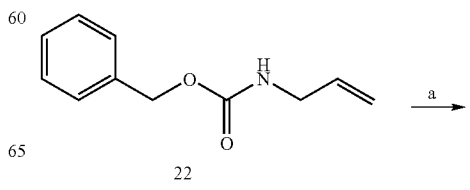

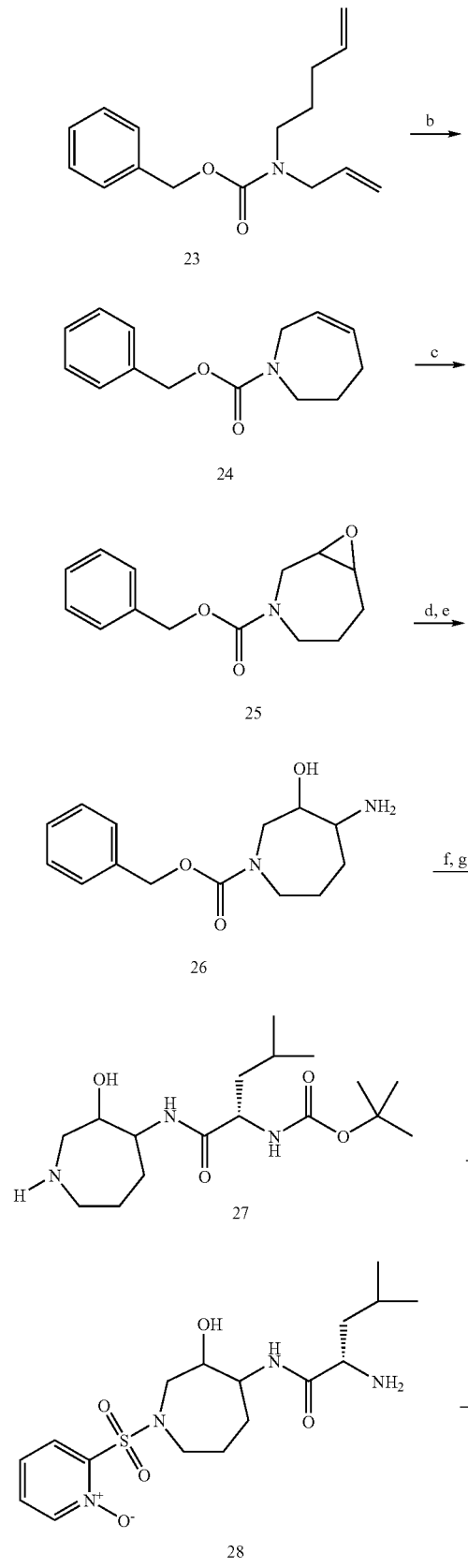
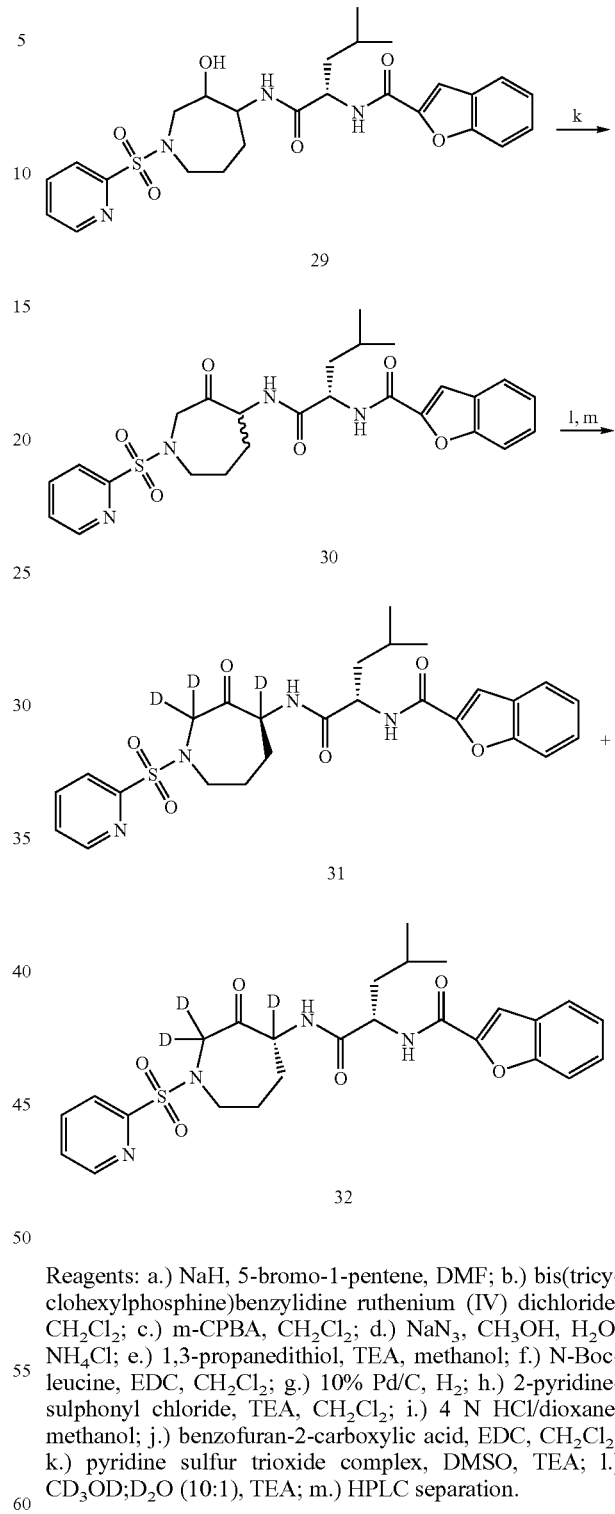

Reagents: a.) NaH, 5-bromo-1-pentene, DMF; b.) bis(tricyclohexylphosphine)benzylidine ruthenium (IV) dichloride, $CH_2Cl_2$; c.) m-CPBA, $CH_2Cl_2$; d.) $NaN_3$, $CH_3OH$, $H_2O$, $NH_4Cl$; e.) 1,3-propanedithiol, TEA, methanol; f.) N-Boc-leucine, EDC, $CH_2Cl_2$; g.) 10% Pd/C, $H_2$; h.) 2-pyridine-sulphonyl chloride, TEA, $CH_2Cl_2$; i.) 4 N HCl/dioxane, methanol; j.) benzofuran-2-carboxylic acid, EDC, $CH_2Cl_2$; k.) pyridine sulfur trioxide complex, DMSO, TEA; l.) $CD_3OD;D_2O$ (10:1), TEA; m.) HPLC separation.

The intermediate azido alcohol may be reduced to the amino alcohol 26 under conditions common to the art such as 1,3-propanedithiol and triethylamine in methanol or with triphenylphosphine in tetrahydrofuran and water. Acylation of 26 may be effected with an acid such as N-Boc-leucine in the presence of a coupling agent such as EDC. Removal of the benzyloxycarbonyl protecting group with hydrogen gas in the presence of 10% Pd/C provides the amine 27. Treatment of the amine 27 with 2-pyridinesulphonyl chloride in the presence of triethylamine or saturated sodium bicarbonate and $CH_2Cl_2$ followed by removal of the tert-butoxycarbonyl protecting group under acidic conditions provides 28. Coupling of 28 with benzofuran-2-carboxylic acid may be effected with a coupling agent such as EDC to provide intermediate alcohol 29. Alcohol 29 may be oxidized with an oxidant such as sulfur trioxide pyridine complex in DMSO and triethylamine to provide the ketone 30 as a mixture of diastereomers. Treatment of ketone 30 with triethylamine in $CD_3OD:D_2O$ at reflux provides the deuterated analog as a mixture of diastereomers which are separated by HPLC to provide the deuterated compounds 31 and 32.

Compounds of the general formula I may also be prepared as outlined in Scheme 5. The amine of compound 12 may be protected with with di-tert-butyldicarbonate to provide the N-Boc derivative 33 (Scheme 2). Removal of the benzyloxycarbonyl protecting group may be effected by treatment of 33 with hydrogen gas in the presence of a catalyst such as 10% Pd/C to provide the amine 34. Treatment of amine 34 with a sulfonyl chloride such as 2-pyridinesulfonyl chloride in the presence of a base such as N-methylmorpholine or triethylamine provides the sulfonamide derivative 35. Removal of the tert-butoxycarbonyl protecting group may be effected with an acid such as hydrochloric acid to provide intermediate 36. Coupling of 36 with an acid such as N-Boc-cyclohexyialanine in the presence of a coupling agent common to the art such as HBTU or polymer supported EDC provides the alcohol intermediate 37. Removal of the tert-butoxycarbonyl protecting group under acidic conditions provides amine 38. Coupling of 38 with an acid such as benzofuran-2-carboxylic acid in the presence of a coupling agent such as HBTU or polymer supported EDC provides alcohol 39. Alcohol 39 may be oxidized with an oxidant common to the art such as pyridine sulfur trioxide complex in DMSO and triethylamine or the Dess-Martin periodinane to provide the ketone 40.

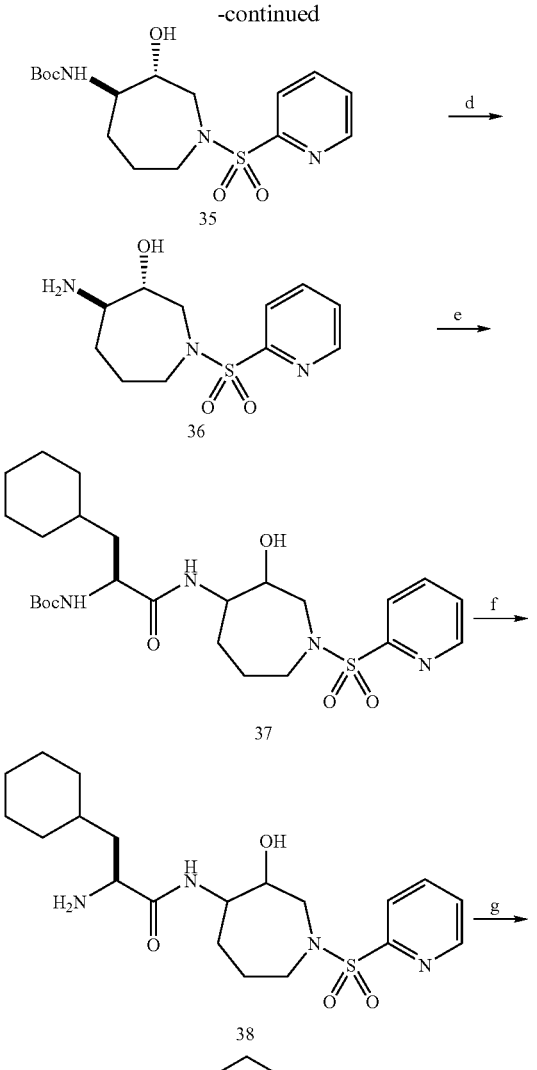

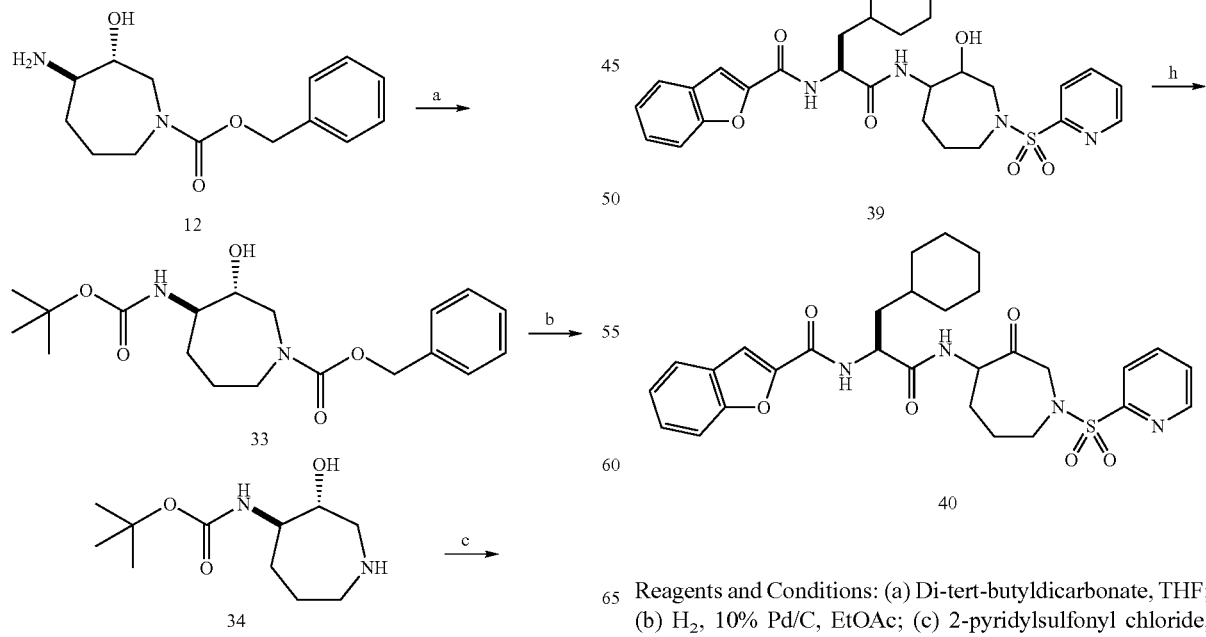

Reagents and Conditions: (a) Di-tert-butyldicarbonate, THF; (b) $H_2$, 10% Pd/C, EtOAc; (c) 2-pyridylsulfonyl chloride, TEA ; (d) HCl, EtOAc; (e) N-Boc-cylohexylalanine, P-EDC, CH$_2$Cl$_2$; (f) HCl, CH$_2$Cl$_2$; (g) benzofuran-2-carboxylic acid, P-EDC, CH$_2$Cl$_2$; (h) Dess-Martin pefiodinane, methylene chloride.

The quatemized, 4-amino-azepan-3-one compounds of the present invention may be conveniently prepared according to Scheme 6. The skilled artisan will understand from Scheme 6 how to make any of the quaternized, 4-amino-azepan-3-one compounds of the present invention. Reductive amination of 13 may be effected by treatment with an aldehyde followed by a reducing agent such as sodium triacetoxyborohydride. Subsequent deprotection of the N-Boc group under acidic conditions provides the amine salt 16. Treatment of 16 with an acid chloride or with a carboxylic acid in the presence of a coupling agent common to the art such as EDC followed by oxidation of the intermediate alcohol (not shown) with an oxidant such as pyridine sulfur trioxide complex provides the ketone 17. Quaternization of the amine of 17 may be effected by treatment with an alkylating agent such as iodomethane to provide the quaternary amine salt 41.

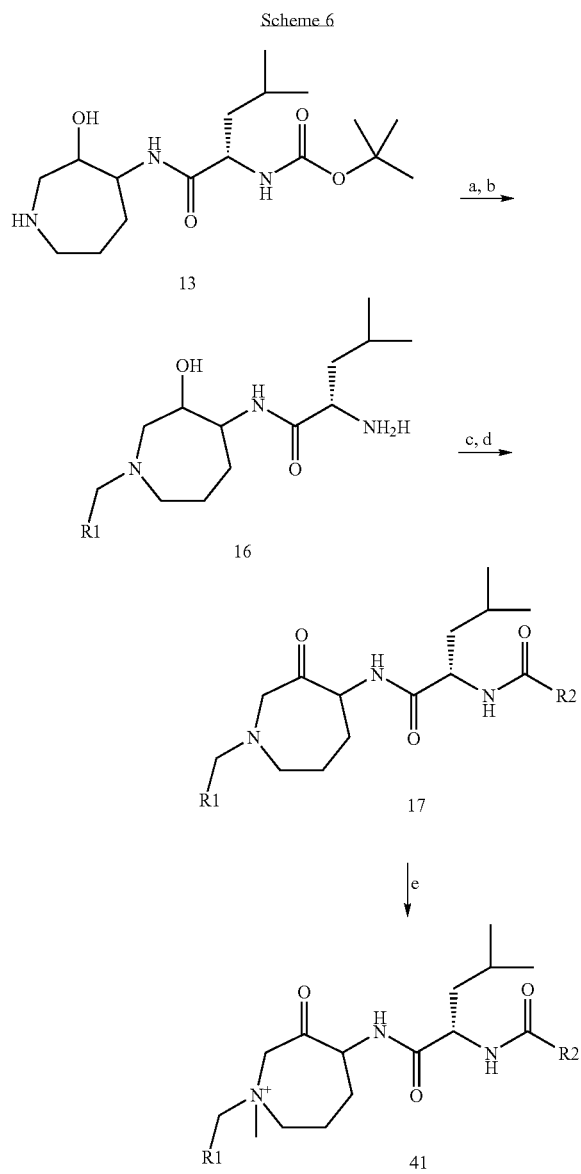

Reagents and conditions: a.) R$_1$CHO, NaBH(OAc)$_3$; b.) HCl; c.) R$_2$CO$_2$H, EDC, CH$_2$Cl$_2$; d.) pyridine sulfur trioxide complex, DMSO, TEA; e.) iodomethane The starting materials used herein are commercially available amino acids or are prepared by routine methods well known to those of ordinary skill in the art and can be found in standard reference books, such as the COMPENDIUM OF ORGANIC SYNTHETIC METHODS, Vol. I-VI (published by Wiley-Interscience).

Coupling methods to form amide bonds herein are generally well known to the art. The methods of peptide synthesis generally set forth by Bodansky et al., THE PRACTICE OF PEPTIDE SYNTHESIS, Springer-Verlag, Berlin, 1984; E. Gross and J. Meienhofer, THE PEPTIDES, Vol. 1, 1-284 (1979); and J. M. Stewart and J. D. Young, SOLID PHASE PEPTIDE SYNTHESIS, 2d Ed., Pierce Chemical Co., Rockford. Ill., 1984. are generally illustrative of the technique and are incorporated herein by reference.

Synthetic methods to prepare the compounds of this invention frequently employ protective groups to mask a reactive functionality or minimize unwanted side reactions. Such protective groups are described generally in Green, T. W, PROTECTIVE GROUPS IN ORGANIC SYNTHESIS, John Wiley & Sons, New York (1981). The term "amino protecting groups" generally refers to the Boc, acetyl, benzoyl, Fmoc and Cbz groups and derivatives thereof as known to the art. Methods for protection and deprotection, and replacement of an amino protecting group with another moiety are well known.

Acid addition salts of the compounds of Formula I are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$ and NH$_4^+$ are specific examples of cations present in pharmaceutically acceptable salts. Halides, sulfate, phosphate, alkanoates (such as acetate and trifluoroacetate), benzoates, and sulfonates (such as mesylate) are examples of anions present in pharmaceutically acceptable salts. Quaternary ammonium salts are prepared by treating a parent amine compound with an excess of alkyl halide, such as methyl iodide.

This invention also provides a pharmaceutical composition which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

Novel Intermediates

Referring to the methods of preparing the compounds of Formula I set forth in Schemes 1-4 above, the skilled artisan will appreciate that the present invention includes all novel intermediates required to make the compounds of Formula I. In particular, the present invention provides the compounds of Formula II:

wherein:
$R^1$ is selected from the group consisting of:

$R^2$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^9$C(O)—, $R^9$C(S)—, $R^9$SO$_2$—, $R^9$OC(O)—, $R^9R^{11}$NC(O)—, $R^9R^{11}$NC(S)—, $R^9(R^{11})$NSO$_2$— and $R^9SO_2R^{11}NC(O)$—;

$R^3$ is selected from the group consisting of: H, $C_{1-6}$alkyl, $C_{3-6}$cycloalkyl-$C_{0-6}$alkyl, $C_{2-6}$alkenyl, $C_{2-6}$alkynyl, Het$C_{0-6}$alkyl and Ar$C_{0-6}$alkyl;

$R^3$ and R' may be connected to form a pyrrolidine, piperidine or morpholine ring;

$R^4$ is selected from the group consisting of: H, $C_{1-6}$alkyl, $C_{3-6}$cyclaakyl-$C_{0-6}$alkyl, Ar—$C_{0-6}$alkyl, Het-$C_{0-6}$alkyl, $R^5$C(O)—, $R^5$C(S)—, $R^5$SO$_2$—, $R^5$OC(O)—, $R^5R^{12}$NC(O)—, and $R^5R^{12}$NC(S)—;

$R^5$ is selected from the group consisting of: H, $C_{1-6}$alkyl, $C_{2-6}$alkenyl, $C_{2-6}$alkynyl, $C_{3-6}$cycloalkyl-$C_{0-6}$alkyl, Ar—$C_{0-6}$ alkyl and Het-$C_{0-6}$alkyl;

$R^6$ is selected from the group consisting of: H, $C_{1-6}$alkyl, Ar—$C_{0-6}$alkyl, or Het-$C_{1-6}$alkyl;

$R^7$ is selected from the group consisting of: H, $C_{1-6}$alkyl, $C_{3-6}$cycloalkyl-$C_{0-6}$alkyl, Ar—$C_{0-6}$alkyl, Het-$C_{0-6}$alkyl, $R^{10}$C(O)—, $R^{10}$C(S)—, $R^{10}$SO$_2$—, $R^{10}$OC(O)—, $R^{10}R^{13}$NC(O)—, and $R^{10}R^{13}$NC(S)—;

$R^8$ is selected from the group consisting of: H, $C_{1-6}$alkyl, $C_{2-6}$alkenyl, $C_{2-6}$alkynyl, Het$C_{0-6}$alkyl and Ar$C_{0-6}$alkyl;

$R^9$ is selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

$R^{10}$ is independently selected from the group consisting of: $C_{1-6}$alkyl, $C_{3-6}$cycloalkyl-$C_{0-6}$alkyl, Ar—$C_{0-6}$alkyl and Het-$C_{0-6}$alkyl;

$R^{11}$ is selected from the group consisting of: H, $C_{1-6}$alkyl, Ar—$C_{0-6}$alkyl, and Het-$C_{0-6}$alkyl;

$R^{12}$ is selected from the group consisting of: H, $C_{1-6}$alkyl, Ar—$C_{0-6}$alkyl, and Het-$C_{0-6}$alkyl;

$R^{13}$ is selected from the group consisting of: H, $C_{1-6}$alkyl, Ar—$C_{0-6}$alkyl; and Het-$C_{0-6}$alkyl;

R' is selected from the group consisting of: H, $C_{1-6}$alkyl, Ar—$C_{0-6}$alkyl, and Het-$C_{0-6}$alkyl;

R" is selected from the group consisting of: H, $C_{1-6}$alkyl, Ar—$C_{0-6}$alkyl, or Het-$C_{0-6}$alkyl;

R''' is selected from the group consisting of: H, $C_{1-6}$alkyl, $C_{3-6}$cycloalkyl-$C_{0-6}$alkyl, Ar—$C_{0-6}$alkyl, and Het-$C_{0-6}$alkyl;

R'''' is selected from the group consisting of: $C_{1-6}$alkyl, $C_{3-6}$cycloalkyl-$C_{0-6}$alkyl $C_{2-6}$alkenyl, $C_{2-6}$alkynyl, Het$C_{0-6}$alkyl and Ar$C_{0-6}$alkyl;

X is selected from the group consisting of: CH$_2$, S, and O;
Z is selected from the group consisting of: C(O) and CH$_2$;
n is an integer of from 1 to 5;

and pharmaceutically acceptable salts, hydrates and solvates thereof.

The following compounds are preferred novel intermediates:

[(S)-1(3-Hydroxy-azepan-4-ylcarbamoyl)-3-methyl-butyl]-carbamic acid benzyl ester;

(S)-2-Amino-4-methyl-pentanoic acid (1-benzyl-3-hydroxy-azepan-4-yl)-amide;

(S)-2-Amino-4-methyl-pentanoic acid {3-hydroxy-1-[2-(3-pyridin-2-yl-phenyl)-acetyl]-azepan-4-yl}-amide;

{(S)-1-[4-((S)-2-Amino-4-methyl-pentanoylamino)-3-hydroxy-azepan-1-ylmethyl]-3-methyl-butyl}-carbamic acid benzyl ester;

(S)-2-Amino-4-methyl-pentanoic acid-(1-benzoyl-3-hydroxy-azepan-4-yl)-amide;

(S)-2-Amino-4-methyl-pentanoic acid [3-hydroxy-1-(4-methyl-pentanoyl)-azepan-4-yl]-amide;

(S)-2-Amino-4-methyl-pentanoic acid (1-benzenesulfonyl-3-hydroxy-azepan-4-yl)-amide;

thieno[3,2-b]thiophene-2-carboxylic acid {(S)-3-methyl-1-[3-hydroxy-1-(1-oxy-pyridine-2-sulfonyl)-azepan-4-yl-carbamoyl]-butyl}amide;

5-methoxybenzofuran-2-carboxylic acid {(S)-3-methyl-1-[3-hydroxy-1-(1-oxy-pyridine-2-sulfonyl)-azepan-4-ylcarbamoyl]-butyl}amide;

thieno[3,2-b]thiophene-2-cbarboxylic acid {(S)-3-methyl-1-[3-hydrbxy-1-(pyridine-2-sulfonyl)-azepan-4-ylcarbamoyl]-butyl}amide;

3-methylbenzofuran-2-carboxylic acid {(S)-3-methyl-1-[3-hydroxy-1-(1-oxy-pyridine-2-sulfonyl)-azepan-4-ylcarbamoyl]-butyl}amide;

quinoline-2-carboxylic acid {(S)-3-methyl-1-[3-hydroxy-1-(1-oxy-pyridine-2-sulfonyl)-azepan-4-ylcarbamoyl]-butyl}amide; and quinoxaline-2-carboxylic acid {(S)-3-methyl-1-[3-hydroxy-1-(1-oxy-pyridine-2-sulfonyl)-azepan-4-ylcarbamoyl]-butyl}amide.

Process for Synthesis of Inventive Compounds

Referring to Schemes 1-6 herein above, the present invention provides a process for the synthesis of compounds of Formula (I) comprising the step of oxidizing the appropriate compound of Formula (II) with an oxidant to provide the compound of Formula (I) as a mixture of diastereomers. Preferably the oxidant is sulfur trioxide pyridine complex in DMSO and triethylamine.

Referring to Scheme 4, the present invention also provides a process for the synthesis of deuterated compounds of Formula (I). Specifically, when a deuterated isomer is desired, an additional step, following the oxidation step, of deuterating the protonated isomer with a deuterating agent to provide the deuterated compound of Formula (I) as a mixture of diastereomers is added to the synthesis. Preferably, the deuterating agent is $CD_3OD:D_2O$ (10:1) in triethylamine.

The process further comprises the step of separating the diasteromers of Formula (I) by separating means, preferably by high presssure liquid chromatography (HPLC).

Referring to Scheme 6, the present invention also provides a process for the synthesis of quaternary salts of the 4-amino-azepan-3-one compounds of Formula (I).

Utility of the Present Invention

The compounds of Formula I are useful as protease inhibitors, particularly as inhibitors of cysteine and serine proteases, more particularly as inhibitors of cysteine proteases, even more particularly as inhibitors of cysteine proteases of the papain superfamily, yet more particularly as inhibitors of cysteine proteases of the cathepsin family, most particularly as inhibitors of cathepsin K. The present invention also provides useful compositions and formulations of said compounds, including pharmaceutical compositions and formulations of said compounds.

The present compounds are useful for treating diseases in which cysteine proteases are implicated, including infections by pneumocystis carinii, *trypsanoma cruzi, trypsanoma brucei,* and Crithidia fusiculata; as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal. most particularly a human in need thereof an inhibitor of cathepsin K, including a compound of the present invention. The present invention particularly provides methods for treating diseases in which cysteine proteases are implicated, including infections by pneumocystis carinii, *trypsanoma cruzi, trypsanoma brucei,* and Crithidia fusiculata; as well as in schistosomiasis, malaria, tumor metastasis, metachromatic leukodystrophy, muscular dystrophy, amytrophy, and-especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

This invention further provides a method for treating osteoporosis or inhibiting bone loss which comprises internal administration to a patient of an effective amount of a compound of Formula I, alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

For acute therapy, parenteral administration of a compound of Formula I is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

Biological Assays

The compounds of this invention may be tested in one of several biological assays to determine the concentration of compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemistry*, 1989, 28, 140):

$$v=V_m A/[K_a(1+I/K_{i,app})+A] \quad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC]=v_{ss}t+(v_0-v_{ss})[1-\exp(-k_{obs}t)]/k_{obs} \quad (2)$$

where [AMC] is the concentration of product formed over time t, $v_0$ is the initial reaction velocity and $v_{ss}$ is the final steady state rate. Values for $k_{obs}$ were then analyzed as a linear function of inhibitor concentration to generate an apparent second order rate constant ($k_{obs}$/inhibitor concentration or $k_{obs}$/[I]) describing the time-dependent inhibition. A complete discussion of this kinetic treatment has been fully described (Morrison et al., *Adv. Enzymol. Relat. Areas Mol. Biol.*, 1988,-61, 201).

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to 1.5× $10^4$/mL in EMEM medium, supplemented with 10% fetal calf serum and 1.7 g/litre of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/mL) and an isotype control (IgG2a diluted to 100 ug/mL). The tubes were incubate at 37° C. for 30 min.

0.5 mL aliquots of the cells were seeded onto sterile dentine slices in a 48-well plate and incubated at 37° C. for 2 h. Each treatment was screened in quadruplicate. The slices were washed in six changes of warm PBS (10 mL/well in a 6-well plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by brightfield microscopy and were then removed from the surface of the dentine by sonication. Pit volumes were determined using the Nikon/Lasertec ILM21W confocal microscope.

General

Nuclear magnetic resonance spectra were recorded at either 250 or 400 MHz using, respectively, a Bruker AM 250 or Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers (cm$^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel.

Where indicated, certain of the materials were purchased from the Aldrich Chemical Co., Milwaukee, Wis., Chemical Dynamics Corp., South Plainfield, N.J., and Advanced Chermtech, Louisville, Ky.

EXAMPLES

In the following synthetic examples, temperature is in degrees Centigrade (° C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of {(S)-1-[1-((S)-2-Benzyloxycarbonylamino-4-methyl-pentanoyl)-3-oxo-azepan-4-ylcarbamoyl}carbamic acid benzyl ester a.) Allyl-pent-4-enyl-carbamic acid tert-butyl ester To a suspension of NaH (3.05 g, 76.33 mmol of 60% NaH in oil; washed with hexanes) in DMF (30 mL) was added tert-butyl N-allylcarbamate (6.0 g, 38.2 mmol) in a dropwise fashion. The mixture was stirred at room temperature for approximately 10 minutes whereupon 5-bromo-1-pentene (6.78 mL, 57.24 mmol) was added in a dropwise fashion. The reaction was heated to 40° C. for approximately 2 hours whereupon the reaction was partitioned between ethyl acetate and water. The organic layer was washed with water (2×'s), brine, dried (MgSO$_4$), filtered and concentrated to give 10 grams of the title compound as an oil: MS(EI) 226 (M+H$^+$).

b.) 2,3,4,7-Tetrahydro-azepine-1-carboxylic acid tert-butyl ester

To a solution of compound of Example 1a (4.5 g) in benzene was added the 2,6-diisopropylphenylimidoneophylidene molybdenum bis(t-butoxide) (600 mg). The reaction was heated to reflux for 1.5 hours whereupon the reaction was concentrated in vacuo. Chromatography (50% CH$_2$Cl$_2$: hexanes) of the residue gave 3.92 g of the product:

c.) 8-Oxa-3-aza-bicyclo[5.1.0]octane-3-carboxylic acid tert-butyl ester

To a solution of the compound of Example 1b (3.0 g, 15.2 mmol) in CH$_2$Cl$_2$ was added m-CPBA (7.8 g, 45.6 mmol). The mixture was stirred overnight at room temperature whereupon it was partitioned between CH$_2$Cl$_2$ and staurated K$_2$CO$_3$. The organic layer was washed with sat. NaHCO$_3$, water, brine, dried (MgSO$_4$), filtered and concentrated to give 3.11 g of the title compound as an oil: MS(EI) 214 (M+H$^+$).

d.) 4-Azido-3-hydroxy-azepane-1-carboxylic acid tert-butyl ester

To a solution of the epoxide from Example 1c (3.92 g, 20 mmol) in methanol:water (180 mL of an 8:1 solution) was added NH$_4$Cl (3.18 g, 60 mmol) and sodium azide (3.9 g, 60 mmol). The reaction was heated to 40° C. until complete consumption of the starting epoxide was observed by TLC analysis. The majority of the solvent was removed in vacuo and the remaining solution was diluted with ethyl acetate and washed with water, brine dried (Na$_2$SO$_4$), filtered and concentrated. Column chromatography (40% ethyl acetate:hexanes) of the residue provided 3.43 g of the title compound.

e.) 4-Amino-3-hydroxy-azepane-1-carboxylic acid tert-butyl ester

To a solution of the azido alcohol of Example 1d (3.4 g) and 10% Pd/C (catalytic) in ethyl acetate:methanol (2:1 solution) was affixed a balloon of hydrogen. The reaction was stirred until complete consumption of the starting material was observed by TLC analysis. The reaction was filtered to remove the catalyst and the filtrate was concentrated in vacuo. Column chromatography of the residue (25% methanol:dichloromethane) provided 2.57 g of the title compound: MS(EI) 231 (M+H$^+$).

f.) 4-((S)-2-benzyloxycarbonylamino-4-methyl-pentanoylamno)-3-hydroxy-azepane-1-carboxylic acid tert butyl ester To a solution of the amino alcohol of Example 1e (160 mg, 0.70 mmol) in CH$_2$Cl$_2$ was added EDC (134 mg), HOBt (94 mg) and Cbz-leucine (185 mg). The reaction was maintained at room temperature until complete consumption of the starting material was observed by TLC analysis. The reaction was diluted with ethyl acetate and washed with 1N HCl, sat. K$_2$CO$_3$, water, brine, dried (MgSO$_4$), filtered and concentrated. Column chromatography of the residue (3% methanol: dichloromethane) gave 200 mg of the title compound: MS(EI) 478 (M+H$^+$), 500 (M+Na$^+$).

g.) [(S)-1-(3-hydroxy-azepan-4-ylcarbamoyl)-3-methyl-butyl]-carbamic acid benzyl ester A solution of the compound of Example 1f (200 mg, 0.42 mmol) in methanol (5 mL) was added 4M HCl in dioxane (5 mL). The reaction was stirred at room temperature for approximately 2 hours whereupon the solvent was removed in vacuo to provide 168 mg of the title compound: MS(EI) 378 (M+H$^+$).

h.) {(S)-1-[4-((S)-2-Benzyloxycarbonylamino-4-methyl-pentanoylamino)-3-hydroxy-azepane-1-carbonyl]-3-methyl-butyl}carbamic acid benzyl ester To a solution of the amine salt of Example 1g (168 mg, 0.42 mmol) in CH$_2$Cl$_2$ was added EDC (81 mg), HOBt (57 mg), triethylamine (0.09 mL) and Cbz-leucine (111 mg). The reaction was stirred until complete by TLC analaysis. Workup followed by column chromatography (5% CH$_3$OH:CH$_2$Cl$_2$) provided 159 mg of the title compound: MS(EI) 625 (M+H$^+$).

i.) {(S)-1-[4-((S)-2-Benzyloxycarbonylamino-4-methyl-pentanoylamino)-3-oxo-azepane-1-carbonyl]-3-methyl-butyl}carbamic acid benzyl ester To a solution of the alcohol of Example 1h (130 mg, 0.21 mmol) in DMSO was added TEA (0.17 mL) and pyridine sulfur trioxide complex (97 mg, 0.62 mmol). The reaction was stirred at room temperature for approximately 2 hours whereupon it was partitioned between ethyl acetate and water. The organic layer was washed with brine, dried (MgSO$_4$), filtered and concentrated. Column chromatography of the residue (5% CH$_3$OH:CH$_2$Cl$_2$) provided 100 mg of the title compound as a mixture of diastereomers: $^1$H NMR (CDCl$_3$): δ 1.0 (m, 12H), 1.5-2.1 (m, 8H), 2.2 (m, 4H), 3.0 (m, 1H), 3.5 (d, 1H). 3.6 (d, 1H), 4.01 (m, 1H), 4.5 (m, 2H), 4.7 (m, 1H), 5.0 (m, 5H), 7.3 (m, 10H): MS (EI) 623(M+H$^+$), 645 (M+Na$^+$). Separation of the diastereomers by HPLC provided diastereomer 1:MS (EI) 623 (M+H$^+$), 645 (M+Na$^+$) and diastereomer 2: MS (ES) 623 (M+H$^+$), 645 (M+Na$^+$).

Example 2

Preparation of Naphthylene-2-carboxylic acid[(S)-1-(1-benzyl-3-oxo-azepan-4-ylcarbamoyl)-3-methyl-butyl]amide a.) Allyl-pent-4-enyl-carbamic acid benzyl ester To a suspension of NaH (1.83 g, 76.33 mmol of 90% NaH) in DMF was added benzyl allyl-carbamic acid benzyl ester (7.3 g, 38.2 mmol) in a dropwise fashion. The mixture was stirred at room temperature for approximately 10 minutes whereupon 5-bromo-1-pentene (6.78 mL, 57.24 mmol) was added in a dropwise fashion. The reaction was heated to 40° C. for approximately 4 hours whereupon the reaction was partitioned between dichloromethane and water. The organic layer was washed with water (2×'s), brine, dried (MgSO$_4$), filtered and concentrated. Column chromatography of the residue (10% ethyl acetate:hexanes) provided 10.3 grams of the title compound as an oil: MS(EI) 260 (M+H$^+$).

b.) 2,3,4,7-Tetrahydro-azepine-1-carboxylic acid benzyl ester

To a solution of compound of Example 2a (50 g) in dichloromethane was added bis(tricyclohexylphosphine)benzylidine ruthenium (IV) dichloride (5.0 g). The reaction was heated to reflux until complete as determined by TLC analysis. The reaction was concentrated in vacuo. Column chromatography of the residue (50% dichloromethane:hexanes) gave 35 g of the title compound: MS(EI) 232 (M+H$^+$).

c.) 8-Oxa-3-aza-bicyclo[5.1.0]octane-3-carboxylic acid benzyl ester

Following the general procedure of Example 1c except substituting the compound of Example 2b the title compound was prepared: MS(EI) 248 (M+H$^+$), 270 (M+Na$^+$).

d.) 4-azido-3-hydroxy-azepane-1-carboxylic acid benzyl ester

To a solution of the epoxide from Example 2c (2.0 g, 8.1 mmol) in methanol:water (8:1 solution) was added NH$_4$Cl (1.29 g, 24.3 mmol) and sodium azide (1.58 g, 24.30 mmol). The reaction was heated to 40° C. until complete consumption of the starting epoxide was observed by TLC analysis. The majority of the solvent was removed in vacuo and the remaining solution was partitioned between ethyl acetate and pH 4 buffer. The organic layer was washed with sat. NaHCO$_3$, water, brine dried (MgSO$_4$), filtered and concentrated. Column chromatography (20% ethyl acetate:hexanes) of the residue provided 1.3 g of the title compound: MS(EI) 291 (M+H$^+$) plus 0.14 g of trans-4-hydroxy-3-azido-hexahydro-1H-azepine e.) 4-amino-3-hydroxy-azepane-1-carboxylic acid benzyl ester To a solution of the azido alcohol of Example 2d (1.1 g, 3.79 mmol) in methanol was added triethylamine (1.5 mL, 11.37 mmol) and 1,3-propanedithiol (1.1 mL, 11.37 mL). The reaction was stirred until complete consumption of the starting material was observed by TLC analysis whereupon the reaction was concentrated in vacuo. Column chromatography of the residue (20% methanol:dichloromethane) provided 0.72 g of the title compound: MS(EI) 265 (M+H$^+$).

f.) 4-((S)-2-tert-Butoxycarbonylamino-4-methyl-pentanoylamino)-3-hydroxy-azepan-1-carboxylic acid benzyl ester To a solution of the amino alcohol of Example 2e (720 mg, 2.72 mmol) in CH$_2$Cl$_2$ was added EDC (521 mg), HOBt (368 mg) and N-Boc-leucine (630 mg). The reaction was maintained at room temperature until complete consumption of the starting material was observed by TLC analysis. The reaction was diluted with ethyl acetate and washed with 1N HCl, sat. K$_2$CO$_3$, water, brine, dried (MgSO$_4$), filtered and concentrated. Column chromatography of the residue (3% methanol:dichloromethane) gave 1.0 g of the title compound: MS(EI) 478 (M+H$^+$).

g.) [(S)-1-(3-Hydroxy-azepan-4-ylcarbamoyl)-3-methyl-butyl]-carbamic acid tert butyl ester To a solution of the compound of Example 2f (1.0 g) and 10% Pd/C (catalytic) in ethyl acetate:methanol (2:1 solution) was affixed a balloon of hydrogen. The reaction was stirred until complete consumption of the starting material was observed by TLC analysis. The reaction was filtered to remove the catalyst and the filtrate was concentrated in vacuo to provide 0.82 g of the title compound: MS(EI) 344 (M+H$^+$).

h.) [(S)-1-(1-Benzyl-3-Hydroxy-azepan-4-ylcarbamoyl)-3-methyl-butyl]-carbamic acid tert butyl ester To a solution of the compound of Example 2g (0.69 g, 2.01 mmol) in CH$_2$Cl$_2$ was added benzaldehyde (0.32 mL, 3.01 mmol) followed by sodium triacetoxyborohydride (0.85 g, 4.02 mmol). The reaction was stirred until complete as determined by TLC analysis whereupon several drops of water were added to the reaction to destroy the excess sodium triacetoxyborohydride. The mixture was diluted with ethyl acetate washed with sat. NaHCO$_3$, water, brine, dried (Na$_2$SO$_4$), filtered and concentrated. Column chromatography of the residue (5% methanol:dichloromethane) gave 800 mg of the title compound: MS(ES) 434 (M+H$^+$).

i.) (S)-2-Amino-4-methyl-pentanoic acid (1-benzyl-3-hydroxy-azepan-4-yl)-amide

To a solution of the compound of Example 2h (800 mg) in methanol (15 mL) was added 4M HCl in dioxane (15 mL). The reaction was stirred at room temperature overnight whereupon it was concentrated-in vacuo to give 800 mg of the title compound: MS(ES) 334 (M+H+).

j.) Naphthylene-2-carboxylic acid [(S)-1-(1-benzyl-3-hydroxy-azepan-4-ylcarbamoyl)-3-methyl-butyl]-amide To a solution of the amine salt of Example 2i (200 mg, 0.49 mmol) in CH$_2$Cl$_2$ was added triethylamine (0.17 mL, 1.22 mmol), EDC (103.5 mg, 0.54 mmol), HOBt (73 mg, 0.54 mmol) and 2-naphthoic acid (93 mg, 0.54 mmol). The reaction was stirred until complete by TLC analysis. The reaction was diluted with ethyl acetate and washed with sat. $NaHCO_3$, water, brine, dried ($Na_2SO_4$), filtered and concentrated. Column chromatography of the residue (5% methanol:dichloromethane) gave 0.14 g of the title compound: MS(EI) 488 ($M+H^+$).

k.) Naphthylene-2-carboxylic acid[(S)-1-(1-benzyl-3-oxo-azepan-4-ylcarbamoyl)-3-methyl-butyl]-amide Following the general procedure of Example 1i except substituting the compound of Example 2j for the compound of Example 1i the title compound was prepared: $^1$H NMR ($CDCl_3$): δ 1.0 (m, 6H), 1.5-2.1 (m, 5H), 2.2 (m, 2H), 2.9 (m, 1H), 3.2 (dd, 1H). 3.4 (m, 1H), 3.7 (m, 2H), 4.7 (m, 1H), 5.2 (m, 1H), 7.2-8.4 (m, 12H); MS(EI): 486 ($M+H^+$, 100%). Separation of the diastereomers by HPLC provided diastereomer 1: MS (EI) 486.3 ($M+H^+$), and diastereomer 2: MS (ES) 486.3 ($M+H^+$).

Example 3

Preparation of Benzo[1,3]dioxole-5-carboxylic acid [(S)-1-(1-benzyl-3-oxo-azepan-4-ylcarbamoyl)-3-methyl-butyl]amide a.) Benzo[1,3]dioxole-5-carboxylic acid [(S)-1-(1-benzyl-3-hydroxy-azepan-4-ylcarbamoyl)-3-methyl-butyl]amide Following the general procedure of Example 2j except substituting piperonylic acid for 2-naphthoic acid the title compound was prepared: MS(ES) 482 ($M+H^+$).

b.) Benzo[1,3]dioxole-5-carboxylic acid [(S)-1-(1-benzyl-3-oxo-azepan-4-ylcarbamoyl)-3-methyl-butyl]amide Following the general procedure of Example 1i except substituting the compound of Example 3a the title compound was prepared: $^1$H NMR ($CDCl_3$): δ 1.0 (m, 6H), 1.5-2.1 (m, 5H), 2.2 (m, 2H), 2.9 (m, 1H), 3.0 (m, 1H). 3.2 (d, 1H), 3.5 (q, 1H), 3.7 (m, 2H), 4.7 (m, 1H), 5.2 (m, 1H), 6.0 (s, 2H), 6.8 (m, 2H).7.2 (m, 6H); MS(EI): 480 ($M+H^+$, 100%). The diastereomers were separated by preparative scale HPLC. Lyophilisation of the eluents provided diastereomer 1: MS (EI) 480.3 ($M+H^+$), 959.6 $2M+H^+$) and diastereomer 2: MS (EI) 480.3 ($M+H^+$), 959.6 $2M+H^+$).

Example 4

Preparation of Benzofuran-2-carboxylic acid [(S)-1-(1-benzyl-3-oxo-azepan-4-ylcarbamoyl)-3-methyl-butyl]amide a.) Benzofuran-2-carboxylic acid [(S)-1-(1-benzyl-3-hydroxy-azepan-4-ylcarbamoyl)-3-methyl-butyl]amide Following the general procedure of Example 2j except substituting benzofuran-2-carboxylic acid for 2-naphthoic acid the title compound was prepared: MS(ES) 478 ($M+H^+$).

b.) Benzofuran-2-carboxylic acid [(S)-1-(1-benzyl-3-oxo-azepan-4-ylcarbamoyl)-3-methyl-butyl]amide Following the general procedure of Example 1i except substituting the compound of Example 4a the title compound was-prepared: 476 MS(EI): 492 ($M+H^+$, 100%). The diastereomers were separated by preparative scale HPLC. Lyophilisation of the eluents provided diastereomer 1: MS (EI) 476.4 ($M+H^+$), 951.6 ($M+H^+$) and diastereomer 2: MS (EI) 476.4 ($M+H^+$), 951.6 $2M+H^+$).

Example 5

Preparation of Benzo[b]thiophene-2-carboxylic acid [(S)-1-(1-benzyl-3-oxo-azepan-4-ylcarbamoyl)-3-methyl-butyl]amide a.) Benzo[b]thiophene-2-carboxylic acid [(S)-1-(1-benzyl-3-hydroxy-azepan-4-ylcarbamoyl)-3-methyl-butyl]amide Following the general procedure of Example 2j except substituting benzothiophene-2-carboxylic acid for 2-naphthoic acid the title compound was prepared: MS(ES) 494 ($M+H^+$).

b.) Benzo[b]thiophene-2-carboxylic acid [(S)-1-(1-benzyl-3-oxo-azepan-4-ylcarbamoyl)-3-methyl-butyl]amide Following the general procedure of Example 1i except substituting the compound of Example 5a the title compound was prepared: $^1$H NMR ($CDCl_3$): δ 1.0 (m, 6H), 1.5-2.1 (m, 5H), 2.2 (m, 2H), 2.9 (m, 1H), 3.2 (dd, 1H). 3.4 (m, 1H), 3.7 (m, 2H), 4.7 (m, 1H), 5.2 (m, 1H), 7.2-8.4 (m, 10H): MS(EI): 492 ($M+H^+$, 100%)

The diastereomers were separated by preparative scale HPLC. Lyophilisation of the eluents provided diastereomer 1: MS (EI) 492.4 ($M+H^+$), 983.7 $2M+H^+$) and diastereomer 2: MS (EI) 492.4 ($M+H^+$), 983.7 $2M+H^+$).

Example 6

Preparation of Naphthylene-2-sulphonyl [(S)-1-(1-benzyl-3-oxo-azepan-4-ylcarbamoyl)-3-methyl-butyl]-amide a.) Naphthylene-2-sulphonyl [(S)-1-(1-benzyl-3-hydroxy-azepan-4-ylcarbamoyl)-3-methyl-butyl]-amide To a solution of the amine salt of Example 2i (200 mg, 0.49 mmol) in $CH_2Cl_2$ was added triethylamine (0.24 mL, 1.72 mmol) and 2-naphthalenesulphonyl chloride (122 mg, 0.54 mmol). The reaction was stirred at room temperature until complete as determined by TLC analysis. The reaction was worked-up, dried.($Na_2SO_4$), filtered and concentrated. Column chromatography of the residue (10% methanol:dichloromethane) provided 52 mg of the title compound: MS(EI) 524 ($M+H^+$).

b.) Naphthylene-2-sulphonyl [(S)-1-(1-benzyl-3-oxo-azepan-4-ylcarbamoyl)-3-methyl-butyl]-amide Following the general procedure of Example 1i except substituting the compound of Example 6a the title compound was prepared:: $^1$H NMR ($CDCl_3$): δ 1.0 (m, 6H), 1.5-2.1 (m, 5H), 2.2 (m, 2H), 2.7 (m, 1H), 3.0 (dd, 1H). 3.3 (m, 1H), 3.6 (m, 2H), 3.7 (m, 1H) 4.7 (m, 1H), 5.3 (m, 1H), 7.2-8.4 (m, 12H): MS(EI): 522 ($M+H^+$, 100%)

Example 7

Preparation of Quinoline-2-carboxylic acid [(S)-1-(1-benzyl-3-oxo-azepan-4-ylcarbamoyl)-3-methyl-butyl]amide a.) Quinoline-2-carboxylic acid [(S)-1-(1-benzyl-3-hydroxy-azepan-4-ylcarbamoyl)-3-methyl-butyl]amide Following the general procedure of Example 2j except substituting 2-quinolinecarboxylic acid for 2-naphthoic acid the title compound was prepared: MS(ES) 489 ($M+H^+$).

b.) Quinoline-2-carboxylic acid [(S)-1-(1-benzyl-3-oxo-azepan-4-ylcarbamoyl)-3-methyl-butyl]amide Following the general procedure of Example 1i except substituting the compound of Example 7a the title compound was prepared: $^1$H NMR (CDCl$_3$): δ 1.0 (m, 6H), 1.5-2.1 (m, 5H), 2.2 (m, 2H), 2.9 (m, 1H), 3.2 (dd, 1H), 3.4 (m, 1H), 3.7 (m, 2H), 4.7 (m, 1H), 5.2 (m, 1H), 7.2-8.4 (m, 11H); MS(EI): 487 (M+H$^+$, 100%). The diastereomers were separated by preparative scale HPLC. Lyophilisation of the eluents provided diastereomer 1: MS (EI) 492.4 (M+H$^+$), 983.7 2M+H$^+$) and diastereomer 2: MS (EI) 492.4 (M+H$^+$), 983.7 2M+H$^+$).

Example 8

Preparation of 3,4-dichlorobenzoic acid [(S)-1-(1-benzyl-3-oxo-azepan-4-ylcarbamoyl)-3-methyl-butyl]amide a.) 3,4-dichlorobenzoic acid [(S)-1-(1-benzyl-3-hydroxy-azepan-4-ylcarbamoyl)-3-methyl-butyl]amide Following the general procedure of Example 2j except substituting 3,4-dichlorbenzoic acid for 2-naphthoic acid the title compound was prepared: MS(ES) 506 (M+H$^+$).

b.) 3,4-dichlorobenzoic acid [(S)-1-(1-benzyl-3-oxo-azepan-4-ylcarbamoyl)-3-methyl-butyl]amide Following the general procedure of Example 1i except substituting the compound of Example 8a the title compound was prepared: $^1$H NMR (CDCl$_3$): δ 1.0 (m, 6H), 1.5-2.1 (m, 5H), 2.2 (m, 2H), 2.9 (m, 1H), 3.2 (dd, 1H), 3.4 (m, 1H), 3.7 (m, 2H), 4.7 (m, 2H), 5.2 (m, 1H), 7.2-8.4 (m, 8H); MS(EI): 504 (M$^+$, 100%).

Example 9

Preparation of 4-{(S)-Methyl-2-[(quinoline-2-carbonyl)-amino]pentanoylamino}-3-oxo-1-[2-(3-pyridin-2-yl-phenyl)-acetyl]azepanium a.) 4-((S)-2-tert-Butoxycarbonylamino-4-methyl-pentanoylamino)-3-hydroxy-1-[2-(3-pyridin-2-yl-phenyl)-acetyl]-azepanium To a solution of the compound of Example 2g (0.5 g, 1.46 mmol) in CH$_2$Cl$_2$ was added EDC (307 mg, 1.60 mmol), HOBt (216 mg, 1.60 mmol) and 3-(2-pyridyl)phenyl acetic acid (341 mg, 1.60 mmol). The reaction was stirred at room temperature until complete as determined by TLC analysis. Workup and column chromatography (2% methanol:dichloromethane) provided the title compound: MS(ES) 539 (M+H$^+$).

b.) 4-((S)-Amino-4-methyl-pentanoylamino)-3-hydroxy-1-[2-(3-pyridin-2-yl-phenyl)-acetyl]-azepanium To a solution of the compound of Example 9a (1.3 g) dissolved in methanol (20 mL was added 4M HCl in dixoane (20 mL). The reaction was stirred until complete by TLC analysis whereupon it was concentrated in vacuo to give 1.1 g of the title compound: MS(EI) 439 (M+H$^+$).

c.) 4-{(S)-Methyl-2-[(quinoline-2-carbonyl)-amino]pentanoylamino}-3-hydroxy-1-[2-(3-pyridin-2-yl-phenyl)-acetyl]azepanium Following the procedure of Example 7a except substituting the compound of Example 9b the title compound was prepared: MS(EI) 594 (M+H$^+$).

d.) 4-{(S)-Methyl-2-[(quinoline-2-carbonyl)-amino]pentanoylamino}-3-oxo-1-[2-(3-pyriddin-2-yl-phenyl)-acetyl] azepanium Following the procedure of Example 1i except substituting the compound of Example 9c the title compound was prepared: $^1$H NMR (CDCl$_3$): δ 1.0 (m, 6H), 1.5-2.1 (m, 5H), 2.2 (m, 2H), 2.9 (m, 1H), 3.4 (dd, 1H). 3.8 (m, 3H), 4.1 (m, 2H), 4.7 (m, 3H), 5.4 (m, 1H), 7.2-8.4 (m, 14H); MS(EI): 592 (M+H$^+$, 100%).

Example 10

Preparation of 1-((S)-2-Benzyloxycarbonylamino-4-methyl-pentyl)-4-{(S)-4-methyl-2-[(2-quinoiline-2-carbonyl)-amino]-pentanoylamino)-3-oxo-azepanium a.) 1-((S)-2-Benzyloxycarbonylamino-4-methyl-pentyl)-4-((S)-2-tert-butoxycarbonylamino-4-methyl-pentanoylamino)-3-hydroxy-azepanium Following the procedure of Example 2h except-substituting Cbz-leucinal for benzaldehyde the title compound was prepared: MS(EI) 577 (M+H$^+$).

b.) 4-((S)-2-Amino-4-methy-pentanoylamino)-1-((S)-2-tert-benzyloxycarbonylamino-4-methyl-pentyl)-3-hydroxy-azepanium Following the procedure of Example 2i except substituting the compound of Example 10a the title compound was prepared: MS(EI) 477 (M+H$^+$).

c.) 1-((S)-2-Benzyloxycarbonylamino-4-methyl-pentyl)-4-{(S)-4-methyl-2-[(2-quinoiline-2-carbonyl)-amino]-pentanoylamino)-3-hydroxy-azepanium Following the procedure of Example 7a except substituting the compound of Example 10b the title compound was prepared: MS(EI) 632 (M+H+).

d.) 1-((S)-2-Benzyloxycarbonylamino-4-methyl-pentyl)-4-{(S)-4-methyl-2-[(2-quinoiline-2-carbonyl)-amino]-pentanoylamino)-3-oxo-azepanium Following the procedure of Example 1i except substituting the compound of Example 10c the title compound was prepared: $^1$H NMR (CDCl$_3$): δ 1.0 (m, 12H), 1.5-2.1 (m, 10H), 2.2 (m, 4H), 2.9 (m, 1H), 3.4 (M. 2H). 3.7 (m, 1H), 4.7 (m, 2H), 5.2 (m, 3H), 7.2 (m, 4H), 7.5 (m, 1H), 7.6 (m, 1H), 7.7 (m, 1H), 8.1 (m, 1H), 8.2 (m. 2H), 8.5 (m, 1H); MS(EI): 630 (M+H$^+$, 100%).

Example 11

Preparation of 1-Benzoyl-4-((S)-2-(benzo[1,3]dioxole-carbonylamino)-4-methyl-pentanoylamino)-3-oxo-azepanium a.) 1-Benzoyl-4-((S)-2-tert-butoxycarbonylamino-4-methyl-pentanoylamino)-3-hydroxy-azepanium Following the procedure of Example 9a except substituting benzoic acid for 3-(2-pyridyl)phenyl acetic acid the title compound was prepared: MS(EI) 448(M+H$^+$).

b.) 4-((S)-2-Amino-4-methyl-pentanoylamino)-1-benzoyl-3-hydroxy-azepanium

Following the procedure of Example 2i except substituting the compound of Example 11a the title compound was prepared: MS(EI) 348 (M+H$^+$).

c.) 1-Benzoyl-4-((S)-2-(benzo[1,3]dioxole-carbonylamino)-4-methyl-pentanoylamino)-3-hydroxy-azepanium Following the procedure of Example 2j except substituting the compound of Example 11b for the compound of Example 2j and piperonylic acid for 2-naphthoic acid the title compound was prepared: MS(EI) 496 (M+H+).

d.) 1-Benzoyl-4-((S)-2-(benzo[1,3]dioxole-carbonylamino)-4-methyl-pentanoylamino)-3-oxo-azepanium Following the procedure of Example 1i except substituting the compound of Example 11c the title compound was prepared: $^1$H NMR (CDCl$_3$): δ 1.0 (m, 6H), 1.5-2.1 (m, 5H), 2.2 (m, 2H), 2.9 (m, 1H), 3.2 (dd, 1H). 3.4 (m, 1H), 3.7 (m, 2H), 4.7 (m, 1H), 5.2 (m, 1H), 6.0 (s, 2H), 7.2-8.4 (m, 8H); MS(EI): 494 (M+H$^+$, 70%).

Example 12

Preparation of 1-Benzoyl-4-((S)-2-(4-fluoro-benzoylamino)-4-methyl-pentanoylamino)-3-oxo-azepanium a.) 1-Benzoyl-4-((S)-2-(4-fluoro-benzoylamino)-4-methyl-pentanoylamino)-3-hydroxy-azepanium Following the procedure of Example 11c except substituting 4-fluorobenzoic acid for piperonylic acid the title compound was prepared: MS(EI) 470 (M+H+).

b.) 1-Benzoyl-4-((S)-2-(4-fluoro-benzoylamino)-4-methyl-pentanoylamino)-3-oxo-azepanium Following the procedure of Example 1i except substituting the compound of Example 12a the title compound was prepared: $^1$H NMR (CDCl$_3$): δ 1.0 (m, 6H), 1.5-2.1 (m, 5H), 2.2 (m, 2H), 2.7 (m, 1H), 3.0 (dd, 1H). 3.6 (m, 1H), 4.0 (m, 2H), 4.7 (m, 1H), 5.2 (m, 1H), 7.2-8.4 (m, 9H); MS(EI): 468 (M+H$^+$, 10%).

Example 13

Preparation of 3-Oxo-4-((S)-4-methyl-2-{[5-(2-morpholino-4-yl-ethoxy)-benzofuran-2-carbonyl]amino}-pentanoylamino)-1-(4-methyl-pentanoyl)-azepanium a.) 4-((S)-2-tert-butoxycarbonylamino-4-methyl-pentanoylamino)-3-hydroxy-1-(4-methyl-pentanoyl)-azepanium Following the procedure of Example 9a except substituting iso-caproic acid for 3-(2-pyridyl)phenyl acetic acid the title compound was prepared: MS(EI) 442 (M+H$^+$).

b.) 4-((S)-2-Amino-4-methyl-pentanoylamino)-3-hydroxy-1-(4-methyl-pentanoyl)-azepanium Following the procedure of Example 2i except substituting the compound of Example 13a the title compound was prepared: MS(EI) 342 (M+H$^+$).

c.) 3-Hydroxy-4-((S)-4-methyl-2-{[5-(2-morpholino-4-yl-ethoxy)-benzofuran-2-carbonyl]amino}-pentanoylamino)-1-(4-methyl-pentanoyl)-azepanium To a solution of the compound of Example 13b (200 mg, 0.53 mmol) in dichloromethane was added EDC (111 mg, 0.58 mmol), HOBt (78 mg, 0.58 mmol), TEA (0.11 mL, 0.79 mmol) and 5-(2-morpholin-4-yl-ethyloxy)benzofuran-2-carboxylic acid. The reaction was stirred at room temperature until complete as indicated by TLC analysis. Workup and column chromatography (5% methanol:dichloromethane) provided 160 mg of the title compound: MS(EI) 615 (M+H$^+$).

d.) 3-Oxo-4-((S)-4-methyl-2-{[5-(2-morpholino-4-yl-ethoxy)-benzofuran-2-carbonyl]amino}-pentanoylamino)-1-(4-methyl-pentanoyl)-azepanium Following the procedure of Example 1i except substituting the compound of Example 13d the title compound was prepared: $^1$H NMR (CDCl$_3$): δ 1.0 (m, 12H), 1.5-2.1 (m, 8H), 2.2 (m, 2H), 2.3 (m, 1H), 2.4-2.5 (m, 2H), 72.6 (m, 5H), 2.7 (m, 2H), 2.9 (m, 1H), 3.4 (m, 1H), 3.7 (m, 4H), 4.1 (m, 2H), 4.5-4.6 (m, 2H), 5.2 (m, 1H), 7.2-8.4 (m, 4H): MS(EI): 613 (M+H$^+$, 100%). The diastereomers were separated by preparative scale HPLC. Lyophilisation of the eluents provided diastereomer 1 and diastereomer 2.

Example 14

Preparation of 3-Oxo-4-((S)-4-methyl-2-{[5-(2-morpholino-4-yl-ethoxy)-benzofuran-2-carbonyl]amino}-pentanoylamino)-1-benzenesulphonyl-azepanium a.) 1-Benzenesulphonyl-4-((S)-2-tert-butoxycarbonylamino-methyl-pentanoylamino)-3-hydroxy-azepanium To a solution of the amine of Example 2g (0.5 g, 1.46 mmol) in dichloromethane was added triethylamine (0.4 mL, 2.92 mmol) followed by benzenesulphonyl chloride (0.28 mL, 2.18 mmol). The reaction was stirred at room temperature until complete as determined by TLC analysis. Workup and column chromatography (10% methanol:dichloromethane) provided 450 mg of the title compound: MS(EI) 484 (M+H$^+$).

b.) 4-((S)-2-Amino-methyl-pentanoylamino) 1-benzenesulphonyl-3-hydroxy-azepanium Following the procedure of Example 2i except substituting the compound of Example 14a the title compound was prepared: MS(EI) 384 (M+H+).

c.) 3-Hydroxy-4-((S)-4-methyl-2-{[5-(2-morpholino-4-yl-ethoxy)-benzofuran-2-carbonyl]amino}-pentanoylamino)-1-benzenesulphonyl-azepanium Following the procedure of Example 13c except substituting the compound of Example 14b the title compound was prepared: MS(EI) 657 (M+H+).

d.) 3-Oxo-4-((S)-4-methyl-2-{[5-(2-morpholino-4-yl-ethoxy)-benzofuran-2-carbonyl]amino}-pentanoylamino)-1-benzenesulphonyl-azepanium Following the procedure of Example 1i except substituting the compound of Example 14c the title comnpound was prepared: $^1$H NMR (CDCl$_3$): δ 1.0 (m, 6H), 1.5-2.1 (m, 5H), 2.2 (m, 2H), 2.4 (m, 1H), 2.7 (m, 4H), 2.8 (m, 2H), 3.5 (m, 1H), 3.8 (m, 4H), 4.0 (m, 1H), 4.1 (m, 2H), 4.4 (m, 1H), 4.5 (m, 1H), 4.7 (m, 1H), 5.1 (m, 1H), 7.0 (m, 3H), 7.3 (m, 2H), 7.5 (m, 3H), 7.7 (m, 2H): MS(EI): 655 (M+H$^+$, 100%).

Analysis of the diastereomeric mixture by analytical HPLC (40:60 to 45:55 CH$_3$CN:20 mm KHPO$_4$ (pH 7 buffer) 60 min. gradient 1 mL/min.; inertsil ODS-3 column 4.6×250 mm; UV detection at 215 nM) showed two peaks (R$_t$=44.6 mins. and 45.9 mins). The diastereomers were separated by preparative scale HPLC (40:60 to 50:50 CH$_3$CN: mm KHPO$_4$ (pH 7 buffer) gradient, 12 mL/min., 60 mins; inertsil ODS-3 column 250×20 mm; UV detection at 215 nM). Lyophilisation of the eluents provided diastereomer 1 (anal. R$_t$=44.6 mins.) and diastereomer 2 (anal. Rt=45.9 mins).

Example 15

Preparation of 4-((S)-4-Methyl-2-{[5-(2-morpholino-4-yl-ethoxy)-benzofuran-2-carbonyl]amino}-pentanoylamino)-3-oxo-azepane-1-carboxylic acid phenylamide a.) [(S)-1-(3-Hydroxy-1-phenylcarbamoyl-azepan-4-ylcarbamoyl)-3-methyl-butyl]-carbamic acid tert-butyl ester To a solution of the amine of Example 2g (0.5 g, 1.46 mmol) in dichloromethane (20 mL) was added phenyl isocyanate (0.24 mL, 2.18 mmol). The reaction was stirred at room temperature until complete as determined by TLC analysis. Workup and column chromatography (5% methanol:dichloromethane) provided 578 mg of the title compound: MS(EI) 463 (M+H$^+$).

b.) 4-((S)-2-Amino-methyl-pentanoylamino)-3-hydroxy-azepane-1-carboxylic acid phenyl amide Following the procedure of Example 2i except substituting the compound of Example 15a the title compound was prepared: MS(EI) 363 (M+H$^+$).

c.) 3-Hydroxy-4-((S)-4-Methyl-2-{[5-(2-morpholino-4-yl-ethoxy)-benzofuran-2-carbonyl]amino}-pentanoylamino)-azepane-1-carboxylic acid phenylamide Following the procedure of Example 13c except substituting the compound of Example 15b the title compound was prepared: MS(EI) 636 (M+H$^+$).

d.) 4-((S)-4-Methyl-2-{[5-(2-morpholino-4-yl-ethoxy)-benzofuran-2-carbonyl]amino}-pentanoylamino)-3-oxo-azepane-1-carboxylic acid phenylamide Following the procedure of Example 1i except substituting the compound of Example 15c the title compound was prepared: $^1$H NMR (CDCl$_3$)): δ 1.0 (m, 6H), 1.5-2.1 (m, 5H), 2.2 (m, 2H), 2.7 (m, 4H), 3.0 (m, 2H), 3.1 (m, 1H), 3.8 (m, 1H), 3.9 (m, 4H), 4.2 (m, 1H), 4.3 (m, 2H), 4.9 (m, 2H), 5.2 (m, 1H), 7.2-8.4 (m, 9H): MS(EI): 634 (M+H$^+$, 100%)

Analysis of the diastereomeric mixture by analytical HPLC (40:60 CH$_3$CN:20 mM KHPO$_4$ (pH 7 buffer) isocratic, 1 mL/min.; inertsil ODS-3 column 4.6×250 mm; UV detection at 215 nM) showed two peaks (R$_t$=27.3 mins. and 30.1 mins). The diastereomers were separated by preparative scale HPLC (40:60 to 50:50 CH$_3$CN: 20 mM KHPO$_4$ (pH 7 buffer) gradient, 12 mL/min., 60 mins; inertsil ODS-3 column 250× 20 mm; UV detection at 215 nM). Lyophilisation and desalting of the eluents by NaHCO$_3$:ethyl acetate extraction provided diastereomer 1 (anal. R$_t$=27.3 mins.) and diastereomer 2 (anal. Rt=30.1 mins).

Example 16

Preparation of 5-(2-Morpholino-4-yl-ethoxy)-benzofuran-2-carboxylic acid ((S)-3-methyl-1-{3-oxo-1-[2-(3-pyridin-2-yl-phenyl)acetyl]-azepan-4-ylcarbamoyl}-butyl)amide a.) 5-(2-Morpholino-4-yl-ethoxy)-benzofuran-2-carboxylic acid ((S)-3-methyl-1-{3-hydroxy-1-[2-(3-pyridin-2-yl-phenyl)acetyl]-azepan-4-ylcarbamoyl}-butyl)amide Following the procedure of Example 13c except substituting the compound of Example 9b the title compound was prepared: MS(EI) 712 (M+H$^+$).

b.) 5-(2-Morpholino-4-yl-ethoxy)-benzofuran-2-carboxylic acid ((S)-3-methyl-1-{3-oxo-1-[2-(3-pyridin-2-yl-phenyl)acetyl]-azepan-4-ylcarbamoyl}-butyl)amide Following the procedure of Example 1i except substituting the compound of Example 16c the title compound was prepared: $^1$H NMR (CDCl$_3$): ): δ 1.0 (m, 6H), 1.5-2.1 (m, 5H), 2.2 (m, 2H), 2.7 (m, 4H), 2.8 (m, 2H), 2.9 (m, 1H), 3.5 (m, 1H), 3.7 (m, 4H), 3.9 (m, 3H), 4.3 (m, 2H), 4.7 (m, 2H), 5.4 (m, 1H), 7.2-8.0 (m, 13H), 8.5 (m, 1H); MS(EI): 710 (M+H$^+$, 100%) MS(EI).

Analysis of the diastereomeric mixture by analytical HPLC (40:60 CH$_3$CN:20 mM KHPO$_4$ (pH 7 buffer) isocratic, 1 mL/min.; inertsil ODS-3 column 4.6×250 mm; UV detection at 215 nM) showed two peaks (R$_t$=33.9 mins. and 37.9 mins). The diastereomers were separated by preparative scale HPLC (40:60 to 45:55 CH$_3$CN: 20 mM KHPO$_4$ (pH 7 buffer) gradient, 12 mL/min., 60 mins; inertsil ODS-3 column 250× 20 mm; UV detection at 215 nM). Lyophilisation and desalting of the eluents by NaHCO$_3$:ethyl acetate extraction provided diastereomer 1: MS(EI) 710.3 (M+H$^+$) (anal. R$_t$=33.9 mins.) and diastereomer 2: MS(EI) 710.3 (M+H$^+$) (anal. Rt=37.9 mins).

Example 17

Preparation of 5-(2-Morpholino-4-yl-ethoxy)-benzofuran-2-carboxylic acid [(S)-1-(benzoyl-3-oxo-azepan-4-ylcarbamoyl)-3-methyl-butyl]amide a.) 5-(2-Morpholino-4-yl-ethoxy)-benzofuran-2-carboxylic acid [(S)-1-(benzoyl-3-hydroxy-azepan-4-ylcarbamoyl)-3-methyl-butyl]amide Following the procedure of Example 13c except substituting the compound of Example 11b the title compound was prepared: MS(EI) 621 (M+H$^+$).

b.) 5-(2-Morpholino-4-yl-ethoxy)-benzofuran-2-carboxylic acid [(S)-1-(benzoyl-3-oxo-azepan-4-ylcarbamoyl)-3-methyl-butyl]amide Following the procedure of Example 1i except substituting the compound of Example 17a the title compound was prepared: $^1$H NMR (CDCl$_3$): δ 1.0 (m, 6H), 1.5-2.1 (m, 5H), 2.2 (m, 2H), 2.7 (m, 4H), 2.9 (m, 2H), 3.0 (m, 1H), 3.7 (m, 5H), 4.0 (m, 1H), 4.1 (m, 2H), 4.7 (m, 2H), 5.4 (m, 1H), 7.2-8.4 (m, 11H): MS(EI): 619 (M+H$^+$, 100%)

Analysis of the diastereomeric mixture by analytical HPLC (40:60 to 55:45 CH$_3$CN:20 mM KHPO$_4$ (pH 7 buffer) 30 min. gradient, 1 mL/min.; inertsil ODS-3 column 4.6×250 mm; UV detection at 215 nM) showed two peaks (R$_t$=mins. 13.5 and 17.6 mins). The diastereomers were separated by preparative scale HPLC (40:60 to 45:55 CH$_3$CN: mM KHPO$_4$ (pH 7 buffer) 60 min. gradient, 15 mL/min., 60 mins; inertsil ODS-3 column 250×20 mm; UV detection at 215 nM). Lyophilisation and desalting of the eluents by NaHCO$_3$: ethyl acetate extraction provided diastereomer 1 (anal. R$_t$=13.5 mins.) and diastereomer 2 (anal. Rt=17.6 mins).

Example 18

Preparation of 5-(2-Pyrrolidin-1-yl-ethoxy)-benzofuran-2-carboxylic acid [(S)-1-(1-benzenesulfonyl-3-oxo-azepan-4-ylcarbamoyl)-3-methyl-butyl]amide a.) 5-(2-Pyrrolidin-1-yl-ethoxy)-benzofuran-2-carboxylic acid [(S)-1-(1-benzenesulfonyl-3-hydroxy-azepan-4-ylcarbamoyl)-3-methyl-butyl]amide Following the procedure of Example 14c except substituting 5-(2-pyrrolidin-1-yl-ethyloxy)-benzofuran-2-carboxylic acid for 5-(2-morpholin-4-yl-ethyloxy)benzofuran-2-carboxylic acid the title compound was prepared: MS(EI) 641 (M+H$^+$).

b.) 5-(2-Morpholino-4-yl-ethoxy)-benzofuran-2-carboxylic acid [(S)-1-(benzoyl-3-oxo-azepan-4-ylcarbamoyl)-3-methyl-butyl]amide Following the procedure of Example 1i except substituting the compound of Example 18a the title compound was prepared: $^1$H NMR (CDCl$_3$) δ 1.0 (m, 6H), 1.5-2.1 (m, 9H), 2.2 (m, 2H), 2.5 (m, 1H), 2.7 (m, 4H), 3.0 (m, 2H), 3.4 (m, 1H), 4.0 (m, 1H), 4.1 (m, 2H), 4.5 (m, 1H), 4.6 (m, 1H), 5.0 (m, 1H), 7.2-8.4 (m, 11H): MS(EI): 639 (M+H$^+$, 100%).

Example 19

Preparation of 5-(2-Piperidin-1-yl-ethoxy)-benzofuran-2-carboxylic acid [(S)-1-(1-benzenesulfonyl-3-oxo-azepan-4-ylcarbamoyl)-3-methyl-butyl]amide a.) 5-(2-Piperidin-1-yl-ethoxy)-benzofuran-2-carboxylic acid [(S)-1-(1-benzenesulfonyl-3-oxo-azepan-4-ylcarbamoyl)-3-methyl-butyl]amide Following the procedure of Example 14c except substituting 5-(2-piperidin-1-yl-ethyloxy)-benzofuran-2-carboxylic acid for 5-(2-morpholin-4-yl-ethyloxy)benzofuran-2-carboxylic acid the title compound was prepared: MS(EI) 655 (M+H$^+$).

b.) 5-(2-Piperidin-1-yl-ethoxy)-benzofuran-2-carboxylic acid [(S)-1-(1-benzenesulfonyl-3-hydroxy-azepan-4-ylcarbamoyl)-3-methyl-butyl]amide Following the procedure of Example 1i except substituting the compound of Example 18a the title compound was prepared: $^1$H NMR (CDCl$_3$): δ 1.0 (m, 6H), 1.5-2.1 (m, 11H), 2.2 (m, 2H), 2.5 (m, 5H), 2.7 (m, 2H), 3.5 (m, 1H), 4.0 (m, 1H), 4.1 (m, 2H), 4.5 (m, 1H), 4.6 (m, 1H), 5.0 (m, 1H), 7.2-8.4 (m, 11H): MS(EI): 653 (M+H$^+$, 100%).

Example 20

Preparation of 5-(2-Morpholino-4-yl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide a.) 5-(2-morpholin-4-yl-ethyloxy)benzofuran-2-carboxylic acid methoxy methyl amide To a solution of 3-(2-pyridyl)phenyl acetic acid (1 g) in dichloromethane was added N,O-dimethylhydroxylamine hydrochloride (0.92 g), triethylamine (1.3 mL), HOBt (0.96 g) and EDC (1.1 g). The reaction was stirred until complete. Workup and column chromatography (40% ethyl acetate: hexanes provided 1.1 g of the title compound: MS(EI) 257 (M+H$^+$).

b.) 5-(2-morpholin-4-yl-ethyloxy)benzofuran-2-carbaldehyde

To a solution of 5-(2-morpholin-4-yl-ethyloxy)benzofuran-2-carboxylic acid methoxy methyl amide (0.2 g) of Example 20a in THF was added LAH (2.0 mL of a 1 M solution in THF). The reaction was stirred until complete consumption of the starting material. Workup gave 160 mg of the title compound.

c.) ((S)-{3-hydroxy-1-[2-(3-pyridin-2-yl-phenyl)-ethyl]-azepan-4-ylcarbamoyl}-3-methyl-butyl)-carbamic acid tert butyl ester Following the general procedure of Example 2g except substituting 5-(2-morpholin-4-yl-ethyloxy)benzofuran-2-carbaldehyde for benzaldehyde the title compound was prepared: MS(EI) 525 (M+H$^+$).

d.) (S)-2-Amino-4-methyl-pentanoic acid-{3-hydroxy-1-[2-(3-pyridin-2-yl-phenyl)-ethyl]-azepan-4-yl}-amide Following the procedure of Example 2i except substituting the compound of Example 20c the title compound was prepared.

e.) 5-(2-Morpholino-4-yl-ethoxy)-benzofuran-2-carboxylic acid ((S)-3-methyl-1-{3hydroxy-1-[2-(3-pyridin-2-yl-phenyl)ethyl]-azepan-4-ylcarbamoyl}-butyl)amide Following the procedure of Example 13c except substituting the compound of Example 20d the title compound was prepared.

f.) 5-(2-Morpholino-4-yl-ethoxy)-benzofuran-2-carboxylic acid ((S)-3-methyl-1-{3-oxy-1-[2-(3-pyridin-2-yl-phenyl)ethyl]-azepan-4-ylcarbamoyl}-butyl)amide Following the procedure of Example 1i except substituting the compound of Example 20e the title compound was prepared: $^1$H NMR (CDCl$_3$): δ 1.0 (m, 6H), 1.5-2.1 (m, 5H), 2.2 (m, 2H), 2.7 (m, 4H), 2.8 (m, 6H), 3.1 (m, 1H), 3.3 (m, 1H); 3.5 (m, 1H), 3.7 (m, 4H), 4.2 (m, 3H), 4.6 (m, 1H), 5.2 (m, 1H), 7.2-8.4 (m, 13H), 8.6 (m, 1H); MS(EI): 696 (M+H$^+$, 80%).

The diastereomeric mixture was separated by HPLC to provide the faster eluting diastereoemer; MS(EI): 696 (M+H$^+$, 100%), and the slower eluting diastereomer; MS(EI): 696 (M+H$^+$, 100%).

Example 21

Preparation of Naphthlene-2-carboxylic acid ((S)-3-methyl-1-{3-oxo-1-[2-(3-pyridin-2-yl-phenyl)ethyl]-azepan-4-ylcarbamoyl}-butyl)amide a.) Naphthlene-2-carboxylic acid ((S)-3-methyl-1-{3-hydroxy-1-[2-(3-pyridin-2-yl-phenyl)ethyl]-azepan-4-ylcarbamoyl}-butyl)amide Following the procedure of Example 20f except substituting 2-naphthoic acid for 5-(2-morpholin-4-yl-ethyloxy)benzofuran-2-carboxylic acid the title compound was prepared: MS(EI) 579 (M+H$^+$).

b.) Naphthlene-2-carboxylic acid ((S)-3-methyl-1-{3-oxo-1-[2-(3-pyridin-2-yl-phenyl)ethyl]-azepan-4-ylcarbamoyl}-butyl)amide Following the procedure of Example 1i except substituting the compound of Example 21b the title compound was prepared: $^1$H NMR (CDCl$_3$): δ 1.0 (m, 6H), 1.5-2.1 (m, 6H), 2.2 (m, 2H), 2.9 (m, 4H), 3.0 (m, 1H), 3.4 (d, 1H), 3.5 (m, 1H), 4.7 (m, 1H), 5.0 (m, 1H), 6.8-7.2 (m, 6H), 7.3 (m, 1H), 7.5 (m, 2H), 7.9 (m, 6H), 8.2 (m, 1H), 8.7 (m, 1H): MS(EI): 577 (M+H$^+$, 100%).

Example 22

Preparation of 1H-Indole-2-carboxylic acid ((S)-3-methyl-1-{3-oxo-1-[2-(3-pyridin-2-yl-phenyl)ethyl]-azepan-4-ylcarbamoyl}-butyl)amide a.) ((S)-3-methyl-1-{3-hydroxy-1-[2-(3-pyridin-2-yl-phenyl)ethyl]-azepan-4-ylcarbamoyl}-butyl)amide Following the procedure of Example 20f except substituting 1H-indole-2-carboxylic acid for 5-(2-morpholin-4-yl-ethyloxy)benzofuran-2-carboxylic acid the title compound was prepared: MS(EI) 568 (M+H$^+$).

b.) ((S)-3-methyl-1-{3-oxo-1-[2-(3-pyridin-2-yl-phenyl)ethyl]-azepan-4-ylcarbamoyl}-butyl)amide Following the procedure of Example 1i except substituting the compound of Example 22b the title compound was prepared:: $^1$H NMR (CDCl$_3$):): δ 1.0 (m, 6H), 1.5-2.1 (m, 5H), 2.2 (m, 2H), 2.9 (m, 4H), 3.0 (m, 1H), 3.4 (d, 1H). 3.5 (m, 1H), 4.7 (m, 1H), 5.0 (m, 1H), 6.8-7.2 (m, 6H), 7.0-7.9 (m, 12H), 8.7 (m, 1H), 9.5 (m, 1H): MS(EI): 566 (M+H$^+$, 100%)

Example 23

Preparation of 1H-Indole-2-carboxylic acid [(S)-1-(1-benzenesulfonyl-3-oxo-azepan-4-ylcarbamoyl)-3-methyl-butyl]amide a.) 1H-Indole-2-carboxylic acid [(S)-1-(1-benzenesulfonyl-3-hydroxy-azepan-4-ylcarbamoyl)-3-methyl-butyl]amide Following the procedure of Example 2j except substituting the compound of Example 14b and substituting 1H-indole-2-carboxylic acid for naphthoic acid the title compound was prepared: MS(EI) 527 (M+H$^+$).

b.) 1H-Indole-2-carboxylic acid [(S)-1-(1-benzenesulfonyl-3-oxo-azepan-4-ylcarbamoyl)-3-methyl-butyl]amide Following the procedure of Example 1i except substituting the compound of Example 23b the title compound was prepared: $^1$H NMR (CDCl$_3$): δ 1.0 (m, 6H), 1.5-2.1 (m, 5H), 2.2 (m, 2H), 2.5 (m, 1H), 3.5 (dd, 1H), 3.9 (m, 1H), 4.5 (dd, 2H), 4.7 (m, 1H), 5.0 (m, 1H), 7.2-7.6 (m, 10H). 9.5 (b, 1H); MS(EI): 525 (M+H$^+$, 10%).

Example 24

Preparation of Benzofuran-2-carboxylic acid [(S)-1-(1-benzenesulfonyl-3-oxo-azepan-4-ylcarbamoyl)-3-methyl-butyl]amide a.) Benzofuran-2-carboxylic acid [(S)-1-(1-benzenesulfonyl-3-hydroxy-azepan-4-ylcarbamoyl)-3-methyl-butyl]amide Following the procedure of Example 23a except substituting benzofuran-2-carboxylic acid for 1H-indole 2-carboxylic acid the title compound was prepared: MS(EI) 528 (M+H$^+$).

b.) Benzofuran-2-carboxylic acid [(S)-1-(1-benzenesulfonyl-3-oxo-azepan-4-ylcarbamoyl)-3-methyl-butyl]amide Following the procedure of Example 1i except substituting the compound of Example 24b the title compound was prepared: $^1$H NMR (CDCl$_3$): δ 1.0 (m, 6H), 1.5-2.1 (m, 5H), 2.2 (m, 2H), 2.6 (m, 1H), 3.5 (d, 1H), 4.1 (m, 1H), 4.7 (m, 2H), 5.0 (m, 1H), 7.2-7.2 (m, 10H).

Example 25

Preparation of Benzofuran-2-carboxylic acid [(S)-3-methyl-1-{3-oxo-1-[2-(3-pyridin-2-yl-phenyl)ethyl]-azepan-4-ylcarbamoyl}-butyl)amide a.) Benzofuran-2-carboxylic acid [(S)-3-methyl-1-{3-hydroxy-1-[2-(3-pyridin-2-yl-phenyl)ethyl]-azepan-4-ylcarbamoyl}-butyl)amide Following the procedure of Example 20e except substituting benzofuran-2-carboxylic acid for 5-(2-morpholin-4-yl-ethyloxy)benzofuran-2-carboxylic the title compound was prepared: MS(EI) 569 (M+H$^+$).

b.) Benzofuran-2-carboxylic acid [(S)-3-methyl-1-{3-oxo-1-[2-(3-pyridin-2-yl-phenyl)ethyl]-azepan-4-ylcarbamoyl}-butyl)amide Following the procedure of Example 1i except substituting the compound of Example 25b the title compound was prepared: $^1$H NMR (CDCl$_3$): δ 1.0 (m, 6H), 1.5-2.1 (m, 5H), 2.2 (m, 2H), 2.7 (m, 5H), 3.0 (m, 1H), 3.3 (m, 1H), 3.5 (m, 1H), 4.7 (m, 1H), 5.2 (m, 1H), 7.2-7.7 (m, 14H), 8.7 (m, 1H); MS(EI): 567 (M+H$^+$, 100%)

The diastereomeric mixture was separated by HPLC to provide the faster eluting diastereoemer; MS(EI): 656 (M+H$^+$, 100%), and the slower eluting diastereomer; MS(EI): 656 (M+H$^+$, 100%).

Example 26

Preparation of 5-(2-Morpholino-4-yl-ethoxy)-benzofuran-2-carboxylic acid [(S)-3-methyl-1-(3-oxo-1-phenethyl-azepan-4-ylcarbamoyl]-butyl}amide Following the procedures of Examples 20c-f except substituting phenylacetaldehyde for 5-(2-morpholin-4-yl-ethyloxy)benzofuran-2-carbaldehyde of Example 20c the title compound was prepared: $^1$H NMR (CDCl$_3$): δ 1.0 (m, 6H), 1.5-2.1 (m, 5H), 2.2 (m, 2H), 2.4 (m, 1H), 2.6 (m, 4H), 2.7 (m, 6H), 3.0 (m, 1H), 3.3 (dd, 1H), 3.5 (q, 1H), 3.7 (m, 4H), 4.2 (m, 2H), 4.7 (m, 1H), 5.0 (m, 1H), 7.2-7.2 (m, 11H); MS(EI): 619 (M+H$^+$, 80%)

The diastereomeric mixture was separated by HPLC to provide the faster eluting diastereoemer; MS(EI): 619 (M+H$^+$, 100%), and the slower eluting diastereomer; MS(EI): 619 (M+H$^+$, 100%).

Example 27

Preparation of Naphthylene-2-carboxylic acid [(S)-3-methyl-1-(3-oxo-1-phenethyl-azepan-4-ylcarbamoyl]-butyl}amide Following the procedures of Examples 2h-k except substituting phenylacetaldehyde for benzaldehyde of Example 2h the title compound was prepared: $^1$H NMR (CDCl$_3$): δ 1.0 (m, 6H), 1.5-2.1 (m, 5H), 2.2 (m, 2H), 2.4 (m, 1H), 2.7 (m, 4H), 3.0 (m, 1H), 3.7 (d, 1H), 3.5 (q, 1H), 4.7 (m, 1H), 5.1 (m, 1H), 6.9-7.2 (m, 7H), 7.5 (m, 2H), 7.9 (m, 4H) 8.4 (m, 1H); MS(EI): 500 (M+H$^+$, 100%).

Example 28

Preparation of Benzofuran-2-carboxylic acid {(S)-3-methyl-1-[3-oxo-1-(pyridine-2-sulfonyl)-azepan-4-ylcarbamoyl]-butyl}amide a.) (S)-2-Amino-4-methyl-pentanoic acid [3-hydroxy-1-(pyridine-2-sulfonyl)-azepan-4-yl]-amide Following the procedure of Examples 14a-b except substituting 2-pyridinesulfonyl chloride for benzenesulfonyl chloride of Example 14a the title compound was prepared: MS(EI) 385 (M+H$^+$).

b.) Benzofuran-2-carboxylic acid {(S)-3-methyl-1-[3-hydroxy-1-(pyridine-2-sulfonyl)-azepan-4-ylcarbamoyl]-butyl}amide To a solution of (S)-2-amino-4-methyl-pentanoic acid [3-hydroxy-1-(pyridine-2-sulfonyl)-azepan-4-yl]-amide of Example 28a (0.15 g) in dichloromethane was added TEA (0.11 mL), HOBt (49 mg), EDC (69 mg) and benzofuran-2- carboxylic acid (58 mg). The reaction was stirred until complete. Workup and column chromatography (5% methanol: ethyl acetate) provided the title compound: MS(EI) 529 (M+H$^+$).

c.) Benzofuran-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 28b the title compound was prepared: $^1$H NMR (CDCl$_3$): δ 1.0 (m, 6H), 1.5-2.1 (m, 5H), 2.2 (m, 2H), 2.7 (m, 1H), 3.7 (dd, 1H), 4.0 (m, 1H), 4.7 (m, 2H), 5.0 (m, 1H), 7.2-7.3 (m, 3H), 7.4 (m, 4H), 7.6 (m, 1H), 8.0 (m, 2H), 8.7 (m, 1H); MS(EI): 527 (M+H$^+$, 40%).

The diastereomeric mixture was separated by HPLC to provide the faster eluting diastereoemer; $^1$HNMR: δ 1.0 (m, 6H), 1.5-2.1 (m, 5H), 2.2 (m, 2H), 2.7 (t, 1H), 3.7 (d, 1H); 4.0 (d, 1H), 4.7 (m, 2H), 5.0 (m, 1H), 7.2-7.3 (m, 3H), 7.4 (m, 4H), 7.6 (m, 1H), 8.0 (m, 2H), 8.7 (m, 1H), MS(EI): 527 (M+H$^+$, 100%), and the slower eluting diastereomer; $^1$HNMR: δ 1.0 (m, 6H), 1.5-2.1 (m, 5H), 2.2 (m, 2H), 2.7 (t, 1H), 3.7 (d, 1H); 4.0 (d, 1H), 4.7 (m, 2H), 5.0 (m, 1H), 7.2-7.3 (m, 3H), 7.4 (m, 4H), 7.6 (m, 1H), 8.0 (m, 2H), 8.7 (m, 1H); MS(EI): 527 (M+H$^+$, 100%).

Example 29

Preparation of Naphthylene-2-carboxylic acid {(S)-3-methyl-1-[3-oxo-1-(pyridine-2-sulfonyl)-azepan-4-ylcarbamoyl]-butyl}amide a.) Naphthylene-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 2-naphthoic acid for benzofuran-2-carboxylic acid the title compound was prepared: MS(EI) 539 (M+H$^+$).

b.) Naphthylene-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 29a the title compound was prepared: $^1$H NMR (CDCl$_3$): δ 1.0 (m, 6H), 1.5-2.1 (m, 5H), 2.2 (m, 2H), 2.7 (m, 1H), 3.7 (dd, 1H), 4.0 (m, 1H), 4.7 (m, 2H), 5.0 (m, 1H), 7.2-7.3 (m, 2H), 7.5 (m, 3H), 7.9 (m, 6H), 8.3 (m, 1H), 8.4 (m, 1H); MS(EI): 537 (M+H$^+$, 50%).

The diastereomeric mixture was separated by HPLC to provide the faster eluting diastereoemer; MS(EI): 537 (M+H$^+$, 100%), and the slower eluting diastereomer; MS(EI): 537 (M+H$^+$, 100%).

Example 30

Preparation of 5-(2-Morpholino-4-yl-ethoxy)-benzofuran-2-carboxylic acid {(S)-3-methyl-1-[3-oxo-1-(pyridine-2-sulfonyl)-azepan-4-ylcarbamoyl]-butyl}amide a.) 5-(2-Morpholino-4-yl-ethoxy)-benzofuran-2-carboxylic acid {(S)-3-methyl-1-[3-hydroxy-1-(pyridine-2-sulfonyl)-azepan-4-ylcarbamoyl]-butyl}amide Following the procedure of Example 13c except substituting the compound of Example 28a the title compound was prepared: MS(EI) 658 (M+H$^+$).

b.) 5-(2-Morpholino-4-yl-ethoxy)-benzofuran-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 29a the title compound was prepared: $^1$H NMR (CDCl$_3$): δ 1.0 (m, 6H), 1.5-2.1 m, 5H), 2.2 (m, 2H), 2.7 (m, 1H), 3.5 (m, 4H), 3.7 (m, 6H), 4.1 (m, 1H), 4.5 (m, 2H), 4.7 (m, 2H), 5.0 (m, 1H), 7.2-7.3 (m, 4H), 7.4 (m, 2H), 8.0 (m, 2H), 8.7 (m, 1H), 8.7 (m, 1H); MS(EI): 656 (M+H$^+$, 100%).

The diastereomeric mixture was separated by HPLC to provide the faster eluting diastereoemer; MS(EI): 656 (M+H$^+$, 100%), and the slower eluting diastereomer; MS(EI): 656 (M+H$^+$, 100%).

Example 31

Preparation of 4-((S)-4-Methyl-2-{[(5-(2-morpholino-4-yl-ethoxy)-benzofuran-2-carbonyl]-amino}-pentanoylamino)-3-oxo-azepane-1-carboxylic acid tert-butyl ester a.) 4-((S)-2-Amino-4-methyl-pentanoylamino)-3-hydroxy-azepane-1-carboxylic acid tert-butyl ester To a solution of the compound of Example 1f (0.89 g) in ethyl acetate:methanol (30 mL of a 2:1 mixture) was added 10% Pd/C and a balloon of hydrogen gas was attached. The reaction was stirred until complete by TLC analysis whereupon it was filtered and concentrated to provide the title compound (0.57 g).

b.) 4-((S)-4-Methyl-2-{[(5-(2-morpholino-4-yl-ethoxy)-benzofuran-2-carbonyl]-amino}-pentanoylamino)-3-hydroxy-azepane-1-carboxylic acid tert-butyl ester Following the procedure of Example 13c except substituting the compound of Example 31a the title compound was prepared.

c.) 4-((S)-4-Methyl-2-{[(5-(2-morpholino-4-yl-ethoxy)-benzofuran-2-carbonyl]-amino}-pentanoylamino)-3-oxo-azepane-1-carboxylic acid tert-butyl ester Following the procedure of Example 1i except substituting the compound of Example 31b the title compound was prepared: $^1$H NMR (CDCl$_3$): δ 1.0 (m, 6H), 1.5 (m, 9H), 1.7 (m, 5H), 2.2 (m, 2H), 2.5 (m, 5H), 2.7 (m, 2H), 3.5 (m, 1H), 3.8 (m, 4H), 4.1 (m, 3H), 4.2 (m, 1H), 4.7 (m, 2H), 5.0 (m, 1H), 7.2-7.3 (m, 5H); MS(EI): 615 (M+H$^+$, 100%).

Example 32

Preparation of 4-((S)-4-Methyl-2-{[(5-(2-morpholino-4-yl-ethoxy)-benzofuran-2-carboxylic acid [(S)-3-methyl-1-(3-oxo-azepan-4-ylcarbamoyl]-butyl}amide To a solution of the compound of Example 31c in THF (5 mL) was added 1M HCl in ether (5 mL). Th reaction was stirred overnight whereupon it was concentrated to provide the title compound: $^1$H NMR (CDCl$_3$): δ 1.0 (m, 6H), 1.5-2.1 (m, 5H), 2.2 (m, 2H), 2.7 (m, 4H), 3.2 (dd, 3H), 3.7 (m, 6H), 4.0 (m, 3H), 4.5 (m, 2H), 5.0 (m, 1H), 7.2-7.3 (m, 6H); MS(EI): 515 (M+H$^+$, 100%).

Example 33

Preparation of 4-Methyl-pentanoic acid {3-oxo-1-[2-(3-pyridin-2-yl-phenyl-acetyl]-azepan-4-yl}-amide a.) 3-Hydroxy-4-(4-methyl-pentanoylamino)-azepane-1-carboxylic acid tert-butyl ester Following the procedure of Example 1f except substituting 4-methylpentanoic acid for Cbz-leucine the title compound was prepared: MS(EI) 329 (M+H$^+$).

b.) 4-Methyl pentanoic acid (3-hydroxy-azepan-4-yl)-amide

To a solution of the compound of Example 33a (200 mg) in methanol (5 mL) was added 4M HCl dioxane (5 mL). The reaction was stirred until complete whereupon it was concentrated to provide the title compound (132 mg): MS(EI) 229 (M+H+).

c.) 4-Methyl-pentanoic acid {3-hydroxy-1-[2-(3-pyridin-2-yl-phenyl-acetyl]-azepan-4-yl}amide Following the procedure of Example 9a except substituting the compound of Example 33b the title compound was prepared: MS(EI) 424 (M+H+).

d.) 4-Methyl-pentanoic acid {3-oxo-1-[2-(3-pyridin-2-yl-phenyl-acetyl]-azepan-4-yl}-amide Following the procedure of Example 1i except substituting the compound of Example 33c the title compound was prepared: $^1$H NMR (CDCl$_3$) δ 1.0 (m, 6H), 1.5-2.1 (m, 5H), 2.2 (m, 2H), 2.7 (m, 1H), 2.9 (m, 1H), 3.5 (m, 1H), 3.7 (m, 2H), 4.1 (m, 3H), 4.6 (m, 1H), 5.3 (m, 1H), 7.2-8.0 (m, 7H), 8.7 (m, 1H); MS(EI): 422 (M+H+, 100%).

Example 34

Preparation of ((S)-3-Methyl-1-{3-oxo-1-[2-(3-pyridin-2-yl-phenyl)-acetyl]-azepan-4-ylcarbamoyl}-butyl)-naphthylene-2-methyl-carbamic acid tert-butyl ester a.) (S)-4-Methyl-2-[naphthalene-2-ylmethyl)-amino]-pentanoic acid methyl ester To a solution of leucine methyl ester hydrochloride (0.5 g) in dichlormethane was added triethylamine (0.9 mL), 2-naphthaldehyde (0.43 g) and sodium triacetoxyborohydride (0.87 g). The mixture was stirred until complete. Workup and column chromatography (5% ethyl acetate:dichloromethane) provided 0.4 g of the title compound: MS(EI) 286 (M+H+).

b.) (S)-2-(tert-Butoxycarbonyl-naphthlen-2-ylmethyl-amino)-4-metyhyl pentanoic acid methyl ester To a solution of the compound of Example 34a (0.35 g) in dichloromethane was added di-tert-butyldicarbonate (0.29 g). After 2 hours at room temperature triethylamine was added and the reaction heated to reflux. Upon completion, the reaction was concentrated and the residue was purified by column chromatography (50% hexane:dichloromethane) to provide 0.17 g of the title compound: MS(EI) 386 (M+H+).

c.) (S)-2-(tert-Butoxycarbonyl-naphthlen-2-ylmethyl-amino)-4-methyl pentanoic acid To a solution of the compound of Example 34b (0.17 g) in THF:methanol (15 mL of a 2:1 solution) was added LiOH (0.019 g). The reaction was stirred overnight whereupon it was concentrated to provide the title compound.

d.) 4-[(S)-tert-butoxycarbonyl-naphthylen-2-ylmethyl-amino)-4-methyl-pentanoylamino]-3-hydroxy-azepane-1-carboxylic acid benzyl ester To a sloution of the compound of Example 2e (0.11 g) in dichloromethane was added EDC (0.08 g), HOBt (0.06 g) and the acid of Example 34c. Upon completion the reaction was worked up and chromatographed (5% methanol:dichloromethane) to provide the title compound (0.18 g): MS(EI) 618 (M+H+).

e.) [(S)-1-(3-Hydroxy-azepan-4-ylcarbamoyl)-3-methyl-butyl]-naphthylen-2-ylmethyl carbamic acid tert-butyl ester To a solution of the compound of Example 34d (0.17 g) in ethyl acetate:methanol (20:10 mL) was added 10% Pd/C. A balloon of hydrogen was attached and the reaction was stirred until complete consumption of the starting material. The reaction was filtered and concentrated to provide the title compound (0.10 g): MS(EI) 484 (M+H+).

f.) ((S)-3-Methyl-1-{3-hydroxy-1-[2-(3-pyridin-2-yl-phenyl)-acetyl]-azepan-4-ylcarbamoyl}-butyl)-naphthylene-2-methyl-carbamic acid tert-butyl ester Following the procedure of Example 9a except substituting the compound of Example 34e the title compound was prepared: MS(EI) 679 (M+H+).

g.) ((S)-3-Methyl-1-{3-oxo-1-[2-(3-pyridin-2-yl-phenyl)-acetyl]-azepan-4-ylcarbamoyl}-butyl)-naphthylene-2-methyl-carbamic acid tert-butyl ester Following the procedure of Example 1i except substituting the compound of Example 34f the title compound was prepared:: $^1$H NMR (CDCl$_3$): δ 1.0 (m, 6H), 1.5-2.2 (m, 16H), 2.7 (m, 1H), 3.2 (m, 1H), 3.7 (m, 3H), 4.0 (m, 1H), 4.7 (m, 2H), 5.2 (m, 1H), 7.2-7.3 (m, 16H), 8.6 (m, 1H); MS(EI): 677 (M+H+, 100%).

Example 35

Preparation of (S)-4-Methyl-2-[(naphthylen-2-ylmethyl)-amino]-pentenoic acid [3-oxo-1-[2-(3-pyridin-2-yl-phenyl)-acetyl]-azepan-4-yl}-amide To a solution of the compound of Example 34g (20 mg) in THF was added 1M HCl in ether. The reaction was stirred until complete consumption of the starting material whereupon it was concentrated to provide the title compound: $^1$H NMR (CDCl$_3$): δ 1.0 (m, 6H), 1.5-2.1 (m, 5H), 2.2 (m, 2H), 2.5 (m, 1H), 3.5 (m, 5H), 4.0 (m, 1H), 4.7 (m, 2H), 4.4 (m, 1H), 7.2-8.0 (m, 16H), 8.7 (m, 1H); MS(EI): 577 (M+H+, 100%).

Example 36

Preparation of 4-[2-(2-{(S)-3-Methyl-1-[3-oxo-1-(pyidine-2-sulfonyl)-azepan-4-ylcarbamoyl]-butyl-carbamoyl}-benzofuran-5-yloxy)-ethyl]-piperazine-1-carboxylic acid tert-butyl ester a.) 4-[2-(2-{(S)-3-Methyl-1-[3-hydroxy-1-(pyidine-2-sulfonyl)-azepan-4-ylcarbamoyl]-butylcarbamoyl}-benzofuran-5-yloxy)-ethyl]-piperazine-1-carboxylic acid tert-butyl ester To a solution of the compound of Example 28a (0.15 g) in dichloromethane was added EDC (0.07 g), HOBt (0.05 g), triethylamine (0.11 mL) and 4-[2-(2-carboxy-benzofuran-5-yloxy)-ethyl]-piperazine-1-carboxylic acid tert-butyl ester. The reaction was stirred until complete. Work up and column chromatography (10% methanol: ethyl acetate) provided the title compound (0.10 g): MS(EI) 757 (M+H+).

b.) 4-[2-(2-{(S)-3-Methyl-1-[3-oxo-1-(pyidine-2-sulfonyl)-azepan-4-ylcarbamoyl]-butylcarbamoyl}-benzofuran-5-yloxy)-ethyl]-piperazine-1-carboxylic acid tert-butyl ester Following the procedure of Example 1i except substituting the compound of Example 36a the title compound was prepared: $^1$H NMR (CDCl$_3$): δ 1.0 (m, 6H), 1.5-2.1 (m, 14H), 2.2 (m, 2H), 2.7 (m, 1H), 3.0 (m, 2H), 3.5 (m, 4H), 3.7 (m, 6H), 4.1 (m, 1H), 4.5 (m, 2H), 4.7 (m, 2H), 5.0 (m, 1H), 7.0-7.6 (m, 6H), 8.0 (m, 2H), 8.7 (m, 1H); MS(EI): 755 (M+H+, 100%).

Example 37

Preparation of 5-(2-Piperizin-1-yl-ethoxy)-benzofuran-2-carboxylic acid {(S)-3-methyl-1-[3-oxo-1-(pyridine-2-sulfonyl)-azepan-4-ylcarbamoyl)-3-butyl]-amide The compound of Example 36b (0.02 g) was dissolved in 4M HCl in dioxane. The reaction was stirred until complete whereupon it was concentrated to provide the title compound: $^1$H NMR (CDCl$_3$): δ 1.0 (m, 6H), 1.5-1.7 (m, 7H), 2.7 (m, 2H), 3.3 (M, 2H), 3.5 (m, 1H), 3.8 (m, 5H), 4.1 (m, 3H), 4.7 (m, 4H), 5.0 (m, 1H), 7.0-7.3 (m, 2H), 7.4 (m, 6H), 8.0 (m, 2H), 8.7 (m, 1H): MS(EI): 655 (M+H$^+$, 100%).

Example 38

Preparation of 5-(2-Cyclohexyl-ethoxy)-benzofuran-2-carboxylic acid {(S)-3-methyl-1-[3-oxo-1-(pyridine-2-sulfonyl)-azepan-4-ylcarbamoyl]-butyl}amide a.) 5-(2-Cyclohexyl-ethoxy)-benzofuran-2-carboxylic acid {(S)-3-methyl-1-[3-hydroxy-1-(pyridine-2-sulfonyl)-azepan-4-ylcarbamoyl]-butyl}amide To a solution of the compound of Example 28a (0.15 g) in dichloromethane was added EDC (0.07 g), HOBt (0.05 g), triethylamine (0.11 mL) and 5-(2-cyclohexyl-ethoxy)-benzofuran carboxylic acid (0.01 g). The reaction was stirred until complete by TLC analysis. Workup and column chromatography (100% ethyl acetate) provided the title compound (0.15 g): MS(EI) 655 (M+H$^+$).

b.) 5-(2-Cyclohexyl-ethoxy)-benzofuran-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 38a the title compound was prepared: MS(EI) 653 (M+H$^+$).

Example 39

Preparation of 5-(2-Cyclohexyl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide a.) 5-(2-Cyclohexyl-ethoxy)-benzofuran-2-carboxylic acid ((S)-3-methyl-1-{3-hydroxy-1-[2-(3-pyridin-2-yl-phenyl)ethyl]-azepan-4-ylcarbamoyl}-butyl)amide To a solution of the compound of Example 20d (0.15 g) in dichloromethane was added EDC (0.06 g), HOBt (0.04 g), triethylamine (0.14 mL) and 5-(2-cyclohexyl-ethoxy)-benzofuran carboxylic acid (0.09 g). The reaction was stirred until complete by TLC analysis. Workup and column chromatography (100% ethyl acetate) provided the title compound (0.10 g): MS(EI) 695 (M+H$^+$).

b.) 5-(2-Cyclohexyl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide Following the procedure of Example 1i except substituting the compound of Example 39a the title compound was prepared: $^1$H NMR (CDCl$_3$): δ 1.0 (m, 6H), 1.5-2.1 (m, 18H), 2.2 (m, 2H), 2.7 (m, 3H), 3.2 (m, 1H), 3.5 (m, 1H), 3.9 (m, 4H), 4.7 (m, 2H), 5.0 (m, 1H), 7.2-7.3 (m, 13H), 8.7 (m, 1H): MS(EI): 693 (M+H$^+$, 100%)

Example 40

Preparation of 4-[2-(2-{(S)-3-Methyl-1-[3-oxo-1-(3-pyridin-2-yl-phenyl)-ethyl [azepan-4-ylcarbamoyl]-butylcarbamoyl}-benzofuran-5-yloxy)-ethyl]-piperazine-1-carboxylic acid tert-butyl ester a.) 4-[2-(2-{(S)-3-Methyl-1-[3-hydroxy-1-(3-pyridin-2-yl-phenyl)-ethyl [azepan-4-ylcarbamoyl]-butylcarbamoyl}-benzofuran-5-yloxy)-ethyl]-piperazine-1-carboxylic acid tert-butyl ester To a solution of the compound of Example 20d (0.15 g) in dichloromethane was added EDC (0.06 g), HOBt (0.04 g), triethylamine (0.14 mL) and 4-[2-(2-carboxy-benzofuran-5-yloxy)-ethyl]-piperazine-1-carboxylic acid tert-butyl ester (0.12 g). The reaction was stirred until complete by TLC analysis. Workup and column chromatography (10% methanol:ethyl acetate) provided the title compound (0.09 g): MS(EI) 797 (M+H$^+$).

b.) 4-[2-(2-{(S)-3-Methyl-1-[3-oxo-1-(3-pyridin-2-yl-phenyl)-ethyl [azepan-4-ylcarbamoyl]-butylcarbamoyl}-benzofuran-5-yloxy)-ethyl]-piperazine-1-carboxylic acid tert-butyl ester Following the procedure of Example 1i except substituting the compound of Example 40a the title compound was prepared: MS(EI) 795.9 (M+H$^+$).

Example 41

Preparation of 5-(2-piperizin-1-yl-ethoxy)-benzofuran-2-carboxylic acid ((S)-3-methyl-1-{3-oxo-1-[2-(3-pyridin-2-yl-phenyl)ethyl]-azepan-4-ylcarbamoyl}-butyl)amide Following the procedure of Example 37 except substituting the compound of Example 40b the title compound was prepared: $^1$H NMR (CDCl$_3$): δ 1.0 (m, 6H), 1.5-2.1 (m, 5H), 2.2 (m, 2H), 3.4-3.6 (m, 19H), 4.5 (m, 1H), 4.7 (m, 2H), 5.0 (m, 1H), 7.2 (m, 1H), 7.4 (m, 1H), 7.5 (m, 2H), 7.7 (m, 2H), 7.8 (m, 1H), 8.1 (m, 2H), 8.4 (m, 1H), 8.7 (m, 1H); MS(EI): 695 (M+H$^+$, 70%).

Example 42

Preparation of (S)-4-Methyl-2-(methyl-naphthalen-2-ylmethyl-amino)pentanoic acid [3-oxo-1-(pyridine-2-sulphonyl)-azepan-4-yl]-amide a.) 4-[(S)-2-(tert-Butoxycarbonyl-methyl-amino)-4-methyl-pentanoylamino]-3-hydroxy-azepane-1-carboxylic acid benzyl ester To a solution of the compound of Example 2e (0.35 g) in dichloromethane was added N-methyl-N-Boc-leucine (0.36 g), HOBt (0.2 g) and EDC (0.28 g). The reaction was stirred until complete. Workup and column chromatography (5% methanol:dichloromethane) provided 0.6 g of the title compound: MS(EI) 492 (M+H$^+$).

b.) [(S)-1-(3-Hydroxy-azepan-4-ylcarbamoyl)-3-methyl-butyl]-methyl-carbamic acid tert-butyl ester To a solution of the compound of Example 42a (0.6 g) in methanol:ethyl acetate (10:20 mL) was added 10% Pd/C and a balloon of hydrogen was attached. The reaction was stirred overnight whereupon it was filtered and concentrated to provide 0.50 g of the title: MS(EI) 358 (M+H$^+$).

c.) {(S)-1-[3-Hydroxy-1-(pyridine-2-sulfonyl)-azepan-4-yl-carbamoyl]-3-methyl-butyl}-methyl-carbamic acid tert-butyl ester To a solution of the compound of Example 42b (0.2 g) in dichloromethane was added triethylamine (0.16 mL) and 2-pyridinesulfonyl chloride (0.15 g). The reaction was stirred until complete. Workup and column chromatography (5% methanol:ethyl acetate) provided the title compound (0.23 g): MS(EI) 499 (M+H$^+$).

d.) (S)-4-Methyl-2-methylamino-pentanoic acid [3-hydroxy-1-(2-pyridine-2-sulfonyl)-azepan-4-yl]-amide To a solution of the compound of Example 42c (0.23 g) in methanol (3.0 mL) was added 4M HCl in dioxane (3.0 mL). The reaction was stirred until complete. Concentration provided the title compound: MS(EI) 399 (M+H$^+$).

e.) (S)-4-Methyl-2-(methyl-naphthalen-2-ylmethyl-amino) pentanoic acid [3-hydroxy-1-(pyridine-2-sulphonyl)-azepan-4-yl]-amide To a solution of the compound of Example 42d (0.05 g) in dichloromethane was added triethylamine (0.07 mL), 2-naphthaldehyde (0.05 g) and sodium triacetoxyborohydride (0.11 g). The reaction was stirred until complete. Workup and column chromatography (5% methanol ethyl acetate) provided the title compound (0.03 g): MS(EI) 539 (M+H$^+$).

f.) (S)-4-Methyl-2-(methyl-naphthalen-2-ylmethyl-amino) pentanoic acid [3-oxo-1-(pyridine-2-sulphonyl)-azepan-4-yl]-amide Following the procedure of Example 1i except substituting the compound of Example 42e the title compound was prepared: $^1$H NMR (CDCl$_3$): δ 1.0 (m, 6H), 1.5-2.1 (m, 5H), 2.2 (m, 5H), 2.6 (m, 1H), 3.3 (m, 1H), 3.7 (m, 2H), 4.1 (m, 1H), 4.7 (m, 1H), 5.2 (m, 1H), 7.2-8.0 (m, 10H), 8.7 (m, 1H); MS(EI): 537 (M+H$^+$, 100%).

Example 43

Preparation of (S)-4-Methyl-2-(methyl-naphthalen-2-ylmethyl-amino)pentanoic acid {3-oxo-1-[2-(3-pyridin-2-yl-2-yl-phenyl)-acetyl]-azepan-4-yl}-amide a.) ((S)-1-{3-Hydroxy-1-[2-(3-pyridin-2-yl-phenyl)-acetyl]-azepan-4-ylcarbamoyl}-3-methyl-butyl)-methyl-carbamic acid tert-butyl ester To a solution of the compound of Example 42b (0.25 g) was added 3-(2-pyridyl)phenyl acetic acid (0.16 g), HOBt (0.12 g) and EDC (0.15 g). The reaction was stirred until complete. Workup and column chromatography (5% methanol:ethyl acetate) provided the title compound (0.24 g): MS(EI) 553 (M+H$^+$).

b.) (S)-4-Methyl-2-methylamino-pentanoic acid {3-hydroxy-1-[2-(3-pyridin-2-yl-phenyl)-acetyl]-azepan-4-yl}-amide Following the procedure of Example 42d except substituting the compound of Example 43a the title compound was produced: MS(EI) 453 (M+H$^+$).

c.) (S)-4-Methyl-2-(methyl-naphthalen-2-ylmethyl-amino) pentanoic acid {3-oxo-1-[2-(3-pyridin-2-yl-phenyl)-acetyl]-azepan-4-yl}-amide Following the procedures of Examples 42e-f except substituting the compound of Example 43b the title compound was produced: $^1$H NMR (CDCl$_3$): δ 1.0 (m, 6H), 1.5-2.1 (m, 5H), 2.2 (m, 5H), 3.0 (m, 1H), 3.5 (m, 1H), 3.7 (m, 4H), 4.1 (m, 1H), 4.7 (m, 2H), 5.2 (m, 1H), 7.2-8.0 (m, 15H), 8.7 (m, 1H); MS(EI): 591 (M+H$^+$, 100%).

Example 44

Preparation of 5-(2-Morpholino-4-yl-ethoxy)-benzofuran-2-carboxylic acid methyl ((S)-3-methyl-1-{3-oxo-1-[2-(3-pyridin-2-yl-phenyl)acetyl]-azepan-4-ylcarbamoyl}-butyl)amide a.) 5-(2-Morpholino-4-yl-ethoxy)-benzofuran-2-carboxylic acid methyl ((S)-3-methyl-1-{3-hydroxy-1-[2-(3-pyridin-2-yl-phenyl)acetyl]-azepan-4-ylcarbamoyl}-butyl)amide To a solution of the compound of Example 43b (0.1 g) in dichloromethane was added 5-(2-morpholin-4-yl-ethyloxy) benzofuran-2-carboxylic acid (0.06 g), HOBt (0.026 g), TEA (0.07 mL) and EDC (0.04 g). The reaction was stirred until complete. Workup and chromatography (20% methanol:ethyl acetate) provided the title compound (0.07 g): MS(EI) 726 (M+H$^+$).

b.) 5-(2-Morpholino-4-yl-ethoxy)-benzofuran-2-carboxylic acid methyl ((S)-3-methyl-1-{3-oxo-1-[2-(3-pyridin-2-yl-phenyl)acetyl]-azepan-4-ylcarbamoyl}-butyl)amide Following the procedure of Example 1i except substituting the compound of Example 44a the title compound was prepared: $^1$H NMR (CDCl$_3$):): δ 1.0 (m, 6H), 1.5-2.1 (m, 5H), 2.2 (m, 5H), 2.7 (m, 4H), 2.8 (m, 2H), 2.9 (m, 1H), 3.5 (m, 1H), 3.7 (m, 4H), 3.9 (m, 3H), 4.3 (m, 2H), 4.7 (m, 2H), 5.4 (m, 1H), 7.2-8.0 (m, 12H), 8.5 (m, 1H); MS(EI): 724 (M+H$^+$, 100%).

Example 45

Preparation of Benzofuran-2-carboxylic acid methyl {(S)-3-methyl-1-[3-oxo-1-(pyridine-2-sulfonyl)-azepan-4-ylcarbamoyl)-3-methyl-butyl]-amide a.) Benzofuran-2-carboxylic acid methyl {(S)-3-methyl-1-[3-hydroxy-1-(pyridine-2-sulfonyl)-azepan-4-ylcarbamoyl)-3-methyl-butyl]-amide To a solution of the compound of Example 42d (0.1 g) in dichloromethane was added benzofuran-2-carboxylic acid (0.04 g), TEA (excess), HOBt (0.03 g), and EDC (0.04 g). The reaction was stirred until complete. Workup and column chromatography (5% methanol:dichloromethane) provided the title compound (0.04 g): MS(EI) 542.9 (M+H$^+$).

b.) Benzofuran-2-carboxylic acid methyl {(S)-3-methyl-1-[3-oxo-1-(pyridine-2-sulfonyl)-azepan-4-ylcarbamoyl)-3-methyl-butyl]-amide Following the procedure of Example 1i except substituting the compound of Example 45a the title compound was prepared: $^1$H NMR (CDCl$_3$): δ 1.0 (m, 6H), 1.5-2.1 (m, 8H), 2.2 (m, 2H), 2.7 (m, 1H), 3.0 (m, 1H), 3.7 (m, 2H), 4.1 (m, 1H), 4.7 (m, 1H), 5.2 (m, 1H), 7.2-8.0 (m, 8H), 8.7 (m, 1H); MS(EI): 541 (M+H$^+$, 10%).

Example 46

Preparation of 2,2,2-Trifluoro-N-((S)-3-methyl-1-{3-oxo-1-[2-(3-pyridin-2-yl-phenyl)-acetyl]-azepan-4-ylcarbamoyl}-butyl)-N-naphthylen-2-ylmethyl-acetamide a.) (S)-4-Methyl-2-[naphthylen-2-ylmethyl-(2,2,2-trifluoro-acetyl)-amino]-pentanoic acid methyl ester To a solution of the compound of Example 34a (0.5 g) in dichloromethane was added potassium carbonate (catalytic amount), and trifluoroacetic acid (0.44 g). The reaction was stirred at room temperature for 1 hour whereupon it was concentrated and chromatographed (20% ethyl acetate:hexane) to provide the title compound.

b.) (S)-4-Methyl-2-[naphthylen-2-ylmethyl-(2,2,2-trifluoro-acetyl)-amino]-pentanoic acid lithium salt To a solution of the compound of Example 46a (0.49 g) in THF:water (3 mL of a 2:1 solution) was added lithium hydroxide monohydrate (0.06 g). The reaction was stirred overnight whereupon it was concentrated to provide the title compound (0.46 g): MS(EI) 366 (M+H$^+$).

c.) 3-Hydroxy-4-{(S)-4-methyl-2-[naphthylen-2-ylmethyl-(2,2,2-trifluoro-acetyl)-amino]-pentanoylamino}-azepane-1-carboxylic acid benzyl ester To a solution of the compound of Example 2e (0.29 g) in dichloromethane was added EDC (0.24 g), HOBt (0.16 g) and the compound of Example 46b (0.46 g). The reaction was stirred until complete. Workup and column chromatography (5% methanol:ethyl acetate) provided the title compound (0.25 g): MS(EI) 614 (M+H$^+$).

d.) 2,2,2-Trifluoro-N-[(S)-1-(3-hydroxy-azepan-ylcarbamoyl)-3-methyl-butyl]-N-naphthlen-2-ylmethyl-acetamide Following the procedure of Example 42b except substituting the compound of Example 46c the title compound was produced: MS(EI) 480 (M+H$^+$).

e.) 2,2,2-Trifluoro-N-((S)-3-methyl-1-{3-hydroxy-1-[2-(3-pyridin-2-yl-phenyl)-acetyl]-azepan-4-ylcarbamoyl}-butyl)-N-naphthylen-2-ylmethyl-acetamide Following the procedure of Example 43a except substituting the compound of Example 46d the title compound was produced: MS(EI) 675 (M+H$^+$).

f.) 2,2,2-Trifluoro-N-((S)-3-methyl-1-{3-oxo-1-[2-(3-pyridin-2-yl-phenyl)-acetyl]-azepan-4-ylcarbamoyl}-butyl)-N-naphthylen-2-ylmethyl-acetamide Following the procedure of Example 1i except substituting the compound of Example 46e the title compound was prepared: $^1$H NMR (CDCl$_3$): δ 1.0 (m, 6H), 1.5-2.1 (m, 5H), 2.2 (m, 2H), 2.7 (m, 1H), 3.2 (m, 1H), 3.7 (m, 3H), 4.1 (m, 1H), 4.5 (m, 2H), 4.7 (m, 2H), 5.2 (m, 1H), 7.2-8.0 (m, 14H), 8.7 (m, 1H): MS(EI): 673 (M+H$^+$, 100%).

Example 47

Preparation of 4-[(S)-(Methanesulphonyl-naphthylen-2-ylmethyl-amino)-4-methyl-pentanoylamino]-3-oxo-azepane-1-carboxylic acid benzyl ester a.) (S)-2-(Methanesulfonyl-naphthylen-2-ylmethyl-amino)-4-methyl-pentanoic acid methyl ester To a solution of the compound of Example 34a (0.5 g) in dichloromethane was added triethylamine (0.36 mL) and methansulfonyl chloride (0.16 mL). The reaction was stirred at room temperature until complete. Workup and chromatography (20% ethyl acetate:hexanes) provided the title compound (0.24 g).

b.) (S)-2-(Methanesulfonyl-naphthylen-2-ylmethyl-amino)-4-methyl-pentanoic acid lithium salt Following the procedure of Example 46b except substituting the compound of Example 47a the title compound was prepared: MS(EI) 348 (M+H$^+$).

c.) 4-[(S)-(Methanesulphonyl-naphthylen-2-ylmethyl-amino)-4-methyl-pentanoylamino]-3-hydroxy-azepane-1-carboxylic acid benzyl ester Following the procedure of Example 46c except substituting the compound of Example 47b the title compound was prepared: MS(EI) 596 (M+H$^+$).

d.) 4-[(S)-(Methanesulphonyl-naphthylen-2-ylmethyl-amino)-4-methyl-pentanoylamino]-3-oxo-azepane-1-carboxylic acid benzyl ester Following the procedure of Example 1i except substituting the compound of Example 47c the title compound was prepared: $^1$H NMR (CDCl$_3$): δ 1.0 (m, 6H), 1.5-2.1 (m, 5H), 2.2 (m, 5H), 3.0 (m, 1H), 3.5 (m, 1H), 4.1 (m, 1H), 4.5 (m, 3H), 4.7 (m, 1H), 5.2 (m, 3H), 7.2-8.0 (m, 13H); MS(EI): 596 (M+3H$^+$, 100%).

Example 48

Preparation of Quinoline-2-carboxylic acid {(S)-3-methyl-1-[3-oxo-1-(pyridine-2-sulfonyl)-azepan-4-ylcarbamoyl]-butyl}amide a.) Quinoline-2-carboxylic acid {(S)-3-methyl-1-[3-hydroxy-1-(pyridine-2-sulfonyl)-azepan-4-ylcarbamoyl]-butyl}amide Following the procedure of Example 28b except substituting quinoline-2-carboxylic acid for benzofuran-2-carboxylic acid the title compound was prepared: MS(EI) 540 (M+H$^+$).

b.) Quinoline-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 48a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.1 (m, 1H), 4.7 (m, 2H), 5.0 (m, 1H), 7.0-7.2 (m, 1H), 7.3 (m, 1H), 7.5 (m, 1H), 7.7 (m, 1H), 7.8 (m, 3H), 8.1 (m, 1H), 8.3 (m, 2H), 8.7 (m, 2H); MS(EI): 538 (M+H$^+$, 100%).

The diastereomeric mixture was separated by HPLC to provide the faster eluting diastereoemer; MS(EI): 538 (M+H$^+$, 100%), and the slower eluting diastereomer; MS(EI): 538 (M+H$^+$, 100%).

Example 49

Preparation of Quinoline-8-carboxylic acid }(S)-3-methyl-1-[3-oxo-1-(pyridine-2-sulfonyl)-azepan-4-ylcarbamoyl]-butyl}amide a.) Quinoline-8-carboxylic acid {(S)-3-methyl-1-[3-hydroxy-1-(pyridine-2-sulfonyl)-azepan-4-ylcarbamoyl]-butyl}amide Following the procedure of Example 28b except substituting quinoline-8-carboxylic acid for benzofuran-2-carboxylic acid the title compound was prepared: MS(EI) 540 (M+H$^+$).

b.) Quinoline-8-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 49a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.5 (m, 4H), 7.6 (m, 1H), 7.7 (m, 3H), 8.2 (m, 1H), 8.6 (m, 1H), 8.7 (m, 1H), 8.9 (m, 1H); MS(EI): 538 (M+H$^+$, 100%).

Example 50

Preparation of Quinoline-6-carboxylic acid {(S)-3-methyl-1-[3-oxo-1-(pyridine-2-sulfonyl)-azepan-4-ylcarbamoyl]-butyl}amide a.) Quinoline-6-carboxylic acid {(S)-3-methyl-1-[3-hydroxy-1-(pyridine-2-sulfonyl)-azepan-4-ylcarbamoyl]-butyl}amide Following the procedure of Example 28b except substituting quinoline-6-carboxylic acid for benzofuran-2-carboxylic acid the title compound was prepared: MS(EI) 540 (M+H$^+$).

b.) Quinoline-6-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 50a the title compound was prepared: $^1$H NMR (CDCl$_3$): δ 10 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.0 (m, 2H), 7.5 (m, 2H), 7.9 (m, 2H), 8.0 (m, 3H), 8.2 (m, 1H), 8.7 (m, 1H), 8.9 (m, 1H); MS(EI): 538 (M+H$^+$, 100%).

The diastereomeric mixture was separated by HPLC to provide the faster eluting diastereoemer; MS(EI): 538 (M+H$^+$, 100%), and the slower eluting diastereomer; MS(EI): 538 (M+H$^+$, 100%).

Example 51

Preparation of Quinoline-4-carboxylic acid {(S)-3-methyl-1-[3-oxo-1-(pyridine-2-sulfonyl)-azepan-4-ylcarbamoyl]-butyl}amide a.) Quinoline-4-carboxylic acid {(S)-3-methyl-1-[3-hydroxy-1-(pyridine-2-sulfonyl)-azepan-4-ylcarbamoyl]-butyl}amide Following the procedure of Example 28b except substituting quinoline-4-carboxylic acid for benzofuran-2-carboxylic acid the title compound was prepared: MS(EI) 540 (M+H$^+$).

b.) Quinoline-4-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 51a the title compound was prepared: $^1$H NMR (CDCl$_3$): δ1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 6.5-7.2 (m, 2H), 7.4 (m, 2H), 7.5 (m, 1H), 7.7 (m, 1H), 7.9 (m, 2H), 8.0 (m, 1H), 8.2 (m, 1H), 8.7 (m, 1H), 8.9 (m, 1H); MS(EI): 538 (M+H$^+$, 100%)

The diastereomeric mixture was separated by HPLC to provide the faster eluting diastereoemer; MS(EI): 538 (M+H$^+$, 100%), and the slower eluting diastereomer; MS(EI): 538 (M+H$^+$, 100%).

Example 52

Preparation of Quinoline-3-carboxylic acid {(S)-3-methyl-1-[3-oxo-1-(pyridine-2-sulfonyl)-azepan-4-ylcarbamoyl]-butyl}amide a.) Quinoline-3-carboxylic acid {(S)-3-methyl-1-[3-hydroxy-1-(pyridine-2-sulfonyl)-azepan-4-ylcarbamoyl]-butyl}amide Following the procedure of Example 28b except substituting quinoline-3-carboxylic acid for benzofuran-2-carboxylic acid the title compound was prepared: MS(EI) 540 (M+H$^+$).

b.) Quinoline-3-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 52a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.2 (m 2H), 7.5 (m, 1H), 7.6 (m, 1H), 7.7-7.9 (m, 4H), 8.1 (m, 1H), 8.5 (m, 1H), 8.6 (m, 1H), 9.3 (m, 1H); MS(EI): 538 (M+H$^+$, 100%).

The diastereomeric mixture was separated by HPLC to provide the faster eluting diastereoemer; MS(EI): 538 (M+H$^+$, 100%), and the slower eluting diastereomer; MS(EI): 538 (M+H$^+$, 100%).

Example 53

Preparation of Isoquinoline-3-carboxylic acid {(S)-3-methyl-1-[3-oxo-1-(pyridine-2-sulfonyl)-azepan-4-ylcarbamoyl]-butyl}amide a.) Isoquinoline-3-carboxylic acid {(S)-3-methyl-1-[3-hydroxy-1-(pyridine-2-sulfonyl)-azepan-4-ylcarbamoyl]-butyl}amide Following the procedure of Example 28b except substituting isoquinoline-3-carboxylic acid for benzofuran-2-carboxylic acid the title compound was prepared: MS(EI) 540 (M+H$^+$).

b.) Isoquinoline-3-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 53a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.0 (m, 1H), 7.5 (m, 1H), 7.7 (m, 2H), 7.9 (m, 4H), 8.7 (m, 3H), 9.2 (m, 1H); MS(EI): 538 (M+H$^+$, 100%).

Example 54

Preparation of Isoquinoline-1-carboxylic acid {(S)-3-methyl-1-[3-oxo-1-(pyridine-2-sulfonyl)-azepan-4-ylcarbamoyl]-butyl}amide a.) Isoquinoline-1-carboxylic acid {(S)-3-methyl-1-[3-hydroxy-1-(pyridine-2-sulfonyl)-azepan-4-ylcarbamoyl]-butyl}amide Following the procedure of Example 28b except substituting isoquinoline-1-carboxylic acid for benzofuran-2-carboxylic acid the title compound was prepared: MS(EI) 540 (M+H$^+$).

b.) Isoquinoline-1-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 54a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.3 (m, 1H), 7.5 (m, 1H), 7.7-8.0 (m, 6H), 8.7 (m, 3H), 9.5 (m, 1H); MS(EI): 538 (M+H$^+$, 100%).

The diastereomeric mixture was separated by HPLC to provide the faster eluting diastereoemer; MS(EI): 537 (M$^+$, 100%), and the slower eluting diastereomer; MS(EI): 537 (M$^+$, 100%).

Example 55

Preparation of Quinoxaline-2-carboxylic acid {(S)-3-methyl-1-[3-oxo-1-(pyridine-2-sulfonyl)-azepan-4-ylcarbamoyl]-butyl}amide a.) Quinoxaline-2-carboxylic acid {(S)-3-methyl-1-[3-hydroxy-1-(pyridine-2-sulfonyl)-azepan-4-ylcarbamoyl]-butyl}amide Following the procedure of Example 28b except substituting quinoxaline-2-carboxylic acid for benzofuran-2-carboxylic acid the title compound was prepared: MS(EI) 541 (M+H$^+$).

b.) Quinoxaline-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 55a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.0-7.2 (m, 2H), 7.5 (m, 1H), 7.7 (m, 3H), 8.2 (m, 2H), 8.3 (m, 1H), 8.7 (m, 1H), 9.5 (m, 1H); MS(EI): 539 (M+H$^+$, 30%).

Example 56

Preparation of Benzo[b]thiophene-2-carboxylic acid {(S)-3-methyl-1-[3-oxo-1-(pyridine-2-sulfonyl)-azepan-4-ylcarbamoyl]-butyl}amide a.) Benzo[b]thiophene-2-carboxylic acid {(S)-3-methyl-1-[3-hydroxy-1-(pyridine-2-sulfonyl)-azepan-4-ylcarbamoyl]-butyl}amide Following the procedure of Example 28b except substituting benzo[b]thiophene-2-carboxylic acid for benzofuran-2-carboxylic acid the title compound was prepared: MS(EI) 545 (M+H$^+$).

b.) Benzo[b]thiophene-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 56a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 6.8-7.2 (m, 1H), 7.5 (m, 3H), 8.0 (m, 6H), 8.7 (m, 1H); MS(EI): 543 (M+H$^+$, 60%).

The diastereomeric mixture was separated by HPLC to provide the faster eluting diastereoemer; $^1$HNMR (CDCl$_3$): δ 1.0 (m, 6H), 1.5-2.2 (m, 6H), 2.7 (m, 1H), 3.8 (m, 1H), 4.1 (m, 1H), 4.7 (m, 2H), 5.1 (m, 1H), 7.4-8.0 (m, 8H), 8.7 (m, 1H); MS(EI): 543 (M+H$^+$, 100%), and the slower eluting diastereomer; 1.0 (m, 6H), 1.5-2.2 (m, 6H), 2.7 (m, 1H), 3.8 (m, 1H), 4.1 (m, 1H), 4.7 (m, 2H), 5.1 (m, 1H), 7.4-8.0 (m, 8H), 8.7 (m, 1H); MS(EI): 543 (M+H$^+$, 100%).

Example 57

Preparation of 1,8-Naphthyridine-2-carboxylic acid {(S)-3-methyl-1-[3-oxo-1-(pyridine-2-sulfonyl)-azepan-4-ylcarbamoyl]-butyl}amide a.) 1,8-Naphthyridine-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 1,8-naphthyridine-2-carboxylic acid for benzofuran-2-carboxylic acid the title compound was prepared: MS(EI) 541 (M+H$^+$).

b.) 1,8-Naphthyridine-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 57a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.2 (m, 1H), 7.6 (m, 2H), 7.9 (m, 2H), 8.3 (m, 1H), 8.4 (m, 2H), 8.5 (m, 2H), 9.2 (m, 1H); MS(EI): 539 (M+H$^+$, 100%)

Example 58

Preparation of 1H-Indole-2-carboxylic acid {(S)-3-methyl-1-[3-oxo-1-(pyridine-2-sulfonyl)-azepan-4-ylcarbamoyl]-butyl}amide a.) 1H-Indole-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 1H-indole-2-carboxylic acid for benzofuran-2-carboxylic acid the title compound was prepared: MS(EI) 528 (M+H$^+$).

b.) 1H-Indole-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 58a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 6.8 (m, 1H), 7.1 (m, 1H), 7.3 (m, 3H), 7.4 (m, 1H), 7.5 (m, 1H), 7.6 (m, 1H), 8.0 (m, 2H), 8.7 (m, 1H), 9.4 (b, 1H); MS(EI): 526 (M+H$^+$, 80%).

Example 59

Preparation of 5-Methoxybenzofuran-2-carboxylic acid {(S)-3-methyl-1-[3-oxo-1-(pyridine-2-sulfonyl)-azepan-4-ylcarbamoyl]-butyl}amide a.) 5-Methoxybenzofuran-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-methoxybenzofuran-2-carboxylic acid for benzofuran-2-carboxylic acid the title compound was prepared: MS(EI) 559 (M+H$^+$).

b.) 5-Methoxybenzofuran-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 59a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 4H), 4.0 (m, 1H), 4.7 (m, 2H), 5.0 (m, 1H), 7.0 (m, 4H), 7.6 (m, 3H), 8.0 (m, 2H), 8.7 (m, 1H); MS(EI): 557 (M+H$^+$, 70%).

The diastereomeric mixture was separated by HPLC to provide the faster eluting diastereoemer; $^1$HNMR (CDCl$_3$): δ 1.0 (m, 6H), 1.5-2.1 (m, 5H), 2.2 (m, 2H), 2.7 (t, 1H), 3.7 (m, 4H), 4.0 (d, 1H), 4.7 (m, 2H), 5.0 (d, 1H), 7.0 (m, 4H), 7.6 (m, 3H), 8.0 (m, 2H), 8.7 (d, 1H); MS(EI): 557 (M+H$^+$, 100%), and the slower eluting diastereomer; MS(EI): 557 (M+H$^+$, 100%).

Example 60

Preparation of 5-Bromo-furan-2-carboxylic acid {(S)-3-methyl-1-[3-oxo-1-(pyridine-2-sulfonyl)-azepan-4-ylcarbamoyl]-butyl}amide a.) 5-Bromo-furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-bromo-2-furoic acid for benzofuran-2-carboxylic acid the title compound was prepared: MS(EI) 558 (M+H$^+$).

b.) 5-Bromo-furan-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 60a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 6.5 (m, 1H), 6.7 (m, 1H), 7.1 (m, 2H), 7.5 (m, 1H), 8.0 (m, 2H), 8.7 (m, 1H); MS(EI): 555 (M+H$^+$, 60%).

The diastereomeric mixture was separated by HPLC to provide the faster eluting diastereoemer; MS(EI): 555 (M+H$^+$, 100%), and the slower eluting diastereomer; MS(EI): 555 (M+H$^+$, 100%).

Example 61

Preparation of Furan-2-carboxylic acid {(S)-3-methyl-1-[3-oxo-1-(pyridine-2-sulfonyl)-azepan-4-ylcarbamoyl]-butyl}amide a.) Furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 2-furoic acid for benzofuran-2-carboxylic acid the title compound was prepared: MS(EI) 479 (M+H$^+$).

b.) Furan-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 61a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 6.5 (m, 1H), 7.2 (m, 3H), 7.5 (m, 2H), 8.0 (m, 2H), 8.7 (m, 1H); MS(EI): 477 (M+H$^+$, 50%).

Example 62

Preparation of 5-Nitro-furan-2-carboxylic acid {(S)-3-methyl-1-[3-oxo-1-(pyridine-2-sulfonyl)-azepan-4-ylcarbamoyl]-butyl}amide a.) 5-Nitro-furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-nitro-2-furoic acid for benzofuran-2-carboxylic acid the title compound was prepared: MS(EI) 524 (M+H$^+$).

b.) 5-Nitro-furan-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 62a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 7.2 (m, 1H), 7.3 (m, 1H), 7.5 (m, 1H), 7.9 (m, 2H), 8.7 (m, 1H); MS(EI): 522 (M+H$^+$, 80%).

Example 63

Preparation of 5-(4-Nitro-phenyl)-furan-2-carboxylic acid {(S)-3-methyl-1-[3-oxo-1-(pyridine-2-sulfonyl)-azepan-4-ylcarbamoyl]-butyl}amide a.) 5-(4-Nitro-phenyl)-furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-(4-nitrophenyl)-2-furoic acid for benzofuran-2-carboxylic acid the title compound was prepared: MS(EI) 600 (M+H$^+$).

b.) 5-(4-Nitro-phenyl)-furan-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 63a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H). 4.0 (m, 1H), 4.7 (m, 2H), 5.0 (m, 1H), 6.9 (m, 1H), 7.2 (m, 1H), 7.5 (m, 2H), 7.9-8.0 (m, 4H), 8.5 (m, 1H), 8.6 (m, 1H); MS(EI): 598 (M+H$^+$, 80%).

Example 64

Preparation of 5-(3-Trifluoromethyl-phenyl)-furan-2-carboxylic acid {(S)-3-methyl-1-[3-oxo-1-(pyridine-2-sulfonyl)-azepan-4-ylcarbamoyl]-butyl}amide a.) 5-(3-Trifluoromethyl-phenyl)-furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-[3-(trifluoromethyl)phenyl]-2-furoic acid for benzofuran-2-carboxylic acid the title compound was prepared: MS(EI) 623 (M+H$^+$).

b.) 5-(3-Trifluoromethyl-phenyl)-furan-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 64a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H). 4.0 (m, 1H), 4.7 (m, 2H), 5.0 (m, 1H), 7.1 (m, 1H), 7.5 (m, 3H), 8.0 (m, 4H) 8.7 (m, 1H); MS(EI): 621 (M+H$^+$, 80%).

The diastereomeric mixture was separated by HPLC to provide the faster eluting diastereoemer; MS(EI): 621 (M+H$^+$, 100%), and the slower eluting diastereomer; MS(EI): 621 (M+H$^+$, 100%).

Example 65

Preparation of Tetrahydro-furan-2-carboxylic acid {(S)-3-methyl-1-[3-oxo-1-(pyridine-2-sulfonyl)-azepan-4-ylcarbamoyl]-butyl}amide a.) Tetrahydro-furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting tetrahydrofuran-2-carboxylic acid for benzofuran-2-carboxylic acid the title compound was prepared: MS(EI) 483 (M+H$^+$).

b.) Tetrahydro-furan-2-carboxylic acid {(S)-3-methyl-1-[3-oxo-1-(pyridine-2-sulfonyl)-azepan-4-ylcarbamoyl]-butyl}amide Following the procedure of Example 1i except substituting the compound of Example 65a the title compound was prepared: $^1$H NMR (CDCl$_3$): δ 1.0 (m, 6H), 1.5-2.2 (m, 12H), 2.7 (m, 1H), 3.8 (m, 3H). 4.0 (m, 1H), 4.5 (m, 2H), 4.8 (m, 1H), 5.0 (m, 1H), 7.0 (m, 1H), 7.5 (m, 1H), 7.9 (m, 2H), 8.7 (m, 1H). MS(EI): 481 (M+H$^+$, 80%).

Example 66

Preparation of (S)-4-Methyl-2-(2-phenoxy-acetylamino)-pentanoic acid [3-oxo-(pyridine-2-sulfonyl)-azepan-4-yl]-amide a.) (S)-4-Methyl-2-(2-phenoxy-acetylamino)-pentanoic acid [3-hydroxy-(pyridine-2-sulfonyl)-azepan-4-yl]-amide Following the procedure of Example 28b except substituting phenoxyacetic acid for benzofuran-2-carboxylic acid the title compound was prepared: MS(EI) 519 (M+H$^+$).

b.) (S)-4-Methyl-2-(2-phenoxy-acetylamino)-pentanoic acid [3-oxo-(pyridine-2-sulfonyl)-azepan-4-yl]-amide Following the procedure of Example 1i except substituting the compound of Example 66a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H). 4.0 (m, 1H), 4.5 (m, 3H), 4.7 (m, 1H), 5.1 (m, 1H), 7.0 (m, 3H), 7.3 (m, 2H), 7.5 (m, 1H), 7.9 (m, 2H), 8.6 (m, 1H); MS(EI): 517 (M+H$^+$, 60%).

Example 67

Preparation of (S)-2-[2-(4-Fluoro-phenoxy)-acetylamino]-4-methyl-pentanoic acid [3-oxo-(pyridine-2-sulfonyl)-azepan-4-yl]-amide a.) (S)-2-[2-(4-Floro-phenoxy)-acetylamino]-4-methyl-pentanoic acid [3-hydroxy-(pyridine-2-sulfonyl)-azepan-4-yl]-amide Following the procedure of Example 28b except substituting 4-fluorophenoxyacetic acid for benzofuran-2-carboxylic acid the title compound was prepared: MS(EI) 537 (M+H$^+$).

b.) (S)-2-[2-(4-Fluoro-phenoxy)-acetylamino]-4-methyl-pentanoic acid [3-oxo-(pyridine-2-sulfonyl)-azepan-4-yl]-amide Following the procedure of Example 1i except substituting the compound of Example 67a the title compound was prepared: $^1$H NMR (CDCl$_3$): δ 1.0 (m, 6H), 1.5-2.1 (m, 5H), 2.2 (m, 2H), 2.7 (m, 1H), 3.6 (d, 1H). 4.0 (m, 1H), 4.5 (, 3H), 4.8 (m, 1H), 5.1 (m, 1H), 7.0 (m, 4H), 7.5 (m, 1H), 7.9 (m, 2H), 8.6 (m, 1H); MS(EI): 535 (M+H$^+$, 50%).

Example 68

Preparation of Benzofuran-2-carboxylic acid {(S)-3-methyl-1-[3-oxo-1-(pyridine-2-carbonyl)-azepan-4-ylcarbamoyl)-3-butyl]-amide a.) {(S)-1-[3-Hydroxy-1-(pyridine-2-carbonyl)-azepan-4-ylcarbamoyl]-3-methyl-butyl}-carbamic acid tert-butyl ester To a solution of the compound of Example 2g (0.25 g) in dichloromethane was added picolinic acid (0.09 g), EDC (0.14 g) and HOBt (0.10 g). The reaction was stirred until complete. Workup and column chromatography (5% methanol:ethyl acetate) provided the title compound (0.35 g).

b.) (S)-2-Amino-4-methylpentanoic acid [3-hydroxy-1-(pyridine-2-carbonyl)-azepan-4-yl]-amide To a solution of the compound of Example 68a (0.34 g) in methanol (6 mL) was added 4M HCl in dioxane (6 mL). The reaction was stirred until complete whereupon it was concentrated to provide the title compound (0.34 g): MS(EI) 349 (M+H$^+$).

c.) Benzofuran-2-carboxylic acid {(S)-3-methyl-1-[3-hydroxy-1-(pyridine-2-carbonyl)-azepan-4-ylcarbamoyl)-3-butyl]-amide Following the procedure of Example 28b except substituting the compound of Example 68b the title compound was prepared: MS(EI) 493 (M+H$^+$).

d.) Benzofuran-2-carboxylic acid {(S)-3-methyl-1-[3-oxo-1-(pyridine-2-carbonyl)-azepan-4-ylcarbamoyl)-3-butyl]-amide Following the procedure of Example 1i except substituting the compound of Example 68c the title compound was prepared: $^1$H NMR (CDCl$_3$): δ 1.0 (m, 6H), 1.5-2.1 (m, 5H), 2.2 (m, 2H), 2.5 (m, 1H), 3.7 (m, 1H), 4.7 (m, 4H), 5.0 (m, 1H), 7.0-7.5 (m, 8H), 8.2 (m, 1H); MS(EI): 491 (M$^+$, 100%).

Example 69

Preparation of Benzofuran-2-carboxylic acid {(S)-3-methyl-1-[3-oxo-1-(1-oxy-pyridine-2-carbonyl)-azepan-4-ylcarbamoyl]-butyl}amide Following the procedures of Examples 68a-d except substituting picolinic acid N-oxide for picolinic acid of Example 68c the title compound was prepared: $^1$H NMR (CDCl$_3$): δ 1.0 (m, 6H), 1.5-2.1 (m, 5H), 2.2 (m, 2H), 2.5 (m, 1H), 3.5 (d, 1H). 4.0 (m, 1H), 4.7 (m, 3H), 5.5 (m, 1H), 7.0 (m, 2H), 7.2-7.5 (m, 7H), 8.1 (m, 2H); MS(EI): 507 (M$^+$, 20%).

Example 70

Preparation of 4-((S)-2-tert-Butylcarbonylamino-4-methyl-pentanoylamino)-3-oxo-azepane-1-carboxylic acid benzyl ester Following the procedure of Example 92j, except substituting 4-((S)-2-tert-Butoxycarbonylamino-4-methyl-pentanoylamino)-3-hydroxy-azepane-1-carboxylic acid benzyl ester for benzofuran-2-carboxylic acid {(S)-1-[3-hydroxy-6,6-dimethyl-1-(pyridine-2-sulfonyl)-azepan-4-ylcarbamoyl]-3-methyl-butyl}-amide, the title compound was prepared. The residue was purified by HPLC. First eluting diastereomer; MS (M+H$^+$): 476.2; $^1$H-NMR (400 MHz, CDCl$_3$): •7.40-6.95 (m, 7H), 5.25-4.60(m, 4H), 4.40-4.06(m, 2H), 3.70-3.58(t, 1H), 2.70-2.50(m, 1H), 2.25-1.30(m, 16H); and the second eluting diastereomer: 1.00-0.85(d, 6H); and the second eluting diastereomer: MS (M+H$^+$) 476.2.

Example 71

Preparation of 5,6-Dimethoxybenzofuran-2-carboxylic acid {(S)-3-methyl-1-[3-oxo-1-(1-methyl-1H-imidazole-4-sulfonyl)-azepan-4-ylcarbamoyl]-butyl}amide a.) {(S)-1-[3-Hydroxy-1-(1-methyl-1H-imidazole-2-sulfonyl)-azepan-4-ylcarbamoyl}-3-methyl-butyl}-carbamic acid tert-butyl ester To a solution of the amine of Example 2g in methylene chloride (5 ml) was added pyridine (92 μL, 1.14 mmol) followed by 1-methylimidazole-4-sulfonylchloride (0.112 g, 0.623 mmol). The reaction was allowed to stir for 16 h at room temperature. The solution was then washed with saturated aqueous NaHCO$_3$, water and brine. The product was purified by column chromatography (silica gel: methanol/methylenechloride) to yield the title compound as a white solid (0.172 g, 68%): $^1$HNMR (400 MHz, CDCl$_3$) δ 7.6 (d, 1H), 7.5 (d, 1H), 6.6 (d, 1H), 3.8 (s, 3H), 1.5 (s, 9H), 1 (d, 6H); MS(ESI): 488.2 (M+H)$^+$ b.) (S)-2-Amino-4-methyl-pentanoic acid [3-hydroxy-1-(1-methyl-1H-imidazole-2-sulfonyl)-azepan-4-yl]-amide To a solution of the compound of Example 71a (0.172 g, 0.353 mmol) in minimal MeOH was added 4M HCl in dioxane (10 mL) and stirred for 4 h at room temperature. The reaction mixture was concentrated and azeotroped with toulene (2×'s) to yield the title compound as an off white solid: MS(ESI): 388.2 (M+H)$^+$ c.) 5,6-Dimethoxybenzofuran-2-carboxylic acid {(S)-3-methyl-1-[3-hydroxyl-1-(1-methyl-1H-imidazole-4-sulfonyl)-azepan-4-ylcarbamoyl]-butyl}amide To a stirring solution of the compound of Example 71b (0.137 g, 0.353 mmol), 5,6-dimethoxybenzofuran-2-carboxylic acid (0.86 g, 0.388 mmol), triethylamine (246 mL, 1.77 mmol) and 1-hydroxybenzotriazole (0.01 g, 0.070 mmol) in DMF (5 mL) was added 1-(3-dimethylaminopropyl)3-ethylcarbodimide hydrochloride (0.074 g, 0.388 mmol). After stirring at room temperature for 16 h, the solution was diluted with EtOAc and washed successively with saturated aqueous sodium bicarbonate, water (2×'s), and saturated brine. The organic layer was dried over Na$_2$SO$_4$, filtered and concentrated. The product was purified by column chromatography (silica gel; methanoudichloromethane) to yield the title compound as a white solid (0.088 g, 42%): MS(ESI): 592.1 (M+H)$^+$ d.) 5,6-Dimethoxybenzofuran-2-carboxylic acid {(S)-3-methyl-1-[3-oxo-1-(1-methyl-1H-imidazole-4-sulfonyl)-azepan-4-ylcarbamoyl]-butyl}amide Oxalyl chloride (52 μL, 0.596 mmol) chloride was cooled to −78°. To this was added dimethyl sulfoxide (106 μL, 1.49 mmol) in methylene chloride dropwise. After stirring for 15 min at −78°, the alcohol in methylene chloride was added slowly and allowed to stir for 1 h when Et$_3$N (416 μL, 2.98 mmol) was added. The solution was then brought to room temperature and quenched with water and extracted into methylene chloride. The organic layer was separated and washed with brine, dried over MgSO$_4$, filtered and concentrated. The product was purified by column chromatography (silica gel: methanol/methylene chloride) to yield the title compound as white solid (0.068 g, 78%): $^1$H NMR (400 MHz, CDCl$_3$) δ 6.8-7.6 (m, 14H), 4 (d, 12H), 1 (d, 12H); MS(ESI): 590.1 (M+H)$^+$ Example 72

Preparation of Benzofuran-2-carboxylic acid {(S)-3-methyl-1-[1-(5-methyl-1H-[1,2,4]triazole-3-sulfonyl)-3-oxo-azepan-4-ylcarbamoyl]-butyl}amide a.) 4-((S)-2-Amino-4-methyl-pentanoylamino)-3-hydroxy-azepane-1-carboxylic acid benzyl ester To a stirring solution of the compound of Example 2f (3.5 g, 7.33 mmol) in EtOAc (0.5 mL) was added 4M HCl in dioxane (12.8 mL). The mixture was stirred for 1 h at room temperature. The reaction mixture was concentrated and azeotroped with toluene (2×20 mL) to yield the title compound as a pale yellow oil (3.13 g, 100%): MS(ESI) 378.4 (M+H)$^+$ b.) 4-{(S)-2-[(Benzofuran-2-carbonyl)-amino]-4-methyl-pentanoylamino}-3-hydroxy-azepane-1-carboxylic acid benzyl ester To a stirring solution of the compound of Example 72a (3.13 g, 7.57 mmol), benzofuran-2-carboxylic acid (1.35 g, 8.32 mmol), triethylamine (1.17 ml, 8.25 mmol) and 1-hydroxybenzotriazole (0.2 g, 1.48 mmol) in DMF (30 mL) was added 1-(3-dimethylaminopropyl)3-ethylcarbodimide hydrochloride (1.6 g, 8.33 mmol). After stirring at room temperature for 16 h, the solution was diluted with EtOAc and washed successively with saturated aqueous sodium bicarbonate, water (2×), and brine. The organic layer was dried over Na$_2$SO$_4$, filtered and concentrated. The product was purified by column chromatography (silica gel; ethylacetate/dichloromethane) to yield the title compound (3.7 g, 93%). $^1$HNMR (400 MHz, CDCl$_3$) δ 6.8-7.7 (m, 12H), 5.35 (s, 2H), 1.0 (d, 6H): MS(ESI): 522 (M+H)$^+$ c.) Benzofuran-2-carboxylic acid [(S)-1-(3-hydroxy-azepan-4-ylcarbamoyl)-3-methyl-butyl]-amide To a solution the compound of Example 72b (2.6 g, 4.9 mmol) in EtOAc (150 mL) was added 10% palladium on carbon (1.3 g) and stirred at room temperature for 64 h under a hydrogen atmosphere. The mixture was then filtered through celite and the filtrate concentrated to yield the title compound as a white solid (1.92 g, 100%): $^1$H NMR (400 MHz, CDCl$_3$) δ 6.8-7.7(m, 7H), 1.02 (d, 6H); MS(ESI) 388 (M+H)$^+$ d.) Benzofuran-2-carboxylic acid {(S)-3-methyl-1-[1-(5-methyl-1H-[1,2,4]triazole-3-sulfonyl)-3-hydroxy-azepan-4-ylcarbamoyl]-butyl}amide To a stirring solution of the compound of Example 72c (0.100 g, 0.25 mmol) and triethylamine (35 μL, 0.25 mmol) in methylene chloride (2 mL) was added 5-methyl-1H-1,2,4-triazolesulfonylchloride (0.043 g, 0.25 mmol). The reaction was allowed to stir for 10 min and washed with saturated aqueous NaHCO$_3$, water and saturated brine. The organic layer was dried over Na$_2$SO$_4$, filtered and concentrated. The compound was purified by column chromatography (silica gel; ethylacetate/hexane) to yield the title compound as a pale yellow oil (0.111, 84%): MS(ESI) 532.73 (M+H)$^+$ e.) Benzofaran-2-carboxylic acid {(S)-3-methyl-1-[1-(5-methyl-1H-[1,2,4]triazole-3-sulfonyl)-3-oxo-azepan-4-ylcarbamoyl}amide To a stirring solution of the compound of Example 72d (0.108 g, 0.206 mmol) in dimethylsulfoxide (2 mL) was added triethylamine (172 μL, 4.23 mmol) followed by sulfur trioxide pyridine (0.116 g, 0.718 mmol) and stirred for 16 h at room temperature. The reaction mixture was diluted with EtOAc and washed with water (×2). The organic layer was dried over Na$_2$SO$_4$, filtered and conentrated. The crude product was purified by column chromatography (silica gel; methanol/methylenechloride) to yield the title compound as a white solid (0.08 g, 81%): $^1$HNMR (400 MHz, CDCl$_3$) δ 7.1-7.7 (m, 7H), 2.65 (s, 3H), 1.0 (d, 6H); MS(ESI): 552.71 (M+Na)$^+$ Example 73

Preparation of Benzofuran-2-carboxylic acid {(S)-3-methyl-1-[1-(1-methyl-1H-imidazole-3-sulfonyl)-3-oxo-azepan-4-ylcarbamoyl]-butyl}amide a.) Benzofuran-2-carboxylic acid {(S)-3-methyl-1-[1-(1-methyl-1H-imidazole-3-sulfonyl)-3-hydroxy-azepan-4-ylcarbamoyl]-butyl}amide To a stirring solution of the compound of Example 72c (0.100 g, 0.25 mmol) and triethylamine (35 μL, 0.25 mmol)

was added 1-methylimidazole sulfonyl chloride (0.046 g, 0.255 mmol). The reaction was allowed to stir for 10 min and washed with saturated aqueous NaHCO$_3$, water and saturated brine. The organic layer was dried over Na$_2$SO$_4$, filtered and concentrated. The compound was purified by column chromatography (silica gel; ethylacetate/hexane) to yield the title compound as a pale yellow oil (0.113 g, 82%): $^1$HNMR (400 MHz, CDCl$_3$) δ 6.9-7.7(m, 9H), 3.9 (2s, 3H), 1.0 (d, 6H); MS(ESI): 531.8 (M+H)$^+$ b.) Benzofuran-2-carboxylic acid {(S)-3-methyl-1-[1-(1-methyl-1H-imidazole-3-sulfonyl)-3-oxo-azepan-4-ylcarbamoyl]-butyl}amide To a stirring solution of the compound of Example 73a (0.085 g, 0.159 mmol) in dimethylsulfoxide was added triethylamine (133 µL, 0.95 mmol) followed by sulfurtrioxide pyridine (0.08 g, 0.5 mmol) and stirred for 16 h at room temperature. The reaction mixture was diluted with EtOAc and washed with water (×2). The organic layer was dried over Na$_2$SO$_4$, filtered and conentrated. The crude product was purified by column chromatography (silica gel; methanol/methylenechloride) to yield the title compound as a white solid (0.072 g, 83%). MS(ESI): 529.76 (M+H)$^+$ Example 74

Preparation of Benzofuran-2-carboxylic acid {(S)-3-methyl-1-[1-(1H-imidazole-2-sulfonyl)-3-oxo-azepan-4-ylcarbamoyl]-butyl}amide a.) Benzofuran-2-carboxylic acid {(S)-3-methyl-[1-(1H-imidazole-2-sulfonyl)-3-oxo-azepan-4-ylcarbamoyl]-butyl}amide To a stirring solution of the compound of Example 72c (0.100 g, 0.25 mmol) and triethylamine (35 µL, 0.25 mmol) was added 2-imidazolesulfonyl chloride (0.046 g, 0.255 mmol). The reaction was allowed to stir for 10 min and washed with saturated aqueous NaHCO$_3$, water and saturated brine. The organic layer was dried over Na$_2$SO$_4$, filtered and concentrated. The compound was purified by column chromatography (silica gel; ethylacetate/hexane) to yield the title compound as a pale yellow oil (0.113 g, 82%): $^1$HNMR (400 MHz, CDCl$_3$) δ 7.1-7.7 (m, 9H), 4.8 (s, 1H), d, 6H); MS(ESI): 517.76 (M+H)$^+$ b.) Benzofuran-2-carboxylic acid {(S)-3-methyl-1-[1-(1H-imidazole-2-sulfonyl)-3-oxo-azepan-4-ylcarbamoyl]-butyl}amide To a stirring solution of the compound of Example 74a (0.107 g, 0.206 mmol) in dimethylsulfoxide (2 mL) was added triethylamine (172 µL, 1.23 mmol) followed by sulfurtrioxide pyridine (0.115 g, 0.718 mmol) and stirred for 16 h at room temperature. The reaction mixture was diluted with EtOAc and washed with water (×2). The organic layer was dried over Na$_2$SO$_4$, filtered and conentrated. The crude product was purified by column chromatography (silica gel; methanol/methylenechloride) to yield the title compound as a white solid (0.09 g, 85%); MS(ESI): 515.84 (M+H)$^+$ Example 75

Preparation of Benzofuran-2-carboxylic acid {(S)-3-methyl-1-[3-oxo-1-(thiazole-2-sulfonyl)-azepan-4-ylcarbamoyl]-butyl}amide a.) {(S)-1-[3-Hydroxy-1-(thiazole-2-sulfonyl)-azepan-4-ylcarbamoyl}-3-methyl-butyl}-carbamic acid tert-butyl ester To a solution of the compound of Example 2g (2.50 g, 7.29 mmol) in DCE (100 mL) was added P—NMM (4.0 g) and thioazole-2-sulphonyl chloride (1.6 g, 8.75 mmol). After shaking at room temperature overnight, the solution was filtered. The filtrate was concentrated to yield the title compound as white solid (2.50 g, 5.10 mmol, 70%); MS: 490.91 (M+H)$^+$.

b.) Benzofuran-2-carboxylic acid {(S)-3-methyl-1-[3-hyroxy-1-(thiazole-2-sulfonyl)-azepan-4-ylcarbamoyl]-butyl}-amide To a solution of the compound of Example 75b (0.15 g, 0.45 mmol) in CH$_2$Cl$_2$ (20 mL) was added benzofuran-2-carboxylic acid (0.109 g, 0.172 mmol), 1-hydroxybenzotriazole (0.106 g, 0.762 mmol), and P-EDC (0.85 g, 1 mmol/g) in CH$_2$Cl$_2$ (10 mL). After shaking at room temperature overnight, the solution was treated with tisamine (0.589 g, 3.75 mmol/g). After shaking for another 2 hr, the solution was filtered and concentrated to yield the title compound as a white solid (166.7 mg, 70%); MS (ESI): 535.3 (M+H)$^+$.

c.) Benzofuran-2-carboxylic acid{S}-3-methyl-1-[3-oxo-1-(thiazole-2-sulfonyl)-azepan-4-ylcarbamoyl]-butyl}-amide To a stirring solution of the compound of Example 75c (166.7 mg, 0.313 mmol) in dichloromethane (4 mL) was added Dess-Martin reagent (265.5 mg, 0.626 mmol). After stirring at room temperature for 2 h, solutions of sodium thiosulfate (2 mL of 10% in water) and saturated aqueous sodium bicarbonate (2 mL) were added simultaneously to the solution. The aqueous was extracted with dichloromethane (2×). The organic phases were combined, washed with saturated brine, dried (MgSO$_4$), filtered and concentrated. The residue was purified by HPLC (50:50 ethanol:hexane, 20 mL/min, 25 min, WhelkO-1(R,R) 21×250 mm column, UV detection at 280 nm and 305 nm) to yield the first elution as a white solid (84.8 mg, 50.8%). MS (ESI): 533.2 (M+H)$^+$ and the second elution as a white solid (50.1 mg, 30.0%) MS: 533.2 (M+H$^+$).

Example 76

Preparation of Benzofuran-2-carboxylic acid {(S)-3-methyl-1-[1-(1-methyl-1H-imidazole-4-sulfonyl)-3-oxo-azepan-4-ylcarbamoyl]-butyl}amide a.) {(S)-1-[3-Hydroxy-1-(1-methyl-1H-imidazole-2-sulfonyl)-azepan-4-ylcarbamoyl}-3-methyl-butyl}-carbamic acid tert-butyl ester To a solution of the amine of Example 2g in methylenechloride (5 ml) was added pyridine (92 µL, 1.14 mmol) followed by 1-methylimidazole-4-sulfonylchloride (0.112 g, 0.623 mmol). The reaction was allowed to stir for 16 h at room temperature. The solution was then washed with satutated aqueous NaHCO$_3$, water and brine. The product was purified by column chromatography (silica gel: methanol/methylenechloride) to yield the title compound as a white solid (0.172 g, 68%): $^1$HNMR (400 MHz, CDCl$_3$) δ 7.6 (d, 1H), 7.5 (d, 1H), 6.6 (d, 1H), 3.8 (s, 3H), 1.5 (s, 9H), 1 (d, 6H); MS(ESI): 488.2 (M+H)$^+$ b.) (S)-2-Amino-4-methyl-pentanoic acid [3-hydroxy-1-(1-methyl-1H-imidazole-2-sulfonyl)-azepan-4-yl]-amide To a solution of the compound of Example 76a (0.172 g, 0.353 mmol) in minimal MeOH was added 4M HCl in dioxane (10 mL) and stirred for 4 h at room temperature. The reaction mixture was concentrated and azeotroped with toulene (2×'s) to yield the title compound as an off white solid. MS(ESI): 388.2 (M+H)$^+$ c.) Benzofuran-2-carboxylic acid {(S)-3-methyl-1-[1-(1-methyl-1H-imidazole-4-sulfonyl)-3-hydroxy-azepan-4-ylcarbamoyl]-butyl}amide To a stirring solution of the compound of Example 72c (0.2 g, 0.471 mmol), benzofuran-2-carboxylic acid (0.084 g, 0.388 mmol), triethylamine (72 μL, 0.517 mmol) and 1-hydroxybenzotriazole (0.012 g, 0.088 mmol) in DMF (5 mL) was added 1-(3-dimethylaminopropyl)3-ethylcarbodimide hydrochloride (0.099 g, 0.515 mmol). After stirring at room temperature for 16 h, the solution was diluted with EtOAc and washed successively with saturated aqueous sodium bicarbonate, water (2×'s), and saturated brine. The organic layer was dried over $Na_2SO_4$, filtered and concentrated. The product was purified by column chromatography (silica gel; methanol/dichloromethane) to yield the title compound as a white solid (0.226 g, 90%): $^1$HNMR (400 MHz, $CDCl_3$) δ 6.9-8.1 (m, 18H), 3.75 (2s, 6H), 1 (d, 12H); MS(ESI): 531.80 $(M+H)^+$ d.) Benzofuran-2-carboxylic acid {(S)-3-methyl-1-[1-(1-methyl-1H-imidazole-4-sulfonyl)-3-oxo-azepan-4-ylcarbamoyl]-butyl}amide To a stirring solution of the compound of Example 76a (0.226 g, 0.426 mmol) in dimethylsulfoxide (2 mL) was added triethylamine (355 μL, 2.55 mmol) followed by sulfur trioxide pyridine (0.238 g, 1.48 mmol) and stirred for 16 h at room temperature. The reaction mixture was diluted with EtOAc and washed with water (×2). The organic layer was dried over $Na_2SO_4$, filtered and conentrated. The crude product was purified by column chromatography (silica gel; methanol/methylenechloride) to yield the title compound as a white solid (0.168 g, 76%): $^1$HNMR (400 MHz, $CDCl_3$) δ 7.1-7.7 9m, 18H), 3.7 (2s, 6H), 0.9 (d, 12H); MS(ESI): 529.80 $(M+H)^+$ Example 77

Preparation of 5-(4-Oxy-morpholino-4-yl-ethoxy)-benzofuran-2-carboxylic acid {(S)-3-methyl-1-[3-oxo-1-(pyridine-2-sulfonyl)-azepan-4-ylcarbamoyl]-butyl}amide To a solution of the compound of Example 30b (0.01 g) in dichloromethane (2 mL) was added m-CPBA (0.008 g). The reaction was stirred overnight. Workup and column chromatography (30% methanol:dichloromethane) provided the title compound: $^1$H NMR ($CDCl_3$): δ 1.0 (m, 6H), 1.5-2.1 (m, 5H), 2.2 (m, 2H), 2.5 (m, 4H), 2.7 (m, 1H), 2.8 (m, 2H), 3.7 (m, 4H), 3.8 (q, 1H). 4.0 (m, 3H), 4.7 (m, 1H), 4.8 (m, 1H), 5.0 (m, 1H), 7.0 (m, 3H), 7.4 (m, 2H), 7.5 (m, 1H), 7.9 (m, 2H), 8.6 (m, 1H); MS(EI): 671 ($M^+$, 100%).

Example 78

Preparation of Benzofuran-2-carboxylic acid {(S)-3-methyl-1-[3-oxo-1-(pyridine-3-sulfonyl)-azepan-4-ylcarbamoyl]-butyl}amide a.) 4-((S)-2-Amino-4-methyl-pentanoylamino)-3-hydroxy-azepane-1-carboxylic acid benzyl ester To a solution of 4-((S)-2-tert-butoxycarbonylamino-4-methyl-pentanoylamino)-3-hydroxy-azepan-1-carboxylic acid benzyl ester of Example 2f (4.0 g) in methanol (20 mL) was added 4M HCl in dioxane (20 mL). The reaction was stirred at room temperature for 2 hours whereupon it was concentrated to provide the title compound (3.8 g): MS(EI) 378 $(M+H^+)$.

b.) 4-{(S)-2-[(Benzofuran-2-carbonyl)-amino]-4-methyl-pentanoylamino}-3-hydroxy-azepane-1-carboxylic acid benzyl ester To a solution of 4-((S)-2-amino-4-methyl-pentanoylamino)-3-hydroxy-azepane-1-carboxylic acid benzyl ester of Example 78a (3.2 g) in dichloromethane (200 mL) was added EDC (1.48 g), HOBt (1.05 g), TEA (1.29 mL) and benzofuran-2-carboxylic acid. The reaction was stirred until complete. Workup and column chromatography (2% methanol:dichloromethane) provided the title compound (3.78 g): MS(EI) 521 $(M+H^+)$.

c.) Benzofuran-2-carboxylic acid [(S)-1-(3-hydroxy-azepan-4-ylcarbamoyl)-3-methyl-butyl]-amide To a solution of 4-{(S)-2-[(benzofuran-2-carbonyl)-amino]-4-methyl-pentanoylamino}-3-hydroxy-azepane-1-carboxylic acid benzyl ester of Example 78b (1.6 g) in methanol:ethyl acetate (50 mL: 100 mL) was added 10% Pd/C. The reaction was stirred under a balloon of hydrogen for 2 hours whereupon it was filtered and concentrated to provide the title compound (1.16 g): MS(EI) 387 $(M+H^+)$.

d.) Benzofuran-2-carboxylic acid {(S)-3-methyl-1-[3-hydroxy-1-(pyridine-3-sulfonyl)-azepan-4-ylcarbamoyl]-butyl}amide To a solution of benzofuran-2-carboxylic acid [(S)-1-(3-hydroxy-azepan-4-ylcarbamoyl)-3-methyl-butyl]-amide of Example 78c (0.3 g) in dichloromethane was added triethylamine (0.17 mL) followed by 3-pyridinesulfonyl chloride (0.25 g). The reaction was stirred at room temperature until complete as determined by TLC analysis. Workup and column chromatography (5% methanol:ethyl acetate) provided 0.32 g of the title compound: MS(EI) 528 $(M+H^+)$.

e.) Benzofuran-2-carboxylic acid {(S)-3-methyl-1-[3-oxo-1-(pyridine-3-sulfonyl)-azepan-4-ylcarbamoyl]-butyl}amide Following the procedure of Example 1i except substituting benzofuran-2-carboxylic acid {(S)-3-methyl-1-[3-hydroxy-1-(pyridine-3-sulfonyl)-azepan-4-ylcarbamoyl]-butyl}amide of Example 78d the title compound was prepared: $^1$H NMR ($CDCl_3$): δ 1.0 (m, 6H), 1.5-2.1 (m, 5H), 2.2 (m, 2H), 2.5 (m, 1H), 3.5 (d, 1H). 4.0 (m, 1H), 4.7 (m, 1H), 4.8 (m, 1H), 5.0 (m, 1H), 7.0 (m, 2H), 7.2-7.5 (m, 6H), 8.1 (m, 1H), 8.9-9.0 (m, 2H); MS(EI): 526 ($M^+$, 100%).

Example 79

Preparation of Benzofuran-2-carboxylic acid {(S)-3-methyl-1-[3-oxo-1-(1-oxy-pyridine-3-sulfonyl)-azepan-4-ylcarbamoyl]-butyl}amide a.) Benzofuran-2-carboxylic acid {(S)-3-methyl-1-[3-hydroxy-1-(1-oxy-pyridine-3-sulfonyl)-azepan-4-ylcarbamoyl]-butyl}amide To a solution of benzofuran-2-carboxylic acid {(S)-3-methyl-1-[3-hydroxy-1-(pyridine-3-sulfonyl)-azepan-4-ylcarbamoyl]-butyl}amide of Example 78d (0.05 g) in dichloromethane was added m-CPBA (0.05 g). The reacrton was stirred overnight. Workup and column chromatography (10% methanol:dichloromethane) provided the title compound (0.03 g): MS(EI) 544 $(M+H^+)$.

b.) Benzofuran-2-carboxylic acid {(S)-3-methyl-1-[3-oxo-1-(1-oxy-pyridine-3-sulfonyl)-azepan-4-ylcarbamoyl]-butyl}amide Following the procedure of Example 1i except substituting benzofuran-2-carboxylic acid {(S)-3-methyl-1-[3-hydroxy-1-(1-oxy-pyridine-3-sulfonyl)-azepan-4-ylcarbamoyl]- butyl}amide of Example 79a the title compound was prepared: $^1$H NMR (CDCl$_3$): δ 1.0 (m, 6H), 1.5-2.1 (m, 5H), 2.2 (m, 2H), 2.5 (m, 1H), 3.5 (d, 1H). 4.0 (m, 1H), 4.5 (m, 1H), 4.8 (m, 1H), 5.0 (m, 1H), 7.2-7.5 (m, 7H), 8.1-8.2 (m, 2H). MS(EI): 542 (M$^+$, 50%).

Example 80

Preparation of Quinoline-3-carboxylic acid {(S)-1-(3,4-dichloro-benzene-sulfonyl)-3-oxo-azepan-4-ylcarbamoyl)]-3-methyl-butyl}-amide Following the procedures of Example 75a-d except substituting 3,4-dichlorosulfonyl chloride for thioazole-2-sulphonyl chloride of Example 75a and quinoline-3-carboxylic acid for benzofura-2-carboxylic acid the title compound was prepared: $^1$H NMR(CDCl$_3$, 400 MHz) δ 9.34 (s, 1H), 8.61 (s, 1H), 8.14 (m, 1H), 7.81 (m, 3H), 7.60 (m, 3H), 7.19 m, 2H), 5.09 (m, 1H), 4.88 (m, 1H), 4.50 (m, 1H), 3.92 (m, 1H), 3.51 (m, 1H), 2.57 (m, 1H), 2.23 (m, 2H), 1.60 (m, 5H), 1.01 (m, 6H).

Example 81

Prepeparation of 5-Hydroxy-benzofuran-2-carboxylic acid {(S)-3-methyl-1-[1-(1-methyl-1H-imidazole-4-sulfonyl)-3-oxo-azepan-4-ylcarbamoyl]-butyl}amide a.) 5-Hydroxy-benzofuran-2-carboxylic acid {(S)-3-methyl-1-[1-(1-methyl-1H-imidazole-4-sulfonyl)-3-hydroxy-azepan-4-ylcarbamoyl]-butyl}amide To a stirring solution of the compound of Example 76b (0.1 g, 0.235 mmol), 5-hydroxybenzofuran-2-carboxylic acid (0.046 g, 0.256 mmol), triethylamine (36 μL, 0.258 mmol) and 1-hydroxybenzotriazole (0.006 g, 0.044 mmol) in DMF (5 mL), was added 1-(3-dimethylaminopropyl)3-ethylcarbodimide hydrochloride (0.05 g, 0.26 mmol). After stirring at room temperature for 16 h, the solution was diluted with EtOAc and washed successively with saturated aqueous sodium bicarbonate, water (2×), and saturated brine. The organic layer was dried over Na$_2$SO$_4$, filtered and concentrated. The product was purified by column chromatography (silica gel; methanol/dichloromethane) to yield the title compound as a white solid (0.129 g, 100%). $^1$HNMR (400 MHz, CDCl$_3$) δ 6.8-8 (m, 16H), 3.6 (2s, 6H), (d, 12H).

MS(ESI): 547.88(M+H)$^+$ b.) 5-Hydroxy-benzofuran-2-carboxylic acid {(S)-3-methyl-1-[1-(1-methyl-1H-imidazole-4-sulfonyl)-3-oxo-azepan-4-ylcarbamoyl]-butyl}amide Oxalyl chloride (13 μL, 0.149 mmol) chloride was taken to −78°. To this was added dimethyl sulfoxide (28 μL, 0.394 mmol) in methylene chloride dropwise. After stirring for 15 min at −78°, the alcohol of Example 81a in methylene chloride was added slowly and allowed to stir for 1 h when Et$_3$N (7 μL, 0.05 mmol) was added. The solution was then brought to room temperature and quenched with water and extracted into methylene chloride. The organic layer was separated and washed with brine, dried over MgSO$_4$, filtered and concentrated. The product was purified by column chromatography (silica gel: methanoumethylene chloride) to yield the title compound as white solid (0.021 g, 78%): MS(ESI) 545.9(M+H)$^+$

Example 82

Preparation of Benzofuran-2-carboxylic acid {(S)-3-methyl-1-[3-oxo-1-(1-oxy-pyridine-2-sulfonyl)-azepan-4-ylcarbamoyl)]-3-methyl-butyl}-amide a.) Benzofuran-2-carboxylic acid {(S)-3-methyl-1-[3-hydroxy-1-(1-oxy-pyridine-2-sulfonyl)-azepan-4-ylcarbamoyl)]-3-methyl-butyl}-amide To a solution of benzofuran-2-carboxylic acid [(S)-1-(3-hydroxy-azepan-4-ylcarbamoyl)-3-methyl-butyl]-amide of Example 78c (0.10 g) in dichloromethane was added triethylamine (0.07 mL) followed by 2-pyidinesulphonylchloride N-oxide. The reaction was stirred at room temperature overnight. Workup and chromatography (10% methanol:dichloromethane) provided the title compound (0.01 g): MS(EI) 544 (M+H$^+$).

b.) {(S)-3-methyl-1-[3-oxo-1-(1-oxy-pyridine-2-sulfonyl)-azepan-4-ylcarbamoyl)]-3-methyl-butyl}-amide Following the procedure of Example 1i except substituting benzofuran-2-carboxylic acid {(S)-3-methyl-1-[3-hydroxy-1-(1-oxy-pyridine-2-sulfonyl)-azepan-4-ylcarbamoyl)]-3-methyl-butyl}-amide of Example 82a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 1H), 4.7 (m, 1H), 4.8 (m, 1H), 5.0 (m, 1H), 7.0-7.5 (m, 9H), 8.1-8.2 (m, 2H). MS(EI): 542 (M$^+$, 20%).

The diastereomeric mixture was separated by HPLC to provide the faster eluting diastereoemer; $^1$HNMR (CDCl$_3$): δ 1.0 (m, 6H), 1.5-2.1 (m, 5H), 2.2 (m, 2H), 2.7 (t, 1H), 3.8 (d, 1H). 4.0 (d, 1H), 4.7 (m, 1H), 4.8 (d, 1H), 5.0 (m, 1H), 7.0-7.5 (m, 9H), 8.1-8.2 (m, 2H); MS(EI): 542 (M$^+$, 100%), and the slower eluting diastereomer; MS(EI): 542 (M+H$^+$, 100%).

Example 83

Preparation of 2-(4-{(S)-2-{(Benzofuran-2-carbonyl)-amino}-4-methyl-pentanoylamino}-3-oxo-azepane-1-sulfonyl)-benzoic acid a.) 2-(4-{(S)-2-[(Benzofuran-2-carbonyl)-amino]-4-methyl-pentanoylamino}-3-hydroxy-azepane-1-sulfonyl)-benzoic acid methyl ester Following the procedure of Example 75a-c, except substituting 2-carboxymethylsulphonyl chloride for 2-thiazolesulfonyl chloride, the title compound was prepared: MS (M+H$^+$)=585.56, M+Na$^+$=607.76, 2M+H$^+$=1170.48.

b.) 2-(4-{(S)-2-[(Benzofuran-2-carbonyl)-amino]-4-methyl-pentanoylamino}-3-hydroxy-azepane-1-sulfonyl)-benzoic acid 2-(4-{(S)-2-[(benzofuran-2-carbonyl)-amino]-4-methyl-pentanoylamino}-3-hydroxy-azepane-1-sulfonyl)-benzoic acid methyl ester (compound 83a, 180 mg, 0.309 mmol) was dissolved in 5:1 MeOH/water (6 ml) LiOH (14 mg, 0.34 mmol) was added and the reaction mixture was stirred and refluxed for 6 h. The reaction mixture was then quenched with water and 6 N HCl (adjusted to pH=2), extracted with EtOAc (3×10 ml), dried with MgSO$_4$, filtered, concentrated, and chromatographed (silica gel, 1% acetic acid/4% MeOH/CH$_2$Cl$_2$) to yield the title compound as a white solid (48 mg, 27%): M+H$^+$=572.2 c.) 2-(4-{(S)-2-[(Benzofuran-2-carbonyl)-amino]-4-methyl-pentanoylamino}-3-oxo-azepane-1-sulfonyl)-benzoic acid Following the procedure of Example 75d, except substituting 2-(4-{(S)-2-[(benzofuran-2-carbonyl)-amino]4-methyl-pentanoylamino}-3-hydroxy-azepane-1-sulfonyl)-benzoic acid for benzofuran-2-carboxylic acid {(S)-3-methyl-1-[3-hydroxy-1-(thiazole-2-sulfonyl)-azepan-4-ylcarbamoyl]-butyl}amide, the title compound was prepared: MS (M+H⁺): 570.2 (M+H⁺). ¹H NMR(400 Hz, CDCl₃—CD₃OD): δ 8.05-7.95 (m, 1H), 7.70-7.15 (m, 8H), 5.15-5.00 (m, 1H), 4.95-4.75 (m, 2H), 4.15-4.00 (m, 1H), 3.65 (d, 1H), 2.85-2.70 (m, 1H), 2.25-2.05 (m, 2H), 1.90-1.70 (m, 4H), 1.60-1.45 (m, 1H), 0.95 (d, 6H).

Example 84

Preparation of 3-(4-{(S)-2-{(Benzofuran-2-carbonyl)-amino]-4-methyl-pentanoylamino}-3-oxo-azepane-1-sulfonyl)-benzoic acid Following the procedure of Example 83, except substituting 3-carboxymethylbenzenesulphonyl chloride for 2-carboxymethylbenzenesulfonyl chloride, the title compound was prepared: MS 570.2 (M+H⁺); ¹H NMR (400 Hz, CDCl₃—CD₃OD): δ 8.46 (d, 1H), 8.31-8.25 (m, 1H), 8.00-7.97 (m, 1H), 7.70-7.62 (m, 2H), 7.55-7.46 (m, 1H), 7.45-7.35 (m, 1H), 7.30-7.25 (m, 1H), 5.10-5.05 (m, 1H), 4.95-4.78 (m, 1H), 4.75-4.55 (q, 1H), 4.00 (d, 1H), 3.5 (d, 1H), 2.60-2.40 (m, 2H), 2.25-2.15 (m, 1H), 1.95-1.70 (m, 4H), 1.55-1.40 (m, 1H), 0.98 (t, 6H).

Example 85

Preparation of Benzo[b]thiophene-2-carboxylic acid {(S)-3-methyl-1-[3-oxo-1-(1-oxy-pyridine-2-sulfonyl)-azepan-4-ylcarbamoyl]-butyl}amide a.) {(S)-1-[3-Hydroxy-1-(1-oxy-pyridine-sulfonyl)-azepan-4-ylcarbamoyl]-3-methyl-butyl-carbamic acid tert-butyl ester To a solution of [(S)-1-(3-hydroxy-azepan-4-ylcarbamoyl)-3-methyl-butyl]-carbamic acid tert butyl ester of Example 2g (2.5 g) in dichloromethane (100 mL) and saturated sodium bicarbonate was added freshly prepared 2-pyidinesulphonyl chloride N-oxide (prepared by bubbling chlorine gas through a solution of 2-mercaptopyridine-N-oxidein 9M HCl for approximately 90 minutes. Removal of excess chlorine under vacuum provided the 2-pyridinesulfonyl chloride-N-oxide). The reaction was stirred at room temperature for 1 hour. Workup and column chromatography (10% methanol:dichloromethane) provided the title compound (2.0 g): MS(EI) 500 (M+H⁺).

b.) (S)-2-Amino-4-methyl-pentanoic acid [3-hydroxy-1-(1-oxy-pyyridine-sulfonyl)-azepan-4-yl]-amide To a solution of {(S)-1-[3-hydroxy-1-(1-oxy-pyridine-sulfonyl)-azepan-4-ylcarbamoyl]-3-methyl-butyl-carbamic acid tert-butyl ester of Example 85a (2.0 g) in methanol (20 mL) was added 4M HCl in dioxane (20 mL). The reaction was stirred at room temperature for 1.5 hours whereupon it was concentrated to provide the title compound (1.8 g): MS(EI) 400 (M+H⁺).

c.) Benzo[b]thiophene-2-carboxylic acid {(S)-3-methyl-1-[3-hydroxy-1-(1-oxy-pyridine-2-sulfonyl)-azepan-4-ylcarbamoyl]-butyl}amide To a solution of (S)-2-amino-4-methyl-pentanoic acid [3-hydroxy-1-(1-oxy-pyyridine-sulfonyl)-azepan-4-yl]-amide of Example 85b (0.25 g) in dichloromethane (12 mL) was added triethylamine (0.12 mL), EDC (0.11 g), HOBt (0.077 g) and benzo[b]thiophene-2-carboxylic acid. The reaction was stirred until complete. Workup and column chromatography (10% methanol:dichloromethane) provided the title compound (0.26 g): MS(EI) 560 (M+H⁺).

d.) Benzo[b]thiophene-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substituting benzo[b]thiophene-2-carboxylic acid {(S)-3-methyl-1-[3-hydroxy-1-(1-oxy-pyridine-2-sulfonyl)-azepan-4-ylcarbamoyl]-butyl}amide of Example 85c the title compound was prepared: ¹H NMR (CDCl₃): δ 1.0 (m, 6H), 1.5-2.1 (m, 5H), 2.2 (m, 2H), 2.7 (m, 1H), 3.8 (q, 1H). 4.0 (m, 1H), 4.7 (m, 1H), 4.8 (m, 1H), 5.0 (m, 1H), 7.5 (m, 4H), 7.8 (m, 3H), 8.1-8.2 (m, 2H). MS(EI): 558 (M⁺, 100%).

The diastereomeric mixture was separated by HPLC to provide the faster eluting diastereoemer; MS(EI): 558 (M⁺, 100%), and the slower eluting diastereomer; MS(EI): 558 (M⁺, 100%).

Example 86

Preparation of 5-Bromo-furan-2-carboxylic acid {(S)-3-methyl-1-[3-oxo-1-(1-oxy-pyridine-2-sulfonyl)-azepan-4-ylcarbamoyl]-butyl}amide a. 5-Bromo-furan-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 5-bromo-2-furoic acid for benzo[b]thiophene-2-carboxylic acid the title compound was prepared: MS(EI) 574 (M+H⁺).

b.) 5-Bromo-furan-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substituting 5-bromo-furan-2-carboxylic acid {(S)-3-methyl-1-[3-hydroxy-1-(1-oxy-pyridine-2-sulfonyl)-azepan-4-ylcarbamoyl]-butyl}amide of Example 86a the title compound was prepared: ¹H NMR (CDCl₃): δ 1.0 (m, 6H), 1.5-2.1 (m, 5H), 2.2 (m, 2H), 2.7 (m, 1H), 3.8 (q, 1H). 4.0 (m, 1H), 4.7 (m, 1H), 4.8 (m, 1H), 5.0 (m, 1H), 7.0 (m, 2H), 7.4 (m, 2H), 8.1-8.2 (m, 2H); MS(EI): 570 (M⁺, 100%)

The diastereomeric mixture was separated by HPLC to provide the faster eluting diastereoemer; MS(EI): 572 (M+H⁺, 100%), and the slower eluting diastereomer; MS(EI): 572 (M+H⁺, 100%).

Example 87

Preparation of 5,6-Dimethoxybenzofuran-2-carboxylic acid {(S)-3-methyl-1-[3-oxo-1-(1-oxy-pyridine-2-sulfonyl)-azepan-4-ylcarbamoyl]-butyl}amide a.) 5,6-Dimethoxybenzofuran-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 5,6-dimethoxybenzofuran-2-carboxylic acid for benzo[b]thiophene-2-carboxylic acid the title compound was prepared: MS(EI) 604 (M+H⁺).

b.) 5,6-Dimethoxybenzofuran-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substituting 5,6-dimethoxybenzofuran-2-carboxylic acid {(S)-3-methyl-1-[3-hydroxy-1-(1-oxy-pyridine-2-sulfonyl)-azepan-4-ylcarbamoyl]-butyl amide of Example 87a the title compound was prepared: $^1$H NMR (CDCl$_3$): δ 1.0 (m, 6H), 1.5-2.1 (m, 5H), 2.2 (m, 2H), 2.7 (m, 1H), 3.8 (m, 7H). 4.0 (m, 1H), 4.7 (m, 1H), 4.8 (m, 1H), 5.0 (m, 1H), 7.0-7.5 (m, 5H), 8.1-8.2 (m, 2H); MS(EI): 602 (M$^+$, 100%).

The diastereomeric mixture was separated by HPLC to provide the faster eluting diastereoemer; MS(EI): 602 (M$^+$, 100%), and the slower eluting diastereomer; MS(EI): 602 (M$^+$, 100%).

Example 88

Preparation of 1-Oxy-pyridine-2-carboxylic acid {(S)-3-methyl-1-[3-oxo-1-(pyridine-2-sulfonyl)-azepan-4-ylcarbamoyl]-butyl}amide a.) 1-Oxy-pyridine-2-carboxylic acid {(S)-3-methyl-1-[3-hydroxy-1-(pyridine-2-sulfonyl)-azepan-4-ylcarbamoyl]-butyl}amide Following the procedure of Example 28b except substituting picolinic acid N-oxide for benzofuran-2-carboxylic acid the title compound was prepared: MS(EI) 505 (M+H$^+$).

b.) 1-Oxy-pyridine-2-carboxylic acid {(S)-3-methyl-1-[3-oxo-1-(pyridine-2-sulfonyl)-azepan-4-ylcarbamoyl]-butyl}amide Following the procedure of Example 1i except substituting 1-oxy-pyridine-2-carboxylic acid {(S)-3-methyl-1-[3-hydroxy-1-(pyridine-2-sulfonyl)-azepan-4-ylcarbamoyl]-butyl}amide of Example 88a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.1 (m, 1H), 4.7 (m, 2H), 5.0 (m, 1H), 7.5 (m, 3H), 7.9 (m 2H), 8.3-8.4 (m, 2H), 8.6 (m, 1H); MS(EI): 503 (M$^+$, 100%)

Example 89

Preparation of (S)-4-Methyl-2-(pyridine-2-sulfonylamino)-pentanoic acid [3-oxo-1-(pyridine-2-sulfonyl)-azepan-4-yl]-amide a.) (S)-4-Methyl-2-(pyridine-2-sulfonylamino)-pentanoic acid [3-hydroxy-1-(pyridine-2-sulfonyl)-azepan-4-yl]-amide To a solution of (S)-2-amino-4-methyl-pentanoic acid [3-hydroxy-1-(pyridine-2-sulfonyl)-azepan-4-yl]-amide of Example 28a (0.25 g) in dichloromethane was added triethylamine (0.27 mL) and 2-pyridinesulfonyl chloride (0.15 g). The reaction was stirred until complete. Workup and column chromatography (5% methanol:dichloromethane) provided the title compound (0.09 g): MS(EI) 525 (M+H$^+$).

b.) (S)-4-Methyl-2-(pyridine-2-sulfonylamino)-pentanoic acid [3-hydroxy-1-(pyridine-2-sulfonyl)-azepan-4-yl]-amide Following the procedure of Example 1i except substituting (S)-4-methyl-2-(pyridine-2-sulfonylamino)-pentanoic acid [3-hydroxy-1-(pyridine-2-sulfonyl)-azepan-4-yl]-amide of Example 89a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 1H), 4.7 (m, 1H), 5.0 (m, 1H), 5.5 (m, 1H), 7.0 (m 1H), 7.5 (m, 2H), 7.9 (m 3H), 8.6 (m, 2H). MS(EI): 523 (M$^+$, 100%).

Example 90

Preparation of (S)-2-(3-Benzyl-ureido)-4-methyl-pentanoic acid [3-oxo-1-(pyridine-2-sulfonyl)-azepan-4-yl]-amide a.) (S)-2-(3-Benzyl-ureido)-4-methyl-pentanoic acid [3-hydroxy-1-(pyridine-2-sulfonyl)-azepan-4-yl]-amide To a solution of (S)-2-amino-4-methyl-pentanoic acid [3-hydroxy-1-(pyyridine-sulfonyl)-azepan-4-yl]-amide of Example 28a (0.25 g) in dichloromethane was added triethylamine (0.17 mL) and benzyl isocyanate (0.088 g). The reaction was stirred until complete. Workup and column chromatography (5% methanol:dichloromethane) provided the title compound (0.12 g).

b.) (S)-2-(3-Benzyl-ureido)-4-methyl-pentanoic acid [3-oxo-1-(pyridine-2-sulfonyl)-azepan-4-yl]-amide Following the procedure of Example 1i except substituting (S)-2-(3-benzyl-ureido)-4-methyl-pentanoic acid [3-hydroxy-1-(pyridine-2-sulfonyl)-azepan-4-yl]-amide of Example 89a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 3H), 4.5 (t, 1H), 4.7 (m, 1H), 5.0 (m, 1H), 7.2 (, 5H), 7.5 (m, 1H), 7.9 (m, 2H), 8.6 (m, 1H); MS(EI): 515 (M$^+$, 60%).

The diastereomeric mixture was separated by HPLC to provide the faster eluting diastereoemer; MS(EI): 516 (M+H$^+$, 100%), and the slower eluting diastereomer; MS(EI): 516 (M+H$^+$, 100%).

Example 91

Preparation of (S)-2-(3-Phenyl-uriedo)-4-methyl pentanoic acid [3-oxo-1-(pyridine-2-sulfonyl)-azepan-4-yl]-amide a.) (S)-2-(3-Phenyl-ureido)-4-methyl-pentanoic acid [3-hydroxy-1-(pyridine-2-sulfonyl)-azepan-4-yl]-amide Following the procedure of Example 90a except substituting phenyl isocyante for benzyl isocyanate the title compound was prepared:: MS(EI) 503 (M+H$^+$).

b.) (S)-2-(3-Phenyl-ureido)-4-methyl-pentanoic acid [3-oxo-1-(pyridine-2-sulfonyl)-azepan-4-yl]-amide Following the procedure of Example 1i except substituting (S)-2-(3-phenyl-ureido)-4-methyl-pentanoic acid [3-hydroxy-1-(pyridine-2-sulfonyl)-azepan-4-yl]-amide of Example 91a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 1H), 4.5 (t, 1H), 4.7 (m, 1H), 5.0 (m, 1H), 7.0-7.9 (m, 8H), 8.6 (m, 1H). MS(EI): 501 (M$^+$, 60%).

Example 92

Preparation of Benzofuran-2-carboxylic acid {(S)-1-[6,6-dimethyl-3-oxo-1(pyridine-sulphonyl)-azepan-4-ylcarbamoyl]-3-methyl-butyl}-amide a.) Allyl-(2,2-dimethyl-pent-4-enylidene)-amine 2,2-Dimethyl-4-pentenal (2.8 g, 25 mmol) was dissolved in 15 mL benzene. To this solution allylamine (2.85 g, 50 mmol) was added. A few molecular sieves were used to absorb water generated during the reaction. The mixture was stirred at room temperature overnight. Removal of the solvent and excess amount of allylamine on rotavapor provided 3.76 g of the title compound as clear liquid (yield 100%). $^1$H-NMR (400 MHz, CDCl$_3$): •7.52(s, 1H), 5.99-5.90(m, 1H), 5.80-5.70(m, 1H), 5.15-4.99(m, 4H), 4.01-3.99(m, 2H), 2.17(d, 2H), 1.06(s, 6H).

b.) Allyl-(2,2-dimethyl-pent-4-enyl)-amine

Allyl-(2,2-dimethyl-pent-4-enylidene)-amine of Example 92a (3.76 g, 25 mmol) was diluted in 5 ml MeOH. To the solution NaBH$_4$ (0.95 g, 25 mmol) was added at 0° C. After addition the mixture was stirred at r.t. for 5 h. Methanol was removed on rotavapor and the residue was partitioned between EtOAc/20% NaOH. The organic layer was dried over Na$_2$SO$_4$, fitered and evaperated to give 2.26 g of the title compound: MS (M+H$^+$): 154.0; $^1$H-NMR (400 MHz, CDCl$_3$): 5.93-5.76(m, 2H), 5.29-4.99(m, 4H), 3.22(d, 2H), 2.34(s, 2H), 2.01(d, 2H), 0.94(s, 6H).

c.) Pyridine-2-sulfonic acid allyl-(2,2-dimethyl-pent-4-enyl)-amide

Allyl-(2,2-dimethyl-pent-4-enyl)-amine (0.43 g, 2.8 mmol) and NMM (0.57 g, 5.6 mmol) were mixed in 30 mL CH$_2$Cl$_2$. 2-pryridinesulphonyl chloride was added slowly to the solution while it was cooled in an ice-water bath. After addition, the reaction mixture was stirred at r.t. overnight. Washed by 10% NaHCO$_3$ and the brine. Purified by column chromatography gave 0.6 g colorless oil in 73% yield. MS (M+H$^+$): 295.2; $^1$H-NMR (400 MHz, CDCl$_3$): •8.71-8.70(d, 1H), 7.98-7.86(m, 2H), 7.48-7.46(m, 1H), 5.88-5.77(m, 1H), 5.55-5.45(m, 1H), 5.13-5.00(m, 4H), 4.05-4.04(d, 2H), 3.24 (s, 2H), 2.07-2.05(d, 2H), 0.96(s, 6H)

d.) .3,3-Dimethyl-1-(pyridine-2-sulfonyl)-2,3,4,7-tetrahydro-1H-azepine

Pyridine-2-sulfonic acid allyl-(2,2-dimethyl-pent-4-enyl)-amide (0.6 g, 2 mmol) was diluted in CH$_2$Cl$_2$ (50 ml) After carefully degass by Ar, Grubbs catalyst (0.17 g, 0.2 mmol) was added under Ar protection. The mixture was then refluxed for 2 h before the solvent was removed on rotavapor. The crude product was purified by column chromatography (5%-20% E/H) to give 0.47 g of the title compound in 87% yield. MS (M+H$^+$): 267.0; $^1$H-NMR (400 MHz, CDCl$_3$): •8.70-8.69(d, 1H), 7.96-7.88(m, 2H), 7.49-7.46(m, 1H), 5.81-5.70(m, 2H), 3.93-3.92(d, 2H), 3.26(s, 2H), 2.13-2.12 (d, 2H), 1.00(s, 6H)

e.) 5,5-Dimethyl-3-(pyridine-2-sulfonyl)-8-oxa-3-aza-bicyclo[5.1.0]octane

To the solution of the compound of Example 92d (1.2 g, 4.5 mmol) in 50 mL CH$_2$Cl$_2$ was added NaHCO$_3$ (2.4 g, 13.5 mmol) and then MCPBA (1.2 g, 13.5 mmol) in portions. The reaction was stirred at r.t. for 4 h before it was worked up by washing with 15% NaOH, saturated K$_2$CO$_3$, brine and dried (Na$_2$SO$_4$) to give 1.0 g crude product in 79% yield (good enough for next reaction without further purification.) MS (M+H$^+$): 283.0; $^1$H-NMR (400 MHz, CDCl$_3$): •8.68-8.67(d, 1H), 8.03-7.87(m, 2H), 7.49-7.40(m, 1H), 4.44-3.89(q, 1H), 3.62-3.59(d, 1H), 3.50(m, 1H), 3.00(m, 1H), 2.78-2.62(m, 2H), 2.12-2.06(m, 1H), 1.52-1.46(q, 1H), 1.20(s, 3H), 0.89(s, 3H).

f.) 4-Azido-6,6-dimethyl-1-(pyridine-2-sulfonyl)-azepan-3-ol 5,5-Dimethyl-3-(pyridine-2-sulfonyl)-8-oxa-3-aza-bicyclo[5.1.0]octane from Example 92e (1.2 g, 4.3 mmol) was dissolved in the mixture of 7 ml MeOH and 1 ml H$_2$O. NaN$_3$ (0.83 g, 13 mmol) and NH$_4$Cl (0.7 g, 13 mmol) were added to the solution. The resulting mixture was refluxed overnight. After the removal of MeOH, the residue was diluted in EtOAc and washed with 10% NaHCO$_3$ and brine. Purified on column chromatography gave 0.4 g 4-azido-6,6-dimethyl-1-(pyridine-2-sulfonyl)-azepan-3-ol (yield 29%); MS (M+H$^+$): 326.2; $^1$H-NMR (400 MHz, CDCl$_3$): •8.68-8.67(m, 1H), 8.05-7.90(m, 2H), 7.53-7.50(m, 1H), 3.75-3.60(m, 3H), 3.49-3.30(m, 3H), 1.73-1.66(m, 1H), 1.56-1.52(d, 1H), 1.07(s, 3H), 0.99(s, 3H)

g.) 4-Amino-6,6-dimethyl-1-(pyridine-2-sulfonyl)-azepan-3-ol

4-Azido-6,6-dimethyl-1-(pyridine-2-sulfonyl)-azepan-3-ol from Example 92f (0.4 g, 1.23 mmol) was dissolved in THF (50 ml) and H$_2$O (0.2 ml). PPh$_3$ (0.48 g, 1.85 mmol) was added to this solution. The reaction mixture was stirred at 45° C. over night. TLC showed no starting material left. THF was evaporated, azeotroped with toluene (2×'s). The resulting thick oil was dissolved in MeOH, treated with HCl in ether to adjust pH to acidic. More ether was added and the solution turned cloudy. 0.22 g white precipitate of the title compound was collected. (45% yield); $^1$H-NMR (400 MHz, CD$_3$OD): •8.68(m, 1H), 8.10-7.93(m, 2H), 7.62(m, 1H), 3.90(m, 1H), 3.68(m, 1H), 3.40-2.90(m, 4H), 1.82(m, 1H), 1.53(d, 1H), 1.05(s, 6H)

h.) {(S)-1-[3-Hydroxy-6,6-dimethyl-1-(pyridine-2-sulfonyl)-azepan-4-ylcarbamoyl]-3-methyl-butyl}-carbamic acid tert-butyl ester 4-Amino-6,6-dimethyl-1-(pyridine-2-sulfonyl)-azepan-3-ol HCl salt from Example 92g (0.22 g, 0.6 mmol) was dissolved in 5 ml DMF. To this solution, was added Boc-Leu-OH (0.22 g, 0.9 mmol) and HBTU (0.34 g, 0.9 mmol) and then NMM (0.24 g, 2.4 mmol). The mixture was stirred at r.t. overnight. DMF was removed under high vacuum. The residue was diluted with EtOAc and washed with H$_2$O, 10% NaHCO$_3$ and brine. Purification by column chromatography gave 0.22 g of the title compound (72% yield); MS (M+H$^+$): 512.9; $^1$H-NMR (400 MHz, CDCl$_3$): •8.68-8.67(d, 1H), 7.97-7.88(m, 2H), 7.69-7.64(m, 1H), 6.62-6.53(m, 1H), 5.06-5.00 (m, 1H), 4.03-3.18(m, 7H), 1.80-1.42(m, 15H), 1.04-0.92(m, 12H).

i.) Benzofuran-2-carboxylic acid {(S)-1-[3-hydroxy-6,6-dimethyl-1-(pyridine-2-sulfonyl)-azepan-4-ylcarbamoyl]-3-methyl-butyl}-amide To {(S)-1-[3-Hydroxy-6,6-dimethyl-1-(pyridine-2-sulfonyl)-azepan-4-ylcarbamoyl]-3-methyl-butyl}-carbamic acid tert-butyl ester of Example 92h (0.22 g, 0.43 mmol) was added HCl/dioxane (4M, 20 ml, 80 mmol). The mixture was stirred at r.t. for 2 h before solvents and excess amount of HCl was removed on rotavapor. The resulting white solid was dissolved in 5 ml DMF. To the solution was added 2-benzofurancarboxylic acid (84 mg, 0.52 mmol), HBTU (0.2 g, 0.52 mmol) and NMM (0.2 g, 2 mmol). The mixture was stirred at r.t. overnight. DMF was then removed and the residue was redissolved in EtOAc (50 ml), washed with 10% NaHCO$_3$ (50 ml×2) and brine (50 ml). Evaporation of the solvent gave crude product 0.26 g. Purification by column chromatograghy gave the title compound 0.15 g in 63% total yield; MS (M+H$^+$): 556.8; $^1$H-NMR (400 MHz, CDCl$_3$): •8.66-8.63(m, 1H), 7.94-7.11(m, 10H), 4.72(m, 1H), 4.01-2.98(m, 7H), 1.78-1.39(m, 5H), 1.02-0.85(m, 12H).

j.) Benzofuran-2-carboxylic acid {(S)-1-[3-oxo-6,6-dimethyl-1-(pyridine-2-sulfonyl)-azepan-4-ylcarbamoyl]-3-methyl-butyl}-amide To a solution of benzofuran-2-carboxylic acid {(S)-1-[3-hydroxy-6,6-dimethyl-1-(pyridine-2-sulfonyl)-azepan-4-ylcarbamoyl]-3-methyl-butyl}-amide from Example 92i (100 mg, 0.18 mmol) in 2 ml CH$_2$Cl$_2$, was added Dess-Martin reagent (76 mg, 0.18 mmol) at r.t. The solution was stirred for 2 h when 20 ml CH$_2$Cl$_2$ was added and then washed with NaHCO$_3$ and brine. Purification by column chromatograghy (50% ethyl acetate in hexane) gave 70 mg of the title compound in 70% yield. MS (M+H$^+$): 555.4; 1H-NMR (400 MHz, CDCl$_3$): •8.68-8.67(d, 1H), 7.97-7.93(m, 2H), 7.69-7.28(m, 6H), 7.32-6.92(m, 2H), 5.24(m, 1H), 4.79-4.69(m, 2H), 3.80-3.71(m, 2H), 2.54-2.50(d, 1H), 1.92-1.76(m, 4H), 1.45-1.40(m, 4H), 1.01-0.91(m, 9H).

The diastereomeric mixture was separated by HPLC to provide the faster eluting diastereoemer; MS (M+H$^+$): 555.2, and the slower eluting diastereomer; MS (M+H$^+$): 555.2.

Example 93

Preparation of 5-Methoxybenzofuran-2-carboxylic acid {(S)-3-methyl-1-[3-oxo-1-(1-oxy-pyridine-2-sulfonyl)-azepan-4-ylcarbamoyl]-butyl}amide a.) 5-Methoxybenzofuran-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 5-methoxybenzofuran-2-carboxylic acid for benzo[b]thiophene-2-carboxylic acid the title compound was prepared: MS(EI) 574 (M+H$^+$).

b.) 5-Methoxybenzofuran-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 5-methoxybenzofuran-2-carboxylic acid {(S)-3-methyl-1-[3-hydroxy-1-(1-oxy-pyridine-2-sulfonyl)-azepan-4-ylcarbamoyl]-butyl}amide of Example 93a the title compound was prepared: $^1$H NMR (CDCl$_3$): δ 1.0 (m, 6H), 1.5-2.1 (m, 5H), 2.2 (m, 2H), 2.7 (m, 1H), 3.8 (m, 4H). 4.0 (m, 1H), 4.5 (t, 1H), 4.7 (m, 1H), 5.0 (m, 1H), 7.4-8.6 (m, 8H) 8.0-8.2 (m, 2H); MS(EI): 572 (M$^+$, 30%).

The diastereomeric mixture was separated by HPLC to provide the faster eluting diastereoemer; $^1$HNMR (CDCl$_3$): δ 1.0 (m, 6H), 1.5-2.1 (m, 5H), 2.2 (m, 2H), 2.7 (t, 1H), 3.7 (s, 3H), 3.8 (d, 1H). 4.0 (d, 1H), 4.7 (m, 1H), 4.8 (d, 1H), 5.0 (m, 1H), 7.4-8.6 (m, 8H) 8.0-8.2 (m, 2H); MS(EI): 573 (M+H$^+$, 100%) and the slower eluting diastereomer; MS(EI): 573 (M+H$^+$, 100%).

Example 94

Preparation of Thieno[3,2-b]thiophene-2-carboxylic acid {(S)-3-methyl-1-[3-oxo-1-(1-oxy-pyridine-2-sulfonyl)-azepan-4-ylcarbamoyl]-butyl}amide a.) Thieno[3,2-b]thiophene-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting thieno[3,2-b]thiophene-2-carboxylic acid for benzo[b]thiophene-2-carboxylic acid the title compound was prepared: MS(EI) 566 (M+H$^+$).

b.) Thieno[3,2-b]thiophene-2-carboxylic acid {(S)-3-methyl-1-[3-oxo-1-(1-oxy-pyridine-2-sulfonyl)-azepan-4-yl-carbamoyl]-butyl}amide Following the procedure of Example 1i except substuting thieno[3,2-b]thiophene-2-carboxylic acid {(S)-3-methyl-1-[3-hydroxy-1-(1-oxy-pyridine-2-sulfonyl)-azepan-4-ylcarbamoyl]-butyl}amide of Example 94a the title compound was prepared: $^1$H NMR (CDCl$_3$): δ 1.0 (m,6H), 1.5-2.1 (m, 5H), 2.2 (m, 2H), 2.7 (m, 1H), 3.8 (q, 1H). 4.0 (m, 1H), 4.5 (t, 1H), 4.7 (m, 1H), 5.0 (m, 1H), 7.4-7.5 (m, 6H), 7.7 (d, 1H), 8.0-8.2 (m, 2H). MS(EI): 564 (M$^+$, 100%).

The diastereomeric mixture was separated by HPLC to provide the faster eluting diastereoemer; $^1$HNMR (CDCl$_3$): δ 1.0 (m, 6H), 1.5-2.1 (m, 5H), 2.2 (m, 2H), 2.7 (t, 1H), 3.8 (d, 1H). 4.0 (d, 1H), 4.5 (m, 1H), 4.7 (d, 1H), 5.0 (m, 1H), 7.4-7.5 (m, 6H), 7.7 (d, 1H), 8.0-8.2 (m, 2H); MS(EI): 565 (M+H$^+$, 100%) and the slower eluting diastereomer; MS(EI): 565 (M+H$^+$, 100%).

Example 95

Preparation of Quinoxaline-2-carboxylic acid {(S)-3-methyl-1-[3-oxo-1-(1-oxy-pyridine-2-sulfonyl)-azepan-4-ylcarbamoyl]-butyl}amide a.) Quinoxaline-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting quinoxaline-2-carboxylic acid for benzo[b]thiophene-2-carboxylic acid the title compound was prepared: MS(EI) 556 (M+H$^+$).

b.) Quinoxaline-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting quinoxaline-2-carboxylic acid {(S)-3-methyl-1-[3-hydroxy-1-(1-oxy-pyridine-2-sulfonyl)-azepan-4-ylcarbamoyl]-butyl}amide of Example 95a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 1H), 4.5 (t, 1H), 4.7 (m, 1H), 5.0 (m, 1H), 7.4-7.5 (m, 2H), 7.9 (m, 1H), 8.0-8.4 (m, 4H, 9.6 (d, 1H); MS(EI): 554 (M$^+$, 100%).

The diastereomeric mixture was separated by HPLC to provide the faster eluting diastereoemer; MS(EI): 555 (M+H$^+$, 100%) and the slower eluting diastereomer; MS(EI): 555 (M+H$^+$, 100%).

Example 96

Preparation of Quinoline-2-carboxylic acid {(S)-3-methyl-1-[3-oxo-1-(1-oxy-2-pyridine-2-sulfonyl)-azepan-4-ylcarbamoyl]-butyl}amide a.) Quinoline-2-carboxylic acid {(S)-3-methyl-1-[3-hydroxy-1-(1-oxy-pyridine-2-sulfonyl)-azepan-4ylcarbamoyl]-butyl}amide Following the procedure of Example 85c except substituting quinoline-2-carboxylic acid for benzo[b]thiophene-2-carboxylic acid the title compound was prepared: MS(EI) 555 (M+H$^+$).

b.) Quinoline-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting quinoline-2-carboxylic acid {(S)-3-methyl-1-[3-hydroxy-1-(1-oxy-pyridine-2-sulfonyl)-azepan-4-ylcarbamoyl]-butyl}amide of Example 96a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 1H), 4.5 (t, 1H), 4.7 (m, 1H), 5.0 (m, 1H), 7.4-8.6 (m, 10H); MS(EI): 553 (M$^+$, 100%).

The diastereomeric mixture was separated by HPLC to provide the faster eluting diastereoemer; MS(EI): 554 (M+H+, 100%) and the slower eluting diastereomer; MS(EI): 554 (M+H+, 100%).

Example 97

Preparation of Thiophene-3-carboxylic-acid {(S)-3-methyl-1-[3-oxo-1-(1-oxy-pyridine-2-sulfonyl)-azepan-4-ylcarbamoyl]-butyl}amide a.) Thiophene-3-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting thiophene-3-carboxylic acid for benzo[b]thiophene-2-carboxylic acid the title compound was prepared: MS(EI) 510 (M+H+).

b.) Thiophene-3-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting thiophene-3-carboxylic acid {(S)-3-methyl-1-[3-hydroxy-1-(1-oxy-pyridine-2-sulfonyl)-azepan-4-ylcarbamoyl]-butyl}amide of Example 97a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H). 4.0 (m, 1H), 4.5 (t, 1H), 4.7 (m, 1H), 5.0 (m, 1H), 7.4-8.0 (m, 4H), 7.8 (m, 1H), 8.1-8.2 (m, 2H); MS(EI): 508 (M+, 80%).

Example 98

Preparation of 1H-Indole-5-carboxylic acid {(S)-3-methyl-1-[3-oxo-1-(1-oxy-pyridine-2-sulfonyl)-azepan-4-ylcarbamoyl]-butyl}amide a.) 1H-Indole-5-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 1H-indole-5-carboxylic acid for benzo[b]thiophene-2-carboxylic acid the title compound was prepared: MS(EI) 543 (M+).

b.) 1H-Indole-5-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting of 1H-indole-5-carboxylic acid {(S)-3-methyl-1-[3-hydroxy-1-(1-oxy-pyridine-2-sulfonyl)-azepan-4-ylcarbamoyl]-butyl}amide of Example 98a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H), 7.4-8.0 (m, 7H), 8.1-8.2 (m, 2H), 8.6 (b, 1H); MS(EI): 541 (M+, 100%).

The diastereomeric mixture was separated by HPLC to provide the faster eluting diastereoemer; MS(EI): 542 (M+H+, 80%) and the slower eluting diastereomer; MS(EI): 542 (M+H+, 80%).

Example 99

Preparation of Benzo[1,3]dioxole-5-carboxylic acid {(S)-3-methyl-1-[3-oxo-1-(1-oxy-pyridine-2-sulfonyl)-azepan-4-ylcarbamoyl]-butyl}amide a.) Benzo[1,3]dioxole-5-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting Benzo[1,3]dioxole-5-carboxylic acid for benzo[b]thiophene-2-carboxylic acid the title compound was prepared: MS(EI) 548 (M+).

b.) Benzo[1,3]dioxole-5-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting benzo[1,3]dioxole-5-carboxylic acid {(S)-3-methyl-1-[3-hydroxy-1-(1-oxy-pyridine-2-sulfonyl)-azepan-4-ylcarbamoyl]-butyl}amide of Example 99a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H), 6.0 (s, 2H), 7.4-8.0 (m, 5H), 8.1-8.2 (m, 2H); MS(EI): 546 (M+, 100%).

The diastereomeric mixture was separated by HPLC to provide the faster eluting diastereoemer; MS(EI): 547 (M+H+, 100%) and the slower eluting diastereomer; MS(EI): 547 (M+H+, 100%).

Example 100

Preparation of Furan-2-carboxylic acid {(S)-3-methyl-1-[3-oxo-1-(1-oxy-pyridine-2-sulfonyl)-azepan-4-ylcarbamoyl]-butyl}amide a.) Furan-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting furoic acid for benzo[b]thiophene-2-carboxylic acid the title compound was prepared: MS(EI) 494 (M+).

b.) Furan-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting furan-2-carboxylic acid {(S)-3-methyl-1-[3-hydroxy-1-(1-oxy-pyridine-2-sulfonyl)-azepan-4-ylcarbamoyl]-butyl}amide of Example 100a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H), 7.4-8.0 (m, 5H), 8.1-8.2 (m, 2H); MS(EI): 492 (M+, 100%).

The diastereomeric mixture was separated by HPLC to provide the faster eluting diastereoemer MS(EI): 493 (M+H+, 100%) and the slower eluting diastereomer; MS(EI): 493 (M+H+, 100%).

Example 101

Preparation of (S)-4-Methyl-2-(2-thiophen-2-yl-acetylamino)-pentanoic acid [3-oxo-1-(1-oxy-pyridine-2-sulfonyl)-azepan-4-yl]-amide a.) (S)-4-Methyl-2-(2-thiophen-2-yl-acetylamino)-pentanoic acid [3-hydroxy-1-(1-oxy-pyridine-2-sulfonyl)-azepan-4-yl]-amide Following the procedure of Example 85c except substituting thiophene-2-acetic acid for benzo[b]thiophene-2-carboxylic acid the title compound was prepared.

b.) (S)-4-Methyl-2-(2-thiophen-2-yl-acetylamino)-pentanoic acid [3-oxo-1-(1-oxy-pyridine-2-sulfonyl)-azepan-4-yl]-amide Following the procedure of Example 1i except substuting (S)-4-methyl-2-(2-thiophen-2-yl-acetylamino)-pentanoic acid [3-hydroxy-1-(1-oxy-pyridine-2-sulfonyl)-azepan-4-yl]-amide of Example 101a the title compound was prepared: $^1$H NMR (CDCl$_3$): δ 1.0 (m, 6H), 1.5-2.1 (m, 5H), 2.2 (m, 2H), 2.7 (m, 1H), 3.8 (m, 3H); 4.0 (m, 1H), 4.5 (t, 1H), 4.7 (m, 1H), 5.0 (m, 1H), 7.4-8.0 (m, 5H), 8.1-8.2 (m, 2H); MS(EI): 522 (M$^+$, 20%).

Example 102

Preparation of 1H-Indole-2-carboxylic acid {(S)-3-methyl-1-[3-oxo-1-(1-oxy-pyridine-2-sulfonyl)-azepan-4-ylcarbamoyl]-butyl}amide a.) 1H-Indole-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 1H-indole-2-carboxylic acid for benzo[b]thiophene-2-carboxylic acid the title compound was prepared: MS(EI) 543 (M$^+$).

b.) 1H-Indole-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 1H-indole-2-carboxylic acid {(S)-3-methyl-1-[3-hydroxy-1-(1-oxy-pyridine-2-sulfonyl)-azepan-4-ylcarbamoyl]-butyl}amide of Example 102a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H),7.4-8.0 (m, 7H), 8.1-8.2 (m, 2H), 9.4 (b, 1H); MS(EI): 541 (M$^+$, 100%).

The diastereomeric mixture was separated by HPLC to provide the faster eluting diastereomer: MS(EI): 542 (M+H$^+$, 100%) and the slower eluting diastereomer; MS(EI): 542 (M+H$^+$, 100%).

Example 103

Preparation of 4-Fluoro-{(S)-3-methyl-1-[3-oxo-1-(1-oxy-pyridine-2-sulphonyl)-azepan-4-carbamoyl]-butyl}-benzamide a). 4-Fluoro-{(S)-3-methyl-1-[3-hydroxy-1-(1-oxy-pyridine-2-sulphonyl)-azepan-4-carbamoyl]-butyl}-benzamide Following the procedure of Example 85c except substituting 4-fluorobenzoic acid for benzo[b]thiophene-2-carboxylic acid the title compound was prepared: MS(EI) 522 (M$^+$).

b.) 4-Fluoro-{(S)-3-methyl-1-[3-oxo-1-(1-oxy-pyridine-2-sulphonyl)-azepan-4-carbamoyl]-butyl}-benzamide Following the procedure of Example 1i except substuting 4-fluoro-{(S)-3-methyl-1-[3-hydroxy-1-(1-oxy-pyridine-2-sulphonyl)-azepan-4-carbamoyl]-butyl}-benzamide of Example 103a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H), 7.4-8.0 (m, 6H), 8.1-8.2 (m, 2H); MS(EI): 520 (M$^+$, 100%).

The diastereomeric mixture was separated by HPLC to provide the faster eluting diastereomer: MS(EI): 521 (M+H$^+$, 100%) and the slower eluting diastereomer MS(EI): 521 (M+H$^+$, 100%).

Example 104

Preparation of 5-(2-Morpholin-4-yl-ethoxy)-benzofuran-2-carboxylic acid {(S)-3-methyl-1-[3-oxo-(1-oxy-pyridine2-sulphonyl)-azepan-4-ylcarbamoyl]-butyl}-amide a.) 5-(2-Morpholin-4-yl-ethoxy)-benzofuran-2-carboxylic acid {(S)-3-methyl-1-[3-hydroxy-(1-oxy-pyridine2-sulphonyl)-azepan-4-ylcarbamoyl]-butyl}-amide Following the procedure of Example 85c except substituting 5-(2-morpholin-4-yl-ethyloxy)benzofuran-2-carboxylic acid for benzo[b]thiophene-2-carboxylic acid the title compound was prepared: MS(EI) 673 (M$^+$).

b.) 5-(2-Morpholin-4-yl-ethoxy)-benzofuran-2-carboxylic acid {(S)-3-methyl-1-[3-oxo-(1-oxy-pyridine2-sulphonyl)-azepan-4-ylcarbamoyl]-butyl}-amide Following the procedure of Example 1i except substuting 5-(2-morpholin-4-yl-ethoxy)-benzofuran-2-carboxylic acid {(S)-3-methyl-1-[3-hydroxy-(1-oxy-pyridine2-sulphonyl)-azepan-4-ylcarbamoyl]-butyl}-amide of Example 104a the title compound was prepared: $^1$H NMR (CDCl$_3$): δ 1.0 (m, 6H), 1.5-2.1 (m, 5H), 2.2 (m, 2H), 2.5 (m, 4H), 2.7 (m, 3H), 3.7 (m, 4H); 3.9 (m, 1H), 4.5 (m, 3H), 4.7 (m, 1H), 5.0 (m, 1H), 7.4-8.0 (m, 6H), 8.1-8.2 (m, 2H); MS(EI): 671 (M$^+$, 100%).

The diastereomeric mixture was separated by HPLC to provide the faster eluting diastereomer: MS(EI): 672 (M+H$^+$, 100%) and the slower eluting diastereomer MS(EI): 672 (M+H$^+$, 100%).

Example 105

Preparation of Thiophene-2-carboxylic acid {(S)-3-methyl-1-[3-oxo-1-(1-oxy-pyridine-2-sulfonyl)-azepan-4-ylcarbamoyl]-butyl}amide a.) Thiophene-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting thiophene-2-carboxylic acid for benzo[b]thiophene-2-carboxylic acid the title compound was prepared: MS(EI) 510 (M$^+$).

b.) Thiophene-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting thiophene-2-carboxylic acid {(S)-3-methyl-1-[3-hydroxy-1-(1-oxy-pyridine-2-sulfonyl)-azepan-4-ylcarbamoyl]-butyl}amide of Example 105a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H), 7.4-8.0 (m, 5H), 8.1-8.2 (m, 2H); MS(EI): 508 (M$^+$, 100%).

The diastereomeric mixture was separated by HPLC to provide the faster eluting diastereomer: MS(EI): 509 (M+H$^+$, 100%) and the slower eluting diastereomer MS(EI): 509 (M+H$^+$, 100%).

Example 106

Preparation of 3-Methylbenzofuran-2-carboxylic acid {(S)-3-methyl-1-[3-oxo-1-(1-oxy-pyridine-2-sulfonyl)-azepan-4-ylcarbamoyl]-butyl}amide a.) 3-Methylbenzofuran-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 3-methylbenzofuran-2-carboxylic acid for benzo[b]thiophene-2-carboxylic acid the title compound was prepared: MS(EI) 558 (M$^+$).

b.) 3-Methylbenzofuran-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 3-methylbenzofuran-2-carboxylic acid {(S)-3-methyl-1-[3-hydroxy-1-(1-oxy-pyridine-2-sulfonyl)-azepan-4-ylcarbamoyl]-butyl}amide of Example 106a the title compound was prepared: $^1$H NMR (CDCl$_3$): δ 1.0 (m, 6H), 1.5-2.1 (m, 5H), 2.2 (m, 2H), 2.5 (d, 3H), 2.7 (m, 1H), 3.8 (q, 1H); 4.0 (m, 1H), 4.5 (t, 1H), 4.7 (m, 1H), 5.0 (m, 1H), 7.4-8.0 (m, 6H), 8.1-8.2 (m, 2H); MS(EI): 556 (M$^+$, 100%).

The diastereomeric mixture was separated by HPLC to provide the faster eluting diastereoemer: $^1$H NMR (CDCl$_3$): δ 1.0 (m, 6H), 1.5-2.1 (m, 5H), 2.2 (m, 2H), 2.6 (s, 3H), 2.7 (t, 1H), 3.8 (d, 1H); 4.1 (d, 1H), 4.7 (m, 1H), 4.7 (d, 1H), 5.0 (m, 1H), 7.0 (m, 2H), 7.3 (m, 2H), 7.4 (m, 4H), 8.1 (d, 1H), 8.2 (d, 1H); MS(EI): 557 (M+H$^+$, 100%) and the slower eluting diastereomer MS(EI): 557 (M+H$^+$, 100%).

Example 107

Preparation of 6-Methyl-N-{(S)-3-methyl-1-[3-oxo-1-(1-oxy-pyridine-2-sulfonyl)-azepan-4-ylcarbamoyl]-butyl}-nicotinamide a.) 6-Methyl-N-{(S)-3-methyl-1-[3-hydroxy-1-(1-oxy-pyridine-2-sulfonyl)-azepan-4-ylcarbamoyl]-butyl}-nicotinamide Following the procedure of Example 85c except substituting 6-methylnicotinic acid for benzo[b]thiophene-2-carboxylic acid the title compound was prepared: MS(EI) 519 (M$^+$).

b.) 6-Methyl-N-{(S)-3-methyl-1-[3-oxo-1-(1-oxy-pyridine-2-sulfonyl)-azepan-4-ylcarbamoyl]-butyl}-nicotinamide Following the procedure of Example 1i except substuting of 6-methyl-N-{(S)-3-methyl-1-[3-hydroxy-1-(1-oxy-pyridine-2-sulfonyl)-azepan-4-ylcarbamoyl]-butyl}-nicotinamide Example 107a the title compound was prepared:: $^1$H NMR (CDCl$_3$): δ 1.0 (m, 6H), 1.5-2.1 (m, 5H), 2.2 (m, 2H), 2.6 (s, 3H), 2.7 (m, 1H), 3.8 (q, 1H); 4.0 (m, 1H), 4.5 (t, 1H), 4.7 (m, 1H), 5.0 (m, 1H), 7.4-8.0 (m, 3H), 8.1-8.2 (m, 3H), 9.0 (m, 1H); MS(EI): 517 (M$^+$, 100%).

The diastereomeric mixture was separated by HPLC to provide the faster eluting diastereoemer: MS(EI): 518 (M+H$^+$, 100%) and the slower eluting diastereomer MS(EI): 518 (M+H$^+$, 100%).

Example 108

Preparation of (S)-4-Methyl-2-(2-thiophen-yl-acetylamino)-pentanoic acid-[3-oxo-1-(pyridine-2-sulfonyl)-azepan-4-yl]-butyl}amide a.) (S)-4-Methyl-2-(2-thiophen-yl-acetylamino)-pentanoic acid-[3-hydroxy-1-(pyridine-2-sulfonyl)-azepan-4-yl]-butyl}amide Following the procedure of Example 28b except substituting thiophene-2-acetic acid for benzofuran-2-carboxylic acid the title compound was prepared: MS(ESI) 508.8 (M+H$^+$).

b.) (S)-4-Methyl-2-(2-thiophen-yl-acetylamino)-pentanoic acid-[3-oxo-1-(pyridine-2-sulfonyl)-azepan-4-yl]-butyl}amide Following the procedure of Example 1i except substuting (S)-4-methyl-2-(2-thiophen-yl-acetylamino)-pentanoic acid-[3-hydroxy-1-(pyridine-2-sulfonyl)-azepan-4-yl]-butyl amide of Example 108a the title compound was prepared: MS(ESI) 506.8 (M+H$^+$).

Example 109

Preparation of 1H-Indole-6-carboxylic acid {(S)-3-methyl-1-[3-oxo-1-(pyridine-2-sulfonyl)-azepan-4-ylcarbamoyl]-butyl}amide a.) 1H-Indole-6-carboxylic acid {(S)-3-methyl-1-[3-hydroxy-1-(pyridine-2-sulfonyl)-azepan-4-ylcarbamoyl]-butyl}amide Following the procedure of Example 28b except substituting 1H-indole-6-carboxylic acid for benzofuran-2-carboxylic acid the title compound was prepared: MS(EI) 527 (M+H$^+$).

b.) 1H-Indole-6-carboxylic acid {(S)-3-methyl-1-[3-oxo-1-(pyridine-2-sulfonyl)-azepan-4-ylcarbamoyl]-butyl}amide Following the procedure of Example 1i except substuting 1H-indole-6-carboxylic acid {(S)-3-methyl-1-[3-hydroxy-1-(pyridine-2-sulfonyl)-azepan-4-ylcarbamoyl]-butyl}amide of Example 109a the title compound was prepared: MS(EI) 525 (M+H$^+$).

Example 110

Preparation of Benzo[1,3]dioxole-5-carboxylic acid {(S)-3-methyl-1-[3-oxo-1-(pyridine-2-sulfonyl)-azepan-4-ylcarbamoyl]-butyl}amide a.) Benzo[1,3]dioxole-5-carboxylic acid {(S)-3-methyl-1-[3-hydroxy-1-(pyridine-2-sulfonyl)-azepan-4-ylcarbamoyl]-butyl}amide Following the procedure of Example 28b except substituting piperonylic acid for benzofuran-2-carboxylic acid the title compound was prepared: MS(EI) 532.7 (M+H$^+$).

b.) Benzo[1,3]dioxole-5-carboxylic acid {(S)-3-methyl-1-[3-oxo-1-(pyridine-2-sulfonyl)-azepan-4-ylcarbamoyl]-butyl}amide Following the procedure of Example 1i except substuting benzo[1,3]dioxole-5-carboxylic acid {(S)-3-methyl-1-[3-hydroxy-1-(pyridine-2-sulfonyl)-azepan-4-ylcarbamoyl]-butyl}amide of Example 110a the title compound was prepared MS(EI) 530.8 (M+H$^+$).

Example 111

Preparation of 3,4-Dihydro-2H-benzo[b][1,4]dioxepine-7-carboxylic acid {(S)-3-methyl-1-[3-oxo-1-(1-oxy-pyridine-2-sulfonyl)-azepan-4-ylcarbamoyl]-butyl}amide a.) 3,4-Dihydro-2H-benzo[b][1,4]dioxepine-7-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 3,4-dihydro-2H-1,5-benzodioxepine-7-carboxylic acid for benzo[b]thiophene-2-carboxylic acid the title compound was prepared: MS(EI) 576 (M+).

b.) 3,4-Dihydro-2H-benzo[b][1,4]dioxepine-7-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 3,4-dihydro-2H-benzo[b][1,4]dioxepine-7-carboxylic acid {(S)-3-methyl-1-[3-hydroxy-1-(1-oxy-pyridine-2-sulfonyl)-azepan-4-ylcarbamoyl]-butyl}amide of Example 111a the title compound was prepared: $^1$H NMR (CDCl$_3$): δ 1.0 (m, 6H), 1.5-2.1 (m, 5H), 2.2 (m, 4H), 2.5 (d, 3H), 2.7 (m, 1H), 3.8 (q, 1H); 4.0 (m, 1H), 4.2 (m, 4H), 4.5 (t, 1H), 4.7 (m, 1H), 5.0 (m, 1H), 7.4-8.0 (m, 5H), 8.1-8.2 (m, 2H); MS(EI): 575 (M+H$^+$, 100%).

The diastereomeric mixture was separated by HPLC to provide the faster eluting diastereoemer: MS(EI): 575 (M+H$^+$, 100%) and the slower eluting diastereomer MS(EI): 575 (M+H$^+$, 100%).

Example 112

Preparation of 5-Methyl-thiophene-2-carboxylic acid {(S)-3-methyl-1-[3-oxo-1-(1-oxy-pyridine-2-sulfonyl)-azepan-4-ylcarbamoyl]-butyl}amide a.) 5-Methyl-thiophene-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 5-methyl thiophene-2-carboxylic acid for benzo[b]thiophene-2-carboxylic acid the title compound was prepared: MS(EI) 524 (M$^+$).

b.) 5-Methyl-thiophene-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 5-methyl-thiophene-2-carboxylic acid {(S)-3-methyl-1-[3-hydroxy-1-(1-oxy-pyridine-2-sulfonyl)-azepan-4-ylcarbamoyl]-butyl}amide of Example 112a the title compound was prepared: $^1$H NMR (CDCl$_3$): δ 1.0 (m, 6H), 1.5-2.1 (m, 5H), 2.2 (m, 2H), 2.5 (d, 3H), 2.7 (m, 1H), 3.8 (q, 1H); 4.0 (m, 1H), 4.5 (t, 1H), 4.7 (m, 1H), 5.0 (m, 1H), 7.4-8.0 (m, 4H), 8.1-8.2 (m, 2H); MS(EI): 523 (M+H$^+$, 100%).

The diastereomeric mixture was separated by HPLC to provide the faster eluting diastereoemer: MS(EI): 523 (M+H$^+$, 100%) and the slower eluting diastereomer MS(EI): 523 (M+H$^+$, 100%).

Example 113

Preparation of 4,5-Dibromo-thiophene-2-carboxylic acid {(S)-3-methyl-1-[3-oxo-1-(1-oxy-pyridine-2-sulfonyl)-azepan-4-ylcarbamoyl]-butyl}amide a.) 4,5-Dibromo-thiophene-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 4,5-dibromo-thiophene-2-carboxylic acid for benzo[b]thiophene-2-carboxylic acid the title compound was prepared: MS(EI) 668 (M$^+$).

b.) 4,5-Dibromo-thiophene-2-carboxylic acid {(S)-3-methyl-1-[3-oxo-1-(1-oxy-pyridine-2-sulfonyl)-azepan-4-ylcarbamoyl]-butyl}amide

**Following the procedure of Example 1i except substuting 4,5-dibromo-thiophene-2-carboxylic acid {(S)-3-methyl-1-[3-hydroxy-1-(1-oxy-pyridine-2-sulfonyl)-azepan-4-ylcarbamoyl]-butyl}amide of Example 113a the title compound was prepared: $^1$H NMR (CDCl$_3$): δ 1.0 (m, 6H), 1.5-2.1 (m, 5H), 2.2 (m, 2H), 2.7 (m, 1H), 3.8 (q, 1H); 4.0 (m, 1H), 4.5 (t, 1H), 4.7 (m, 1H), 5.0 (m, 1H), 7.4-8.0 (m, 3H), 8.1-8.2 (m, 2H); MS(EI): 665 (M+H$^+$, 100%).

Example 114

Preparation of 3,5-Dimethyl-isoxazole-4-carboxylic acid {(S)-3-methyl-1-[3-oxo-1-(1-oxy-pyridine-2-sulfonyl)-azepan-4-ylcarbamoyl]-butyl}amide a.) 3,5-Dimethyl-isoxazole-4-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 3,5-dimethyl-isoxazole-4-carboxylic acid for benzo[b]thiophene-2-carboxylic acid the title compound was prepared: MS(EI) 524 (M+H$^+$).

b.) 3,5-Dimethyl-isoxazole-4-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 3,5-dimethyl-isoxazole-4-carboxylic acid {(S)-3-methyl-1-[3-hydroxy-1-(1-oxy-pyridine-2-sulfonyl)-azepan-4-ylcarbamoyl]-butyl}amide of Example 114a the title compound was prepared: $^1$H NMR (CDCl$_3$): δ 1.0 (m, 6H), 1.5-2.1 (m, 5H), 2.2 (m, 2H), 2.4 (m, 3H), 2.6 (m, 3H), 2.7 (m, 1H), 3.8 (q, 1H); 4.0 (m, 1H), 4.5 (t, 1H), 4.7 (m, 1H), 5.0 (m; 1H), 7.4-8.0 (m, 5H), 8.1-8.2 (m, 2H); MS(EI): 521 (M$^+$, 100%).

Example 115

Preparation of (S)-2-(2-Benzyloxy-acetylamino)-4-methyl-pentanoic acid[1-(4-methoxy-benzenesulfonyl)-3-oxo-azepan-4-yl]-amide a.) {(S)-1-[3-Hydroxy-1-(4-methoxy-benzenesulfonyl)-azepan-4-ylcarbamoyl]-3-methyl-butyl}-carbamic acid-tert-butyl ester

[(S)-1-(3-Hydroxy-azepan-4-ylcarbamoyl)-3-methyl-butyl]-carbamic acid-tert-butyl ester (compound 2g, 0.8 g, 2.33 mmol) was dissolved in 1,2-dichloroethane (DCE, 20 ml). Then, morpholinemethyl polystyrene resin beads (1.26 g, 3.7 mmol/g, Nova) were added and the solution was shaken for 5 minutes. Then, p-methoxybenzenesulfonyl chloride (0.48 g, 2.33 mmol) was dissolved in DCE (10 ml), and this solution was added to the reaction mixture. The reaction was shaken overnight, filtered, washed with DCE (2×10 ml), then CH$_2$Cl$_2$ (10 ml). The combined organics were concentrated in vacuo, and used in the next reaction without further purification: M+H$^+$=514.2.

b.) (S)-2-Amino-4-methyl-pentanoic acid [3-hydroxy-1-(4-methoxy-benzenesulfonyl)-azepan-4-yl]-amide·HCl salt {(S)-1-[3-Hydroxy-1-(4-methoxy-benzenesulfonyl)-azepan-4-ylcarbamoyl]-3-methyl-butyl}-carbamic acid-tert-butyl ester (compound 207a, 0.59 g, 1.15 mmol) was dissolved in CH$_2$Cl$_2$ (8 ml), then a solution of 4 M HCl in dioxane (8 ml) was added and the reaction was stirred at RT for 4 h. The reaction mixture was concentrated in vacuo, azeotroped from toluene twice (10 ml) in vacuo, and was used in the next reaction without further purification: M+H$^+$=413.8.

c.) (S)-2-(2-Benzyloxy-acetylamino)-4-methyl-pentanoic acid [3-hydroxy-1-(4-methoxy-benzenesulfonyl)-4-yl]-amide (S)-2-Amino-4-methyl-pentanoic acid [3-hydroxy-1-(4-methoxy-benzenesulfonyl)-azepan-4-yl]-amide·HCl salt (crude product from reaction mixture of 115b) was dissolved in MeOH (10 ml) and was treated with carbonate-polystyrene resin beads (1.75 g 2.63 mmol/g, 4.6 mmol) and was shaken for 2 h, filtered, washed with MeOH (10 ml) and the combined organics were concentrated in vacuo. The product was then dissolved in DCE (2 ml) and morpholinemethyl polystyrene resin beads (0.25 g, 3.77 mmol/g, 0.91 mmol, Nova) were added and the reaction was shaken for 5 minutes. Then, benzylacetyl chloride (0.081 g, 0.44 mmol) was added and the reaction mixture was shaken overnight. Then, trisamine polystyrene beads (0.1 g, 3.66 mmol/g, 0.366 mmol) was added and the reaction mixture was shaken for 1.5 h. The reaction mixture was then filtered, washed with DCE (2×10 ml) and CH$_2$Cl$_2$ (10 ml), and the combined organics were concentrated in vacuo. The crude product was used in the next reaction without further purification: M+H$^+$=562.2.

d.) (S)-2-(2-Benzyloxy-acetylamino)-4-methyl-pentanoic acid [1-(4-methoxy-benzenesulfonyl)-3-oxo-azepan-4-yl]-amide (S)-2-(2-Benzyloxy-acetylamino)-4-methyl-pentanoic acid [3-hydroxy-1-(4-methoxy-benzenesulfonyl)-azepan-4-yl]-amide (compound 207c, 0.24 g, 0.44 mmol) was dissolved in CH$_2$Cl$_2$ (5 ml), then Dess-Martin periodinane (0.3 g, 0.7 mmol) was added and the reaction was stirred for 30 min. The reaction was diluted with CH$_2$Cl$_2$ (20 ml), then was extracted with aqueous 10% Na$_2$S$_2$O$_5$ (10 ml), then aqueous 10% NaHCO$_3$ (10 ml), water (10 ml), brine (10 ml). The combined organics were concentrated in vacuo. The residue was purified by HPLC (50:50 Ethanol:hexanes, 20 mL/min, 25 min, WhelkO-1(R,R) 21×250 mm column, UV detection at 280 nm and 305 nm) to yield the first elution as a white solid (47 mg, 43%): MS 560.4 (M+H$^+$). $^1$H NMR (400 Hz,CDCl$_3$): δ 7.73 (d, 2H), 7.40-7.30 (m, 5H), 7.05 (d, 2H), 3.99 (s, 2H), 3.88 (s, 3H), 2.28-2.10 (m, 2H), 0.95 (t, 6H), and second eluting diastereomer: MS 560.2 (M+H$^+$).

Example 116

Preparation of 5-(3-Trifluoromethyl-phenyl)-furan-2-carboxylic acid {(S)-3-methyl-1-[3-oxo-1-(1-oxy-pyridine-2-sulfonyl)-azepan-4-ylcarbamoyl]-butyl}amide a.) 5-(3-Trifluoromethyl-phenyl)-furan-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 5-(3-trifluoromethyl-phenyl)-furan-2-carboxylic acid for benzo[b]thiophene-2-carboxylic acid the title compound was prepared: MS(EI) 638 (M$^+$).

b.) 5-(3-Trifluoromethyl-phenyl)-furan-2-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 5-(3-trifluoromethyl-phenyl)-furan-2-carboxylic acid {(S)-3-methyl-1-[3-hydroxy-1-(1-oxy-pyridine-2-sulfonyl)-azepan-4-ylcarbamoyl]-butyl}amide of Example 116a the title compound was prepared: $^1$H NMR (CDCl$_3$): δ 1.0 (m, 6H), 1.5-2.1 (m, 5H), 2.2 (m, 2H), 2.6 (d, 3H), 2.7 (m, 1H), 3.8 (q, 1H); 4.1 (m, 1H), 4,7 (t, 1H), 4.8 (m, 1H), 5.0 (m, 1H), 7.4-8.0 (m, 9H), 8.1-8.2 (m, 2H); MS(EI): 637 (M+H$^+$, 100%).

The diastereomeric mixture was separated by HPLC to provide the faster eluting diastereoemer: MS(EI): 637 (M+H$^+$, 100%) and the slower eluting diastereomer MS(EI): 637 (M+H$^+$, 100%).

Example 117

Preparation of 5-Methyl-2-2-phenyl-oxazole-4-carboxylic acid {(S)-3-methyl-1-[3-oxo-1-(1-oxy-pyridine-2-sulfonyl)-azepan-4-ylcarbamoyl]-butyl}amide a.) 5-Methyl-2-phenyl-oxazole-4-carboxylic acid {(S)-3-methyl-1-[3-hydroxy-1-(1-oxy-pyridine-2-sulfonyl)-azepan-4-ylcarbamoyl]-butyl}amide Following the procedure of Example 85c except substituting 5-methyl-2-phenyl-oxazole-4-carboxylic acid for benzo[b]thiophene-2-carboxylic acid the title compound was prepared: MS(EI) 585 (M$^+$).

b.) 5-Methyl-2-phenyl-oxazole-4-carboxylic acid {(S)-3-methyl-1-[3-oxo-1-(1-oxy-pyridine-2-sulfonyl)-azepan-4-ylcarbamoyl]-butyl}amide Following the procedure of Example 1i except substuting 5-methyl-2-phenyl-oxazole-4-carboxylic acid {(S)-3-methyl-1-[3-hydroxy-1-(1-oxy-pyridine-2-sulfonyl)-azepan-4-ylcarbamoyl]-butyl}amide of Example 117a the title compound was prepared: $^1$H NMR (CDCl$_3$): δ 1.0 (m, 6H), 1.5-2.1 (m, 5H), 2.2 (m, 2H), 2.6 (d, 3H), 2.7 (m, 1H), 3.8 (q, 1H); 4.0 (m, 1H), 4.5 (t, 1H), 4.7 (m, 1H), 5.0 (m, 1H), 7.4-8.0 (m, 7H), 8.1-8.2 (m, 2H); MS(EI): 584 (M+H$^+$, 100%).

The diastereomeric mixture was separated by HPLC to provide the faster eluting diastereoemer: MS(EI): 584 (M+H$^+$, 100%) and the slower eluting diastereomer MS(EI): 584 (M+H$^+$, 100%).

Example 118

Preparation of Benzofuran-2-carboxylic acid {(S)-1-[1-(3,4-dimethoxy-benzenesulfonyl)-3-oxo-azepan-4-ylcarbamoyl]-butyl}-amide a.) Benzofuran-2-carboxylic acid {(S)-1-[1-(3,4-dimethoxy-benzenesulfonyl)-3-hydroxy-azepan-4-ylcarbamoyl]-butyl}-amide To a solution of benzofuran-2-carboxylic acid {(S)-1-[1-(3,4-dimethoxy-benzenesulfonyl)-3-oxo-azepan-4-ylcarbamoyl]-butyl}-amide of Example 78c (0.175 g) in dichloromethane was added triethylamine (0.1 mL) and 3,4-dimethoxy-benzenesulfonyl chloride (0.12 g). The reaction was stirred until complete. Workup and column chromatography (5% methanol:dicloromethane) provided the title compound (0.21 g): MS(EI) 587 (M+).

b.) Benzofuran-2-carboxylic acid {(S)-1-[1-(3,4-dimethoxy-benzenesulfonyl)-3-oxo-azepan-4-ylcarbamoyl]-butyl}-amide Following the procedure of Example 1i except substuting benzofuran-2-carboxylic acid {(S)-1-[1-(3,4-dimethoxy-benzenesulfonyl)-3-hydroxy-azepan-4-ylcarbamoyl]-butyl}-amide of Example 118a the title compound was prepared: 1H NMR (CDCl₃): δ 1.0 (m, 6H), 1.5-2.1 (m, 6H), 2.6 (m, 1H), 3.5 (d, 1H); 3.7 (t, 6H), 4.0 (m, 1H), 4.5 (t, 1H), 4.7 (m, 1H), 5.0 (m, 1H), 7.4-8.0 (m, 8H); MS(EI): 586 (M+H+, 100%).

Example 119

Preparation of Benzofuran-2-carboxylic acid {(S)-1-[1-(4-bromo-benzenesulfonyl)-3-oxo-azepan-4-ylcarbamoyl]-3-methyl-butyl}-amide a.) Benzofuran-2-carboxylic acid {(S)-1-[1-(4-bromo-benzenesulfonyl)-3-hydroxy-azepan-4-ylcarbamoyl]-3-methyl-butyl}-amide Following the procedure of Example 118a except substituting 4-bromobenzenesulfonyl chloride for 3,4-dimethoxybenzenesulfonyl chloride the title compound was prepared: MS(EI) 606 (M+).

b.) Benzofuran-2-carboxylic acid {(S)-1-[1-(4-bromo-benzenesulfonyl)-3-oxo-azepan-4-ylcarbamoyl]-3-methyl-butyl}-amide Following the procedure of Example 1i except substituting benzofuran-2-carboxylic acid {(S)-1-[1-(4-bromo-benzenesulfonyl)-3-hydroxy-azepan-4-ylcarbamoyl]-3-methyl-butyl}-amide of Example 119a the title compound was prepared: ¹H NMR (CDCl₃): δ 1.0 (m, 6H), 1.5-2.1 (m, 6H), 2.6 (m, 1H), 3.5 (d, 1H); 4.0 (m, 1H), 4.5 (t, 1H), 4.7 (m, 1H), 5.0 (m, 1H), 7.4-8.0 (m, 9H); MS(EI): 604 (M+, 100%).

Example 120

Preparation of Benzofuran-2-carboxylic acid {(S)-1-[1-(benzo[1,2,5]oxadiazole-4-sulfonyl)-3-oxo-azepan-4-ylcarbamoyl]-3-methyl-butyl}-amide a.) Benzofuran-2-carboxylic acid {(S)-1-[1-(benzo[1,2,5]oxadiazole-4-sulfonyl)-3-hydroxy-azepan-4-ylcarbamoyl]-3-methyl-butyl}-amide Following the procedure of Example 118a except substituting benzofurazan-4-sulfonyl chloride for 3,4-dimethoxybenzenesulfonyl chloride the title compound was prepared: MS(EI) 569 (M+).

b.) Benzofuran-2-carboxylic acid {(S)-1-[1-(benzo[1,2,5]oxadiazole-4-sulfonyl)-3-oxo-azepan-4-ylcarbamoyl]-3-methyl-butyl}-amide Following the procedure of Example 1i except substituting Benzofuran-2-carboxylic acid {(S)-1-[1-(benzo[1,2,5]oxadiazole-4-sulfonyl)-3-hydroxy-azepan-4-ylcarbamoyl]-3-methyl-butyl}-amide of Example 120a the title compound was prepared: ¹H NMR (CDCl₃): δ 1.0 (m, 6H), 1.5-2.1 (m, 6H), 2.6 (m, 1H), 3.7 (m, 1H); 4.1 (m, 1H), 4.7 (m, 2H), 5.2 (m, 1H), 7.4-8.0 (m, 8H); MS(EI): 568 (M+H+, 100%).

Example 121

Preparation of Benzofuran-2-carboxylic acid {(S)-1-[1-(3,5-dimethyl-oxazole-4-sulfonyl)-3-oxo-azepan-4-ylcarbamoyl]-3-methyl-butyl}-amide a.) Benzofuran-2-carboxylic acid {(S)-1-[1-(3,5-dimethyl-oxazole-4-sulfonyl)-3-hydroxy-azepan-4-ylcarbamoyl]-3-methyl-butyl}-amide Following the procedure of Example 118a except substituting 3,5-dimethyloxazole-4-sulphonyl chloride for 3,4-dimethoxybenzenesulfonyl chloride the title compound was prepared: MS(EI) 546 (M+).

b.) Benzofuran-2-carboxylic acid {(S)-1-[1-(3,5-dimethyl-oxazole-4-sulfonyl)-3-oxo-azepan-4-ylcarbamoyl]-3-methyl-butyl}-amide Following the procedure of Example 1i except substituting benzofuran-2-carboxylic acid {(S)-1-[1-(3,5-dimethyl-oxazole-4-sulfonyl)-3-hydroxy-azepan-4-ylcarbamoyl]-3-methyl-butyl}-amide of Example 121a the title compound was prepared: ¹H NMR (CDCl₃): δ 1.0 (m, 6H), 1.5-2.2 (m, 6H), 2.2 (m, 2H), 2.4 (d, 3H), 2.7 (t, 3H), 3.6 (d, 1H), 4.1 (m, 1H), 4.4 (t, 1H), 4.7 (m, 1H), 5.2 (m, 1H), 7.4-8.0 (m, 5H); MS(EI): 544 (M+, 100%).

Example 122

Preparation of 3-Methylbenzofuran-2-carboxylic acid {(S)-3-methyl-1-[3-oxo-1-(pyridine-2-sulfonyl)-azepan-4-ylcarbamoyl]-butyl}amide a.) 3-Methylbenzofuran-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 3-methylbenzofuran-2-carboxylic acid for benzofuran-2-carboxylic acid the title compound was prepared: MS(EI) 542 (M+).

b.) 3-Methylbenzofuran-2-carboxylic acid {(S)-3-methyl-1-[3-oxo-1-(pyridine-2-sulfonyl)-azepan-4-ylcarbamoyl]-butyl}amide Following the procedure of Example 1i except substituting 3-methylbenzofuran-2-carboxylic acid {(S)-3-methyl-1-[3-hydroxy-1-(pyridine-2-sulfonyl)-azepan-4-ylcarbamoyl]-butyl}amide of Example 122a the title compound was prepared: ¹H NMR (CDCl₃): δ 1.0 (m, 6H), 1.5-2.2 (m, 6H), 2.2 (m, 2H), 2.6 (d, 3H), 2.7 (m, 1H), 3.8 (m, 1H), 4.1 (m, 1H), 4.7 (m, 2H), 5.2 (m, 1H), 7.4-8.0 (m, 7H); 8.7 (m, 1H); MS(EI): 540 (M+, 100%).

The diastereomeric mixture was separated by HPLC to provide the faster eluting diastereoemer: ¹H NMR (CDCl₃): δ 1.0 (m, 6H), 1.5-2.2 (m, 6H), 2.2 (m, 2H), 2.6 (s, 3H), 2.7 (m, 1H), 3.8 (d, 1H); 4.1 (d, 1H), 4.7 (m, 2H), 5.2 (m, 1H), 7.4-8.0 (m, 7H); 8.7 (m, 1H); MS(EI): 541 (M+H+, 100%) and the slower eluting diastereomer MS(EI): 541 (M+H+, 100%).

Example 123

Preparation of Thieno[3,2-b]thiophene-2-carboxylic acid {(S)-3-methyl-1-[3-oxo-1-(pyridine-2-sulfonyl)-azepan-4-ylcarbamoyl]-butyl}amide a.) Thieno[3,2-b]thiophene-2-carboxylic acid {(S)-3-methyl-1-[3-hydroxy-1-(pyridine-2-sulfonyl)-azepan-4-ylcarbamoyl]-butyl}amide Following the procedure of Example 28b except substituting thieno[3,2-b]thiophene-2-carboxylic acid for benzofuran-2-carboxylic acid the title compound was prepared: MS(EI) 550 (M$^+$).

b.) Thieno[3,2-b]thiophene-2-carboxylic acid {(S)-3-methyl-1-[3-oxo-1-(pyridine-2-sulfonyl)-azepan-4-ylcarbamoyl]-butyl}amide Following the procedure of Example 1i except substituting thieno[3,2-b]thiophene-2-carboxylic acid {(S)-3-methyl-1-[3-hydroxy-1-(pyridine-2-sulfonyl)-azepan-4-ylcarbamoyl]-butyl}amide of Example 123a the title compound was prepared: $^1$H NMR (CDCl$_3$): δ 1.0 (m, 6H), 1.5-2.2 (m, 6H), 2.2 (m, 2H), 2.7 (m, 1H), 3.8 (m, 1H); 4.1 (m, 1H), 4.7 (m, 2H), 5.2 (m, 1H), 7.4-8.0 (m, 8H); 8.7 (m, 1H); MS(EI): 548 (M$^+$, 100%).

The diastereomeric mixture was separated by HPLC to provide the faster eluting diastereoemer: $^1$HNMR (CDCl$_3$): δ 1.0 (m, 6H), 1.5-2.2 (m, 6H), 2.2 (m, 2H), 2.7 (t, 1H), 3.8 (d, 1H); 4.1 (d, 1H), 4.7 (m, 2H), 5.2 (m, 1H), 7.4-8.0 (m, 8H); 8.7 (d, 1H); MS(EI): 549 (M+H$^+$, 100%) and the slower eluting diastereomer MS(EI): 549 (M+H$^+$, 100%).

Example 124

Preparation of 5-tert-Butyl-3-methyl-thieno[3,2-b]thiophene-2-carboxylic acid {(S)-3-methyl-1-[3-oxo-1-(pyridine-2-sulfonyl)-azepan-4-ylcarbamoyl]-butyl}amide a.) 5-tert-Butyl-3-methyl-thieno[3,2-b]thiophene-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-tert-butyl-3-methyl-thieno[3,2-b]thiophene-2-carboxylic acid for benzofuran-2-carboxylic acid the title compound was prepared: MS(EI) 620 (M$^+$).

b.) 5-tert-Butyl-3-methyl-thieno[3,2-b]thiophene-2-carboxylic acid {(S)-3-methyl-1-[3-oxo-1-(pyridine-2-sulfonyl)-azepan-4-ylcarbamoyl]-butyl}amide Following the procedure of Example 1i except substituting 5-tert-butyl-3-methyl-thieno[3,2-b]thiophene-2-carboxylic acid {(S)-3-methyl-1-[3-hydroxy-1-(pyridine-2-sulfonyl)-azepan-4-ylcarbamoyl]-butyl}amide of Example 124a the title compound was prepared: $^1$H NMR (CDCl$_3$): δ 1.0 (m, 6H), 1.45 (s, 9H), 1.5-2.2 (m, 6H), 2.2 (m, 2H), 2.4 (d, 3H), 2.7 (m, 1H), 3.8 (m, 1H); 4.1 (m, 1H), 4.7 (m, 2H), 5.2 (m, 1H), 7.4-8.0 (m, 4H); 8.7 (m, 1H); MS(EI): 618 (M$^+$, 100%).

Example 125

Preparation of 5-Methyl-2-phenyl-oxazole-4-carboxylic acid {(S)-3-methyl-1-[3-oxo-1-(pyridine-2-sulfonyl)-azepan-4-ylcarbamoyl]-butyl}amide a.) 5-Methyl-2-phenyl-oxazole-4-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-methyl-2-phenyl-oxazole-4-carboxylic acid for benzofuran-2-carboxylic acid the title compound was prepared: MS(EI) 569 (M$^+$).

b.) 5-Methyl-2-phenyl-oxazole-4-carboxylic acid {(S)-3-methyl-1-[3-oxo-1-(pyridine-2-sulfonyl)-azepan-4-ylcarbamoyl]-butyl}amide Following the procedure of Example 1i except substituting 5-methyl-2-phenyl-oxazole-4-carboxylic acid {(S)-3-methyl-1-[3-hydroxy-1-(pyridine-2-sulfonyl)-azepan-4-ylcarbamoyl]-butyl}amide of Example 125a the title compound was prepared: $^1$H NMR (CDCl$_3$): δ 1.0 (m, 6H), 1.5-2.2 (m, 6H), 2.2 (m, 2H), 2.7 (m, 1H), 2.6 (m, 3H), 3.8 (m, 1H); 4.1 (m, 1H), 4.7 (m, 2H), 5.2 (m, 1H), 7.4-8.0 (m, 8H); 8.7 (m, 1H); MS(EI): 567 (M$^+$, 100%).

The diastereomeric mixture was separated by HPLC to provide the faster eluting diastereoemer: MS(EI): 568 (M+H$^+$, 100%) and the slower eluting diastereomer MS(EI): 568 (M+H$^+$, 100%)

Example 126

Preparation of 2-Phenyl-5-trifluoromethyl-oxazole-4-carboxylic acid {(S)-3-methyl-1-[3-oxo-1-(pyridine-2-sulfonyl)-azepan-4-ylcarbamoyl]-butyl}amide a.) 2-Phenyl-5-trifluoromethyl-oxazole-4-carboxylic acid {(S)-3-methyl-1-[3-hydrox-1-(pyridine-2-sulfonyl)-azepan-4-ylcarbamoyl]-butyl}amide Following the procedure of Example 28b except substituting 2-phenyl-5-trifluoromethyl-oxazole-4-carboxylic acid for benzofuran-2-carboxylic acid the title compound was prepared: MS(EI) 623 (M$^+$).

b.) 2-Phenyl-5-trifluoromethyl-oxazole-4-carboxylic acid {(S)-3-methyl-1-[3-oxo-1-(pyridine-2-sulfonyl)-azepan-4-ylcarbamoyl]-butyl}amide Following the procedure of Example 1i except substituting 2-phenyl-5-trifluoromethyl-oxazole-4-carboxylic acid {(S)-3-methyl-1-[3-hydrox-1-(pyridine-2-sulfonyl)-azepan-4-ylcarbamoyl]-butyl}amide of Example 126a the title compound was prepared: $^1$H NMR (CDCl$_3$): δ 1.0 (m, 6H), 1.5-2.2 (m, 6H), 2.2 (m, 2H), 2.7 (m, 1H), 3.8 (m, 1H); 4.1 (m, 1H), 4.7 (m, 2H), 5.2 (m, 1H), 7.4-8.0 (m, 8H); 8.7 (m, 1H); MS(EI): 621 (M$^+$, 100%).

The diastereomeric mixture was separated by HPLC to provide the faster eluting diastereoemer: MS(EI): 622 (M+H$^+$, 100%) and the slower eluting diastereomer: MS(EI): 622 (M+H$^+$, 100%).

Example 127

Preparation of Quinoline-2-carboxylic acid [(S)-1-(1-methanesulfonyl-3-oxo-azepan-4-ylcarbamoyl)-3-methyl-butyl]-amide Following the procedure of Example 75, except substituting methanesulfonyl chloride for thiazole-2-sulfonyl chloride and 2-quinoline carboxylic acid for benzofuran-2-carboxylic acid, the title compound was prepared. The residue was purified by HPLC. First eluting diastereomer; MS (M+H$^+$): 475.2; $^1$H-NMR (400 MHz, CDCl$_3$): . 8.65(d, 1H), 8.35-8.28 (q, 2H), 8.20-8.18(d, 1H), 7.91-7.89(d, 1H), 7.80-7.78(t, 1H), 7.67-7.65(t, 1H), 7.10(d, 1H), 5.08(m, 1H), 4.73 (m, 1H), 4.56-4.51(d, 1H), 4.00(m, 1H), 3.67-3.62(d, 1H), 2.91(s, 3H), 2.70(m, 1H), 2.32-2.10(m, 2H), 1.95-1.40(m, 5H), 1.02-1.00 (m, 6H); and the second eluting diastereomer: MS (M+H$^+$): 475.2

Example 128

Preparation of 1-Methyl-1H-indole-2-carboxylic acid [(S)-1-(1-methanesulfonyl-3-oxo-azepan-4-ylcarbamoyl)-3-methyl-butyl]-amide Following the procedure of Example 75, except substituting methanesulfonyl chloride for thiazole-2-sulfonyl chloride and N-methylindole-2-carboxylic acid for benzofuran-2-carboxylic acid, the title compound was prepared. The residue was purified by HPLC. First eluting diastereomer; MS (M+H$^+$): 477.2; $^1$H-NMR (400 MHz, CDCl$_3$): •7.65-7.63(d, 1H), 7.39-7.33(m, 2H), 7.17-7.14(t, 1H), 6.98-6.95(m, 2H), 6.65(d, 1H), 5.08(m, 1H), 4.68 (m, 1H) 4.56-4.52(d, 1H), 4.03(m, 4H), 3.67-3.63(d, 1H), 2.92(s, 3H), 2.71(m, 1H), 2.32-2.10(m, 2H), 1.95-1.40(m, 5H), 1.02-1.00(d, 6H); and the second eluting diastereomer: MS (M+H$^+$): 477.2

Example 129

Preparation of Furan-2-carboxylic acid {[(S)-1-(1-methanesulfonyl-3-oxo-azepan-4-ylcarbamoyl)-3-methyl-butylcarbamoyl]-methyl}-amide Following the procedure of Example 75, except substituting methanesulfonyl chloride for thiazole-2-sulfonyl chloride and N-(2-furan-carbonyl)-glycine for benzofuran-2-carboxylic acid, the title compound was prepared. The residue was purified by HPLC. First eluting diastereomer; MS (M+H$^+$): 471.2; $^1$H-NMR (400 MHz, CDCl$_3$): •7.50(m, 1H), 7.15(m, 1H), 7.05(m, 1H), 6.90(d, 1H), 6.55(m, 2H), 5.08(m, 1H), 4.55 (m, 2H), 4.12(m, 2H), 4.05(m, 1H), 3.70(d, 1H), 2.92(s, 3H), 2.75(m, 1H), 2.20-1.40(m, 7H), 0.95 (m, 6H); and the second eluting diastereomer: MS (M+H$^+$): 471.4.

Example 130

Preparation of 5-Methoxybenzofuran-2-carboxylic acid [(S)-1-(1-methanesulfonyl-3-oxo-azepan-4-ylcarbamoyl)-3-methyl-butyl]-amide Following the procedure of Example 75, except substituting methanesulfonyl chloride for thiazole-2-sulfonyl chloride and 5-methoxybenzofuran-2-carboxylic acid for benzofuran-2-carboxylic acid, the title compound was prepared. The residue was purified by HPLC. First eluting diastereomer; MS (M+H$^+$): 494.2; $^1$H-NMR (400 MHz, CDCl$_3$): •7.42-7.40(d, 2H), 7.08-6.94(m, 4H), 5.10(m, 1H), 4.71(m, 1H), 4.56-4.52 (d, 1H), 4.02(m, 1H), 3.86(s, 3H), 3.68-3.63(d, 1H), 2.92(s, 3H), 2.72(m, 1H), 2.30-1.15(m, 2H), 1.95-1.40(m, 5H), 0.99 (d, 6H); and the second eluting diastereomer: MS (M+H$^+$): 494.2.

Example 131

Preparation of Quinoxaline-2-carboxylic acid [(S)-1-(1-methanesulfonyl-3-oxo-azepan-4-ylcarbamoyl)-3-methyl-butyl]-amide Following the procedure of Example 75, except substituting methanesulfonyl chloride for thiazole-2-sulfonyl chloride and-quinoxaline-2-carboxylic acid for benzofuran-2-carboxylic acid, the title compound was prepared. The residue was purified by HPLC. First eluting diastereomer; MS (M+H$^+$): 476.2; $^1$H-NMR (400 MHz, CDCl$_3$): •9.66(s, 1H), 8.38(d, 1H), 8.20-8.18(m, 2H), 7.88(m, 2H), 7.01(d, 1H), 5.10(m, 1H), 4.77(m, 1H), 4.57-4.52(d, 1H), 4.08-4.00(m, 1H), 3.69-3.64(d, 1H), 2.92(s, 3H), 2.71(m, 1H), 2.42-2.15 (m, 2H), 1.95-1.42(m, 5H), 1.02-1.01(d, 6H); and the second eluting diastereomer: MS (M+H$^+$): 476.2.

Example 132

Preparation of 5-(4-Chloro-phenyl)-furan-2-carboxylic acid {(S)-3-methyl-1-[3-oxo-1-(pyridine-2-sulfonyl)-azepan-4-ylcarbamoyl]-butyl}amide a.) 5-(4-Chloro-phenyl)-furan-2-carboxylic acid {(S)-3-methyl-1-[3-hydroxy-1-(pyridine-2-sulfonyl)-azepan-4-ylcarbamoyl]-butyl}amide Following the procedure of Example 28b except substituting 5-(4-chlorophenyl)-2-furoic acid for benzofuran-2-carboxylic acid the title compound was prepared: MS(EI) 590 (M+H$^+$).

b.) 5-(4-Chloro-phenyl)-furan-2-carboxylic acid {(S)-3-methyl-1-[3-oxo-1-(pyridine-2-sulfonyl)-azepan-4-ylcarbamoyl]-butyl}amide Following the procedure of Example 1i except substituting 5-(4-chloro-phenyl)-furan-2-carboxylic acid {(S)-3-methyl-1-[3-hydroxy-1-(pyridine-2-sulfonyl)-azepan-4-ylcarbamoyl]-butyl}amide of Example 132a the title compound was prepared: $^1$H NMR (CDCl$_3$): δ 1.0 (m, 6H), 1.5-2.1 (m, 5H), 2.2 (m, 2H), 2.7 (m, 1H), 3.7 (d, 1H), 4.0 (m, 1H), 4.7 (m, 2H), 5.0 (m, 1H), 6.7 (m, 1H), 7.2 (m, 1H), 7.3 (m, 2H), 7.5 (m, 1H), 7.7 (m, 2H), 8.0 (m, 2H), 8.7 (m, 1H); MS(EI): 587 (M$^+$, 80%)

The diastereomeric mixture was separated by HPLC to provide the faster eluting diastereoemer: MS(EI): 587 (M+H$^+$, 100%) and the slower eluting diastereomer: MS(EI): 587 (M+H$^+$, 100%).

Example 133

Preparation of (S)-2-[2-(4-Methoxy-phenyl)-acetylamino)-4-methyl-pentanoic acid (1-methanesulfonyl-3-oxo-azepan-4-yl)-amide Following the procedure of Example 75, except substituting 4-methanesulfonyl chloride for thiazole-2-sulfonyl chloride and 2-(4-methoxyphenyl)-acetic acid for benzofuran-2-carboxylic acid, the title compound was prepared. The residue was purified by HPLC. First eluting diastereomer; MS (M+H$^+$): 468.2; $^1$H-NMR (400 MHz, CDCl$_3$): •7.19-7.17 (d, 2H), 6.90-6.88(d, 3H), 5.83-5.81(d, 1H), 5.00(m, 1H), 4.53-4.40(m, 2H), 4.03-3.99(m, 1H), 3.81(s, 3H), 3.66-3.61 (d, 1H), 3.53(s, 2H), 2.91(s, 3H), 2.73(t, 1H), 2.22-2.10(m, 2H), 1.99(m, 1H), 1.62-1.35(m, 4H), 0.90-0.88(d, 6H); and the second eluting diastereomer: MS (M+H$^+$): 468.2.

Example 134

Preparation of Quinoline-2-carboxylic acid {[(S)-1-[1-(2-cyano-benzenesulfonyl)-3-oxo-azepan-4-ylcarbamoyl]-3-methyl-butyl}-amide Following the procedure of Example 75, except substituting 2-cyanobenzenesulfonyl chloride for thiazole-2-sulfonyl chloride and quinoline-2-carboxylic acid for benzofuran-2-carboxylic acid, the title compound was prepared. The residue was purified by HPLC. First eluting diastereomer; MS (M+H⁺): 562.2; ¹H-NMR (400 MHz, CDCl₃): •8.65(d, 1H), 8.48-8.40(q, 2H), 8.25-8.10(q, 2H), 7.91-7.65(m, 6H); and the second eluting diastereomer:, 7.12(d, 1H), 5.10(m, 1H), 4.73 (m, 1H) 4,61-4.56(d, 1H),4.20(m, 1H),3.73-3.68(d, 1H), 2.80(m, 1H), 2.27(m, 2H), 1.91-1.40(m, 5H), 1.03-1.01(m, 6H); and the second eluting diastereomer: MS (M+H⁺): 562.2.

Example 135

Preparation of 1-Methyl-1H-indole -2-carboxylic acid {[(S)-1-[1-(2-cyano-benzenesulfonyl)-3-oxo-azepan-4-ylcarbamoyl]-3-methyl-butyl}-amide Following the procedure of Example 75, except substituting 2-cyanophenylsulfonyl chloride for thiazole-2-sulfonyl chloride and N-methylindole-2-carboxylic acid for benzofuran-2-carboxylic acid, the title compound was prepared. The residue was purified by HPLC. First eluting diastereomer; MS (M+H⁺): 564.2; ¹H-NMR (400 MHz, CDCl₃): •8.13(d, 1H), 7.89(d, 1H), 7.77-7.67(m, 3H), 7.38-7.16(m, 4H), 6.97 (s, 1H), 6.70(d, 1H), 5.05(m, 1H), 4.70-4.60 (m, 1H), 4.55-4.50(d, 1H), 4.07(m, 1H), 4.05(s, 3H), 3.76-3.71(d, 1H), 2.75 (m, 1H), 2.30(m, 2H), 2.00-1.45(m, 5H), 1.00(d, 6H); and the second eluting diastereomer: MS (M+H⁺) 564.2.

Example 136

Preparation of Furan-2-carboxylic acid ({(S)-1-[1-(2-cyano-benzenesulfonyl)-3-oxo-azepan-4-ylcarbamoyl]-3-methyl-butylcarbamoyl}-methyl)-amide Following the procedure of Example 75, except substituting 2-cyanophenylsulfonyl chloride for thiazole-2-sulfonyl chloride and N-(2-furan-carbonyl)-glycine for benzofuran-2-carboxylic acid, the title compound was prepared. The residue was purified by HPLC. First eluting diastereomer; MS (M+H⁺): 558.2; ¹H-NMR (400 MHz, CDCl₃): •8.14-8.12(d, 1H), 7.91-7.90(d, 1H), 7.80-7.72(m, 2H), 7.48(s, 1H), 7.14(d, 2H), 6.98(d, 1H), 6.80(d, 1H), 6.52-6.51(t, 1H), 5.03(m, 1H), 4.60-4.53 (m, 2H), 4.17-4.14(m, 3H), 3.74-3.69(d, 1H), 2.80 (m, 1H), 2.25(m, 2H), 2.00-1.40(m, 5H), 1.03-1.01(m, 6H); and the second eluting diastereomer: MS (M+H⁺) 558.2.

Example 137

Preparation of 5-Methoxybenzofuran-2-carboxylic acid {(S)-1-[1-(2-cyano-benzenesulfonyl)-3-oxo-azepan-4-ylcarbamoyl]-3-methyl-butyl}-amide Following the procedure of Example 75, except substituting 2-cyanophenylsulfonyl chloride for thiazole-2-sulfonyl chloride and 5-methoxybenzofuran-2-carboxylic acid for benzofuran-2-carboxylic acid, the title compound was prepared. The residue was purified by HPLC. First eluting diastereomer; MS (M+H⁺): 581.4; ¹H-NMR (400 MHz, CDCl₃): •8.15-8.13(d, 1H), 7.92-7.90(d, 1H), 7.81-7.74(m, 2H), 7.42-7.40(m, 2H), 7.08-7.03(m, 3H), 6.96(d, 1H), 5.10(m, 1H), 4.72-4.60 (m, 2H), 4.17 (d, 1H), 3.85(s, 3H), 3.75-3.70(d, 1H), 2.83-2.76(t, 1H), 2.27(m, 2H), 1.92-1.51 (m, 5H), 1.02-1.01(m, 6H); and the second eluting diastereomer: MS (M+H⁺) 581.2.

Example 138

Preparation of Quinoxaline-2-carboxylic acid {(S)-1-[1-(2-cyano-benzenesulfonyl)-3-oxo-azepan-4-ylcarbamoyl]-3-methyl-butyl}-amide Following the procedure of Example 75, except substituting 2-cyanophenylsulfonyl chloride for thiazole-2-sulfonyl chloride and quinoxaline-2-carboxylic acid for benzofuran-2-carboxylic acid, the title compound was prepared. The residue was purified by HPLC. First eluting diastereomer; MS (M+H⁺): 563.2; ¹H-NMR (400 MHz, CDCl₃): •9.65(s, 1H), 8.40(m, 1H), 8.22-8.10(m, 3H), 7.90-7.22(m, 5H), 7.00(d, 1H), 5.10(m, 1H), 4.75(m, 1H), 4.65-4.60(d, 1H), 4.20-4.10 (m, 1H), 3.72-3.70(d, 1H), 2.70(m, 1H), 2.38(m, 2H), 1.95-1.40(m, 5H), 1.02(d, 6H); and the second eluting diastereomer: MS (M+H⁺) 563.2.

Example 139

Preparation of (S)-2-[2-(4-Methoxy-phenyl)-acetylamino)-4-methyl-pentanoic acid [1-(2-cyano-benzenesulfonyl)-3-oxo-azepan-4-yl]-amide Following the procedure of Example 75, except substituting 2-cyanophenylsulfonyl chloride for thiazole-2-sulfonyl chloride and 2-(4-methoxyphenyl)-acetic acid for benzofuran-2-carboxylic acid, the title compound was prepared. The residue was purified by HPLC. First eluting diastereomer; MS (M+H⁺): 555.2; ¹H-NMR (400 MHz, CDCl₃): •8.14-8.12 (d, 1H), 7.91-7.89(d, 1H), 7.79-7.73(m, 2H), 7.19-7.17(d, 2H), 6.90-6.88(d, 3H), 5.80(d, 1H), 5.02(m, 1H), 4.59-4.55 (d, 1H), 4.45-4.42(m, 1H), 4.18-4.15(m, 1H), 3.82(s, 3H), 3.72-3.67(d, 1H), 3.53(s, 2H), 2.82-2.79(t, 1H), 2.22(m, 2H), 1.92(m, 1H), 1.60-1.30(m, 4H), 0.91-0.89(d, 6H); and the second eluting diastereomer: MS (M+H⁺) 555.2.

Example 140

Preparation of Quinoline-2-carboxylic acid {[(S)-1-[1-(4-methoxy-benzenesulfonyl)-3-oxo-azepan-4-ylcarbamoyl]-3-methyl-butyl}-amide Following the procedure of Example 75, except substituting 4-methoxybenzenesulfonyl chloride for thiazole-2-sulfonyl chloride and 2-quinoline carboxylic acid for benzofuran-2-carboxylic acid, the title compound was prepared. The residue was purified by HPLC. First eluting diastereomer; MS (M+H⁺): 567.2; ¹H-NMR (400 MHz, CDCl₃): •8.72-8.61 (d, 1H), 8.35-8.28(q, 2H) 8.21-8.18(d, 1H), 7.91-7.60(m, 5H), 7.10-6.99(m, 3H), 5.05(m, 1H), 4.73 (m, 1H) 4.59-4.52 (d, 1H),4.00(m, 1H), 3.88(s, 3H), 3.45-3.38(d, 1H), 2.42(m, 1H), 2.30-1.35 (m, 7H), 1.03-1.01(m, 6H); and the second eluting diastereomer: MS (M+H⁺) 567.2.

Example 141

Preparation of 1-Methyl-1H-indole-2-carboxylic acid {[(S)-1-[1-(4-methoxy-benzenesulfonyl)-3-oxo-azepan-4-ylcarbamoyl]-3-methyl-butyl}-amide Following the procedure of Example 75, except substituting 4-methoxyphenylsulfonyl chloride for thiazole-2-sulfonyl chloride and N-methyl-indole-2-carboxylic acid for benzofuran-2-carboxylic acid, the title compound was prepared. The residue was purified by HPLC. First eluting diastereomer; MS (M+H⁺): 569.2; ¹H-NMR (400 MHz, CDCl₃): •7.78-7.72(d, 2H), 7.70-7.65(d, 1H), 7.42-7.30(m, 2H), 7.17-7.14(t, 1H), 7.05-6.95(m, 4H), 6.65(d, 1H), 5.05(m, 1H), 4.70-4.50 (m, 2H), 4.03(s, 3H), 3.88(s, 3H), 3.45-3.40(d, 1H), 2.45(m, 1H), 2.30-2.10(m, 2H), 1.90-1.35(m, 6H); and the second eluting diastereomer:, 1.00(d, 6H); and the second eluting diastereomer: MS (M+H$^+$) 569.2.

Example 142

Preparation of Furan-2-carboxylic acid ({(S)-1-[1-(4-methoxy-benzenesulfonyl)-3-oxo-azepan-4-ylcarbamoyl]-3-methyl-butylcarbamoyl}-methyl)-amide Following the procedure of Example 75, except substituting 4-methoxyphenylsulfonyl chloride for thiazole-2-sulfonyl chloride and N-(2-furan-carbonyl)-glycine for benzofuran-2-carboxylic acid, the title compound was prepared. The residue was purified by HPLC. First eluting diastereomer; MS (M+H$^+$): 563.2; $^1$H-NMR (400 MHz, CDCl$_3$): •7.74-7.72 (d, 2H), 7.47 (s, 1H), 7.15-6.99(m, 4H), 6.91(d, 1H), 6.70(d, 1H), 6.52-6.51(m, 1H), 5.01(m, 1H), 4.53-4.49 (m, 2H), 4.17-4.14(m, 2H), 4.00-3.90(m, 1H), 3.88(s, 3H), 3.45-3.41(d, 1H), 2.47(m, 1H), 2.17(m, 2H), 1.85-1.40(m, 5H), 0.95(m, 6H); and the second eluting diastereomer: MS (M+H$^+$) 563.2.

Example 143

Preparation of 5-Methoxybenzofuran-2-carboxylic acid {[(S)-1-[1-(4-methoxy-benzenesulfonyl)-3-oxo-azepan-4-ylcarbamoyl]-3-methyl-butyl}-amide Following the procedure of Example 75, except substituting 4-methoxyphenylsulfonyl chloride for thiazole-2-sulfonyl chloride and 5-methoxybenzofuran-2-carboxylic acid for benzofuran-2-carboxylic acid, the title compound was prepared. The residue was purified by HPLC. First eluting diastereomer; MS (M+H$^+$): 586.2; $^1$H-NMR (400 MHz, CDCl$_3$): •7.75-7.73(d, 2H), 7.42-7.40(m, 2H), 7.08-6.99(m, 5H), 6.91 (d, 1H), 5.05(m, 1H), 4.70-4.55(m, 2H), 4.05-4.00(m, 1H), 3.89(s, 3H), 3.86(s, 3H), 3.45-3.40(d, 1H), 2.50-2.40(m, 1H), 2.30-2.10(m, 2H), 1.90-1.35(m, 5H), 1.01(m, 6H); and the second eluting diastereomer: MS (M+H$^+$) 586.2.

Example 144

Preparation of Quinoxaline-2-carboxylic acid {[(S)-1-[1-(4-methoxy-benzenesulfonyl)-3-oxo-azepan-4-ylcarbamoyl]-3-methyl-butyl}-amide Following the procedure of Example 75, except substituting 4-methoxyphenylsulfonyl chloride for thiazole-2-sulfonyl chloride and quinoxaline-2-carboxylic acid for benzofuran-2-carboxylic acid, the title compound was prepared. The residue was purified by HPLC. First eluting diastereomer; MS (M+H$^+$): 568.2; $^1$H-NMR (400 MHz, CDCl$_3$): •9.66(s, 1H), 8.40-8.35(m, 1H), 8.19(m, 2H), 7.88(m, 2H), 7.75-7.73 (d, 2H), 7.02-6.90(m, 3H), 5.10-5.05(m, 1H), 4.75(m, 1H), 4.60-4.55(d, 1H), 4.05-3.95(m, 1H), 3.89(s, 3H), 3.45-3.41 (d, 1H), 2.45(m, 1H), 2.30-2.10(m, 2H), 1.95-1.40(m, 5H), 1.04-1.02(d, 6H); and the second eluting diastereomer: MS (M+H$^+$) 568.2.

Example 145

Preparation of (S)-2-[2-(4-Methoxy-phenyl)-acetylamino)-4-methyl-pentanoic acid [1-(4-methoxy-benzenesulfonyl)-3-oxo-azepan-4-yl]-amide Following the procedure of Example 75, except substituting 4-methoxyphenylsulfonyl chloride for thiazole-2-sulfonyl chloride and 2-(4-methoxyphenyl)-acetic acid for benzofuran-2-carboxylic acid, the title compound was prepared. The residue was purified by HPLC. First eluting diastereomer; MS (M+H$^+$): 560.4; $^1$H-NMR (400 MHz, CDCl$_3$): •7.74-7.71(d, 2H), 7.19-7.17(d, 2H), 7.01-6.99(d, 2H), 6.90-6.88(d, 2H), 6.85(d, 1H), 5.81(d, 1H), 4.99(m, 1H), 4.55-4.44 (m, 2H), 3.97(m, 1H), 3.88(s, 3H), 3.81(s, 3H), 3.53(s, 2H), 3.43-3.38(d, 1H), 2.43(t, 1H), 2.14(m, 2H), 1.85-1.35(m, 5H), 0.90-0.89(d, 6H); and the second eluting diastereomer: MS (M+H$^+$) 560.2.

Example 146

Preparation of 1-Methyl-1H-indole-2-carboxylic acid {[(S)-1-[1-(4-fluoro-benzenesulfonyl)-3-oxo-azepan-4-ylcarbamoyl]-3-methyl-butyl}-amide Following the procedure of Example 75, except substituting 4-fluorophenylsulfonyl chloride for thiazole-2-sulfonyl chloride and N-methyl-indole-2-carboxylic acid for benzofuran-2-carboxylic acid, the title compound was prepared. The residue was purified by HPLC. First eluting diastereomer; MS (M+H$^+$): 557.2; $^1$H-NMR (400 MHz, CDCl$_3$): •7.84-7.80 (m, 2H), 7.66-7.65(d, 1H), 7.40-7.14(m, 5H), 6.95(m, 2H), 6.65-6.63(d, 1H), 5.07(m, 1H), 4.68-4.55 (m, 2H), 4.04(s, 3H), 3.48-3.43(d, 1H), 2.49(m, 1H), 2.25(m, 2H), 1.89-1.38 (m, 6H); and the second eluting diastereomer:, 1.01(d, 6H); and the second eluting diastereomer: MS (M+H$^+$) 557.4.

Example 147

Preparation of Furan-2-carboxylic acid ({(S)-1-[1-(4-fluoro-benzenesulfonyl)-3-oxo-azepan-4-ylcarbamoyl]-3-methyl-butylcarbamoyl}-methyl)-amide Following the procedure of Example 75, except substituting 4-fluorophenylsulfonyl chloride for thiazole-2-sulfonyl chloride and N-(2-furan-carbonyl)-glycine for benzofuran-2-carboxylic acid, the title compound was prepared. The residue was purified by HPLC. First eluting diastereomer; MS (M+H$^+$): 551.4; $^1$H-NMR (400 MHz, CDCl$_3$): 7.81(m, 2H), 7.48(s, 1H), 7.27-7.16(m, 3H), 7.05(m, 1H), 6.90(d, 1H), 6.52(m, 2H), 5.00(m, 1H), 4.60-4.48 (m, 2H), 4.14(m, 2H), 4.00-3.90(d, 1H), 3.48-3.44(d, 1H), 2.50(m, 1H), 2.20(m, 2H), 1.90-1.40(m, 5H), 0.95(m, 6H); and the second eluting diastereomer: MS (M+H$^+$) 551.2.

Example 148

Preparation of 5-Methoxybenzofuran-2-carboxylic acid {[(S)-1-[1-(4-fluoro-benzenesulfonyl)-3-oxo-azepan-4-ylcarbamoyl]-3-methyl-butyl}-amide Following the procedure of Example 75, except substituting 4-fluorophenylsulfonyl chloride for thiazole-2-sulfonyl chloride and 5-methoxybenzofuran-2-carboxylic acid for benzofuran-2-carboxylic acid, the title compound was prepared. The residue was purified by HPLC. First eluting diastereomer; MS (M+H$^+$): 574.2; $^1$H-NMR (400 MHz, CDCl$_3$): •7.84-7.81 (m, 2H), 7.42-7.40(m, 2H), 7.27-7.22(m, 2H), 7.08-7.04(m, 3H), 6.93(d, 1H), 5.10-5.02(m, 1H), 4.69-4.55 (m, 2H), 4.05-4.00(m, 1H), 3.86(s, 3H), 3.47-3.43(d, 1H), 2.49(m, 1H), 2.24(m, 2H), 1.90-1.40(m, 5H), 1.01(m, 6H); and the second eluting diastereomer: MS (M+H$^+$): 574.2

Example 149

Preparation of Quinoxaline-2-carboxylic acid {[(S)-1-[1-(4-fluoro-benzenesulfonyl)-3-oxo-azepan-4-ylcarbamoyl]-3-methyl-butyl}-amide Following the procedure of Example 75, except substituting 4-fluorophenylsulfonyl chloride for thiazole-2-sulfonyl chloride and quinoxaline-2-carboxylic acid for benzofuran-2-carboxylic acid, the title compound was prepared. The residue was purified by HPLC. First eluting diastereomer; MS (M+H$^+$): 556.2; $^1$H-NMR (400 MHz, CDCl$_3$): •9.66(s, 1H), 8.40-8.35(d, 1H), 8.21-8.18(m, 2H), 7.90-7.81(m, 4H), 7.27-7.22(m, 2H), 6.97(d, 1H), 5.10-5.02(m, 1H), 4.75(m, 1H), 4.59-4.55(d, 1H), 4.05-4.39(m, 1H), 3.48-3.44(d, 1H), 2.49 (m, 1H), 2.32-2.10(m, 2H), 1.90-1.40(m, 5H), 1.03-1.02(d, 6H); and the second eluting diastereomer: MS (M+H$^+$) 556.2.

Example 150

Preparation of (S)-2-[2-(4-Methoxy-2-phenyl)-acetylamino]-4-methyl-pentanoic acid [1-(4-fluoro-benzenesulfonyl)-3-oxo-azepan-4-yl]-amide Following the procedure of Example 75, except substituting 4-fluorophenylsulfonyl chloride for thiazole-2-sulfonyl chloride and 2-(4-methoxyphenyl)-acetic acid for benzofuran-2-carboxylic acid, the title compound was prepared. The residue was purified by HPLC. First eluting diastereomer; MS (M+H$^+$): 548.2; $^1$H-NMR (400 MHz, CDCl$_3$): •7.83-7.80 (m, 2H), 7.27-7.17(m, 4H), 6.90-6.88(d, 3H), 5.85(d, 1H), 4.98(m, 1H), 4.55-4.43(m, 2H), 4.00-3.97(m, 1H), 3.81(s, 3H), 3.53(s, 2H), 3.45-3.41(d, 1H), 2.48(t, 1H), 2.17-2.14(m, 2H), 1.90-1.30(m, 5H), 0.90-0.88(d, 6H); and the second eluting diastereomer: MS (M+H$^+$): 548.4.

Example 151

Preparation of Benzofuran-2-carboxylic acid-{(S)-1-[1-(3-chloro-benzenesulphonyl)-3-oxo-azepan-4-ylcarbamoyl]-3-methyl-butyl}-amide a.) {(S)-1-[1-(3-Chloro-benzenesulfonyl)-3-hydroxy-azepan-4-ylcarbamoyl]-3-methyl-butyl}-carbamic acid tert-butyl ester To a solution of the compound of Example 2g (2.50 g, 7.29 mmol) in DCE (100 ml) was added P—NMM (4.0 g) and 3-chlorobenzenesulphonyl chloride (1.85 g, 8.75 mmol). After shaking at room temperature overnight, the solution was filtered. The filtrate was concentrated to yield the title compound as white solid (3.13 g, 83.3%). MS: 539.78 (M+Na)$^+$.

b.) (S)-2-Amino-4-methyl-pentanoic acid [1-(3-chloro-benzenesulfonyl)-3-hydroxy-azepan-4-yl]-amide To a stirring solution of the compound of Example 151a (1.0 g, 1.93 mmol) in methnol (10 ml) was added HCl (4M in Dioxane) (10 ml). After stirring at room temperature for 3 hr the solution was concentrated to provide a white solid. To a solution of the white solid (0.68 g, 1.50 mmol, 78%) in methnol (37 ml) was added P—CO$_3$ (2.85 g, 2.63 mmol/g). After shaking for 2 hr, the solution was filtered and concentrated to yield the title compound as white solid (0.59 g, 1.42 mmol, 95%). MS: 417.86 (M+H)$^+$.

c.) Benzofuran-2-carboxylic acid-{(S)-1-[1-(3-chloro-benzenesulphonyl)-3-hydroxy-azepan-4-ylcarbamoyl]-3-methyl-butyl}-amide To a solution of the compound of Example 151b (0.14 g, 0.33 mmol) in CH$_2$Cl$_2$ (20 mL) was added benzofuran-2-carboxylic acid (0.81, 0.50 mmol), 1-hydroxybenzotriazole (0.77 g, 0.57 mmol), and P-EDC (0.67 g, 1 mmol/g) in CH$_2$Cl$_2$ (10 mL). After shaking at room temperature overnight, the solution was treated with tisamine (0.45 g, 3.75 mmol/g). After shaking for another 2 hr, the solution was filtered and concentrated to yield the title compound as a white solid (122 mg, 65%). MS (ESI): 562.2 (M+H)$^+$.

d.) Benzofuran-2-carboxylic acid-{(S)-1-[1-(3-chloro-benzenesulphonyl)-3-oxo-azepan-4-ylcarbamoyl]-3-methyl-butyl}-amide To a stirring solution of the compound of Example 151c (122 mg, 0.22 mmol) in dichloromethane (4 mL) was added Dess-Martin reagent (185 mg, 0.44 mmol). After stirring at room temperature for 2 h, solutions of sodium thiosulfate (2 mL of 10% in water) and saturated aqueous sodium bicarbonate (2 mL) were added simultaneously to the solution. The aqueous layer was extracted with dichloromethane (2×). The organic phases were combined, washed with saturated brine, dried (MgSO$_4$), filtered and concentrated. The residue was purified by HPLC to yield the first eluting diastereomer as a white solid (62.7 mg, 51.6%), MS (ESI): 560.2 (M+H)$^+$ and the second eluting diastereomer as a white solid (40.2 mg, 33.1%). MS (ESI): 560.2 (M+H)$^+$

Example 152

Preparation of 5-Methoxybenzofuran-2-carboxylic acid-{(S)-1-[1-(3-chloro-benzenesulphonyl)-3-oxo-azepan-4-ylcarbamoyl]-3-methyl-butyl}-amide Following the procedure of Example 151c-d, except substituting 5-methoxybenzofuran-2-carboxylic acid for benzofuran-2-carboxylic acid of Example 151c provided the title compound which was separated by HPLC to give the first eluting diastereomer as a white solid (64.4 mg, 50.3%): MS (ESI): 590.2 (M+H)$^+$ and the second eluting distereomer as a white solid (44.4 mg, 34.7%): MS (ESI): 590.2 (M+H)$^+$

Example 153

Preparation of 7-Methoxybenzofuran-2-carboxylic acid-{(S)-1-[1-(3-chloro-benzenesulphonyl)-3-oxo-azepan-4-ylcarbamoyl]-3-methyl-butyl}-amide Following the procedure of Example 151c-d except substituting 7-methoxybenzofuran-2-carboxylic acid for benzofuran-2-carboxylic acid of Example 151c provided the title compound which was separated by HPLC to give first eluting diastereomer as a white solid (51.1 mg, 39.9%), MS (ESI): 590.2 (M+H)$^+$ and the second eluting diastereomer as a white solid (36.7 mg, 28.7%): MS (ESI): 590.2 (M+H)$^+$

Example 154

Preparation of 5,6-Dimethoxybenzofuran-2-carboxylic acid-{(S)-1-[1-(3-chloro-benzenesulphonyl)-3-oxo-azepan-4-ylcarbamoyl]-3-methyl-butyl}-amide Following the procedure of Example 151c-d except substituting 5,6-dimethoxybenzofuran-2-carboxylic acid for benzofuran-2-carboxylic acid of Example 151c provided the title compound which was separated by HPLC to give first eluting diastereomer as a white solid (51.1 mg, 39.9%), MS (ESI): 622.2 (M+H)+ and the second eluting diastereomer as a white solid (36.7 mg, 28.7%): MS (ESI): 622.2 (M+H)+

Example 155

Preparation of 3-Methylbenzofuran-2-carboxylic acid-{(S)-1-[1-(3-chloro-benzenesulphonyl)-3-oxo-azepan-4-ylcarbamoyl]-3-methyl-butyl}-amide Following the procedure of Example 151c-d except substituting 3-methylbenzofuran-2-carboxylic acid for benzofuran-2-carboxylic acid in step 151c provided the title compound which was separated by HPLC to give the first eluting diastereomer as a white solid (78.6 mg, 63.1%), MS (ESI): 574.2 (M+H)+ the second eluting diastereomer as a white solid (40.7 mg, 32.6%). MS (ESI): 574.2 (M+H)+

Example 156

Preparation of Benzo[b]thiophene-2-carboxylic acid-{(S)-1-[1-(3-chloro-benzenesulphonyl)-3-oxo-azepan-4-ylcarbamoyl]-3-methyl-butyl}-amide Following the procedure of Example 151c-d except substituting benzo[b]thiophene-2-carboxylic acid for benzofuran-2-carboxylic acid in step 151c provided the title compound which was separated by HPLC to give the first eluting diastereomer as a white solid (41.0 mg, 32.8%), MS (ESI): 576.2 (M+H)+ the second eluting diastereomer as a white solid (31.0 mg, 24.8%). MS (ESI): 576.4 (M+H)+

Example 157

Preparation of 1-Methyl-1H-indole-2-carboxylic acid-{(S)-1-[1-(3-chloro-benzenesulphonyl)-3-oxo-azepan-4-ylcarbamoyl]-3-methyl-butyl}-amide Following the procedure of Example 151c-d except substituting 1-methylindole-2-carboxylic acid for benzofuran-2-carboxylic acid in step 151c provided the title compound which was separated by HPLC to give the first eluting diastereomer as a white solid (28.5 mg, 22.9%), MS (ESI): 573.2 (M+H)+ the second eluting diastereomer as a white solid (28.5 mg, 22.9%). MS (ESI): 573.2 (M+H)+

Example 158

Preparation of Quinoxaline-2-carboxylic acid-{(S)-1-[1-(3-chloro-benzenesulphonyl)-3-oxo-azepan-4-ylcarbamoyl]-3-methyl-butyl}-amide Following the procedure of Example 151c-d except substituting quinoxaline-2-carboxylic acid for benzofuran-2-carboxylic acid in step 151c provided the title compound which was separated by HPLC to give the first eluting diastereomer as a white solid (63.1 mg, 50.8%), MS (ESI): 572.2 (M+H)+ the second eluting distereomer as a white solid (43.2 mg, 34.8%), MS (ESI): 572.2 (M+H)+

Example 159

Preparation of Benzofuran-2-carboxylic acid-{(S)-1-[1-(2-fluoro-benzenesulphonyl)-3-oxo-azepan-4-ylcarbamoyl]-3-methyl-butyl}-amide a.) {(S)-1-[1-(2-Fluoro-benzenesulfonyl)-3-hydroxy-azepan-4-ylcarbamoyl]-3-methyl-butyl}-carbamic acid tert-butyl ester To a solution of the compound of Example 2g (1.03 g, 3.00 mmol) in DCE (20 ml) was added P—NMM (1.65 g, 3.64 mmol/g) and 2-fluorobenzenesulphonylchloride (0.70 g, 3.60 mmol). After shaking at room temperature overnight, the solution was filtered. The filtrate was concentrated to yield the title compound as white solid (1.13 g, 75.1%): MS: 523.88 (M+Na)+.

b.) (S)-2-Amino-4-methyl-pentanoic acid [1-(2-fluoro-benzenesulfonyl)-3-hydroxy-azepan-4-yl]-amide To a stirring solution of the compound of Example 159a (1.13 g, 2.25 mmol) in methnol (15 ml) was added HCl (4M in dioxane) (15 ml). After stirring at room temperature for 3 hr, the solution was concentrated to get white solid. To a solution of the white solid (1.11 g, 2.60 mmol, 75%) in methnol (50 ml) was added P—CO₃ (5.70 g, 2.63 mmol/g). After shaking for 2 hr, the solution was filtered and concentrated to yield the title compound as white solid (0.868 g, 2.16 mmol, 96%): MS: 401.96 (M+H)+.

c.) Benzofuran-2-carboxylic acid-{(S)-1-[1-(2-fluoro-benzenesulphonyl)-3-hydroxy-azepan-4-ylcarbamoyl]-3-methyl-butyl}-amide To a solution of the compound of Example 159b (0.11 g, 0.26 mmol) in CH₂Cl₂ (10 mL) was added benzofuran-2-carboxylic acid (64.7 mg, 0.39 mmol), 1-hydroxybenzotriazole (61.1 g, 0.45 mmol), and P-EDC (0.53 g, 1 mmol/g) in CH₂Cl₂ (10 mL). After shaking at room temperature overnight, the solution was treated with tisamine (0.35 g, 3.75 mmol/g). After shaking for another 2 hr, the solution was filtered and concentrated to yield the title compound as a white solid (103.5 mg, 70%): MS (ESI) 546.2 (M+H)+.

d.) Benzofuran-2-carboxylic acid-{(S)-1-[1-(2-fluoro-benzenesulphonyl)-3-oxo-azepan-4-ylcarbamoyl]-3-methyl-butyl}-amide To a stirring solution of the compound of Example 159c (103.5 mg, 0.19 mmol) in dichloromethane (4 mL) was added Dess-Martin reagent (164.7 mg, 0.39 mmol). After stirring at room temperature for 2 h, solutions of sodium thiosulfate (2 mL of 10% in water) and saturated aqueous sodium bicarbonate (2 mL) were added simultaneously to the solution. The aqueous was extracted with dichloromethane (2x). The organic phases were combined, washed with saturated brine, dried (MgSO₄), filtered and concentrated. The residue was purified by HPLC to yield the first eluting diastereomer as a white solid (76.2 mg, 73.6%): MS (ES[) 544.2 (M+H)+ the second eluting diastereomer as a white solid (20.7 mg, 20.0%) MS (ESI) 544.4 (M+H)+

Example 160

Preparation of 5-Methoxybenzofuran-2-carboxylic acid-{(S)-1-[1-(2-fluoro-benzenesulphonyl)-3-oxo-azepan-4-ylcarbamoyl]-3-methyl-butyl}-amide Following the procedure of Example 159c-d, except substituting 5-methoxybenzofuran-2-carboxylic acid for benzofuran-2-carboxylic acid in step 159c provided the title compound which was separated by HPLC to give the first eluting diastereomer as a white solid (48.3 mg, 59.2%) MS (ESI): 574.2 (M+H)+ the second eluting diastereomer as a white solid (24.2 mg, 29.6%) MS (ESI): 574.2 (M+H)+

Example 161

Preparation of 7-Methoxybenzofuran-2-carboxylic-acid-{(S)-1-[1-(2-fluoro-benzenesulphonyl)-3-oxo-azepan-4-ylcarbamoyl]-3-methyl-butyl}-amide Following the procedure of Example 159c-d except substituting 7-methoxybenzofuran-2-carboxylic acid for benzofuran-2-carboxylic acid in step 159c provided the title compound which was separated by HPLC to give the first eluting diastereomer as a white solid (47.7 mg, 58.5%): MS (ESI) 574.2 (M+H)$^+$ the second eluting diastereomer as a white solid (27.7 mg, 33.9%).

Example 162

Preparation of 5,6-Dimethoxybenzofuran-2-carboxylic acid-{(S)-1-[1-(2-fluoro-benzenesulphonyl)-3-oxo-azepan-4-ylcarbamoyl]-3-methyl-butyl}-amide Following the procedure of Example 159c-d except substituting 5,6-dimethoxybenzofuran-2-carboxylic acid for benzofuran-2-carboxylic acid in step 159c provided the title compound which was separated by HPLC to give the first eluting diastereomer: MS (ESI) 606.4 (M+H)$^+$ the second eluting diastereomer as a white solid MS(ESI) 606.4 (M+H$^+$).

Example 163

Preparation of 3-Methylbenzofuran-2-carboxylic acid-{(S)-1-[1-(2-fluoro-benzenesulphonyl)-3-oxo-azepan-4-ylcarbamoyl]-3-methyl-butyl}-amide Following the procedure of Example 159c-d except substituting 3-methylbenzofuran-2-carboxylic acid for benzofuran-2-carboxylic acid in step 160c provided the title compound which was separated by HPLC to give the first eluting diastereomer as a white solid (50.5 mg, 63.7%): MS (ESI) 558.2 and the second eluting diastereoemer as a white solid (20.6 mg); MS 558.2 (M+H)$^+$.

Example 164

Preparation of Benzo[b]thiophene-2-carboxylic acid-{(S)-1-[1-(2-fluoro-benzenesulphonyl)-3-oxo-azepan-4-ylcarbamoyl]-3-methyl-butyl}-amide Following the procedure of Example 159c-d except substituting benzo[b]thiophene-2-carboxylic acid for benzofuran-2-carboxylic acid in step 159c provided the title compound which was separated by HPLC to give the first eluting diastereomer as a white solid (52.5 mg, 65.9%): MS (ESI) 560.2 (M+H)$^+$ the second eluting diastereomer as a white solid (20.7 mg, 26.0%): MS(ESI) 560.2 (M+H)$^+$

Example 165

Preparation of 1-Methyl-1H-indole-2-carboxylic acid-{(S)-1-[1-(2-fluoro-benzenesulphonyl)-3-oxo-azepan-4-ylcarbamoyl]-3-methyl-butyl}-amide Following the procedure of Example 159c-d except substituting 1-methylindole-2-carboxylic acid, for benzofuran-2-carboxylic acid in step 159c provided the title compound which was separated by HPLC to give the first eluting diastereomer as a white solid (51.4 mg, 64.9%): MS (ESI) 557.2 (M+H)$^+$ the seond eluting diastereoemer as a white solid (21.0 mg, 26.5%): MS 557.2 (M+H)$^+$

Example 166

Preparation of (S)-4-Methyl-2-(1-oxy-pyridine-2-sulfonylamino)-pentanoic acid [3-oxo-1-(pyridine-2-sulfonyl)-azepan-4-yl]-amide a.) (S)-4-Methyl-2-(1-oxy-pyridine-2-sulfonylamino)-pentanoic acid [3-hydroxy-1-(pyridine-2-sulfonyl)-azepan-4-yl]-amide To a solution of the compound of Example 28a (0.1 ) in dichlorormethane (10 mL) and saturated NaHCO$_3$ was added 2-pryridinesulfonyl chloride N-oxide (0.9 mL) in a dropwise fashion over 3 minutes. The reaction was stirred at room temperature for 30 minutes. Workup and columnn chromatography provided 9.2 mg of the title compound: MS (ESI) 541 (M+H$^+$).

b.) (S)-4-Methyl-2-(1-oxy-pyridine-2-sulfonylamino)-pentanoic acid [3-oxo-1-(pyridine-2-sulfonyl)-azepan-4-yl]-amide Following the procedure of Example 1i except substituting the compound of Example 166a the title compound was prepared: MS (ESI) 539 (M+H$^+$).

Example 167

Preparation of Quinoxaline-2-carboxylic acid-{(S)-1-[1-(2-fluoro-benzenesulphonyl)-3-oxo-azepan-4-ylcarbamoyl]-3-methyl-butyl}-amide Following the procedure of Example 159c-d except substituting quinoxaline-2-carboxylic acid for benzofuran-2-carboxylic acid in step 159c provided the title compound which was purified by HPLC to give the first eluting diastereomer as a white solid (49.7 mg, 62.9%): MS (ESI) 556.2 (M+H)$^+$ and the second eluting diastereomer as a white solid (19.9 mg, 25.1%): MS 556.4 (M+H)$^+$

Example 168

Preparation of 5-Methoxybenzofuran-2-carboxylic acid-{(S)-3-methyl-1-[3-oxo-1-(thiophene-2-sulfonyl)-azepan-4-ylcarbamoyl]-butyl}-amide Following the procedure of Example 75a-d except substituting 2-thiophensulfonyl chloride for 2-thiazolesupfonyl chloride of Example 75a and 5-methoxybenzofuran-2-carboxylic acid for benzofuran-2-carboxylic acid in step 75c provided the title compound which was purified by HPLC to give the first eluting diastereomer as a white solid (71 mg, 65%): MS (ESI) 562.2 (M+H)$^+$ the second eluting diastereomer as a white solid (21.6 mg, 20.0%) MS (ESI): 562.2 (M+H)$^+$

Example 169

Preparation of 7-Methoxybenzofuran-2-carboxylic acid-{(S)-3-methyl-1-[3-oxo-1-(thiophene-2-sulfonyl)-azepan-4-ylcarbamoyl]-butyl}-amide Following the procedure of Example 168 except substituting 7-methoxybenzofuran-2-carboxylic acid for 5-methoxybenzofuran-2-carboxylic acid provided the title compound which ws purified by HPLC to give the first eluting diastereomer as a white solid (88 mg, 80%): MS (ESI) 562.2 (M+H)+ the second eluting diastereomer as a white solid (18 mg, 16%) MS (ESI): 562.2 (M+H)+

Example 170

Preparation of 5,6-Dimethoxybenzofuran-2-carboxylic acid-{(S)-3-methyl-1-[3-oxo-1-(thiophene-2-sulfonyl)-azepan-4-ylcarbamoyl]-butyl}-amide Following the procedure of Example 168 except substituting 5,6-dimethoxybenzofuran-2-carboxylic acid for 5-methoxybenzofuran-2-carboxylic acid provided the title compound which was purified by HPLC to give the first eluting diastereomer MS (ESI) 594.2 (M+H)+ the second eluting diastereomer.

Example 171

Preparation of 3-Methylbenzofuran-2-carboxylic acid-{(S)-3-methyl-1-[3-oxo-1-(thiophene-2-sulfonyl)-azepan-4-ylcarbamoyl]-butyl}-amide Following the procedure of Example 168 except substituting 3-methybenzofuran-2-carboxylic acid for 5-methoxybenzofuran-2-carboxylic acid provided the title compound which was purified by HPLC to give the first eluting diastereomer as a white solid (88 mg, 83%): MS (ESI) 546.2 (M+H)+ the second eluting diastereomer as a white solid (16 mg, 15%): MS (ESI) 546.2 (M+H)+

Example 172

Preparation of Benzo[b]thiophene-2-carboxylic acid-{(S)-3-methyl-1-[3-oxo-1-(thiophene-2-sulfonyl)-azepan-4-ylcarbamoyl]-butyl}-amide Following the procedure of Example 168 except substituting benzo[b]thiophene-2-carboxylic acid 5-methoxybenzofuran-2-carboxylic acid provided the title compound which was purified by HPLC to give the first eluting diastereomer as a white solid (43.4 mg, 41%): MS (ESI) 548.4 (M+H)+ the second eluting diastereomer as a white solid (33.4 mg, 31.5%): MS (ESI) 548.2 (M+H)+

Example 173

Preparation of 1-Methyl-1H-indole-2-carboxylic acid-{(S)-3-methyl-1-[3-oxo-1-(thiophene-2-sulfonyl)-azepan-4-ylcarbamoyl]-butyl}-amide Following the procedure of Example 168 except substituting 1-methylindole-2-carboxylic acid for 5-methoxybenzofuran-2-carboxylic acid provided the title compound which was separated by HPLC to give the first eluting diastereomer as a white solid (35.8 mg, 34.0%): MS (ESI) 545.2 (M+H)+ the second eluting diastereomer as a white solid (45.8 mg, 43%): MS (ESI) 545.2 (M+H)+

Example 174

Preparation of Quinoxaline-2-carboxylic acid-{(S)-3-methyl-1-[3-oxo-1-(thiophene-2-sulfonyl)-azepan-4-ylcarbamoyl]-butyl}-amide Following the procedure of Example 168 except substituting quinoxaline-2-carboxylic acid for 5-methoxybenzofuran-2-carboxylic acid provided the title compound which was separated by HPLC to give the first eluting diastereomer as a white solid (60 mg, 56%): MS (ESI) 544.4 (M+H)+ the second eluting diastereomer as a white solid (38.7 mg, 37%): MS (ESI) 544.4 (M+H)+

Example 175

Preparation of Benzofuran-2-carboxylic acid-{(S)-1-[1-(4-chloro-benzenesulphonyl)-3-oxo-azepan-4-ylcarbamoyl]-3-methyl-butyl}-amide a.) {(S)-1-[1-(3-Chloro-benzenesulfonyl)-3-hydroxy-azepan-4-ylcarbamoyl]-3-methyl-butyl}-carbamic acid tert-butyl ester To a solution of the compound of Example 2 (2.50 g, 7.29 mmol) in DCE (100 ml) was added P—NMM (4.0 g) and 4-chlorobenzenesulphonyl chloride (1.85 g, 8.75 mmol). After shaking at room temperature for over night, the solution was filtered. The filtrate was concentrated to yield the title compound as white solid (3.13 g, 83.3%). MS: 539.78 (M+Na)+.

b.) (S)-2-Amino-4-methyl-pentanoic acid (1-(3-chloro-benzenesulfonyl)-3-hydroxy-azepan-4-yl]-amide To a stirring solution of the compound of example 175a (1.0 g, 1.93 mmol) in methnol (10 ml) was added HCl (4M in dioxane) (10 ml). After stirring at room temperature for 3 hr, the solution was concentrated to provide a white solid. To a solution of the white solid (0.68 g, 1.50 mmol, 78%) in methnol (37 ml) was added P—CO$_3$ (2.85 g, 2.63 mmol/g). After shaking for 2 hr, the solution was filtered and concentrated to yield the title compound as white solid (0.59 g, 1.42 mmol, 95%): MS: 417.86 (M+H)+.

c.) Benzofuran-2-carboxylic acid-{(S)-1-[1-(4-chloro-benzenesulphonyl)-3-hydroxy-azepan-4-ylcarbamoyl]-3-methyl-butyl}-amide To a solution of the compound of Example 175b (0.14 g, 0.335 mmol) in CH$_2$Cl$_2$ (20 mL) was added benzofuran-2-carboxylic acid (0.81, 0.50 mmol), 1-hydroxybenzotriazole (0.77 g, 0.569 mmol), and P-EDC (0.67 g, 1 mmol/g) in CH$_2$Cl$_2$ (10 mL). After shaking at room temperature overnight, the solution was treated with tisamine (0.446 g, 3.75 mmol/g). After shaking for another 2 hr, the solution was filtered and concentrated to yield the title compound as a white solid (122.2 mg, 65%). MS (ESI): 562.2 (M+H)+.

d.) Benzofuran-2-carboxylic acid-{(S)-1-[1-(4-chloro-benzenesulphonyl)-3-oxo-azepan-4-ylcarbamoyl]-3-methyl-butyl}-amide To a stirring solution of the compound of Example 175c (122.2 mg, 0.217 mmol) in dichloromethane (4 mL) was added Dess-Martin reagent (184.8 mg, 0.436 mmol). After stirring at room temperature for 2 h, solutions of sodium thiosulfate (2 mL of 10% in water) and saturated aqueous sodium bicarbonate (2 mL) were added simultaneously to the solution. The aqueous was extracted with dichloromethane (2×). The organic phases were combined, washed with saturated brine, dried (MgSO$_4$), filtered and concentrated. The residue was purified by HPLC to yield the first eluting diastereomer as a white solid (62.7 mg, 51.6%): MS (ESI) 560.2 (M+H)+ the second elution as a white solid (32.7 mg, 26.9%): MS (ESI) 560.2 (M+H)+

Example 176

Preparation of 5-Methoxybenzofuran-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting 5-methoxybenzofuran-2-carboxylic acid for benzofuran-2-carboxylic acid in step 175c provided the title compound which was separated by HPLC to give the first eluting diastereomer as a white solid (64.4 mg, 50%): MS (ESI) 590.2 (M+H)$^+$ the second eluting diastereoemer as a white solid (32.2 mg, 25.2%): MS (ESI) 590.0 (M+H)$^+$

Example 177

Preparation of 7-Methoxybenzofuran-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting 7-methoxybenzofuran-2-carboxylic acid for benzofuran-2-carboxylic acid in step 175c provided the title compound which was separated by HPLC to give the first eluting diastereomer as a white solid (51.1 mg, 40%): MS (ESI) 590.2 (M+H)$^+$ the second eluting diastereoemer as a white solid (41 mg, 32%): MS (ESI) 590.2 (M+H)$^+$

Example 178

Preparation of 5,6-Dimethoxybenzofuran-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting 5,6-dimethoxybenzofuran-2-carboxylic acid for benzofuran-2-carboxylic acid in step 175c provided the title compound which was separated by HPLC to give the first eluting diastereomer: MS (ESI) 622.2 (M+H)$^+$ the second eluting diastereoemer: MS (ESI) 622.2 (M+H)$^+$

Example 179

Preparation of 3-Methylbenzofuran-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting 3-methylbenzofuran-2-carboxylic acid for benzofuran-2-carboxylic acid in step 175c provided the title compound which was separated by HPLC to give the first eluting diastereomer as a white solid (78.6 mg, 63%): MS (ESI) 574.2 (M+H)$^+$ the second eluting diastereoemer as a white solid (27.6 mg, 22%): MS (ESI) 574.2 (M+H)$^+$

Example 180

Preparation of Benzo[b]thiophene-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting benzo[b]thiophene-2-carboxylic acid for benzofuran-2-carboxylic acid in step 175c provided the title compound which was separated by HPLC to give the first eluting diastereomer as a white solid (41 mg, 33%): MS (ESI) 576.2 (M+H)$^+$ the second eluting diastereoemer as a white solid (32.6 mg, 26%): MS (ESI) 576.2 (M+H)$^+$

Example 181

Preparation of 1-Methyl-1H-indole-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting 1-methylindole-2-carboxylic acid for benzofuran-2-carboxylic acid in step 175c provided the title compound which was separated by HPLC to give the first eluting diastereomer as a white solid (28.5 mg, 23%): MS (ESI) 573.2 (M+H)$^+$ the second eluting diastereoemer as a white solid (38.5 mg, 31%): MS (ESI) 573.2 (M+H)$^+$

Example 182

Preparation of Quinoxaline-2-carboxylic acid-{(S)-1-[1-(4-chloro-benzenesulphonyl)-3-oxo-azepan-4-ylcarbamoyl]-3-methyl-butyl}-amide Following the procedure of Example 175c-d except substituting quinoxaline-2-carboxylic acid for benzofuran-2-carboxylic acid in step 175c provided the title compound which was separated by HPLC to give the first eluting diastereomer as a white solid (63 mg, 51%): MS (ESI) 572.2 (M+H)$^+$ the second eluting diastereoemer as a white solid (44.5 mg, 36%): MS (ESI) 572.2 (M+H)$^+$

Example 183

Preparation of Benzofuran-2-carboxylic acid-{(S)-1-[1-(3-methoxy-benzenesulphonyl)-3-oxo-azepan-4-ylcarbamoyl]-3-methyl-butyl}-amide a.) {(S)-1-[1-(3-Methoxy-benzenesulfonyl)-3-hydroxy-azepan-4-ylcarbamoyl]-3-methyl-butyl}-carbamic acid tert-butyl ester To a solution of the compound of Example 2g (1.60 g, 4.66 mmol) in DCE (50 ml) was added P—NMM (2.56 g, 3.64 mmol/g) and 3-methoxy-benzenesulphonyl chloride (1.15 g, 5.59 mmol). After shaking at room temperature for over night, the solution was filtered. The filtrate was concentrated to yield the title compound as white solid (1.70 g, 71.1%): MS 535.8 (M+Na)$^+$.

b.) (S)-2-Amino-4-methyl-pentanoic acid [1-(3-methoxy-benzenesulfonyl)-3-hydroxy-azepan-4-yl]-amide To a stirring solution of the compound of example 183a (1.70 g, 3.31 mmol) in methnol (22 ml) was added HCl (4M in dioxane) (22 ml). After stirring at room temperature for 3 hr, the solution was concentrated to get white solid. To a solution of the white solid (1.19 g, 2.64 mmol, 80%) in methanol (50 ml) was added P—CO$_3$ (5.02 g, 2.63 mmol/g). After shaking for 2 hr the solution was filtered and concentrated to yield the title compound as white solid (1.03 g, 2.49 mmol, 96%): MS 413.90 (M+H)$^+$.

c.) Benzofuran-2-carboxylic acid-{(S)-1-[1-(3-methoxy-benzenesulphonyl)-3-hydroxy-azepan-4-ylcarbamoyl]-3-methyl-butyl}-amide To a solution of the compound of Example 183b (0.11 g, 0.26 mmol) in CH$_2$Cl$_2$ (10 mL) was added benzofuran-2-carboxylic acid (64.69 mg, 0.399 mmol), 1-hydroxybenzotriazole (61.1 g, 0.452 mmol), and P-EDC (0.532 g, 1 mmol/g)

in CH$_2$Cl$_2$ (10 mL). After shaking at room temperature for over night, the solution was treated with tisamine (0.355 g, 3.75 mmol/g). After shaking for another 2 hr, the solution was filtered and concentrated to yield the title compound as a white solid (103.5 mg, 70%): MS (ESI) 558.2 (M+H)$^+$.

d.) Benzofuran-2-carboxylic acid-{(S)-1-[1-(3-methoxy-benzenesulphonyl)-3-oxo-azepan-4-ylcarbamoyl]-3-methyl-butyl}-amide To a stirring solution of the compound of Example 183c (103 mg, 0.19 mmol) in dichloromethane (4 mL) was added Dess-Martin reagent (157 mg, 0.37 mmol). After stirring at room temperature for 2 h, solutions of sodium thiosulfate (2 mL of 10% in water) and saturated aqueous sodium bicarbonate (2 mL) were added simultaneously to the solution. The aqueous was extracted with dichloromethane (2×). The organic phases were combined, washed with saturated brine, dried (MgSO$_4$), filtered and concentrated. The residue was purified by HPLC to yield the first eluting diastereomer as a white solid (76.2 mg, 73.6%): MS (ESI: 556.2 (M+H)$^+$ the second eluting diastereomer as a white solid (24.1 mg, 23.3%): MS (ESI) 556.2 (M+H)$^+$

Example 184

Preparation of 5-Methoxybenzofuran-2-carboxylic acid-{(S)-1-[1-(3-methoxy-benzenesulphonyl)-3-oxo-azepan-4-ylcarbamoyl]-3-methyl-butyl}-amide Following the procedure of Example 183c-d except substituting 5-methoxybenzofuran-2-carboxylic acid for benzofuran-2-carboxylic acid in step 183c provided the title compound which was separated by HPLC to give the first eluting diastereomer as a white solid (33 mg, 31%): MS (ESI) 586.2 (M+H)$^+$ the second eluting diastereoemer as a white solid (35.2 mg, 32%): MS (ESI) 586.2 (M+H)$^+$

Example 185

Preparation of 7-Methoxybenzofuran-2-carboxylic acid-{(S)-1-[1-(3-methoxy-benzenesulphonyl)-3-oxo-azepan-4-ylcarbamoyl]-3-methyl-butyl}-amide Following the procedure of Example 183c-d except substituting 7-methoxybenzofuran-2-carboxylic acid for benzofuran-2-carboxylic acid in step 183c provided the title compound which was separated by HPLC to give the first eluting diastereomer as a white solid (41 mg, 38%): MS (ESI) 586.4 (M+H)$^+$ the second eluting diastereoemer as a white solid (39.5 mg, 36%): MS (ESI) 586.2 (M+H)$^+$

Example 186

Preparation of 4,5-Dimethoxybenzofuran-2-carboxylic acid-{(S)-1-[1-(3-methoxy-benzenesulphonyl)-3-oxo-azepan-4-ylcarbamoyl]-3-methyl-butyl}-amide Following the procedure of Example 183c-d except substituting 5,6-dimethoxybenzofuran-2-carboxylic acid for benzofuran-2-carboxylic acid in step 183c provided the title compound which was separated by HPLC to give the first eluting diastereomer: MS (ESI) 618.4 (M+H)$^+$ the second eluting diastereoemer.

Example 187

Preparation of 3-Methylbenzofuran-2-carboxylic acid-{(S)-1-[1-(3-methoxy-benzenesulphonyl)-3-oxo-azepan-4-ylcarbamoyl]-3-methyl-butyl}-amide Following the procedure of Example 183c-d except substituting 3-methylbenzofuran-2-carboxylic acid for benzofuran-2-carboxylic acid in step 183c provided the title compound which was separated by HPLC to give the first eluting diastereomer as a white solid (76 mg, 72%): MS (ESI) 570.2 (M+H)$^+$ the second eluting diastereoemer as a white solid (23.2 mg, 22%): MS (ESI) 570.2 (M+H)$^+$

Example 188

Preparation of Benzo[b]thiophene-2-carboxylic acid-{(S)-1-[1-(3-methoxy-benzenesulphonyl)-3-oxo-azepan-4-ylcarbamoyl]-3-methyl-butyl}-amide Following the procedure of Example 183c-d except substituting benzo[b]thiophene-2-carboxylic acid for benzofuran-2-carboxylic acid in step 183c provided the title compound which was separated by HPLC to give the first eluting diastereomer as a white solid (37 mg, 35%): MS (ESI) 572.2 (M+H)$^+$ the second eluting diastereoemer as a white solid (31 mg, 29%): MS (ESI) 572.2 (M+H)$^+$

Example 189

Preparation of 1-Methyl-1H-indole-2-carboxylic acid-{(S)-1-[1-(3-methoxy-benzenesulphonyl)-3-oxo-azepan-4-ylcarbamoyl]-3-methyl-butyl}-amide Following the procedure of Example 183c-d except substituting 1-methylindole-2-carboxylic acid for benzofuran-2-carboxylic acid in step 183c provided the title compound which was separated by HPLC to give the first eluting diastereomer as a white solid (34 mg, 32%): MS (ESI) 569.2 (M+H)$^+$ the second eluting diastereoemer as a white solid (38 mg, 38%): MS (ESI) 569.4 (M+H)$^+$

Example 190

Preparation of Quinoxaline-{(S)-1-[1-(3-methoxy-benzenesulphonyl)-3-oxo-azepan-4-ylcarbamoyl]-3-methyl-butyl}-amide Following the procedure of Example 183c-d except substituting quinoxaline-2-carboxylic acid for benzofuran-2-carboxylic acid in step 183c provided the title compound which was separated by HPLC to give the first eluting diastereomer as a white solid (71 mg, 67%): MS (ESI) 568.2 (M+H)$^+$ the second eluting diastereoemer as a white solid (27 mg, 24%): MS (ESI) 568.2 (M+H)$^+$

Example 191

Preparation of Benzofuran-2-carboxylic acid-{(S)-3-methyl-1-[3-oxo-1-(thiophene-2-sulfonyl)-azepan-4-ylcarbamoyl]-butyl}-amide Following the procedure of Example 168 except substituting benzofuran-2-carboxylic acid for 5-methoxybenzofuran-2-carboxylic acid provided the title compound which ws purified by HPLC to give the first eluting diastereomer as a white solid (76 mg, 73%): MS (ESI) 532.2 (M+H)$^+$ the second eluting diastereomer as a white solid (25 mg, 23%) MS (ESI): 532.2 (M+H)$^+$

Example 192

Preparation of Benzofuran-2-carboxylic acid {(S)-3-methyl-1-[(2,2',4-trideuterio)-3-oxo-1-(pyridine-2-sulfonyl)-azepan-4-ylcarbamoyl]-butyl}amide To a solution of benzofuran-2-carboxylic acid {(S)-3-methyl-1-[3-oxo-1-(pyridine-2-sulfonyl)-azepan-4-ylcarbamoyl]-butyl}amide of Example 28c (0.03 g) in $D_2O:CD_3OD$ (0.4:4 mL) was added triethylamine (0.04 mL). The reaction was heated to reflux for 2 hours whereupon it was concentrated and dried under vacuum. The residue was the redissolved in the same mixture and heated to reflux overnight. The reaction was concentrated and the residue purified by column chromatography (5% methanol:dichloromethane) to provide the title compound (0.02 ): $^1$HNMR: δ 1.0 (m, 6H), 1.5-2.2 (m, 6H), 2.7 (m, 1H), 4.1 (m, 1H), 4.7 (m, 2H), 7.4-8.0 (m, 8H), 8.7 (m, 1H); MS(EI): 529 ($M^+$, 45%).

The diastereomeric mixture was separated by HPLC to provide the faster eluting diastereoemer: MS(EI): 530 $(M+H^+, 100\%)$ and the slower eluting diastereomer: MS(EI): 530 $(M+H^+, 100\%)$.

Example 193

Preparation of Benzofuran-2-carboxylic acid {(S)-2-methyl-1-[3-oxo-1-(pyridine-2-sulfonyl)-azepan-4-ylcarbamoyl]-butyl}-amide a.) 4-tert-Butoxycarbonylamino-3-hydroxy-azepane-1-carboxylicacid benzyl ester To a stirring solution of compound of Example 2e (1.04 g, 3.92 mmol) in THF was added di-tert-butyldicarbonate (0.864 g). After stirring at room temperature for 30 minutes, the reaction mixture was diluted with diethylether and extracted with saturated $NaHCO_3$. The organic layer was dried over anhydrous $Na_2SO_4$, filtered, concentrated, and purified by silica gel column to give the title compound as a yellow oil (0.963 g, 2.64 mmol, 67%). MS (ESI): 365.03 $(M+H)^+$.

b.) (3-Hydroxy-azepan-4-yl)-carbamic acid tert-butyl ester

To a solution of compound of Example 193a (0.963 g, 2.64 mmol) in ethyl acetate (16 ml) was added 10% palladium on carbon (500 mg). After stirring the solution at room temperature for 48 hours, the mixture was filtered through celite. The filtrate was concentrated to yield the title compound (0.529 g, 2.29 mmol, 87%): MS(ESI): 231.92 $(M+H)^+$.

c.) [3-Hydroxy-1-(pyridine-2-sulfonyl)-azepan-4-yl]-carbamic acid tert-butyl ester To a solution of the compound of Example 193b (0.53, 2.29 mmol) in dichloromethane (20 ml) was added triethylamine (232 mg) and pyridine-2-sulfonyl chloride (410 mg, 2.32 mmol). After stirring at room temperature for 30 minutes, the mixture was washed with saturated $NaHCO_3$. The organic layer was dried, filtered, concentrated and purified on a silica gel column to give the title compound as a solid (0.58 g, 1.57 mmol, 68%): MS(ESI): 372.95 $(M+H)^+$.

d.) 4-Amino-1-(pryidine-2-sulfonyl)-azepan-3-ol

To a stirring solution of the compound of Example 193c (0.583 g, 1.57 mmol) in ethyl acetate (0.5 ml) was added HCl (4M in dioxane, 3.9 ml). After stirring the reaction mixture for 30 minutes at room temperature, the mixture was concentrated to yield a white solid. The solid was treated with NaOH and then extracted with ethylacetate. The organic layer was dried, filtered, and concentrated to yield a yellow solid (0.35 g, 1.28 mmol, 81%): MS (ESI) 272.93 $(M+H)^+$.

e.) {(S)-1-[3-Hydroxy-1-(pryidine-2-sulfonyl)-azepan-4-ylcarbamoyl]-2-meth-butyl}-carbamic acid tert-butyl ester To a solution of the compound of example 193d (19 mg, 0.070 mmol) in $CH_2Cl_2$ was added N-Boc-isoleucine (24.5 mg, 0.10 mmol), 1-hydroxybenzotriazole (16.1 mg, 0.12 mmol), and P-EDC (140 mg, 0.14 mmol) in $CH_2Cl_2$. After shaking at room temperature overnight, the mixture was treated with PS-Trisamine. After shaking for another 2 hours, the mixture was filtered and concentrated to yield the title compound as a solid. MS (ESI) 484.97 $(M+H)^+$.

f.) (S)-2-Amino-3-methyl-penatanoic acid [3-hydroxy-1-(pyridine-2-sulfonyl)-azepan-4-yl]-amide To a stirring solution of the compound of example 193e (34 mg, 0.07 mmol) in $CH_2Cl_2$ (0.50 ml) was added HCl (4M in dioxane) (0.165 ml). After stirring at room temperature for 30 minutes, the mixture was concentrated, giving a white solid. The white solid was azeotroped with toluene then treated with MP-carbonate (0.35 mmol) in methanol. After four hours of shaking, the mixture was filtered and concentrated to give the title compound as a solid.: MS(ESI) 384.9 $(M+H)^+$.

g.) Benzofuran-2-carboxylic acid {(S)-2-methyl-1-[3-hydroxy-1-(pyridine-2-sulfonyl)-azepan-4-ylcarbamoyl]-butyl}-amide To a solution of the compound of example 193f (27 mg, 0.070 mmol) in $CH_2Cl_2$ was added 2-benzofurancarboxylic acid (17.0 mg, 0.106 mmol), 1-hydroxybenzotriazole (16.1 mg, 0.12 mmol), and P-EDC (140 mg, 0.14 mmol) in $CH_2Cl_2$. After shaking at room temperature overnight, the mixture was treated with PS-Trisamine. After shaking for another 2 hours, the mixture was filtered and concentrated to yield the title compound as a solid: MS (ESI) 528.9 $(M+H)^+$.

h.) Benzofuran-2-carboxylic acid {(S)-2-methyl-1-[3-oxo-1-(pyridine-2-sulfonyl)-azepan-4-ylcarbamoyl]-butyl}-amide To a stirring solution of the compound of example 193 (37 mg, 0.07 mmol) in $CH_2Cl_2$ (0.5 ml) was added Dess-Martin reagent (45 mg, 0.105 mmol). After stirring for 30 minutes, solutions of sodium thiosulfate (10% in water, 0.50 ml) and saturated aqueous sodium bicarbonate (0.50 ml) were added simultaneously to the reaction. The mixture was then extracted with dichloromethane (2 times). The organic layer was dried, filtered, and concentrated. The residue was purified by HPLC to yield the two diastereomers of the title compound as solids (first eluting: 7 mg, second eluting: 5.5 mg): MS (ESI) 526.91 $(M+H)^+$.

Example 194

Preparation of Benzofuran-2-carboxylic acid {(S)-1-[3-oxo-1-(pyridine-2-sulfonyl)-azepan-4-ylcarbamoyl]-propyl}-amide Following the procedure of Example 193e-h, except substituting N-Boc-alpha-aminobutyric acid in step 193e the title compound was purified to yield two diastereomers as solids (first eluting: 5 mg, second eluting: 5 mg) MS(ESI) 543.8 $(M+H)^+$.

Example 195

Preparation of Benzofuran-2-carboxylic acid {(S)-2-cyclohexyl-1-[3-oxo-1-(pyridine-2-sulfonyl)-azepan-4-ylcarbamoyl]-ethyl}-amide Following the procedure of Example 193e-h, except substituting N-Boc-cyclohexylalanine in step 193e, the title compound was purified to yield two diastereomers as solids (first eluting: 4.5 mg second eluting: 4.5 mg): MS(ESI): 566.87 (M+H)+.

Example 196

Preparation of Benzofuran-2-carboxylic acid {(S)-1-[3-oxo-1-(pyridine-2-sulfonyl)-azepan-4-ylcarbamoyl]-ethyl}-amide Following the procedure of Example 193e-h, except substituting N-Boc-alanine for step 193e, the title compound was purified to yield two diastereomers as solids (first eluting: 5.5 mg, second eluting: 5 mg).

Example 197

Preparation of Benzofuran-2-carboxylic acid {(S)-3-methanesulfinyl-1-[3-oxo-1-(pyridine-2-sulfonyl)-azepan-4-ylcarbamoyl]-propyl}-amide Following the procedure of Example 193e-h, except substituting N-Boc-L-methionine for step 1(f), the title compound was purified to yield two diastereomers as solids (first eluting: 3 mg, second eluting: 3 mg). MS(ESI): 560.7 (M+H)+.

Example 198

Preparation of Benzofuran-2-carboxylic acid {[3-oxo-1-(pyridine-2-sulfonyl)-azepan-4-ylcarbamoyl]-methyl}-amide Following the procedure of Example 193e-h, except substituting N-Boc-glycine for step 193e, the title compound was purified to yield two diastereomers as solids (first eluting: 3 mg, second eluting: 3 mg). MS(ESI): 470.81 (M+H)+.

Example 199

Preparation of Benzofuran-2-carboxylic acid {(S)-1-[3-oxo-1-(pyridine-2-sulfonyl)-azepan-4-ylcarbamoyl]-pentyl}-amide Following the procedure of Example 193e-h, except substituting N-Boc-norleucine for step 193e, the title compound was purified to yield two diastereomers as solids (first eluting: 4 mg, second eluting: 5 mg). MS(ESI): 526.85 (M+H)+.

Example 200

Preparation of Benzofuran-2-carboxylic acid {(S)-1-[3-oxo-1-(pyridine-2-sulfonyl)-azepan-4-ylcarbamoyl]-butyl}-amide Following the procedure of Example-193e-h, except substituting N-Boc-norvaline for step 193e, the title compound was purified to yield two diastereomers as solids (first eluting: 7.5 mg, second eluting: 3.5 mg). MS(ESI): 512.8 (M+H)+.

Example 201

Preparation of Benzofuran-2-carboxylic acid {(S)-2-methyl-1-[3-oxo-1-(pyridine-2-sulfonyl)-azepan-4-ylcarbamoyl]-propyl}-amide Following the procedure of Example 193e-h, except substituting N-Boc-valine for step 193e, the title compound was purified to yield two diastereomers as solids (first eluting: 6 mg, second eluting: 4.5 mg). MS(ESI): 512.8 (M+H)+.

Example 202

Preparation of Benzofuran-2-carboxylic acid {(S)-2-hydroxy-1-[3-oxo-1-(pyridine-2-sulfonyl)-azepan-4-ylcarbamoyl]-propyl}-amide Following the procedure of Example 193e-h, except substituting N-Boc-L-threonine for step 193e, the title compound was purified to yield two diastereomers as solids (first eluting: 3 mg, second eluting: 3 mg).

Example 203

Preparation of Benzofuran-2-carboxylic acid {(S)-1-[3-oxo-1-(pyridine-2-sulfonyl)-azepan-4-ylcarbamoyl]-2-phenyl-ethyl}-amide Following the procedure of Example 193e-h, except substituting N-Boc-phenylalanine for step 193e, the title compound was purified to yield two diastereomers as solids (first eluting:5 mg, second eluting: 5 mg). MS(ESI): 560.8 (M+H)+.

Example 204

Preparation of 1(Benzofuran-2-carbonyl)-pyrrolidine-2-carboxylic acid [3-oxo-1-(pyridine-2-sulfonyl)-azepan-4-yl]-amide Following the procedure of Example 193e-h, except substituting N-Boc-L-proline for step 193e, the title compound was purified to yield two diastereomers as solids (first eluting: 4 mg, second eluting: 5 mg). MS(ESI): (M+H)+.

Example 205

Preparation of 3,4-Dimethoxy-N-{(S)-1-[1-(4-imethoxy-benzenesulfonyl)-3-oxo-azepan-4-ylcarbamoyl]-3-methyl-butyl}-benzamide Following the procedure of Example 115, except substituting 3,4-dimethoxybenzoyl chloride for benzyloxyacetyl chloride, the title compound was prepared.

The residue was purified by HPLC. First eluting diastereomer: MS 576.4(M+H+). $^1$H NMR (500 MHz, CDCl$_3$): δ 7.68 (d, 2H), 7.00 (d,1H), 6.89 (s, 2H), 3.84 (s, 3H), 3.77 (s, 6H), 2.38 (t, 1H), 0.94 (d, 6H): MS 576.4 (M+H+).

Example 206

Preparation of Benzo[b]thiophene-2-carboxylic acid-{(S)-1-[1-(4-imethoxy-benzenesulfonyl)-3-oxo-azepan-4-ylcarbamoyl]-3-methyl-butyl}-amide Following the procedure of Example 115, except substituting 2-thiophene-carbonyl chloride for benzyloxyacetyl chloride, the title compound was prepared. The residue was purified by HPLC. First eluting diastereomer: MS 572.2 (M+H+). $^1$H NMR (500 MHz, CDCl$_3$): δ 7.80-7.68 (m, 5H), 7.38-7.34 (m, 2H), 7.01-6.93 (m, 4H), 3.83 (s, 3H), 2.38 (t, 1H), 0.97 (d, 6H). Second eluting diastereomer: MS 572.2 (M+H+).

Example 207

Preparation of Benzo[1,3]dioxole-5-carboxylic acid {(S)-1-[1-(4-fluoro-benzenesulfonyl)-3-oxo-azepan-4-ylcarbamoyl]-3-methyl-butyl}-amide Following the procedure of Example 115, except substituting 4-fluorobenzenesulphonyl chloride for 4-methoxybenzenesulfonyl chloride and 3,4-methylenedioxybenzoyl chloride for benzyloxyacetyl chloride, the title compound was prepared. The residue was purified by HPLC. First eluting diastereomer; MS 548.2 (M+H$^+$); $^1$H NMR (400 Hz,CDCl$_3$): δ 7.85-7.78 (m, 2H), 7.38-7.20 (m, 4H), 7.05 (d, 1H), 2.52-2.40 (m,1H), 1.0 (d, 6H). Second eluting diastereomer: MS 548.2 (M+H$^+$).

Example 208

Preparation of (S)-2-(2-Benzyloxy-acetylamino)-4-methyl-pentanoic acid [1-(4-fluoro-benzenesulfonyl)-3-oxo-azepan-4-yl]-amide Following the procedure of Example 115, except substituting 4-fluorobenzenesulphonyl chloride for 4-methoxybenzenesulfonyl chloride, the title compound was prepared. The residue was purified by HPLC. First eluting diastereomer: MS 548.2 (M+H$^+$). $^1$H NMR (400 Hz,CDCl$_3$-CD$_3$OD) δ 7.88-7.80 (m, 2H), 7.45-7.30 (m, 5H), 7.30-7.20 (m, 2H), 4.00 (s, 2H), 2.60-2.48 (m, 1H), 0.96 (t, 6H): MS 548.2 (M+H$^+$).

Example 209

Preparation of Benzo[b]thiophene-2-carboxylic acid-{(S)-1-[1-(4-fluoro-benzenesulfonyl)-3-oxo-azepan-4-yl carbamoyl]-3-methyl-butyl}-amide Following the procedure of Example 115, except substituting 4-fluorobenzenesulphonyl chloride for 4-methoxybenzenesulfonyl chloride and benzo[b]thiophenecarbonyl chloride for benzyloxyacetyl chloride, the title compound was prepared. The residue was purified by HPLC. First eluting diastereomer: MS 560.2 (M+H$^+$). $^1$H NMR (500 MHz, CDCl$_3$): δ 7.80-7.72 (m, 5H).7.37-7.34 (m, 2H), 7.33-7.15 (m, 4H), 2.43 (t, 1H), 0.96 (d, 6H). Second eluting diastereomer: MS 560.2 (M+H$^+$).

Example 210

Preparation of Benzofuran-2-carboxylic acid {(S)-1-[1-benzoyl-3-oxo-azepan-4-ylcarbamoyl]-3-methyl-butyl}-amide a.) Benzofuran-2-carboxylic acid {(S)-1-[1-benzoyl-3-hydroxy-azepan-4-ylcarbamoyl]-3-methyl-butyl}-amide To a solution of benzofuran-2-carboxylic acid [(S)-1-(3-hydroxy-azepan-4-ylcarbamoyl)-3-methyl-butyl]-amide of Example 78c (0.2 ) in dichloromethane was added benzoic acid (0.12 g), HOBt (0.07 g) and EDC (0.99 g). The reaction was stirred until complete. Workup and column chromatography (5% methanol:dichloromethane) provided the title compound (0.2 g): $^1$H NMR (CDCl$_3$): δ 1.0 (m, 6H), 1.5-2.2 (m, 6H), 2.7 (m, 1H), 3.8 (m,1H), 4.1 (m, 1H), 4.7 (m, 2H), 5.1 (m, 1H), 7.0-7.7 (m, 10H), 8.7 (m, 1H); MS(EI): 492 (M+H$^+$, 100%).

b.) Benzofuran-2-carboxylic acid {(S)-1-[1-benzoyl-3-oxo-azepan-4-ylcarbamoyl]-3-methyl-butyl}-amide Following the procedure of Example 1i except substituting benzofuran-2-carboxylic acid {(S)-1-[1-benzoyl-3-hydroxy-azepan-4-ylcarbamoyl]-3-methyl-butyl}-amide of Example 210a the title compound was prepared: $^1$H NMR (CDCl$_3$): δ 1.0 (m, 6H), 1.5-2.2 (m, 6H), 2.7 (m, 1H), 3.7 (m,1H), 4.0 (m, 1H), 4.7 (m, 2H), 5.1 (m, 1H), 7.4-8.0 (m, 8H); MS(EI): 490 (M+H$^+$, 100%).

Example 211

Preparation of (S)4-Methyl-2-(quinoline-8-sulfonylamino)-pentanoic acid [3-oxo-1-(pyridine-2-sulfonyl)-azepan-4-yl]-amide a.) (S)-4-Methyl-2-(quinoline-8-sulfonylamino)-pentanoic acid [3-hydroxy-1-(pyridine-2-sulfonyl)-azepan-4-yl]-amide Following the procedure of Example 89a except substituting 8-quinolinesulfonyl chloride for 2-pyridinesulfonyl chloride the title compound was prepared: MS(EI) 576 (M+H$^+$).

b.) (S)-4-Methyl-2-(quinoline-8-sulfonylamino)-pentanoic acid [3-oxo-1-(pyridine-2-sulfonyl)-azepan-4-yl]-amide Following the procedure of Example 1i except substituting (S)-4-methyl-2-(quinoline-8-sulfonylamino)-pentanoic acid [3-hydroxy-1-(pyridine-2-sulfonyl)-azepan-4-yl]-amide of Example 211a the title compound was prepared: $^1$H NMR (CDCl$_3$): δ 0.5-0.8 (m, 6H), 1.4-1.8 (m, 7H), 2.5 (m, 1H), 3.5-3.9 (m, 3H), 4.4 (m, 1H), 4.6 (m, 1H), 5.5 (m, 1H), 6.7-7.0 (m, 2H), 7.5 (m, 3H), 8.0 (m, 2H), 8.3 (m, 2H), 8.6 (m, 1H), 9.0 (m, 1H); MS(EI): 674 (M+H$^+$, 100%).

Example 212

Preparation of (S)-4-Methyl-2-(naphthylene-2-sulfonylamino)-pentanoic acid [3-oxo-1-(pyridine-2-sulfonyl)-azepan-4-yl]-amide a.) (S)4-Methyl-2-(naphthylene-2-sulfonylamino)-pentanoic acid [3-hydroxy-1-(pyridine-2-sulfonyl)-azepan-4-yl]-amide Following the procedure of Example 89a except substituting 2-naphthylenesulfonyl chloride for 2-pyridinesulfonyl chloride the title compound was prepared: MS(EI) 575 (M+H$^+$).

b.) (S)-4-Methyl-2-(naphthylene-2-sulfonylamino)-pentanoic acid [3-oxo-1-(pyridine-2-sulfonyl)-azepan-4-yl]-amide Following the procedure of Example 1i except substituting (S)-4-methyl-2-(naphthylene-2-sulfonylamino)-pentanoic acid [3-hydroxy-1-(pyridine-2-sulfonyl)-azepan-4-yl]-amide of Example 212a the title compound was prepared: $^1$H NMR (CDCl$_3$): δ 0.5-0.8 (m, 6H), 1.4-1.8 (m, 7H), 2.5 (m, 1H), 3.5-3.9 (m, 3H), 4.5 (m, 1H), 4.6 (m, 1H), 5.5 (m, 1H), 6.7 (m, 1H), 7.5-8.0 (m, 9H), 8.5-8.6 (m, 2H); MS(EI): 673 (M+H$^+$, 100%).

Example 213

Preparation of Benzofuran-2-carboxylic acid-{(S)-1-[1-(4-fluoro-benzenesulfonyl)-3-oxo-azepan-4-yl carbamoyl]-3-methyl-butyl}-amide Following the procedure of Example 115, except substituting 4-fluorobenzenesulphonyl chloride for 4-methoxybenzenesulfonyl chloride and 2-benzofurancarbonyl chloride for benzyloxyacetyl chloride, the title compound was prepared. The residue was purified by HPLC. First eluting diastereomer: MS 544.2.(M+H$^+$). $^1$H NMR (500 MHz, CDCl$_3$): δ 7.79-7.77 (m, 2H), 7.61 (d, 1H), 7.46-7.38 (m, 3H), 7.25-7.06 (m, 5H), 2.43 (t, 1H), 0.95 (d, 6H). Second eluting diastereomer: MS 544.4 (M+H$^+$).

Example 214

Preparation of N-{(S)-1-[1-(4-Fluoro-benzenesulfonyl)-3-oxo-azepan-4-ylcarbamoyl}-3-methyl-butyl}-3,4-dimethoxy-benzamide Following the procedure of Example 115, except substituting 4-fluorobenzenesulphonyl chloride for 4-methoxybenzenesulfonyl chloride and 3,4-dimethoxybenzoyl chloride for benzyloxyacetyl chloride, the title compound was prepared. The residue was purified by HPLC. First eluting diastereomer: MS 564.2.(M+H$^+$). $^1$H NMR (500 MHz, CDCl$_3$): δ 7.80-7.76 (m, 2H), 7.19 (t, 2H), 7.05 (d, 1H), 6.88 (s, 2H), 6.78 (d, 1H), 6.53 (s, 1H), 3.77 (s, 6H), 2.43 (t, 1H), 0.94 (d, 6H). Second eluting diastereomer: MS 546.2 (M+H$^+$).

Example 215

Preparation of Cyclohexanecarboxylic acid {(S)-1-[1-(4-fluoro-benzenesulfonyl)-3-oxo-azepan-4-ylcarbamoyl}-3-methyl-butyl}-amide Following the procedure of Example 115, except substituting 4-fluorobenzenesulphonyl chloride for 4-methoxybenzenesulfonyl chloride and cyclohexylcarbonyl chloride for benzyloxyacetyl chloride, the title compound was prepared. The residue was purified by HPLC. First eluting diastereomer: MS 510.4.(M+H$^+$). $^1$H NMR (400 Hz,CDCl$_3$): δ 7.83-7.80 (m, 2H), 7.27-7.20 (m, 2H), 6.92 (d, 1H), 6.95 (d, 1H). 2.50 (t, 1H), 1.90-1.20 (m, 15H), 0.94 (t, 6H). Second eluting diastereomer: MS 510.2 (M+H$^+$).

Example 216

Preparation of (S)-2-(2-Benzyloxy-acetylamino)-4-methyl-pentanoic acid[1-(methanesulfonyl)-3-oxo-azepan-4-yl]-amide Following the procedure of Example 115, except substituting methanesulphonyl chloride for 4-methoxybenzenesulfonyl chloride, the title compound was prepared. The residue was purified by HPLC. First eluting diastereomer: MS 468.2 (M+H$^+$). $^1$H NMR (500 MHz, CDCl$_3$): δ 7.37-7.24 (m, 4H), 6.93-6.91 (m, 2H), 5.02-5.00 (m, 1H), 2.88 (s, 3H), 2.70 (t, 1H), 0.92 (t, 6H). Second eluting diastereomer: MS 468.2 (M+H$^+$).

Example 217

Preparation of Benzo[b]thiophene-2-carboxylic acid-{(S)-1-(1-methanesulfonyl-3-oxo-azepan-4-yl carbamoyl)-3-methyl-butyl]-amide Following the procedure of Example 115, except substituting methanesulphonyl chloride for 4-methoxybenzenesulfonyl chloride and benzo[b]thiophenecarbonyl chloride for benzyloxyacetyl chloride, the title compound was prepared. The residue was purified by HPLC. First eluting diastereomer: MS 480.2 (M+H$^+$). $^1$H NMR (500 MHz, CDCl$_3$): δ 7.83-7.78 (m, 3H), 7.42-7.37 (m, 2H), 6.94 (d; 1H), 6.75 (d,1H), 2.89 (s, 3H), 2.68 (t, 1H), 0.97 (d, 6H). Second eluting diastereomer: MS 480.2 (M+H$^+$).

Example 218

Preparation of Benzo[1,3]dioxole-5-carboxylic acid-{(S)-1-(1-methanesulfonyl-3-oxo-azepan-4-yl carbamoyl)-3-methyl-butyl]-amide Following the procedure of Example 115, except substituting methanesulphonyl chloride for 4-methoxybenzenesulfonyl chloride and piperonylcarbonyl chloride for benzyloxyacetyl chloride, the title compound was prepared. The residue was purified by HPLC. First eluting diastereomer: MS 468.2 (M+H$^+$). $^1$H NMR (500 MHz, CDCl$_3$): δ 7.31-7.24 (m, 2H), 6.91 (d, 1H), 6.00 (s, 2H), 2.89 (s, 3H), 2.67 (t, 1H), 0.95 (d, 6H), Second eluting diastereomer: MS 468.2 (M+H$^+$).

Example 219

Preparation of Benzofuran-2-carboxylic acid-{(S)-1-(1-methanesulfonyl-3-oxo-azepan-4-yl carbamoyl)-3-methyl-butyl]-amide Following the procedure of Example 115, except substituting methanesulphonyl chloride for 4-methoxybenzenesulfonyl chloride and 2-benzofurancarbonyl chloride for benzyloxyacetyl chloride, the title compound was prepared. The residue was purified by HPLC. First eluting diastereomer: MS 464.2 (M+H$^+$). $^1$H NMR (500 MHz, CDCl$_3$): δ 7.64 (d, 1H), 7.51-7.37 (m, 3H), 7.29-7.28 (m, 1H), 2.89 (s, 3H), 2.67 (t, 1H), 0.97 (d, 6H). Second eluting diastereomer: MS 464.2 (M+H$^+$).

Example 220

Preparation of N-[(S)-1-(1-Methanesulfonyl)-3-oxo-azepan-4-ylcarbamoyl}-3-methyl-butyl}-3,4-dimethoxy-benzamide Following the procedure of Example 115, except substituting methanesulphonyl chloride for 4-methoxybenzenesulfonyl chloride and 3,4-dimethoxybenzoyl chloride for benzyloxyacetyl chloride, the title compound was prepared. The residue was purified by HPLC. First eluting diastereomer: MS 484.2 (M+H$^+$). $^1$H NMR (500 MHz, CDCl$_3$): δ 6.94-6.88 (m, 3H), 6.58-6.55 (m, 2H), 3.80 (s, 6H), 2.89 (s, 3H), 0.95 (d, 6H). Second eluting diastereomer: MS 484.2 (M+H$^+$).

Example 221

Preparation of (S)-2-(2-Benzyloxy-acetylamino)-4-methyl-pentanoic acid[1-(2-cyano-benzensulfonyl)-3-oxo-azepan-4-yl]-amide Following the procedure of Example 115, except substituting 2-cyanophenylsulphonyl chloride for 4-methoxybenzenesulfonyl chloride, the title compound was prepared. The residue was purified by HPLC. First eluting diastereomer: MS 555.2 (M+H$^+$). $^1$H NMR (500 MHz, CDCl$_3$): δ 8.10 (d, 1H), 7.86 (d, 1H), 7.76-7.70 (m, 2H), 7.35-7.31 (m, 5H), 6.93 (d. 2H), 4.61-4.47 (m, 4H), 2.77 (t, 1H), 0.92 (t, 6H). Second eluting diastereomer: MS 555.2 (M+H$^+$).

Example 222

Preparation of N-{(S)-1-[1-(2-Cyano-benzenesulfonyl)-3-oxo-azepan-4-ylcarbamoyl}-3-methyl-butyl}-4-methanesulfonyl-1-benzamide Following the procedure of Example 115, except substituting 2-cyanophenylsulphonyl chloride for 4-methoxybenzenesulfonyl chloride and 4-methanesulfonylbenzoyl chloride for benzyloxyacetyl chloride, the title compound was prepared. The residue was purified by HPLC. First eluting diastereomer: MS 589.2 (M+H$^+$). $^1$H NMR (500 MHz, CDCl$_3$): δ 8.10 (d, 1H), 7.96 (s, 4H), 7.88 (d, 1H), 7.78-7.71 (m, 2H), 3.05 (s, 3H), 2.79 (t, 1H), 0.97 (t, 6H). Second eluting diastereomer: MS 589.2 (M+H$^+$).

Example 223

Preparation of Benzo[b]thiophene-2-carboxylic acid-{(S)-1-[1-(2-cyano-benzenesulfonyl)-3-oxo-azepan-4-yl carbamoyl)-3-methyl-butyl]-amide Following the procedure of Example 115, except substituting 2-cyanophenylsulphonyl chloride for 4-methoxybenzenesulfonyl chloride and benzo[b]thiophene-2-carbonyl chloride for benzyloxyacetyl chloride, the title compound was prepared. The residue was purified by HPLC. First eluting diastereomer: MS 567.2 (M+H$^+$). $^1$H NMR (500 MHz, CDCl$_3$): δ 8.10 (d, 1H), 7.86-7.70 (m, 6H), 7.37-7.30 (m, 2H), 2.76 (t, 1H), 0.98 (d, 6H). Second eluting diastereomer: MS 567.2 (M+H$^+$).

Example 224

Preparation of Benzo[1,3]dioxole-5-carboxylic acid-{(S)-1-[1-(2-cyano-benzenesulfonyl)-3-oxo-azepan-4-ylcarbamoyl)-3-methyl-butyl]-amide Following the procedure of Example 115, except substituting 2-cyanophenylsulphonyl chloride for 4-methoxybenzenesulfonyl chloride and piperonyloyl chloride for benzyloxyacetyl chloride, the title compound was prepared. The residue was purified by HPLC. First eluting diastereomer: MS 555.2 (M+H$^+$). $^1$H NMR (500 MHz, CDCl$_3$): δ 8.11 (d, 1H), 7.87 (d, 1H), 7.76-7.71 (m, 2H), 7.31-7.24 (m, 2H), 6.00 (s, 2H), 2.77 (t, 1H), 0.97 (d, 6H). Second eluting diastereomer: MS 555.4 (M+H$^+$).

Example 225

Preparation of (S)-4-Methyl-2-[4-oxo-4-((4-phenoxy-phenyl)-butyrylamino}-pentanoic acid [3-oxo-1-(pyridine-2-sulfonyl)-azepan-4-yl]-amide Following the procedure of Example 75, except substituting 2-pyridylsulfonyl chloride for thiaxole-2-sulfonyl chloride and 4-phenoxyphenyl-carboxylic acid for benzofuran-2-carboxylic acid, the title compound was prepared. The residue was purified by HPLC. First eluting diastereomer; MS (M+H$^+$) 635.4; $^1$H-NMR (400 MHz, CDCl$_3$): •8.69(d, 1H), 7.99-7.94(m, 4H), 7.53-7.39(m, 3H), 7.23-6.95(m, 7H), 6.20(d, 1H), 5.07(m, 1H), 4.77-4.72(d, 1H), 4.46(m, 1H), 4.13-4.09(m, 1H), 3.85-3.80(d, 1H), 3.33(m, 2H), 2.70-2.64 (m, 3H), 2.20-1.40(m, 6H); and the second eluting diastereomer:, 0.96-0.92(m, 6H); and the second eluting diastereomer: MS (M+H$^+$) 635.4.

Example 226

Preparation of N-{(S)-1-[(1-(2-cyano-benzenesulfonyl)-3-oxo-azepan-4-ylcarbamoyl}-3-methyl-butyl}-3,4-dimethoxy-benzamide Following the procedure of Example 115, except substituting 2-cyanophenylsulphonyl chloride for 4-methoxybenzenesulfonyl chloride and 3,4-dimethoxybenzoyl chloride for benzyloxyacetyl chloride, the title compound was prepared. The residue was purified by HPLC. First eluting diastereomer: MS 571.4 (M+H$^+$). $^1$H NMR (500 MHz, CDCl$_3$): δ 8.10 (d, 1H), 7.87 (d, 1H), 7.76-7.70 (m, 2H), 6.98 (s, 2H), 6.89 (s, 2H), 3.79 (s, 6H), 2.76 (t, 1H), 0.96 (d, 6H). Second eluting diastereomer: MS 571.4 (M+H$^+$).

Example 227

Preparation of Cyclohexanecarboxylic acid {(S)-1-[1-(4-methoxy-benzenesulfonyl)-3-oxo-azepan-4-ylcarbamoyl}-3-methyl-butyl}-amide Following the procedure of Example 115, except substituting cyclohexylcarbonyl chloride for benzyloxyacetyl chloride, the title compound was prepared. The residue was purified by HPLC. First eluting diastereomer: MS 522.4 (M+H$^+$). $^1$H NMR (500 MHz, CDCl$_3$): δ 7.70 (d, 2H), 6.97 (d, 2H), 2.40 (t, 1H), 1.90-1.20 (m, 16H), 0.92 (d, 6H). Second eluting diastereomer: MS 522.4 (M+H$^+$).

Example 228

Preparation of 4-Methansulfonyl-N-{(S)-1-[4-methoxy-benzenesulfonyl)-3-oxo-azepan-4-carbamoyl]-3-methyl-butyl-benzamide Following the procedure of Example 115, except substituting 4-methanesulfonylbenzoyl chloride for benzyloxyacetyl chloride, the title compound was prepared. The residue was purified by HPLC. First eluting diastereomer: MS 594.2 (M+H$^+$). $^1$H NMR (500 MHz, CDCl$_3$): δ 7.96 (s, 4H), 7.69 (d, 2H), 7.25 (d,1H), 6.98 (d,3H), 3.85 (s, 3H), 3.04 (d, 3H), 2.42 (t, 1H), 0.95 (d, 6H). Second eluting diastereomer: MS 594.2 (M+H$^+$).

Example 229

Preparation of 4-Methansulfonyl-N-{(S)-1-[4-fluoro-benzenesulfonyl)-3-oxo-azepan-4-carbamoyl]-3-methyl-butyl-benzamide Following the procedure of Example 115, except substituting 4-fluorophenylsulphonyl chloride for 4-methoxybenzenesulfonyl chloride and substituting 4-methanesulfonylbenzoyl chloride for benzyloxyacetyl chloride, the title compound was prepared. The residue was purified by HPLC. First eluting diastereomer: MS 582.2 (M+H$^+$). $^1$H NMR (500 MHz, CDCl$_3$): δ 7.94 (s, 4H), 7.80-7.77 (m, 2H), 7.25-7.19 (m, 3H), 7.00 (d, 1H), 3.04 (s, 3H), 0.96 (d, 6H). Second eluting diastereomer: MS 582.2 (M+H$^+$).

Example 230

Preparation of ({(S)-3-Methyl-1-[3-oxo-1-(pyridine-2-sulfonyl)-azepan-4-ylcarbamoyl]-butylcarbamoyl}-carbamic acid benzyl ester Following the procedure of Example 75, except substituting 2-pyridylsulfonyl chloride for benzenesulfonyl chloride and N-carbobenzyloxycarbonyl-glycine for benzofuran-2-carboxylic acid, the title compound was prepared. The residue was purified by HPLC. First eluting diastereomer; MS (M+H$^+$): 574.2; $^1$H-NMR (400 MHz, CDCl$_3$): •8.60(d, 1H), 7.97-7.90(m, 2H), 7.50(m, 1H), 7.42-7.25(m, 5H), 6.90(m, 1H), 6.42(m, 1H), 5.38(m, 1H), 5.18-5.10(m, 4H), 4.78-4.72 (d, 1H), 4.50(m, 1H), 4.12-4.05(m, 1H), 3.95-3.85(m, 2H), 2.72(m, 1H), 2.25-2.10(m, 2H), 1.90-1.40(m, 5H), 0.92(m, 6H); and the second eluting diastereomer: MS (M+H$^+$) 574.2.

Example 231

Preparation of (S)-2-[5-(4-Methoxy-phenyl)-pentanoylamnio]-4-methyl-pentanoic acid [3-oxo-1-(pyridine-2-sulfonyl)-azepan-4-yl]-amide Following the procedure of Example 75, except substituting 2-pyridylsulfonyl chloride for benzenesulfonyl chloride and 5-(4-methoxyphenyl)-pentanoic acid for benzofuran-2-carboxylic acid, the title compound was prepared. The residue was purified by HPLC. First eluting diastereomer; MS (M+H$^+$): 573.4; $^1$H-NMR (400 MHz, CDCl$_3$): •8.59(d, 1H), 7.97-7.94(m, 2H), 7.53(m, 1H), 7.09-7.07(d, 2H), 6.89-6.81 (m, 3H), 5.90(m, 1H), 5.12(m, 1H), 4.79-4.74(d, 1H), 4.48 (m, 1H), 4.12(m, 1H), 3.86-3.81(d, 1H), 3.79(s, 3H), 2.69(m, 1H), 2.59-2.57(m, 2H), 2.23-2.10(m, 3H), 1.75-1.45(m, 10H), 0.96-0.95(m, 6H); and the second eluting diastereomer: MS (M+H$^+$) 573.4.

Example 232

Preparation of (S)-2-[2-(3-Benzyloxy-4-methoxy-phenyl)-acetylamnio]4-methylpentanoic acid [3-oxo-1-(pyridine-2-sulfonyl)-azepan-4-yl]-amide Following the procedure of Example 75, except substituting 2-pyridylsulfonyl chloride for benzenesulfonyl chloride and (3-benzyloxy-4-methoxy-phenyl)-acetic acid for benzofuran-2-carboxylic acid, the title compound was prepared. The residue was purified by HPLC. First eluting diastereomer; MS (M+H$^+$): 637.4; $^1$H-NMR (400 MHz, CDCl$_3$): •8.69(d, 1H), 7.98-7.91(m, 2H), 7.53-7.30(m, 6H); and the second eluting diastereomer:, 6.89-6.82(m, 4H), 5.82(m, 1H), 5.14-5.07(m, 3H), 4.78-4.73(d, 1H), 4.43(m, 1H), 4.09 (m, 1H), 3.89(s, 3H), 3.82(d, 1H), 3.49(s, 2H), 2.69(m, 1H), 2.14(m, 2H), 1.82-1.40(m, 5H), 0.89(d, 6H); and the second eluting diastereomer: MS (M+H$^+$) 637.4.

Example 233

Preparation of 5,6-Difluoro-benzofuran-2-carboxylic acid {(S)-3-methyl-1-[1-(pyridine-2-sulfonyl)-3-oxo-azepan-4-ylcarbamoyl]-butyl}amide a.) 5,6-Difluoro-benzofuran-2-carboxylic acid {(S)-3-methyl-1-[1-(pyridine-2-sulfonyl)-3-hydroxy-azepan-4-ylcarbamoyl]-butyl}amide Following the procedure of Example 28b except substituting 5,6-difluorobenzofuran-2-carboxylic acid for bernzofuran-2-carboxylic acid provided the title compound: MS (M+H$^+$): 564 b.) 5,6-Difluoro-benzofuran-2-carboxylic acid {(S)-3-methyl-1-[1-(pyridine-2-sulfonyl)-3-oxo-azepan-4-ylcarbamoyl]-butyl}amide Following the procedure of Example 1i except substituting the compound of Example 233a provided the title compound. The residue was purified by HPLC. First eluting diastereomer; MS (M+H$^+$): 562; and the second eluting diastereomer: MS (M+H$^+$) 562.

Example 234

Preparation of (S)-4-Methyl-2-(5-oxo-hexanoylamino)-pentanoic acid [3-oxo-1-(pyridine-2-sulfonyl)-azepan-4-yl]-amide Following the procedure of Example 115, except substituting 2-pyridinesulphonyl chloride for 4-methoxybenzenesulfonyl chloride and substituting 5-oxo-hexanoyl chloride for benzyloxyacetyl chloride, the title compound was prepared. The residue was purified by HPLC. First eluting diastereomer: MS 495.4 (M+H$^+$); Second eluting diastereomer: MS 495.4 (M+H$^+$).

Example 235

Preparation of Benzofuran-2-carboxylic acid {(S)-3-methyl-1-[1-(6-methyl-pyridine-2-sulfonyl)-3-oxo-azepan-4-ylcarbamoyl]-butyl}amide a.) 6-methyl-pyridine-2-sulphonyl chloride The title compound was prepared in a similar fashion as that described in Example 85a for the preparation of 2-pyridinesulfonyl chloride-N-oxide.

b.) {(S)-1-[3-Hydroxy-1-(6-methyl-pyridine-2-sulfonyl)-azepan-4-ylcarbamoyl]-3-methyl-butyl}-carbamic acid tert-butylester To a solution of [(S)-1-(3-hydroxy-azepan-4-ylcarbamoyl)-3-methyl-butyl]-carbamic acid tert-butyl ester of Example 2 (1.0 g) in dichloromethane (20 mL) was added saturated sodium bicarbonate (50 mL). To this solution was added 6-methyl-pyridine-2-sulphonyl chloride (6.44 mL of a 0.13 g/mL solution in 9M HCl). The reaction was stirred until complete. Workup and column chromatography (5% methanol:dichloromethane) provided the title compound (1.2 g).

c.) (S)-2-Amino-4-methyl-pentanoic acid [3-hydroxy-1-(6-methyl-pyridine-2-sulfonyl)-azepan-4-yl]-amide To a solution of (S)-2-amino-4-methyl-pentanoic acid [3-hydroxy-1-(6-methyl-pyridine-2-sulfonyl)-azepan-4-yl]-amide of Example 235a (1.2 g) in methanol (20 mL) was added 4M HCl in diopxane (20 mL). The reaction was stirred until complete whereupon it was concentrated to provide the title compound (1 g).

d.) Benzofuran-2-carboxylic acid {(S)-3-methyl-1-[1-(6-methyl-pyridine-2-sulfonyl)-3-hydroxy-azepan-4-ylcarbamoyl]-butyl}amide Following the procedure of Example 28b except substituting (S)-2-amino-4-methyl-pentanoic acid [3-hydroxy-1-(6-methyl-pyridine-2-sulfonyl)-azepan-4-yl]-amide of Example 235c the title compound was prepared: MS(EI) 542 (M$^+$).

e.) Benzofuran-2-carboxylic acid {(S)-3-methyl-1-[1-(6-methyl-pyridine-2-sulfonyl)-3-oxo-azepan-4-ylcarbamoyl]-butyl}amide Following the procedure of Example 1i except substituting benzofuran-2-carboxylic acid {(S)-3-methyl-1-[1-(6-methyl-pyridine-2-sulfonyl)-3-hydroxy-azepan-4-ylcarbamoyl]-butyl}amide of Example 235d the title compound was prepared: $^1$H NMR (CDCl$_3$): δ 1.0 (m, 6H), 1.5-2.2 (m, 6H), 2.6 (m, 3H), 2.7 (m, 1H), 4.1 (m, 1H), 4.7 (m, 2H), 5.3 (m, 1H), 7.4-8.0 (m, 8H); MS(EI); 540 (M$^+$, 100%).

Example 236

Preparation of 5-Methoxybenzofuran-2-carboxylic acid {(S)-3-methyl-1-[1-(6-methyl-pyridine-2-sulfonyl)-3-oxo-azepan-4-ylcarbamoyl]-butyl}amide a.) 5-Methoxybenzofuran-2-carboxylic acid {(S)-3-methyl-1-[1-(6-methyl-pyridine-2-sulfonyl)-3-hydroxy-azepan-4-ylcarbamoyl]-butyl}amide Following the procedure of Example 28b except substituting 5-methoxybenzofuran-2-carboxylic acid for benzofuran-2-carboxylic acid and (S)-2-amino-4-methyl-pentanoic acid [3-hydroxy-1-(6-methyl-pyridine-2-sulfonyl)-azepan-4-yl]-amide of Example 235c for (S)-2-amino-4-methyl-pentanoic acid [3-hydroxy-1-(pyridine-2-sulfonyl)-azepan-4-yl]-amide of Example 28b the title compound was prepared: MS(EI) 572 (M$^+$).

b.) 5-Methoxybenzofuran-2-carboxylic acid {(S)-3-methyl-1-[1-(6-methyl-pyridine-2-sulfonyl)-3-oxo-azepan-4-ylcarbamoyl]-butyl}amide Following the procedure of Example 1i except substituting 5-methoxybenzofuran-2-carboxylic acid {(S)-3-methyl-1-[1-(6-methyl-pyridine-2-sulfonyl)-3-hydroxy-azepan-4-ylcarbamoyl]-butyl}amide of Example 236a the title compound was prepared: $^1$H NMR (CDCl$_3$): δ 1.0 (m, 6H), 1.5-2.2 (m, 6H), 2.6 (m, 3H), 2.7 (m, 1H), 3.8 (s, 3H); 4.1 (m, 1H), 4.7 (m, 2H), 5.3 (m, 1H), 7.4-8.0, (m, 7H); MS(EI): 570 (M$^+$, 100%).

Example 237

Preparation of 3-Methylbenzofuran-2-carboxylic acid {(S)-3-methyl-1-[1-(6-methyl-pyridine-2-sulfonyl)-3-oxo-azepan-4-ylcarbamoyl]-butyl}amide a.) 3-Methylbenzofuran-2-carboxylic acid {(S)-3-methyl-1-[1-(6-methyl-pyridine-2-sulfonyl)-3-hydroxy-azepan-4-ylcarbamoyl]-butyl}amide Following the procedure of Example 236a except substituting 3-methylbenzofuran-2-carboxylic acid for 5-methoxybenzofuran-2-carboxylic acid the title compound was prepared: MS(EI) 556 (M$^+$).

b.) 3-Methylbenzofuran-2-carboxylic acid {(S)-3-methyl-1-[1-(6-methyl-pyridine-2-sulfonyl)-3-oxo-azepan-4-ylcarbamoyl]-butyl}amide Following the procedure of Example 1i except substituting 3-methylbenzofuran-2-carboxylic acid {(S)-3-methyl-1-[1-(6-methyl-pyridine-2-sulfonyl)-3-hydroxy-azepan-4-ylcarbamoyl]-butyl}amide of Example 237a the title compound was prepared: $^1$H NMR (CDCl$_3$): δ 1.0 (m, 6H), 1.5-2.2 (m, 6H), 2.6 (m, 3H), 2.7 (m, 1H), 3.8 (s, 1H); 4.1 (m, 1H), 4.7 (m, 2H), 5.3 (m, 1H), 7.4-8.0 (m, 6H); MS(EI): 564-(M$^+$, 100%).

Example 238

Preparation of 7-Methoxybenzofuran-2-carboxylic acid {(S)-3-methyl-1-[1-(pyridine-2-sulfonyl)-3-oxo-azepan-4-ylcarbamoyl]-butyl}amide a.) 7-Methoxybenzofuran-2-carboxylic acid {(S)-3-methyl-1-[1-(6-methyl-pyridine-2-sulfonyl)-3-hydroxy-azepan-4-ylcarbamoyl]-butyl}amide Following the procedure of Example 28b except substituting 7-methoxybenzofuran-2-carboxylic acid for benzofuran-2-carboxylic acid the title compound was prepared: MS(EI) 559 (M+H$^+$).

b.) 7-Methoxybenzofuran-2-carboxylic acid {(S)-3-methyl-1-[1-(6-methyl-pyridine-2-sulfonyl)-3-oxo-azepan-4-ylcarbamoyl]-butyl}amide Following the procedure of Example 1i except substituting 7-methoxybenzofuran-2-carboxylic acid {(S)-3-methyl-1-[1-(6-methyl-pyridine-2-sulfonyl)-3-hydroxy-azepan-4-ylcarbamoyl]-butyl}amide of Example 238a the title compound was prepared: MS(EI) 557 (M+H$^+$).

Example 239

Preparation of 5,6-Dimethoxy-benzo[b]thiophene-2-carboxylic acid {(S)-3-methyl-1-[1-(pyridine-2-sulfonyl)-3-oxo-azepan-4-ylcarbamoyl]-butyl}amide a.) 5,6-Dimethoxy-benzo[b]thiophene-2-carboxylic acid {(S)-3-methyl-1-[1-(6-methyl-pyridine-2-sulfonyl)-3-hydroxy-azepan-4-ylcarbamoyl]-butyl}amide Following the procedure of Example 28b except substituting 5,6-dimethoxy-benzo[b]thiophene-2-carboxylic acid for benzofuran-2-carboxylic acid the title compound was prepared: MS(EI) 604 (M$^{30}$).

b.) 5,6-Dimethoxy-benzo[b]thiophene-2-carboxylic acid {(S)-3-methyl-1-[1-(6-methyl-pyridine-2-sulfonyl)-3-oxo-azepan-4-ylcarbamoyl]-butyl}amide Following the procedure of Example 1i except substituting 5,6-dimethoxy-benzo[b]thiophene-2-carboxylic acid {(S)-3-methyl-1-[1-(6-methyl-pyridine-2-sulfonyl)-3-hydroxy-azepan-4-ylcarbamoyl]-butyl}amide of Example 239a the title compound was prepared: MS(EI) 602.9 (M+H$^+$).

Example 240

Preparation of (R)-1-Benzyl-5-oxo-pyrrolidine-2-carboxylic acid {(S)-3-methyl-1-[3-oxo-(pyridine-2-sulfonyl)-azepan-4-ylcarbamoyl]-butyl}amide Following the procedure of Example 75, except substituting 2-pyridylsulfonyl chloride for thiazole-2-sulfonyl chloride and (R)-1-benzyl-5-oxo-pyrrolidine-2-carboxylic acid for benzofuran-2-carboxylic acid, the title compound was prepared. The residue was purified by HPLC. First eluting diastereomer; MS (M+H$^+$): 584.4; $^1$H-NMR (400 MHz, CDCl$_3$): •8.69(d, 1H), 7.99-7.92(m, 2H), 7.52(m, 1H), 7.32-7.22(m, 5H), 6.92(d, 1H), 6.38(d, 1H), 5.15-5.08(m, 2H), 4.80-4.75(d, 1), 4.47-4.44(m, 1H), 4.14-4.10(m, 1H), 3.89-3.80(m, 3H), 2.75-2.63(m, 2H), 2.46-1.44(m, 10H), 0.95(d, 6H); and the second eluting diastereomer: MS (M+H$^+$) 584.4.

Example 241

Preparation of (S)-1-Benzyl-5-oxo-pyrrolidine-2-carboxylic acid {(S)-3-methyl-1-{3-oxo-(pyridine-2-sulfonyl)-azepan-4-ylcarbamoyl]-butyl}amide Following the procedure of Example 75, except substituting 2-pyridylsulfonyl chloride for benzenesulfonyl chloride and (S)-1-benzyl-5-oxo-pyrrolidine-2-carboxylic acid for benzofuran-2-carboxylic acid, the title compound was prepared. The residue was purified by HPLC. First eluting diastereomer; MS (M+H$^+$): 584.4; $^1$H-NMR (400 MHz, CDCl$_3$): •8.69(d, 1H), 7.98-7.92(m, 2H), 7.52(m, 1H), 7.32-7.22(m, 5H), 6.92(d, 1H), 6.38(d, 1H), 5.22-5.18(d, 1H), 5.10(m, 1H), 4.80-4.75(d, 1H), 4.51(m, 1H), 4.12-4.08 (m, 1H), 3.91-3.79 (m, 3H), 2.71-1.38(m, 12H), 0.97(d, 6H); and the second eluting diastereomer: MS (M+H$^+$): 584.4.

Example 242

Preparation of Benzofuran-2-carboxylic acid {(S)-2-cyclopropyl-1-[3-oxo-1-(pyridine-2-sulfonyl)-azepan-4-ylcarbamoyl)-ethyl]-amide Following the procedure of Example 193e-h except substituting N-Boc-cyclopropylalanine for step 193e, the title compound was purified to yield two diastereomers as solids (first eluting: 8 mg, second eluting: 8 mg): MS(ESI): 525 (M+H)$^+$.

Example 243

Preparation of Benzofuran-2-carboxylic acid {(S)-3-methylsulfanyl-1-[3-oxo-1-(pyridine-2-sulfonyl)-azepan-4-ylcarbamoyl)-propyl]-amide Following the procedures of Examples 193e-g except substituted N-Boc-L-methionine in step 193e. The oxidation of Example 193 was performed by adding sulfur trioxide-pyridine complex (34 mg, 0.211 mmol) and triethylamine (0.077 ml) to the alcohol intermediate in DMSO solvent (0.200 ml). After stirring at room temperature for two hours, the mixture was diluted with water and extracted with ethyl acetate. The organic layer was dried, filtered, concentrated, and purified by HPLC to yield two diastereomers of the title compound as solids (first eluting: 8 mg, second eluting: 5 mg). MS(ESI): 545 (M+H)$^+$.

Example 244

Preparation of Benzofuran-2-carboxylic acid {(S)-2-naphthylen-2-yl-1-[3-oxo-1-(pyridine-2-sulfonyl)-azepan-4-ylcarbamoyl)-ethyl]-amide Following the procedure of Example 193e-h except substituting except substituting N-(t-butoxycarbonyl)-3-(2-naphthyl)-L-alanine, the title compound was purified to yield two diastereomers as solids (first eluting: 5.3 mg, second eluting: 3.3 mg): MS(ESI): 610.8 (M+H)$^+$.

Example 245

Preparation of Thieno[3,2-b]thiophene-2-carboxylic acid {(S)-3-methyl-1-[1-(6-methyl-pyridine-2-sulfonyl)-3-oxo-azepan-4-ylcarbamoyl]-butyl}amide a.) Thieno[3,2-b]thiophene-2-carboxylic acid {(S)-3-methyl-1-[1-(6-methyl-pyridine-2-sulfonyl)-3-hydroxy-azepan-4-ylcarbamoyl]-butyl}amide Following the procedure of Example 236a except substituting thieno[3,2-b]thiophene-2-carboxylic acid for 5-methoxybenzofuran-2-carboxylic acid the title compound was prepared: MS(EI) 564 (M$^+$).

b.) Thieno[3,2-b]thiophene-2-carboxylic acid {(S)-3-methyl-1-[1-(6-methyl-pyridine-2-sulfonyl)-3-oxo-azepan-4-ylcarbamoyl]-butyl}amide Following the procedure of Example 1i except substituting thieno[3,2-b]thiophene-2-carboxylic acid {(S)-3-methyl-1-[1-(6-methyl-pyridine-2-sulfonyl)-3-hydroxy-azepan-4-ylcarbamoyl]-butyl}amide of Example 245a the title compound was prepared: $^1$H NMR (CDCl$_3$): δ 1.0 (m, 6H), 1.5-2.2 (m, 6H), 2.6 (m, 3H) 2.7 (m, 1H), 3.8 (s, 1H); 4.1 (m, 1H), 4.7 (m, 2H), 5.3 (m, 1H), 7.4-8.0 (m, 6H); MS(EI): 562 (M$^+$, 100%).

Example 246

Preparation of Thieno[3,2-b]thiophene-2-carboxylic acid {(S)-3-methyl-1-[1-(3-methyl-pyridine-2-sulfonyl)-3-oxo-azepan-4-ylcarbamoyl]-butyl}amide a.) (S)-2-Amino-4-methyl-pentanoic acid [3-hydroxy-1-(3-methyl-pyridine-2-sulfonyl)-azepan-4-yl]-amide Following the procedure of Examples 235b-c except substituting 3-methyl-pyridine-2-sulfonyl chloride for 6-methyl-pyridine-2-sulfonyl chloride the title compound was prepared: MS(EI) 399 (M$^+$).

b.) Thieno[3,2-b]thiophene-2-carboxylic acid {(S)-3-methyl-1-[1-(3-methyl-pyridine-2-sulfonyl)-3-hydroxy-azepan-4-ylcarbamoyl]-butyl}amide To a solution of (S)-2-amino-4-methyl-pentanoic acid [3-hydroxy-1-(3-methyl-pyridine-2-sulfonyl)-azepan-4-yl]-amide of Example 246a (0.25 ) in dichloromethane was added thieno[3,2-b]thiophene (0.10 g), triethylamine (0.12 mL), HOBt (0.085 g) and EDC (0.12 g). The reaction was stirred until complete. Workup and column chromatography (5% methanol: dichloromethane) provided the title compound (0.18 ): MS(EI) 564 (M$^+$).

c.) Thieno[3,2-b]thiophene-2-carboxylic acid {(S)-3-methyl-1-[1-(3-methyl-pyridine-2-sulfonyl)-3-oxo-azepan-4-ylcarbamoyl]-butyl}amide Following the procedure of Example 1i except substituting thieno[3,2-b]thiophene-2-carboxylic acid {(S)-3-methyl-1-[1-(3-methyl-pyridine-2-sulfonyl)-3-hydroxy-azepan-4-ylcarbamoyl]-butyl}amide of Example 245a the title compound was prepared: $^1$H NMR (CDCl$_3$): δ 1.0 (m, 6H), 1.5-2.2 (m, 6H), 2.6 (m, 3H) 3.0 (m, 1H), 3.8 (s, 3H); 4.1 (m, 2H), 4.7 (m, 2H), 5.3 (m, 1H), 7.4-8.0 (m, 5H), 8.4 (m, 1H); MS(EI): 562 (M$^+$, 100%).

Example 247

Preparation of 3-Methylbenzofuran-2-carboxylic acid {(S)-3-methyl-1-[1-(3-methyl-pyridine-2-sulfonyl)-3-oxo-azepan-4-ylcarbamoyl]-butyl}amide a.) 3-Methylbenzofuran-2-carboxylic acid {(S)-3-methyl-1-[1-(3-methyl-pyridine-2-sulfonyl)-3-hydroxy-azepan-4-ylcarbamoyl]-butyl}amide Following the procedure of Example 246c except substituting 3-methylbenzofuran-2-carboxylic acid for thieno[3,2-b]thiophene the title compound was prepared: MS(EI) 556 (M$^+$).

b.) 3-Methylbenzofuran-2-carboxylic acid {(S)-3-methyl-1-[1-(3-methyl-pyridine-2-sulfonyl)-3-oxo-azepan-4-ylcarbamoyl]-butyl}amide Following the procedure of Example 1i except substituting 3-methylbenzofuran-2-carboxylic acid {(S)-3-methyl-1-[1-(3-methyl-pyridine-2-sulfonyl)-3-hydroxy-azepan-4-ylcarbamoyl]-butyl}amide of Example 247a the title compound was prepared: $^1$H NMR (CDCl$_3$): δ 1.0 (m, 6H), 1.5-2.2 (m, 6H), 2.6 (d, 3H), 2.6 (m, 3H), 3.0 (m, 1H), 4.1 (m, 2H), 4.7 (m, 2H), 5.3 (m, 1H), 7.4-8.0 (m, 6H), 8.4 (m, 1H); MS(EI): 554 (M$^+$, 100%).

Example 248

Preparation of 5-Methoxybenzofuran-2-carboxylic acid {(S)-3-methyl-1-[1-(3-methyl-pyridine-2-sulfonyl)-3-oxo-azepan-4-ylcarbamoyl]-butyl}amide a.) 5-Methoxybenzofuran-2-carboxylic acid {(S)-3-methyl-1-[1-(3-methyl-pyridine-2-sulfonyl)-3-hydroxy-azepan-4-ylcarbamoyl]-butyl}amide Following the procedure of Example 246c except substituting 5-methoxybenzofuran-2-carboxylic acid for thieno[3,2-b]thiophene the title compound was prepared: MS(EI) 572 (M$^+$).

b.) 5-Methoxybenzofuran-2-carboxylic acid {(S)-3-methyl-1-[1-(3-methyl-pyridine-2-sulfonyl)-3-oxo-azepan-4-ylcarbamoyl]-butyl}amide Following the procedure of Example 1i except substituting 5-methoxybenzofuran-2-carboxylic acid {(S)-3-methyl-1-[1-(3-methyl-pyridine-2-sulfonyl)-3-hydroxy-azepan-4-ylcarbamoyl]-butyl}amide of Example 247a the title compound was prepared: $^1$H NMR (CDCl$_3$): δ 1.0 (m, 6H), 1.5-2.2 (m, 6H), 2.6 (d, 3H), 3.0 (m, 1H), 3.8 (s, 3H), 4.1 (m, 2H), 4.7 (m, 2H), 5.3 (m, 1H), 7.4-8.0 (m, 6H), 8.4 (m, 1H); MS(EI): 570 (M$^+$, 100%).

Example 249

Preparation of 5,6-Difluoro-benzofuran-2-carboxylic acid {(S)-3-methyl-1-[3-oxo-1-(1-oxy-pyridine-2-sulfonyl)-azepan-4-ylcarbamoyl]-butyl}amide a.) 5,6-Difluoro-benzofuran-2-carboxylic acid {(S)-3-methyl-1-[3-hydroxy-1-(1-oxy-pyridine-2-sulfonyl)-azepan-4-ylcarbamoyl]-butyl}amide Following the procedure of Example 85c exept substituting 5,6-difluorobenzofuran-2-carboxylic acid for benzo[b]thiophene-2-carboxylic acid the title compound was prepared: MS(ESI) 580.9 (M+H$^+$).

b.) 5,6-Difluoro-benzofuran-2-carboxylic acid {(S)-3-methyl-1-[3-oxo-1-(1-oxy-pyridine-2-sulfonyl)-azepan-4-ylcarbamoyl]-butyl}amide Following the procedure of Example 1i exept substituting the compound of Example 249a the title compound was prepared: MS(ESI) 578.87 (M+H$^+$).

Example 250

Preparation of 5-(3-Trifluoromethyl-phenyl)-furan-2-carboxylic acid {(S)-2-cyclohexyl-1-[3-oxo-1-(pyridine-2-sulfonyl)-azepan-4-ylcarbamoyl]-ethyl}-amide a.) 4-((S)-2-tert-Butoxycarbonylamino-3-cyclohexyl-proprionylamino)-3-hydroxy-azepane-1-carboxylic acid benzyl ester To a solution of the compound of Example 2e (3.2 g, 12.2 mmol) in DMF (35 mL) was added N-Boc-cyclohexylalanine (3.3 g), HOBt (1.8 g) and EDC (2.56 g). The reaction was stirred until complete. Workup and column chromatography of the residue (65% hexanes:ethyl acetate) provided 5.5 g of the title compound.

b.) [(S)-Cyclohexyl-1-(3-hydroxy-azepan-4-ylcarbamoyl)-ethyl]-carbamic acid tert-butyl ester To a solution of the compound of Example 250a (5.5 g) in etyhl acetate:methanol (185 mL:40 mL) was added 10% Pd/C. This mixture was stirred under an atmosphere of hydrogen until complete consumption of the starting material was observed. The reaction was filtered and concentrated to provide 3.75 g of the title compound.

c.) {(S)-2-Cyclohexyl-1-[3-hydroxy-1-(pyridine-2-sulfonyl)-azepan-4-ylcarbamoyl]-ethyl}-carbamic acid tert-butyl ester To a solution of the compound of Example 250b (1.0 g, 1.91 mmol) in dichloromethane (5 mL) was added water (10 mL) and sodium bicarbonate (1 g). To this mixture was added 2-pryidinesulfonyl chloride (0.55 g in 5 mL dichloromethane) dropwise. The mixture was stirred for 20 minutes whereupon the organic layer was separated and washed with water, brine, dried filtered and concentrated. Column chromatography (2% methanol:dichloromethane) of the residue provided 1.0 g of the title compound: MS (ESI) 525 (M+H$^+$).

d.) (S)-2-Amino-3-cyclohexyl-N-[3-hydroxy-(pyridine-2-sulfonyl)-azepan yl]-proprionamide To a solution of the compound of Example 250c (1.0 g) in methanol (10 mL) was added HCl (10 mL of 4M HCl in dioxane). The reaction was stirred until complete consumption of the starting material whereupon it was concentrated. The residue was azeotroped with toluene then washed with ether to provide 0.95 g of the title compound.

e.) 5-(3-Trifluoromethyl-phenyl)-furan-2-carboxylic acid {(S)-2-cyclohexyl-1-{3-hydroxy-1-(pyridine-2-sulfonyl)-azepan-4-ylcarbamoyl]-ethyl}-amide To a solution of the compound of Example 250d (0.20 g, 0.4 mmol) in DMF (0.5 mL) was added diisopropylethylamine (0.16 mL), HOBt (0.06 g), EDC (0.084 g) and 5-[3-(trifluoromethyl)phenyl]-2-furoic acid (0.11 g). ). The reaction was stirred until complete consumption of the starting material. Workup and column chromatography 4% methanol:dichloromethane) provided 0.23 g of the title compound.

f.) 5-(3-Trifluoromethyl-phenyl)-furan-2-carboxylic acid {(S)-2-cyclohexyl-1-{3-oxo-1-(pyridine-2-sulfonyl)-azepan-4-ylcarbamoyl]-ethyl}-amide Following the procedure of Example 75d except substituting the compound of Example 250e the title compound was prepared. Separation of the diastereomers by HPLC provided the first eluting disatereomer (52 mg): MS (ESI) 661.4 and the second eluting diastereomer (45.8 mg): MS (ESI) 661.6.

Example 251

Preparation of 5-(4-Chloro-phenyl)-furan-2-carboxylic acid {(S)-2-cyclohexyl-1-{3-oxo-1-(pyridine-2-sulfonyl)-azepan-4-ylcarbamoyl]-ethyl}-amide Following the procedures of Example 250e-f except substituting 5-(4-chlorophenyl)-2-furoic acid for 5-[3-(trifluoromethyl)phenyl]-2-furoic acid of Example 252e the title compound was prepared. Separation of the diastereomers by HPLC provided the first eluting diastereomer (57 mg): MS (ESI) 627.4 and the second eluting-diastereomer (53 mg): MS (ESI) 627.4.

Example 252

Preparation of Benzofuran-2-carboxylic acid {(S)-3-methyl-1-[6-methyl-3-oxo-1-(pyridine-sulphonyl)-azepan-4-ylcarbamoyl]-butyl}-amide Following the procedure of Example 92, except substituting, 2-methyl-4-pentenal for 2,2-dimethyl-4-pentenal the title compound was prepared. The residue was purified by HPLC. First eluting diastereomer; MS (M+H$^+$): 541.2; $^1$H-NMR (400 MHz, CDCl$_3$): •8.71-8.66(m, 1H), 7.98-7.93 (m, 2H), 7.91(d, 1H), 7.67-7.29(m, 5H), 7.15-6.92(m, 2H), 5.28-5.20(m, 1H), 4.82-4.47(m, 2H), 3.97-3.78(m, 1H), 3.65-2.98(m, 1H), 2.37-2.34(m, 1H), 2.20-1.55(m, 3H), 1.22-1.19 (m, 3H), 1.00-0.86(m, 9H).

Example 253

Preparation of 5-(4-Chloro-phenyl)-furan-2-carboxylic acid {(S)-2-cyclohexyl-1-[3-oxo-1-(1-oxy-pyridine-2-sulfonyl)-azepan-4-ylcarbamoyl]-ethyl}-amide Following the procedures of Example 250c-f except substituting 2-pyridinesulfonyl chloride N-oxide for 2-pyridinesulfonyl chloride of Example 250c and substituting 5-(4-chlorophenyl)-2-furoic acid for 5-[3-(trifluoromethyl)phenyl]-2-furoic acid of Example 252e the title compound was prepared. Separation of the diastereomers by HPLC provided the first eluting diastereomer: MS (ESI) 643.4 and the second eluting diastereomer: MS (ESI) 643.2.

Example 254

Preparation of 5-(3-Trifluoromethyl-phenyl)-furan-2-carboxylic acids {(S)-2-cyclohexyl-1-[3-oxo-1-(1-oxy-pyridine-2-sulfonyl)-azepan-4-ylcarbamoyl]-ethyl}-amide Following the procedures of Example 250c-f except substituting 2-pyridinesulfonyl chloride N-oxide for 2-pyridinesulfonyl chloride of Example 250c the title compound was prepared. Separation of the diastereomers by HPLC provided the first eluting diastereomer: MS (EST) 677.2 and the second eluting diastereomer: MS (ESI) 677.4.

Example 255

Preparation of 5-Fluoro-benzofuran-2-carboxylic acid {(S)-3-methyl-1-[3-oxo-1-(pyridine-2-sulfonyl)-azepan-4-ylcarbamoyl]-butyl}-amide a.) 5-Fluoro-benzofuran-2-carboxylic acid {(S)-3-methyl-1-[3-hydroxy-1-(pyridine-2-sulfonyl)-azepan-4-ylcarbamoyl]-butyl}-amide Following the procedure of Example 28b except substituting 5-fluorobenzofuran-2-carboxylic acid for benzofuran-2-carboxylic acid the title compound was prepared: MS (ESI) 547 (M+H$^+$).

b.) 5-Fluoro-benzofuran-2-carboxylic acid {(S)-3-methyl-1-[3-oxo-1-(pyridine-2-sulfonyl)-azepan-4-ylcarbamoyl]-butyl}-amide Following the procedure of Example 1i except substituting the compound of Example 255a the title compound was prepared: MS(ESI) 544.9 (M+H$^+$).

Example 256

Preparation of 5,6-Dimethoxybenzofuran-2-carboxylic acid {(S)-2-cyclohexyl-1-[3-oxo-1-(1-oxy-pyridine-2-sulfonyl)-azepan-4-ylcarbamoyl]-ethyl}-amide Following the procedures of Example 250c-f except substituting 2-pyridinesulfonyl chloride N-oxide for 2-pyridinesulfonyl chloride of Example 250c and substituting 5,6-dimethoxybenzofuran-2-carboxylic acid for 5-[3-(trifluoromethyl)phenyl]-2-furoic acid of Example 252e the title compound was prepared. Separation of the diastereomers by HPLC provided the first eluting diastereomer: MS (ESI) 643.4 and the second-eluting diastereomer: MS (ESI) 643.2.

Example 257

Preparation of 5,5-Bis-(4-methoxy-phenyl)-pent-4-enoic acid {(S)-3-methyl-1-[3-oxo-1-(pyridine-2-sulfonyl)-azepan-4-ylcarbamoyl]}-butyl}-amide Following the procedure of Example 75 except substituting 2-pyridylsulfonyl chloride for thiazole-2-sulfonyl chloride and 5,5-bis-(4-methoxy-phenyl)-pent-4-enoic acid for benzofuran-2-carboxylic acid, the title compound was prepared. The residue was purified by HPLC. First eluting diastereomer; MS (M+H$^+$) 677.4; $^1$H-NMR (400 MHz, CDCl$_3$): •8.69(d, 1H), 7.98-7.92(m, 2H), 7.53-7.50(m, 1H), 7.27-6.77 (m, 10H), 6.00-5.87(m, 2H), 5.08(m, 1H), 4.76-4.72(d, 1H), 4.48(m, 1H), 4.08(m, 1H), 3.83(s, 3H), 3.78(s, 3H), 2.70-1.35 (m, 12H), 0.91(d, 6H); and the second eluting diastereomer: MS (M+H$^+$) 677.4.

Example 258

Preparation of Quinoline-8-carboxylic acid {(S)-2-naphthylen-2-yl-1-[3-oxo-1-(pyridine-2-sulfonyl)-azepan-4-ylcarbamoyl)-ethyl]-amide a.) 4-Amino-1-(pyridine-2-sulfonyl)-azepan-3-ol To a solution of the compound of Example 193c (1.5 g) in methanol (10 mL) was added HCl (10 mL of 4M HCl in dioxane). The reaction was stirred until complete by TLC analysis whereupon it was concentrated to provide 1.2 g of the title compound as a white solid.

b.) {(S)-1-[3-hydroxy-1-(pyridine-2-sulfonyl)-azepan-4-yl-carbamoyl]-2-napthylene-2-yl-ethyl}-carbamic acid tert-butyl ester To a solution of the compound of Example 258a (225 mg) in dichloromethane was added TEA (0.15 mL), HOBt (99 mg), EDC (140 mg) and N-Boc-L-2-naphthylalanine (230 mg). The reaction was stirred until complete. Workup and column chromatography of the residue (3% methanol:dichloromethane) provided 0.35 g of the title compound: MS(ESI) 569 (M+H$^+$).

c.) (S)-2-Amino-N-[3-hydroxy-1-(pyridine-2-sulfonyl)-azepan-4-yl]-3-naphthylen-2-yl-proprionamide To a solution of the compound of Example 258b (0.35 g) in methanol (5 mL) was added HCl (5 mL of 4M HCl in dioxane). The reaction was stirred until complete by TLC analysis whereupon it was concentrated to provide 0.31 g of the title compound as a white solid.

d.) Quinoline-8-carboxylic acid {(S)-2-naphthylen-2-yl-1-[3-hydroxy-1-(pyridine-2-sulfonyl)-azepan-4-ylcarbamoyl)-ethyl]-amide To a solution of the compound of Example 258c (131 mg) in dichloromethane was added TEA, HOBt (39 mg), EDC (55 mg) and quinoline-8-carboxylic acid (51 mg). The reaction was stirred until complete. Workup and column chromatography of the residue (5% methanol:dichloromethane) provided 0.35 g of the title compound: MS(ESI) 574 (M+H$^+$).

e.) Quinoline-8-carboxylic acid {(S)-2-naphthylen-2-yl-1-[3-oxo-1-(pyridine-2-sulfonyl)-azepan-4-ylcarbamoyl)-ethyl]-amide Following the procedure of Example 1i except substituting the compound of Example 258d the title compound was prepared.

Example 259

Preparation of Naphthylene-1-carboxylic acid {(S)-2-naphthylen-2-yl-1-[3-oxo-1-(pyridine-2-sulfonyl)-azepan-4-ylcarbamoyl)-ethyl]-amide Following the procedures of Examples 258d-e except subsituting 1-naphthoic acid for quinoline-8-carboxylic acid the title compound was prepared.

Example 260

Preparation of Quinoline-8-carboxylic acid {(S)-1-[3-oxo-1-(pyridine-2-sulfonyl)-azepan-4-ylcarbamoyl]-2-phenyl-ethyl}-amide Following the procedures of Examples 258a-e except subsituting N-Boc-phenylalanine for N-Boc-L-2-naphthylalanine the title compound was prepared.

Example 261

Preparation of Naphthyridine-2-carboxylic acid {(S)-3-methyl-1-[3-oxo-1-(pyridine-2-sulfonyl)-azepan-4-ylcarbamoyl]-butyl}-amide Following the procedure of Example 28b-c exept subsituting 1,6-naphthyridine-2-carboxylic acid for benzofuran-2-carboxylic acid the title compound was prepared.

Example 262

Preparation of Naphthylene-1-carboxylic acid {(S)-1-[3-oxo-1-(pyridine-2-sulfonyl)-azepan-4-ylcarbamoyl]-2-phenyl-ethyl}-amide Following the procedure of Example 260 except substituting 1-naphthoic acid for quinoline-8-carboxylic acid the title compound was prepared.

Example 263

Preparation of 3-Methylbenzofuran-2-carboxylic acid {(S)-3-methyl-1-[3-oxo-1-(cyclohexyl-proprionyl)-azepan-4-ylcarbamoyl]-butyl}-amide a.) 4-{(S)-2-[(3-Methylbenzofuran-2-carbonyl)-amino]-4-methyl-pentanoylamino}-3-hydroxy-azepane-1-carboxylic-acid benzyl ester To a solution of the compound of Example 72a (1.2 g, 2.67 mmol) was added EDC (0.56 g), HOBt (0.36 g), TEA (0.67 g) and 3-methylbenzofuran-2-carboxylic acid (0.47 g). The reaction was stirred until complete consumption of the starting material was observed. Workup and colum chromatography (4:1 hexanes:ethyl acetate) provided 1.05 g of the title compound: MS (ESI) 536 (M+H$^+$).

b.) 3-Methylbenzofuran-2-carboxylic acid [(S)-1-(3-hydroxy-azepan-4-ylcarbamoyl)-3-methyl-butyl]-amide Following the procedure of Example 2g except substituting the compound of Example 263a the title compound was prepared: MS (ESI) 402 (M+H$^+$).

c.) 3-Methylbenzofuran-2-carboxylic acid {(S)-3-methyl-1-[3-hydroxy-1-(cyclohexyl-proprionyl)-azepan-4-ylcarbamoyl]-butyl}-amide Following the procedure of Example 263a except substituting the compound of Example 263b and 3-cyclohexylpropionic acid for 3-methylbenzofuran-2-carboxylic acid the title compound was prepared: MS (ESI) 540 (M+H$^+$).

d.) 3-Methylbenzofuran-2-carboxylic acid {(S)-3-methyl-1-[3-oxo-1-(cyclohexyl-proprionyl)-azepan-4-ylcarbamoyl]-butyl}-amide Following the procedure of Example 1i except substituting the compound of Example 263c the title compound was prepared: MS (ESI) 538 (M+H$^+$).

Example 264

Preparation of 3-Methylbenzofuran-2-carboxylic acid {(S)-3-methyl-1-[3-oxo-1-(4-methyl-pentanoyl)-azepan-4-ylcarbamoyl]-butyl}-amide Following the procedures of Example 263c-d except substituting 4-methylpentanoic acid for 3-cyclohexylpropionic acid the title compound was prepared: MS (ESI) 498 (M+H$^+$).

Example 265

Preparation of 3-Methylbenzofuran-2-carboxylic acid {(S)-3-methyl-1-[3-oxo-1-(1-oxy-pyridine-2-carbonyl)-azepan-4-ylcarbamoyl]-butyl}-amide Following the procedures of Example 263c-d except substituting picolinic acid N-oxide for 3-cyclohexylpropionic acid the title compound was prepared: MS (ESI) 498 (M+H$^+$).

Example 266

Preparation of (S)-Acetylamino-4-methyl-pentanoic acid [3-oxo-1-(pyridine-2-sulfonyl)-azepan-4-yl]-amide Following the procedure of Example 75c-d except substituting acetic acid for benzofuran-2-carboxylic acid in step 75c provided the title compound which was separated by HPLC to give the first eluting diastereoemer: MS (M+H$^+$) 425.2; $^1$H-NMR (400 Hz, CDCl$_3$): •8.69(d, 1H), 7.96-7.94 (m, 2H), 7.53-7.52(m, 1H), 7.05(m, 1H), 5.92(m, 1H), 5.08 (m, 1H), 4.69-4.53(m, 2H), 4.05-3.90(m, 2H), 2.80(m, 1H), 2.25-2.12(m, 2H), 1.64(s, 3H), 1.90-1.40(m, 5H), 0.95(m, 6H); and the second eluting distereomer: MS (M+H$^+$): 425.2

Example 267

Preparation of Quinoline-2-carboxylic acid {(S)-1-[3-oxo-1-(pyridine-2-sulfonyl)-azepan-4-ylcarbamoyl]-pentyl}-amide a.) 4-((S)-2-tert-Butoxycarbonylamino-hexanoylamino)-3-hydroxy-azepane-1-carboxylic acid benzyl ester To a stirring solution of compound of the amino alcohol of Example 2e (200 mg, 0.74 mmol) in DMF (4 ml) was added N-Boc-norleucine (175 mg, 0.76 mmol), EDC-HCl (145 mg, 0.76 mmol), and 1-hydroxybenzotriazole (21 mg, 0.16 mmol). Reaction allowed to proceed overnight at room temperature. The following morning the mixture was diluted with ethyl acetate, washed with sat. NaHCO$_3$, H$_2$O, and brine. Dried on MgSO$_4$, filtered and purified by column chromatography to give 300 mg of the title compound: MS(ESI) 478.11 (M+H)$^+$.

b.) [(S)-1-(3-Hydroxy-azepan-4-ylcarbamoyl)-pentyl]-carbamic acid tert-butyl ester To a solution of compound of Example 267a (300 mg, 0.63 mmol) in ethyl acetate (5 ml) was added 10% palladium on carbon (160 mg) and H$_2$ from a filled balloon. After stirring the solution at room temperature for 48 hours, the mixture was filtered through celite. The filterate was concentrated to yield the title compound (crude, 161 mg, 0.47 mmol): MS(ESI): 344.19 (M+H)$^+$.

c.) {(S)-1-[3-Hydroxy-1-(pyridine-2-sulfonyl)-azepan-4-ylcarbamoyl]-pentyl}-carbamic acid tert-butyl ester To a solution of the compound of Example 267b (161 mg,0.47 mmol) in dichloromethane (6 ml) was added triethylamine (0.065 ml, 0.47 mmol) and pyridine-2-sulfonyl chloride (83 mg, 0.47 mmol). After stirring at room temperature for 1 hr the mixture was washed with saturated NaHCO$_3$. The organic layer was dried, filtered, concentrated and purified on a silica gel column to give the title compound (142 mg, 0.29 mmol): MS(ESI): 485.10 (M+H)$^+$.

d.) (S)-2-Amino-hexanoic acid {3-hydroxy-1-(pyridine-2-sulfonyl)-azepan-4-yl}-amide To a stirring solution of the compound of Example 267c (142 mg, 0.29 mmol) in ethyl acetate was added HCl (4M in dioxane) (0.760 ml, 3.0 mmol). After stirring the reaction mixture for 1 hr at room temperature, the mixture was concentrated to yield a white solid. The solid was azeotroped with toluene twice on rotavap and then treated with a resin bound carbonate (1.47 mmol) in methanol and placed on a shaker. After 4 hr the suspension was filtered and concentrated to yield 104 mg crude product: MS (ESI) 385.08 (M+H)$^+$.

e.) Quinoline-2-carboxylic acid {(S)-1-[3-hydroxy-1-(pyridine-2-sulfonyl)-azepan-4-ylcarbamoyl]-pentyl}-amide To a solution of the compound of Example 267d (104 mg, 0.27 mmol) in CH$_2$Cl$_2$ was added quinaldic acid (47 mg, 0.27 mmol), 1-hydroxybenzotriazole (7.4, 0.055 mmol); EDC-HCL (52 mg, 0.27 mmol) in DMF (2 ml). After stirring at room temperature overnight, the mixture was diluted with ethylacetate, washed with sat. NaHCO$_3$, H$_2$O, dried on MgSO$_4$, and filtered to obtain 172 mg crude product: MS(ESI) 539.90 (M+H)$^+$.

f.) Quinoline-2-carboxylic acid {(S)-1-[3-oxo-1-(pyridine-2-sulfonyl)-azepan-4-ylcarbamoyl]-pentyl}-amide To a stirring solution of the compound of Example 267e (172 mg crude, 0.32 mmol) in 1 ml DMSO was added sulfur trioxide-pyridine complex (260 mg, 1.6 mmol)) and triethylamine (0.88 ml, 3.2 mmol). After stirring at room temperature for two hours, the mixture was diluted with water and extracted with ethyl acetate. The organic layer was dried, filtered, concentrated, and purified by HPLC to yield two diastereomers of the title compound as solids (first: 40 mg: second:43 mg): MS(ESI) 537.86 (M+H)$^+$.

Example 268

Preparation of Benzofuran-2-carboxylic acid {(S)-3-methyl-1-[3-oxo-1-(cyclohexyl-proprionyl)-azepan-4-ylcarbamoyl]-butyl}-amide Following the procedures of Example 263a-d except substituting benzofuran-2-carboxylic acid for 3-methylbenzofuran-2-carboxylic acid of Example 263a the title compound was prepared: MS(ESI) 524 (M+H$^+$).

Example 269

Preparation of Benzofuran-2-carboxylic acid {(S)-3-methyl-1-[3-oxo-1-(4-methyl-pentanoyl)-azepan-4-ylcarbamoyl]-butyl}-amide Following the procedures of Example 263a-d except subsituting benzofuran-2-carboxylic acid for 3-methylbenzofuran-2-carboxylic acid of Example 263a and 5-methyl pentanoic aicd for cyclohexyl propionic acid the title compound was prepared: MS(ESI) 484 (M+H$^+$).

Example 270

Preparation of Quinoline-2-carboxylic acid {(S)-1-[3-oxo-1-(pyridine-2-sulfonyl)-azepan-4-ylcarbamoyl]-2-phenyl-ethyl}-amide Following the procedure of Example 267a-f except substituting N-Boc-phenylalanine for N-Boc-norleucine in step 267a the title compound was prepared. Separation of the mixture by HPLC provided two diastereomers as solids (first eluting: 20.5 mg; second eluting: 27 mg): MS(ESI) 571.95 (M+H)$^+$.

Example 271

Preparation of Benzofuran-2-carboxylic acid {(S)-2-benzyloxy-1-[3-oxo-1-(pyridine-2-sulfonyl)-azepane-4-ylcarbamoyl]-ethyl}-amide Following the procedure of Example 193e-h, except substituting N-Boc-O-benzyl-L-serine in step 193e the title compound was prepared as a mixture of distereoemers. To a solution of benzofuran-2-carboxylic acid {(S)-2-benzyloxy-1-[3-oxo-1-(pyridine-2-sulfonyl)-azepane-4-ylcarbamoyl]-ethyl)-amide (90 mg) in ethyl acetate (2 mL) was added 10% Pd/C (50 mg). Upon hydrogenolysis of approximately 50% of the starting benzyl ether the reaction was filtered and concentrated. Purification of this 4 component mixture by HPLC provided the first eluting diastereomer of the title compound (1 mg) and the second eluting diastereomer of the title compound (0.3 mg): MS(ESI): 590.94(M+H)$^+$. Additionally the two individual diastereoemers of benzofuran-2-carboxylic acid {(S)-2-hydroxy-1-[3-oxo-1-(pyridine-2-sulfonyl)-azepane-4-ylcarbamoyl]-ethyl}-amide were also isolated as described below in Example 272.

Example 272

Preparation of Benzofuran-2-carboxylic acid {(S)-2-hydroxy-1-[3-oxo-1-(pyridine-2-sulfonyl)-azepane-4-ylcarbamoyl]-ethyl}-amide The title compound was obtained as discussed above in Example 271. Purification of the mixture by HPLC provided the two diastereomers in solid form (first eluting: 1.6 mg; second eluting 2.1 mg): MS(ESI): 500.9 (M+H)$^+$.

Example 273

Preparation of 5-Methoxybenzofuran-2-carboxylic acid {(S)-3-methyl-1-[3-oxo-1-(thiazole-2-sulfonyl)-azepan-4-ylcarbamoyl]-butyl}amide Following the procedure of Example 75c-d except substituting 5-methoxybenzofuran-2-carboxylic acid for benzofuran-2-carboxylic acid in step 75c provided the title compound which was separated by HPLC to give the first eluting diastereoemer as a white solid (144.3 mg, 85.1%): MS (ESI) 563.2 (M+H)$^+$ and the second eluting diastereomer as a white solid (16.9 mg, 10.0%) MS (ESI): 563.0 (M+H)$^+$ Example 274

Preparation of 7-Methoxybenzofuran-2-carboxylic acid {(S)-3-methyl-1-[3-oxo-1-(thiazole-2-sulfonyl)-azepan-4-ylcarbamoyl]-butyl}amide Following the procedure of Example 75c-d except substituting 7-methoxybenzofuran-2-carboxylic acid for benzofuran-2-carboxylic acid in step 75c provided the title compound which was separated by HPLC to give the first eluting diastereoemer as a white solid (75 mg, 47%): MS (ESI) 563.2 (M+H)$^+$ and the second eluting diastereomer as a white solid (57 mg, 35%): MS (ESI) 563.0 (M+H)$^+$ Example 275

Preparation of 3-Methylbenzofuran-2-carboxylic acid {(S)-3-methyl-1-[3-oxo-1-(thiazole-2-sulfonyl)-azepan-4-ylcarbamoyl]-butyl}amide Following the procedure of Example 75c-d except substituting 3-methylbenzofuran-2-carboxylic acid for benzofuran-2-carboxylic acid in step 75c provided the title compound which was separated by HPLC to give the first eluting diastereoemer as a white solid (69.5 mg, 42%): MS (ESI) 547.2 (M+H)$^+$ and the second eluting diastereomer as a white solid (65 mg, 40%): MS (ESI) 547.2 (M+H)$^+$ Example 276

Preparation of Benzo[b]thiophene-2-carboxylic acid {(S)-3-methyl-1-[3-oxo-1-(thiazole-2-sulfonyl)-azepan-4-ylcarbamoyl]-butyl}amide Following the procedure of Example 75c-d except substituting benzo[b]thiophene-2-carboxylic acid for benzofuran-2-carboxylic acid in step 75c provided the title compound which was separated by HPLC to give the first eluting diastereoemer as a white solid (79.5 mg, 48%): MS (ESI) 549.3 (M+H)$^+$ and the second eluting diastereomer as a white solid (50.5 mg, 31%): MS (ESI) 549.2 (M+H)$^+$ Example 277

Preparation of 1-Methyl-1H-indole-2-carboxylic acid {(S)-3-methyl-1-[3-oxo-1-(thiazole-2-sulfonyl)-azepan-4-ylcarbamoyl]-butyl}amide Following the procedure of Example 75c-d except substituting 1-methylindole-2-carboxylic acid for benzofuran-2-carboxylic acid in step 75c provided the title compound which was separated by HPLC to give the first eluting diastereoemer as a white solid (75 mg, 47%): MS (ESI) 563.2 (M+H)$^+$ and the second eluting diastereomer as a white solid (57 mg, 35%): MS (ESI) 563.0 (M+H)$^+$ Example 278

Preparation of Quinoxaline-2-carboxylic acid {(S)-3-methyl-1-[3-oxo-1-(thiazole-2-sulfonyl)-azepan-4-ylcarbamoyl]-butyl}amide Following the procedure of Example 75c-d except substituting quinoxaline-2-carboxylic acid for benzofuran-2-carboxylic acid in step 75c provided the title compound which was separated by HPLC to give the first eluting diastereoemer as a white solid (126 mg, 77%): MS (ESI) 545.2 (M+H)$^+$ and the second eluting diastereomer as a white solid (25 mg, 15%): MS (ESI) 545.2 (M+H)$^+$ Example 279

Preparation of Quinoline-2-carboxylic acid {[(S)-1-[1-(4-fluoro-benzenesulfonyl)-3-oxo-azepan-4-ylcarbamoyl]-3-methyl-butyl}-amide Following the procedure of Example 75, except substituting 4-fluorophenylsulfonyl chloride for benzenesulfonyl chloride and 2-quinoline carboxylic acid-for benzofuran-2-carboxylic acid, the title compound was prepared. The residue was purified by HPLC. First eluting diastereomer; MS (M+H$^+$): 555.2; $^1$H-NMR (400 Hz, CDCl$_3$): •8.62(d, 1H), 8.34-8.23(q, 2H) 8.19-8.17(d, 1H), 7.90-7.88(d, 1H), 7.88-7.80(m, 3H), 7.66-7.64(t, 1H), 7.25-7.07(m, 3H), 5.08(m, 1H), 4.72 (m, 1H), 4.58-4.53(d, 1H),4.00(m, 1H), 3.46-3.42 (d, 1H), 2.47(m, 1H), 2.27-2.12(m, 2H), 1.90-1.40(m, 5H), 1.03-1.01(m, 6H); and the second eluting diastereomer: MS (M+H$^+$): 555.4.

Example 280

Preparation of Benzofuran-2-carboxylic acid {(S)-1-[-(3-fluoro-benzensulfonyl)-3-oxo-azepan-4-ylcarbamoyl]-3-methyl-1-butyl}-amide a.) Allyl-pent-4-enyl-carbamic acid benzyl ester To a suspension of NaH (1.83 g, 76.33 mmol of 90% NaH) in DMF was added allyl-carbamic acid benzyl ester (7.3 g, 38.2 mmol) in a dropwise fashion. The mixture was stirred at room temperature for approximately 10 minutes whereupon 5-bromo-1-pentene (6.78 mL, 57.24 mmol) was added in a dropwise fashion. The reaction was heated to 40° C. for approximately 4 hours whereupon the reaction was partitioned between dichloromethane and water. The organic layer was washed with water (2×'s), brine, dried (MgSO$_4$), filtered and concentrated. Column chromatography of the residue (10% ethyl acetate:hexanes) provided 10.3 grams of the title compound as an oil: MS(ES) 260 (M+H$^+$).

b.) 2,3,4,7-Tetrahydro-azepine-1-carboxylic acid benzyl ester

To a solution of compound of Example 280a (50 g) in dichloromethane was added bis(tricyclohexylphosphine)benzylidine ruthenium (IV) dichloride (5.0 g). The reaction was heated to reflux until complete as determined by TLC analysis. The reaction was concentrated in vacuo. Column chromatography of the residue (50% dichloromethane:hexanes) gave 35 g of the title compound: MS(ES) 232 (M+H$^+$).

c.) 8-Oxa-3-aza-bicyclo[5.1.0]octane-3-carboxylic acid benzyl ester

To a solution of the compound of Example 280b (35 g, 1.5 mol) in CH$_2$Cl$_2$ was added m-CPBA (78 g, 0.45 mol). The mixture was stirred overnight at room temperature whereupon it was filtered to remove the solids. The filtrate was washed with saturated water and saturated NaHCO$_3$ (several times). The organic layer was dried (MgSO$_4$), filtered and concentrated to give 35 g of the title compound which was of sufficient purity to carry on to the next step: MS(ES) 248 (M+H$^+$), 270 (M+Na$^+$).

d.) 4-Azido-3-hydroxy-azepane-1-carboxylic acid benzyl ester

To a solution of the epoxide from Example 280c (2.0 g, 8.1 mmol) in methanol:water (8:1 solution) was added NH$_4$Cl (1.29 g, 24.3 mmol) and sodium azide (1.58 g, 24.30 mmol). The reaction was heated to 40° C. until complete consumption of the starting epoxide was observed by TLC analysis. The majority of the solvent was removed in vacuo and the remaining solution was partitioned between ethyl acetate and pH 4 buffer. The organic layer was washed with sat. NaHCO$_3$, water, brine dried (MgSO$_4$), filtered and concentrated. Column chromatography (20% ethyl acetate:hexanes) of the residue provided 1.3 g of the title compound: MS(ES) 291 (M+H$^+$) plus 0.14 g of trans-4-hydroxy-3-azido-hexahydro-1H-azepine.

e.) 4-Amino-3-hydroxy-azepane-1-carboxylic acid benzyl ester

To a solution of the azido alcohol of Example 280d (1.1 g, 3.79 mmol) in methanol was added triethyamine (1.5 mL, 11.37 mmol) and 1,3-propanedithiol (1.1 mL, 11.37 mmoL). The reaction was stirred until complete consumption of the starting material was observed by TLC analysis whereupon the reaction was concentrated in vacuo. Column chromatography of the residue (20% methanol:dichloromethane) provided 0.72 g of the title compound: MS(ES) 265 (M+H$^+$).

f.) 4-((S)-2-tert-Butoxycarbonylamino-4-methyl-pentanoylamino)-3-hydroxy-azepan-1-carboxylic acid benzyl ester To a solution of the amino alcohol of Example 280e (720 mg, 2.72 mmol) in CH$_2$Cl$_2$ was added EDC (521 mg), HOBt (368 mg) and N-Boc-leucine (630 mg). The reaction was maintained at room temperature until complete consumption of the starting material was observed by TLC analysis. The reaction was diluted with ethyl acetate and washed with 1N HCl, sat. K$_2$CO$_3$, water, brine, dried (MgSO$_4$), filtered and concentrated. Column chromatography of the residue (3% methanol:dichloromethane) gave 1.0 g of the title compound: MS(ES) 478 (M+H$^+$).

g.) [(S)-1-(3-Hydroxy-azepan-4-ylcarbamoyl)-3-methyl-butyl]-carbamic acid tert butyl ester To a solution of the compound of Example 280f (1.0 g) and 10% Pd/C (catalytic) in ethyl acetate:methanol (2:1 solution) was affixed a balloon of hydrogen. The reaction was stirred until complete consumption of the starting material was observed by TLC analysis. The reaction was filtered to remove the catalyst and the filtrate was concentrated to provide 0.82 g of the title compound: MS(ES) 344 (M+H$^+$).

h.) (S)-2-Amino-4-methyl-pentanoic acid [1-(3-fluoro-benzenesulfonyl)-3-hydroxy-azepan-4-yl]-amide To a solution of the compound of Example 280g (0.2 g) in dichloroethane (20 mL) was added p-NMM (0.32 g) and 3-fluorobenzenesulfonyl chloride (0.11 g). The reaction was stirred until complete as determined by MS analysis whereupon it was filtered, concentrated. The residue was dissolved in methanol (10 mL) and 4M HCl in dioxane (10 mL) was added. The reaction was maintained at room temperature until complete consumption of the starting material whereupon it was concentrated. The residue was dissolved in methanol whereupon p-carbonate resin was added. The mixture was shaken at room temperature for 4 hours then filtered and concentrated to provide 0.64 g of the title compound.

i.) Benzofuran-2-carboxylic acid {(S)-1-[1-(3-fluoro-benzenesulfonyl)-3-hydroxy-azepan-4-ylcarbamoyl]3-methyl-butyl}-amide To a solution of the compound of Example 280h (0.15 g) in CH$_2$Cl$_2$ was added benzofuran-2-carboxylic acid (0.56 mmol), HOBt (0.09 mg), and p-EDC (0.75 mg). The reaction was stirred overnight whereupon trisamine (0.50 g) was added and stirred an additional 1.5 hours. The reaction was filtered and concentrated to provide the title compound.

j.) Benzofuran-2-carboxylic acid {(S)-1-[1-(3-fluoro-benzenesulfonyl)-3-oxo-azepan-4-ylcarbamoyl]3-methyl-butyl}-amide To a solution of the compound of Example 280i (0.3 mmol) in CH$_2$Cl$_2$ was added Dess-Martin periodinane (0.25 g). The reaction was stirred until complete as determined by MS analysis. Workup and HPLC chromatography provided diastereomer 1: MS(ES) 543.2 (M+H)$^+$ and diastereomer 2: MS(ES) 543.2 (M+H)$^+$.

Example 281

Preparation of (S)-4-Methyl-2-(3-piperidin-1-yl-propanoylamino)-pentanoic acid [3-oxo-1-(pyridine-2-sulfonyl)-azepan-4-yl]-amide Following the general procedures of Examples 280h-j except substituting 2-pyridinesulfonyl chloride for 3-fluorobenzenesulfonyl chloride and 1-piperidinepropionoic acid for benzofuran-2-carboxylic acid the title compound was prepared: MS(ES) 521.9 (M+H)$^+$.

Example 282

Preparation of Benzofuran-2-carboxylic acid {(S)-1-[-(4-ethyl-benzensulfonyl)-3-oxo-azepan-4-ylcarbamoyl]-3-methyl-1-butyl}-amide Following the general procedures of Examples 280h-j except sunstituitng 4-ethylnezenesulfonyl chloride for 3-fluorobenzenesulfonyl chloride the title compound was prepared: Separation of the diastereomers provided diastereomer 1 MS(ES) 554.4 (M+H)$^{30}$ and distereomer 2 MS(ES) 554.4 (M+H)$^+$.

Example 283

Preparation of 5-(3-Trifluoromethyl-phenyl)-furan-2-carboxylic acid ((S)-3-methyl-1-{3-oxo-1-[1-(1-oxy-pyridin-2-yl)-methanoyl]-azepan-4-ylcarbamoyl}-butyl)-amide a.) 4-((S)-2-Amino-4-methyl-pentanoylamino)-3-hydroxy-azepane-1-carboxylic acid benzyl ester To a solution of the compound of Example 280f (7.32 g) in methanol was added 4M HCl in dioxane (38 mL). The reaction was stirred until complete whereupon it was concentrated to give 6.9 g of the title compound as a white solid.

b.) 3-Hydroxy-4-[(S)-methyl-2-({1-[5-(3-trifluromethyl-phenyl)-furan-2-yl]-methanoyl}-amino)-pentanoylamino]azepane-1-carboxylic acid benzyl ester To a solution of the compound of Example 283a (1.2 g) in dichloromethane was added TEA (0.93 mL), EDC (0.56 g), HOBt (0.36 g) and 5-[3-(trifluoromethyl) phenyl]-2-furoic acid (0.68 g). The reaction was stirred at room temperature until complete as determined by TLC analysis. Workup and column chromatography provided 1.35 g of the title compound: MS (ES) 616 (M+H)$^+$.

c.) 5-[3-(Trifluoromethyl)phenyl]-furan-2-carboxylic acid [(S)-1-(3-hydroxy-azepan-4-ylcarbamoyl)-3-methyl-butyl]-amide To a solution of the compound of Example 283b (1.3 g) in ethyl acetate:methanol (20 mL of an 8:1 mixture) was added 10% Pd\C. The mixture was stirred under a balloon of hydrogen gas until complete consumption of the starting material was observed by TLC analysis. The reaction was filtered and concentrated to provide 0.96 g of the title compound which was used directly in the following reaction with no further purification.

d.) 5-(3-Trifluoromethyl-phenyl)-furan-2-carboxylic acid ((S)-3-methyl-1-{3-hydroxy-1-[1-(1-oxy-pyridin-2-yl)-methanoyl]-azepan-4-ylcarbamoyl}-butyl)-amide To a solution of the compound of Example 283c (0.3 g) in dichloromethane was added TEA (0.22 mL), EDC (0.13 g), HOBt (0.8 g) and picolinic acid N-oxide (0.09 g). The reaction was stirred at room temperature until complete as determined by TLC analysis. Workup and column chromatography provided 0.16 g of the title compound: MS (ES) 603 (M+H)$^+$.

e.) 5-(3-Trifluoromethyl-phenyl)-furan-2-carboxylic acid ((S)-3-methyl-1-{3-oxo-1-[1-(1-oxy-pyridin-2-yl)-methanoyl]-azepan-4-ylcarbamoyl}-butyl)-amide To a solution of the compound of Example 283d (0.15 g) in DMSO (1.5 mL) was added TEA (0.37 mL) and pyridine sulfur trioxide complex (0.21 g) the reaction was stirred until complete as determined by LCMS. Workup and column chromatography (10% methanol:dichloromethane) provided 0.12 g of the title compound: MS (ES) 601 (M+H)$^+$.

The diastereomers were separated by HPLC to provide diastereomer 1 and diastereomer 2.

Example 284

Preparation of Benzo[1,3]-dioxole-5-carboxylic acid ((S)-3-methyl-1-{3-oxo-1-[1-oxy-pyridin-2-yl)-methanoyl]-azepan-4-ylcarbamoyl}-butyl)-amide Following the general procedures of Examples 283b-e except substituting piperonylic acid for 5-[3-(trifluoromethyl)phenyl]-2-furoic acid the title compound was prepared: MS(ES) 511 (M+H)$^+$.

The diastereomers were separated by HPLC to provide diastereomer 1 and diastereomer 2.

Example 285

Preparation of 5-(3-Trifluoromethyl-phenyl)-furan-2-carboxylic acid {(S)-1-[1-(3-cyclohexyl-propanoyl)-3-oxo-azepan-4-ylcarbamoyl]-3-methyl-butyl}-amide Following the general procedures of Examples 283b-e except substituting 3-cyclohexylpropionic acid for picolinic acid N-oxide the title compound was prepared: MS(ES) 618 (M+H)$^+$.

The diastereomers were separated by HPLC to provide diastereomer 1 and diastereomer 2.

Example 286

Preparation of Benzo[1,3]-dioxole-5-carboxylic acid {(S)-1-[1-(3-cyclohexyl-propanoyl)-3-oxo-azepan-4-ylcarbamoyl]-3-methyl-butyl}-amide Following the general procedures of Examples 283b-e except substituting 3-cyclohexylpropionic acid for picolinic acid N-oxide and piperonylic acid for 5-[3-(trifluoromethyl) phenyl]-2-furoic acid the title compound was prepared: MS(ES) 528 (M+H)$^+$.

The diastereomers were separated by HPLC to provide diastereomer 1 and diastereomer 2.

Example 287

Preparation of 5-(3-Trifluoromethyl-phenyl)-furan-2-carboxylic acid {(S)-1-[1-(4-methyl-pentanoyl)-3-oxo-azepan-4-ylcarbamoyl]-3-methyl-butyl}-amide Following the general procedures of Examples 283b-e except substituting 4-methyl-pentanoic acid for picolinic acid N-oxide the title compound was prepared: MS(ES) 578 (M+H)$^+$.

The diastereomers were separated by HPLC to provide diastereomer 1 and diastereomer 2.

Example 288

Preparation of Benzo[1,3]-dioxole-5-carboxylic acid {(S)-1-[1-(4-methyl-pentanoyl)-3-oxo-azepan-4-ylcarbamoyl]-3-methyl-butyl}-amide Following the general procedures of Examples 283b-e except substituting 4-methyl-pentanoic acid for picolinic acid N-oxide and piperonylic acid for 5-[3-(trifluoromethyl)phenyl]-2-furoic acid the title compound was prepared: MS(ES) 488 (M+H)+.

The diastereomers were separated by HPLC to provide diastereomer 1 and diastereomer 2.

Example 289

Preparation of Benzofuran-2-carboxylic acid {(S)1-[3-oxo-1-(propane-1-sulfonyl)-azepan-4-ylcarbamoyl]-3-methyl-1-butyl}-amide Following the general procedures of Examples 280h-j except substituting propanesulfonyl chloride for 3-fluorosulfonyl chloride the title compound was prepared.

Separation of the diastereomers by HPLC provided diastereomer 1: MS(ES) 491.2 (M+H)+ and diastereomer 2: MS(ES) 491.2 (M+H)+.

Example 290

Preparation of Benzofuran-2-carboxylic acid [(S)-1-[3-oxo-1-(ethanesulfonyl-azepan-4-ylcarbamoyl)-3-methyl-1-butyl]-amide Following the general procedures of Examples 280h-j except substituting ethanesulfonyl chloride for 3-fluorobenzenesulfonyl chloride the title compound was prepared.

Separation of the diastereomers by HPLC provided diastereomer 1: MS(ES) 477.4 (M+H)+ and diastereomer 2: MS(ES) 477.4 (M+H)+.

Example 291

Preparation of 5-Fluoro-benzofuran-2-carboxylic acid {(S)-3-methyl-1-[3-oxo-1-(1-oxy-pyridine-2-sulfonyl)-azepan-4-ylcarbamoyl]-butyl}-amide a.) {(S)-1-[3-Hydroxy-1-(1-oxy-pyridine-2-sulfonyl)-azepan-4-ylcarbamoyl]-3-methyl-butyl}-carbamic acid tert-butyl ester Generation of 2-pyridinesulfonylchloride-N-oxide: To a 0° C. solution of 2-mercaptopyridine-N-oxide (2.23 g, 17.55 mmol) in 9M HCl (33 mL) was bubbled chlorine gas for approximately 90 minutes. The dissolved chlorine was removed under vacuum at 0° C.

To a solution of [(S)-1-(3-hydroxy-azepan-4-ylcarbamoyl)-3-methyl-butyl]-carbamic acid tert butyl ester of Example 280 g (2.5 g, 7.28 mmol) in CH₂Cl₂ (100 mL) and sat. NaHCO₃ (400 mL) was added the solution of 2-pyridinesulfonylchloride-N-oxide (27 mL, 102 mg/mL) dropwise in portions. As the addition proceeds additional sat. NaHCO₃ is added in order to maintain the pH at approximately 8-9. Upon complete addition of the sulfonylchloride the reaction is stirred for an additional hour whereupon the organic layer was removed and washed with brine. The organic layer was evaporated and the residue chromatographed (5% methanol: dichloromethane) to provide 2.5 g of the title compound: MS (ES) 500 (M+H+).

b.) (S)-2-Amino-4-methyl-pentanoic acid-[3-hydroxy-1-(1-oxy-pyridine-2-sulfonyl)-azepan-4-yl]-amide To a solution of {(S)-1-[3-hydroxy-1-(1-oxy-pyridine-2-sulfonyl)-azepan-4-ylcarbamoyl]-3-methyl-butyl}-carbamic acid tert-butyl ester of Example 291a (2.0 g) in methanol (20 mL) was added 4 M HCl in dioxane (20 mL). The reaction was stirred at room temperature for 1.5 hours whereupon it was concentrated to provide 1.8 g of the title compound: MS (ES) 400 (M+H+).

c.) 5-Fluoro-benzofuran-2-carboxylic acid {(S)-3-methyl-1-[3-hydroxy-1-(1-oxy-pyridine-2-sulfonyl)-azepan-4-ylcarbamoyl]-butyl}-amide To a solution of the compound of Example 291b (0.30 g) in CH₂Cl₂ was added 5-fluoro-benzofuran-2-carboxylic acid (0.11 g), EDC (0.13 g), HOBt (0.086 g), and TEA (0.22 mL). The reaction was stirred until complete as determined by LCMS whereupon it was diluted with ethyl acetate and washed with water, sat. K₂CO₃, 1N HCl, brine, dried (MgSO₄), filtered and concentrated. Column chromatography (10% methanol: dichloromethane) of the residue provided 0.27 g of the title compound: MS(ES) 563 (M+H)+.

d.) 5-Fluoro-benzofuran-2-carboxylic acid {(S)-3-methyl-1-[3-oxo-1-(1-oxy-pyridine-2-sulfonyl)-azepan-4-ylcarbamoyl]-butyl}-amide To a solution of the compound of Example 291c (0.19 g) in DMSO (1.5 mL) was added sulfur trioxide pyridine complex (0.26 g). The reaction was stirred until complete as determined by LCMS whereupon it was diluted with ethyl acetate and washed with sat. NaHCO₃, brine dried, filtered and concentrated. Column chromatography of the residue provided 0.15 g of the title compound as a mixture of diastereomers; MS(ES) 561 (M+H)+.

Separation of the diastereomers by HPLC provided diastereomer 1 and diastereomer 2.

Example 292

Preparation of 5-Fluoro-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 5-fluoro-3-methyl benzofuran-2-carboxylic acid for 5-fluoro-benzofuran-2-carboxylic acid provided the title compound as a mixture of diastereomers: MS(ES) 575 (M+H)+.

Separation of the diastereomers by HPLC provided diastereomer 1 and diastereomer 2.

Example 293

Preparation of 6-Fluoro-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 6-fluoro-3-methyl benzofuran-2-carboxylic acid for 5-fluoro-benzofuran-2-carboxylic acid provided the title compound as a mixture of diastereomers: MS(ES) 575 (M+H)+.

Separation of the diastereomers by HPLC provided diastereomer 1 and diastereomer 2.

Example 294

Preparation of 3-Methyl-benzofuran-2-carboxylic acid {(R)-3-methyl-1-[3-oxo-1-(1-oxy-pyridine-2-sulfonyl)-azepan-4-ylcarbamoyl]-butyl}-amide Following the general procedures of Examples 280f-i except substituting N-Boc-D-leucine for N-Boc-L-leucine, 2-pyridinesulfonylchloride N-oxide for 3-fluorobenzenesulfonyl chloride and 3-methyl-benzofuran-2-carboxylic

Example 295

Preparation of 3-Methyl-furo[3,2-b]-pyridine-2-carboxylic acid {(S)-3-methyl-1-[-3-oxo-1-(1-oxy-pyridine-2-sulfonyl)-azepan-4-ylcarbamoyl]-butyl}-amide Following the general procedure of Examples 291c-d except substituting 3-methyl-furo[3,2-b]-pyridine-2-carboxylic acid for 5-fluoro-benzofuran-2-carboxylic acid provided the title compound as a mixture of diastereomers: MS(ES) 558 (M+H)$^+$.

Separation of the diastereomers by HPLC provided diastereomer 1 and diastereomer 2.

Example 296

Preparation of 5-Methoxy-benzofuran-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting 5-methoxy-benzofuran-2-carboxylic acid for benzofuran-2-carboxylic acid provided the title compound as a mixture of diastereomers.

Separation of the diastereomers by HPLC provided diastereomer 1: MS(ES) 574.5 (M+H)$^+$ and diastereomer 2 574.5 (M+H)$^+$.

Example 297

Preparation of 3-Methyl-benzofuran-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting 3-methyl-benzofuran-2-carboxylic acid for benzofuran-2-carboxylic acid provided the title compound as a mixture of diastereomers.

Separation of the diastereomers by HPLC provided diastereomer 1: MS(ES) 557.4 (M+H)$^+$ and diastereomer 2 557.4 (M+H)$^+$.

Example 298

Preparation of Benzo[b]thiophene-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting benzo[b]thiophene-2-carboxylic acid_for benzofuran-2-carboxylic acid provided the title compound as a mixture of diastereomers.

Separation of the diastereomers by HPLC provided diastereomer 1: MS(ES) 559.4 (M+H)$^+$ and diastereomer 2 559.4 (M+H)$^+$.

Example 299

Preparation of 3-Methyl-furan-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting 3-methyl-furan-2-carboxylic acid for benzofuran-2-carboxylic acid provided the title compound as a mixture of diastereomers.

Separation of the diastereomers by HPLC provided diastereomer 1: MS(ES) 507.2 (M+H)$^+$ and diastereomer 2 507.4 (M+H)$^+$.

Example 300

Preparation of Quinoline-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting quinoline-2-carboxylic acid for benzofuran-2-carboxylic acid provided the title compound as a mixture of diastereomers.

Separation of the diastereomers by HPLC provided diastereomer 1: MS(ES) 554.2 (M+H)$^+$ and diastereomer 2 MS(ES) 545.2 (M+H)$^+$.

Example 301

Preparation of Thieno[3,2-b]thiophene-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting thieno[3,2-b]thiophene-2-carboxylic acid for benzofuran-2-carboxylic acid provided the title compound as a mixture of diastereomers.

Separation of the diastereomers by HPLC provided diastereomer 1: MS(ES) 565.2 (M+H)$^+$ and diastereomer 2 MS(ES) 565.2 (M+H)$^+$.

Example 302

Preparation of Quinoxaline-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting quinoxaline-2-carboxylic acid for benzofuran-2-carboxylic acid provided the title compound as a mixture of diastereomers.

Separation of the diastereomers by HPLC provided diastereomer 1: MS(ES) 555.4 (M+H)$^+$ and diastereomer 2 MS(ES) 555.4 (M+H)$^+$.

Example 303

Preparation of Thiophene-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting thiophene-2-carboxylic acid for benzofuran-2-carboxylic acid provided the title compound as a mixture of diastereomers.

Separation of the diastereomers by HPLC provided diastereomer 1: MS(ES) 509.4 (M+H)⁺ and diastereomer 2 MS(ES) 509.2 (M+H)⁺.

Example 304

Preparation of 5-Methyl-thiophene-2-carboxylic acid {(S)-1-[1-(3-fluoro-benzenesulfonyl)-3-oxo-azepan-4-ylcarbamoyl]-3-methyl-butyl}-amide Following the general procedure of Examples 280h-j except substituting 5-methyl-thiophene-2-carboxylic acid for benzofuran-2-carboxylic acid provided the title compound as a mixture of diastereomers.

Separation of the diastereomers by HPLC provided diastereomer 1: MS(ES) 523.2 (M+H)⁺ and diastereomer 2 MS(ES) 523.4 (M+H)⁺.

Example 305

Preparation of 5-Methoxy-benzofuran-2-carboxylic acid [(S)-1-(1-ethanesulfonyl-3-oxo-azepan-4-ylcarbamoyl)-3-methyl-butyl]-amide Following the general procedure of Examples 280h-j except substituting 5-methoxy-benzofuran-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 507.4 (M+H)⁺ and diastereomer 2 MS(ES) 507.4 (M+H)⁺.

Example 306

Preparation of 3-Methyl-benzofuran-2-carboxylic acid [(S)-1-(1-ethanesulfonyl-3-oxo-azepan-4-ylcarbamoyl)-3-methyl-butyl]-amide Following the general procedure of Examples 280h-j except substituting 3-methyl-benzofuran-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 491.2 (M+H)⁺ and diastereomer 2 MS(ES) 491.2 (M+H)⁺.

Example 307

Preparation of Benzo[b]thiophene-2-carboxylic acid [(S)-1-(1-ethanesulfonyl-3-oxo-azepan-4-ylcarbamoyl)-3-methyl-butyl]-amide Following the general procedure of Examples 280h-j except substituting benzo[b]thiophene-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 493.4 (M+H)⁺ and diastereomer 2 MS(ES) 493.4 (M+H)⁺.

Example 308

Preparation of 3-Methyl-furan-2-carboxylic acid [(S)-1-(1-ethanesulfonyl-3-oxo-azepan-4-ylcarbamoyl)-3-methyl-butyl]-amide Following the general procedure of Examples 280h-j except substituting 3-methyl-furan-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 441.2 (M+H)⁺ and diastereomer 2 MS(ES) 441.2 (M+H)⁺.

Example 309

Preparation of Quinoline-2-carboxylic acid [(S)-1-(1-ethanesulfonyl-3-oxo-azepan-4-ylcarbamoyl)-3-methyl-butyl]-amide Following the general procedure of Examples 280h-j except substituting quinoline-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 488.2 (M+H)⁺ and diastereomer 2 MS(ES) 488.2 (M+H)⁺.

Example 310

Preparation of Thieno[3,2-b]thiophene-2-carboxylic acid {(S)-1-(1-ethanesulfonyl-3-oxo-azepan-4-ylcarbamoyl)-3-methyl-butyl]-amide Following the general procedure of Examples 280h-j except substituting thieno[3,2-b]thiophene-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 499.4 (M+H)⁺ and diastereomer 2 MS(ES) 499.4 (M+H)⁺.

Example 311

Preparation of Quinoxaline-2-carboxylic acid [(S)-1-(1-ethanesulfonyl-3-oxo-azepan-4-ylcarbamoyl)-3-methyl-butyl]-amide Following the general procedure of Examples 280h-j except substituting quinoxaline-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 489.2 (M+H)⁺ and diastereomer 2 MS(ES) 489.2 (M+H)⁺.

Example 312

Preparation of Thiophene-2-carboxylic acid [(S)-1-(1-ethanesulfonyl-3-oxo-azepan-4-ylcarbamoyl)-3-methyl-butyl]-amide Following the general procedure of Examples 280h-j except substituting thiophene-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 443.4 (M+H)$^+$ and diastereomer 2 MS(ES) 443.2 (M+H)$^+$.

Example 313

Preparation of 5-Methyl-thiophene-2-carboxylic acid [(S)-1-(1-ethanesulfonyl-3-oxo-azepan-4-ylcarbamoyl)-3-methyl-butyl]-amide Following the general procedure of Examples 280h-j except substituting 5-methyl-thiophene-2-carboxylic acid for benzofuran-2-carboxylic acid and ethanesulfonyl chloride for 3-flurobenzenesulfonyl chloride provided the title compound as a mixture of diastereomers.

Separation of the diastereomers by HPLC provided diastereomer 1: MS(ES) 457.2 (M+H)$^+$ and diastereomer 2 MS(ES) 457.4 (M+H)$^+$.

Example 314

Preparation of 5-Methoxy-benzofuran-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting 5-methoxy-benzofuran-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 521.4 (M+H)$^+$ and diastereomer 2 MS(ES) 521.2 (M+H)$^+$.

Example 315

Preparation of 3-Methyl-benzofuran-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting 3-methyl-benzofuran-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 505.4 (M+H)$^+$ and diastereomer 2 MS(ES) 505.2 (M+H)$^+$.

Example 316

Preparation of Benzo[b]thiophene-2-carboxylic acid {(S)-1-[3-oxo-1-(propane-1-sulfonyl)-azepan-4-yl-carbamoyl]-3-methyl-1-butyl}-amide Following the general procedure of Examples 280h-j except substituting benzo[b]thiophene-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 507.4 (M+H)$^+$ and diastereomer 2 MS(ES) 507.4 (M+H)$^+$.

Example 317

Preparation of 3-Methyl-furan-2-carboxylic acid {(S)-1-[3-oxo-1-(propane-1-sulfonyl)-azepan-4-yl-carbamoyl]-3-methyl-1-butyl}-amide Following the general procedure of Examples 280h-j except substituting 3-methyl-furan-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 455.2 (M+H)$^+$ and diastereomer 2 MS(ES) 455.4 (M+H)$^+$.

Example 318

Preparation of 2,5-Dimethyl-benzofuran-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting 2,5-dimethyl-benzofuran-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 469.4 (M+H)$^+$ and diastereomer 2 MS(ES) 469.2 (M+H)$^+$.

Example 319

Preparation of Quinoline-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting quinoline-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 565.2 (M+H)$^+$ and diastereomer 2 MS(ES) 565.2 (M+H)$^+$.

Example 320

Preparation of Thieno[3,2-b]thiophene-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting thieno[3,2-b]thiophene-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 513.2 (M+H)$^+$ and diastereomer 2 MS(ES) 513.2 (M+H)$^+$.

Example 321

Preparation of Quinoxaline-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting quinoxaline-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 503.4 (M+H)+ and diastereomer 2 MS(ES) 503.4 (M+H)+.

Example 322

Preparation of Thiophene-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting thiophene-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 457.4 (M+H)+ and diastereomer 2 MS(ES) 457.4 (M+H)+.

Example 323

Preparation of 5-Methyl-thiophene-2-carboxylic acid {(S)-1-[3-oxo-1-(propane-1-sulfonyl)-azepan-4-ylcarbamoyl]-3-methyl-1-butyl}-amide Following the general procedure of Examples 280h-j except substituting 5-methyl-thiophene-2-carboxylic acid for benzofuran-2-carboxylic acid and 1-propanesulfonyl chloride for 3-flurobenzenesulfonyl chloride provided the title compound as a mixture of diastereomers.

Separation of the diastereomers by HPLC provided diastereomer 1: MS(ES) 471.4 (M+H)+ and diastereomer 2 MS(ES) 471.4 (M+H)+.

Example 324

Preparation of 5-Methoxy-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 5-methoxy-3-methyl-benzofuran-2-carboxylic acid for 5-fluoro-benzofuran-2-carboxylic acid provided the title compound as a mixture of diastereomers: MS(ES) 587 (M+H)+.

Separation of the diastereomers by HPLC provided diastereomer 1: MS(ES) 565.2 (M+H)+ and diastereomer 2 MS(ES) 565.2 (M+H)+.

Example 325

Preparation of 3,5-Dimethyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 3,5-dimethyl-benzofuran-2-carboxylic acid for 5-fluoro-benzofuran-2-carboxylic acid provided the title compound as a mixture of diastereomers: MS(ES) 571 (M+H)+.

Separation of the diastereomers by HPLC provided diastereomer 1 and diastereomer 2.

Example 326

Preparation of 3-Ethyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 3-ethyl-benzofuran-2-carboxylic acid for 5-fluoro-benzofuran-2-carboxylic acid provided the title compound as a mixture of diastereomers: MS(ES) 571 (M+H)+.

Separation of the diastereomers by HPLC provided diastereomer 1 and diastereomer 2.

Example 327

Preparation of 4-Methoxy-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 4-methoxy-3-methyl-benzofuran-2-carboxylic acid for 5-fluoro-benzofuran-2-carboxylic acid provided the title compound as a mixture of diastereomers: MS(ES) 587 (M+H)+.

Separation of the diastereomers by HPLC provided diastereomer 1 and diastereomer 2.

Example 328

Preparation of 1-Methyl-naphtho[2,1-b]-furan-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 1-methyl-naphtho[2,1-b]-furan-2-carboxylic acid for 5-fluoro-benzofuran-2-carboxylic acid provided the title compound as a mixture of diastereomers: MS(ES) 607 (M+H)+.

Separation of the diastereomers by HPLC provided diastereomer 1 and diastereomer 2.

Example 329

Preparation of 6-Methoxy-3-methyl-benzofuran-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting 6-methoxy-3-methyl-benzofuran-2-carboxylic acid for 5-fluoro-benzofuran-2-carboxylic acid provided the title compound as a mixture of diastereomers: MS(ES) 587 (M+H)+.

Separation of the diastereomers by HPLC provided diastereomer 1 and diastereomer 2.

Example 330

Preparation of 3-Methyl-benzofuran-2-carboxylic acid {1,3-dimethyl-1-[3-oxo-1-(1-oxy-pyridine-2-sulfonyl)-azepan-4-ylcarbamoyl]-butyl}-amide a.) 4-(2-tert-Butoxycarbonylamino-2,4-dimethyl-pentanoylamino)-3-hydroxy-azepane-1-carboxylic acid benzyl ester To a solution of N-[(1,1-dimethylethoxy)carbonyl]-2-methyl-(d,l)-leucine (3.0 g) in methlene chloride was added EDC (2.34 g), HOBt (1.65 g), $Et_3N$ (1.7 ml) and the compound of Example 1e (3.23 g). After stirring at room temperature over night the mixture was washed with 0.1 N HCl, Sat. $NaHCO_3$, $H_2O$, Brine. The organic layer was concentrated and residue was purified by flash column chromatography eluting with $CH_2Cl_2$: $CH_3OH$ (95:5) to give the title compound as a white solid (4.0 g, 66.6%). MS: 492.4 (M+H)$^+$ b.) [1-(3-Hydroxy-azepan-4-ylcarbamoyl)-1,3-dimethyl-butyl]-carbamic acid tert-butyl ester To a solution of the compound of Example 330(a) (3.04 g, 8.00 mmol) in ethyl acetate (50 mL) was added 10% palladium on carbon (1.5 g). After stirring at room temperature under a hydrogen atmosphere for 16 h, the mixture was filtered through celite. The filtrate was concentrated to yield the title compound as a yellow oil (1.97 g, 100%). MS (ESI): 358.4 (M+H)$^+$.

c.) {1-[3-Hydroxy-1-(1-hydroxy-pyridine-2-sulfonyl)-azepan-4-ylcarbamoyl]-1,3-dimethyl-butyl}-carbamic acid tert-butyl ester 2-Mercaptane N-oxide (1.25 g) was disolved in concentrated HCl (5.5 ml). After cooled to 0° C. water (3 ml) was added. $Cl_2$ gas was bubbled through this solution for 1.5 h. Water solution was extacted with cold $CH_2Cl_2$ then the combined organic layer was washed with Sat.$NaHCO_3$, brine. To a solution of the compound of Example 330b (1.20 g) and $Et_3N$ (1.3 ml) in DCE (10 ml) was added the sulfonyl chloride which was freshly prepared above at 0° C. Stirring was kept for 1 h then the reaction mixture was washed with brine, dried over $Na_2SO_4$, concentrated and purified through flash column chromatograpghy eluting with $CH_2Cl_2$: $CH_3OH$ (95:5). The filtrate was concentrated to yield the title compound as white solid (1.2 g, 70%). MS: 515.4 (M+H)$^+$.

d.) 2-Amino-2,4-dimethyl-pentanoic acid [3-hydroxy-1-(hydroxy-pyridine-2-sulfonyl)-azepan-4-yl]-amide To a stirring solution of the compound of Example 330c (1.0 g, 2.04 mmol) in methnol (10 ml) was added HCl (4M in Dioxane) (10 ml). After stirring at room temperature for 3 hr, the solution was concentrated to get white solide. To a solution of the white solid (0.81 g, 1.53 mmol, 75%) in methnol (30 ml) was added P—$CO_3$ (2.9 g, 2.63 mmol/g). After shaking for 2 hr, the solution was filtered and concentrated to yield the title compound as white solid (0.57 g, 1.45 mmol, 95%). MS: 415.4 (M+H)$^+$.

e.) 3-Methyl-benzofuran-2-carboxylic acid {1,3-dimethyl-1-[3-hydroxy-1-(1-oxy-pyridine-2-sulfonyl)-azepan-4-ylcarbamoyl]-butyl}-amide To a solution of the compound of Example 330d (0.150 g, 0.448 mmol) in $CH_2Cl_2$ (20 mL) was added 3-methyl benzofuran-2-carboxylic acid (0.109 g), 1-hydroxybenzotriazole (0.106 g, 0.762 mmol), and P-EDC (0.85 g, 1 mmol/g) in $CH_2Cl_2$ (10 mL). After shaking at room temperature for over night, the solution was treated with tisamine (0.589 g, 3.75 mmol/g). After shaking for another 2 hr, the solution was filtered and concentrated to yield the title compound as a white solid (166.7 mg, 70%). MS (ESI): 573.2(M+H)$^+$.

f.) 3-Methyl-benzofuran-2-carboxylic acid{1,3-dimethyl-1-[3-oxo-1-(oxy-pyridine-2-sulfonyl)-azepan-4-ylcarbamoyl]-butyl}-amide To a stirring solution of the compound of Example 330e (140.7 mg, 0.245 mmol) in DMSO (2 mL) was added Py—$SO_3$ (155.7 mg, 0.98 mmol) and $Et_3N$ (0.27 ml, 1.96 mmol). After stirring at room temperature for 2 h. Sat. $NaHCO_3$ and ethyl acetate was added to quench the reaction. Organic layer was washed with brine, dried over $Na_2SO_4$ and concentrated. The residue was purified through flash column chromatograghy eluting with $CH_2Cl_2$:$CH_3OH$ (95:5) to yield the title compound as a white solid (69.9 mg, 50.8%). MS (ESI): 571.2(M+H)$^+$.

Example 331

Preparation of Benzofuran-2-carboxylic acid [(S)-3-methyl-1-[3-oxo-1-quinolin-2-ylmethyl-azepan-4-ylcarbamoyl]-butyl}-amide a.) [(S)-1-(3-Hydroxy-1-quinoline-2-ylmethyl-azepan-4-ylcarbamoyl)-3-methyl-butyl]-carbamic acid tert-butyl ester To a solution of the compound of Example 280g (1.0 g) in $CH_2Cl_2$ was added α-quinoline carbaldehyde (0.68 g) and $NaBH(OAc)_3$ (1.2 g). Workup and column chromatography (6% methanol:dichloromethane) provided 1.4 g of the title compound: MS(ES) 485 (M+H)$^+$.

b.) (S)-2-Amino-4-methyl-pentanoic acid (3-hydroxy-1-quinolin-2-methyl-azepan-4-yl)-amide To a solution of the compound of Example 331a (1.4 g) in methanol (20 mL) was added 4M HCl in dioxane (20 mL). The reaction was stirred until complete whereupon the reaction was concentrated to provide 1.3 g of the title compound: MS(ES) 385 (M+H)$^+$.

c.) Benzofuran-2-carboxylic acid [(S)-3-methyl-1-[3-hydroxy-1-quinolin-2-ylmethyl-azepan-4-ylcarbamoyl]-butyl}-amide Following the general procedure of Example 291c except substituting the compound of Example 331b and benzofuran-2-carboxylic acid for 5-fluoro-benzofuran-2-carboxylic acid the title compound was prepared: MS(ES) 545 (M+H)$^+$.

d.) Benzofuran-2-carboxylic acid [(S)-3-methyl-1-[3-oxo-1-quinolin-2-ylmethyl-azepan-4-ylcarbamoyl]-butyl}-amide Following the general procedure of Example 291d except substituting the compound of Example 332c the title compound was prepared: MS(ES) 543 (M+H)$^+$.

Example 332

Preparation of 3-Methyl-benzofuran-2-carboxylic acid [(S)-3-methyl-1-[3-oxo-1-quinolin-2-ylmethyl-azepan-4-ylcarbamoyl]-butyl}-amide Following the procedure of Example 331c-d except substituting 3-methyl-benzofuran-2-carboxylic acid for benzofuran-2-carboxylic acid the title compound was prepared: MS(ES) 541 (M+H)$^+$.

Example 333

Preparation of Benzo[b]thiophene-2-carboxylic acid [(S)-3-methyl-1-[3-oxo-1-quinolin-2-ylmethyl-azepan-4-ylcarbamoyl]-butyl}-amide Following the procedure of Example 331c-d except substituting benzo[b]thiophene-2-carboxylic acid for benzofuran-2-carboxylic acid the title compound was prepared: MS(ES) 541 (M+H)$^+$.

Example 334

Preparation of Benzofuran-2-carboxylic acid ((S)-3-methyl-1-{3-oxo-1-[1-toluene-2-sulfonylamino)-methanoyl]-azepan-4-ylcarbamoyl}-butyl)-amide a.) ((S)-1-{3-Hydroxy-1-[1-(toluene-2-sulfonylamino)-methanoyl]-azepan-4-ylcarbamoyl}-3-methyl-butyl)-carbamic acid tert-butyl ester To a solution of the compound of Example 280g (1.0 g) in CH$_2$Cl$_2$ was added o-toluenesulfonyl isocyanate (0.68 g). The reaction was stirred until complete consumption of the starting material was observed. Workup and column chromatography (6% methanol:dichloromethane) provided 1.28 g of the title compound: MS(ES) 541 (M+H)$^+$.

b.) (S)-2-Amino-4-methyl-pentanoic acid {3-hydroxy-1-[1-(toluene-2-sulfonylamino)-methanoyl]-azepan-4-yl}-amide Following the procedure of Example 280g except substituting the compound of Example 334a the title compound was prepared: MS(ES) 441 (M+H)$^+$.

c.) Benzofuran-2-carboxylic acid ((S)-3-methyl-1-{3-hydroxy-1-[1-toluene-2-sulfonylamino)-methanoyl]-azepan-4-ylcarbamoyl}-butyl)-amide Following the procedure of Example 280i except substituting the compound of Example 334b the title compound was prepared: MS(ES) 585 (M+H)$^+$.

d.) Benzofuran-2-carboxylic acid ((S)-3-methyl-1-{3-oxo-1-[1-toluene-2-sulfonylamino)-methanoyl]-azepan-4-ylcarbamoyl}-butyl)-amide Following the procedure of Example 291d except substituting the compound of Example 334c the title compound was prepared: MS(ES) 583 (M+H)$^+$.

Example 335

Preparation of 3-Methyl-benzofuran-2-carboxylic acid ((S)-3-methyl-1-{3-oxo-1-[1-toluene-2-sulfonylamino)-methanoyl]-azepan-4-ylcarbamoyl}-butyl)-amide Following the procedures of Example 334c-d except substituting 3-methyl-benzofuran-2-carboxylic acid for benzofuran-2-carboxylic acid the title compound was prepared: MS(ES) 597 (M+H)$^+$.

Example 336

Preparation of Benzo[b]thiophene-2-carboxylic acid ((S)-3-methyl-1-{3-oxo-1-[1-toluene-2-sulfonylamino)-methanoyl]-azepan-4-ylcarbamoyl}-butyl)-amide Following the procedures of Example 334c-d except substituting Benzo[b]thiophene-2-carboxylic acid for benzofuran-2-carboxylic acid the title compound was prepared: MS(ES) 599 (M+H)$^+$.

Example 337

Preparation of Benzofuran-2-carboxylic acid ((S)-3-methyl-1-{3-oxo-1-[2-chloro-benzenesulfonylamino)-methanoyl]-azepan-4-ylcarbamoyl}-butyl)-amide Following the procedures of Example 334a-d except substituting 2-chlorobenzenesulfonyl isocyanate for o-toluenesulfonyl isocyanate the title compound was prepared: MS(ES) 603 (M+H)$^+$.

Example 338

Preparation of 3-Methyl-benzofuran-2-carboxylic acid ((S)-3-methyl-1-{3-oxo-1-[2-chloro-benzenesulfonylamino)-methanoyl]-azepan-4-ylcarbamoyl}-butyl)-amide Following the procedures of Example 334a-d except substituting 2-chlorobenzenesulfonyl isocyanate for o-toluenesulfonyl isocyanate and 3-methyl-benzofuran-2-carboxylic acid for benzofuran-2-carboxylic acid the title compound was prepared: MS(ES) 617 (M+H)$^+$.

Example 339

Preparation of Benzo[b]thiophene-2-carboxylic acid ((S)-3-methyl-1-{3-oxo-1-[2-chloro-benzenesulfonylamino)-methanoyl]-azepan-4-ylcarbamoyl}-butyl)-amide Following the procedures of Example 334a-d except substituting 2-chlorobenzene sulfonyl isocyanate for o-toluenesulfonyl isocyanate and benzo[b]thiophene-2-carboxylic acid for benzofuran-2-carboxylic acid the title compound was prepared: MS(ES) 619 (M+H)$^+$.

Example 340

Preparation of Benzofuran-2-carboxylic acid ((S)-3-methyl-1-{3-oxo-1-[4-fluoro-benzenesulfonylamino)-methanoyl]-azepan-4-ylcarbamoyl}-butyl)-amide Following the procedures of Example 334a-d except substituting 4-fluorobenzene sulfonyl isocyanate for o-toluenesulfonyl isocyanate the title compound was prepared: MS(ES) 587 (M+H)$^+$.

Example 341

Preparation of 3-Methyl-benzofuran-2-carboxylic acid ((S)-3-methyl-1-{3-oxo-1-[4-fluoro-benzenesulfonylamino)-methanoyl]-azepan-4-ylcarbamoyl}-butyl)-amide Following the procedures of Example 334-d except substituting 4-fluorobenzene sulfonyl isocyanate for o-toluenesulfonyl isocyanate and 3-methyl-benzofuran-2-carboxylic acid for benzofuran-2-carboxylic acid the title compound was prepared: MS(ES) 601 (M+H)$^+$.

Example 342

Preparation of Benzo[b]thiophene-2-carboxylic acid ((S)-3-methyl-1-{3-oxo-1-[4-fluoro-benzenesulfonylamino)-methanoyl]-azepan-4-ylcarbamoyl}-butyl)-amide Following the procedures of Example 334a-d except substituting 4-fluorobenzene sulfonyl isocyanate for o-toluenesulfonyl isocyanate and benzo[b]thiophene-2-carboxylic acid for benzofuran-2-carboxylic acid the title compound was prepared: MS(ES) 603 (M+H)$^+$.

Example 343

Preparation of Benzofuran-2-carboxylic acid ((S)-3-methyl-1-{3-oxo-1-[1-toluene-4-sulfonylamino)-methanoyl]-azepan-4-ylcarbamoyl}-butyl)-amide Following the procedures of Example 334a-d except substituting p-toluenesulfonyl isocyanate for o-toluenesulfonyl isocyanate the title compound was prepared: MS(ES) 583 (M+H)$^+$.

Example 344

Preparation of 3-Methyl-benzofuran-2-carboxylic acid ((S)-3-methyl-1-{3-oxo-1-[1-toluene-4-sulfonylamino)-methanoyl]-azepan-4-ylcarbamoyl}-butyl)-amide Following the procedures of Example 334a-d except substituting p-toluenesulfonyl isocyanate for o-toluenesulfonyl isocyanate and 3-methyl-benzofuran-2-carboxylic acid for benzofuran-2-carboxylic acid the title compound was prepared: MS(ES) 597 (M+H)$^+$.

Example 345

Preparation of Benzo[b]thiophene-2-carboxylic acid ((S)-3-methyl-1-{3-oxo-1-[1-toluene-4-sulfonylamino)-methanoyl]-azepan-4-ylcarbamoyl}-butyl)-amide Following the procedures of Example 334a-d except substituting p-toluenesulfonyl isocyanate for o-toluenesulfonyl isocyanate and benzo[b]thiophene-2-carboxylic acid for benzofuran-2-carboxylic acid the title compound was prepared: MS(ES) 597 (M+H)$^+$.

Example 346

Preparation of Benzofuran-2-carboxylic acid {(S)-3-methyl-1-[1-(6-methyl-pyridin-2-ylmethyl)-3-oxo-azepan-4-ylcarbamoyl]-butyl}-amide Following the general procedures of Example 331a-d except-substituting 6-methylpyridine-2-aldehyde for α-quinoline carbaldehyde the title compound was prepared: MS(ES) 491 (M+H)+.

The diastereomers were separated by HPLC to provide diastereomer 1 and diastereomer 2.

Example 347

Preparation of 3-Methyl-benzofuran-2-carboxylic acid {(S)-3-methyl-1-[1-(6-methyl-pyridin-2-ylmethyl)-3-oxo-azepan-4-ylcarbamoyl]-butyl}-amide Following the general procedures of Example 331a-d except substituting 6-methylpyridine-2-aldehyde for α-quinoline carbaldehyde and 3-methyl-benzofuran-2-carboxylic acid for benzofuran carboxylic acid the title compound was prepared: MS(ES) 505 (M+H)+.

The diastereomers were separated by HPLC to provide diastereoemr 1 and diastereomer 2.

Example 348

Preparation of Benzo[b]thiophene-2-carboxylic acid {(S)-3-methyl-1-[1-(6-methyl-pyridin-2-ylmethyl)-3-oxo-azepan-4-ylcarbamoyl]-butyl}-amide Following the general procedures of Example 331a-d except substituting 6-methylpyridine-2-aldehyde for α-quinoline carbaldehyde and benzo[b]thiophene-2-carboxylic acid for benzofuran carboxylic acid the title compound was prepared: MS(ES) 507 (M+H)+.

The diastereomers were separated by HPLC to provide diastereomer 1 and diastereomer 2.

Example 349

Preparation of Benzo[b]thiophene-2-carboxylic acid {(S)-1-[1-(2-fluoro-phenylcarbamoyl)-3-oxo-azepan-4-ylcarbamoyl]-3-methyl-butyl}-amide a.) {(S)-1-[1-(2-fluorophenylcarbamoyl)-3-hydroxy-azepan-4-ylcarbamoyl]-3-methyl-butyl}-carbamic acid tert-butyl ester To a solution of the compound of Example 280 g (0.1 gm, 0.29 mmol) dissolved in THF was added 2-flurophenyl isocyanate (32 ml, 0.29 mmol) and stirred for 1 hr. THF was removed in vaccuo and the compound was directly used in the next step: MS(ES): 481.02(M+H)+.

b.) 4-((S)-2-Amino-4-methyl-pentanoylamino)-3-hydroxy-azepane-1-carboxylic acid (2-fluoro-phenyl)-amide To a solution of the compound of Example 349a (1.96 g, 4.1 mmol) dissolved in MeOH was added 4M HCl/dioxane (5 ml, 20.3 mmol) and allowed to stir at RT for 2 hr. Excess reagent was removed in vaccuo and azeotroped with toluene to yield 1.84 gm of the product.

c.) Benzo[b]thiophene-2-carboxylic acid {(S)-1-[1-(2-fluoro-phenylcarbamoyl)-3-hydroxy-azepan-4-ylcarbamoyl]-3-methyl-butyl}-amide To a solution of the compound of Example 349b (0.11 g, 0.28 mmol) dissolved in dichloromethane were added P-EDC (0.35 g, 1.8 mmol/g), HOBT (0.06 g, 0.49 mmol) and 2-benzothiophene carboxylic acid (0.077 gm, 0.432 mmol). The reaction mixture was shaken for 16 hr. The reaction was continued for one more hour by the addition of trisamine(0.38 gm, 3.7 mmol/g), followed by the filtration of the product. The product was purified on a silica gel column to yield 112.5 mg of the product: MS(ES): 541.2(M+H)$^+$.

d.) Benzo[b]thiophene-2-carboxylic acid {(S)-1-[1-(2-fluoro-phenylcarbamoyl)-3-oxo-azepan-4-ylcarbamoyl]-3-methyl-butyl}-amide To a solution of the compound of example 349c (0.112 g, 0.2 mmol) was dissolved in dichloromethane followed by the addition of Dess-Martin periodinane (0.175 g, 0.41 mmol). The reaction was stirred for 1 hr followed whereupon it was washed with $Na_2S_2O_3$, $NaHCO_3$ and brine. The compound was purified on a silica gel column to yield 78 mg of the product as a mixture of diastereomers; Separation of the diastereomers by HPLC provided diastereomer 1: MS (ES) 539 (M+H)$^+$ and diastereomer 2: 539 MS(ES) (M+H)$^+$.

Example 350

Preparation of 3-Methyl-benzofuran-2-carboxylic acid {(S)-1-[1-(2-fluoro-phenylcarbamoyl)-3-oxo-azepan-4-ylcarbamoyl]-3-methyl-butyl}-amide Following the general procedures of example 349c-d except substituting 3-methyl-benzofuran-2-carboxylic acid for benzo[b]thiophene-2-carboxylic acid the title compound was prepared.

Separation of the diastereomers by HPLC provided diastereomer 1: MS(ES) 537 (M+H)$^+$ and diastereomer 2: MS(ES) 537 (M+H)$^+$.

Example 351

Preparation of 2,4-Dimethylfuran-3-carboxylic acid {(S)-1-[1-(2-fluoro-phenylcarbamoyl)-3-oxo-azepan-4-ylcarbamoyl]-3-methyl-butyl}-amide Following the general procedures of example 349c-d except substituting 2,4-dimethylfuran-3-carboxylic acid for benzo[b]thiophene-2-carboxylic acid the title compound was prepared.

Separation of the diastereomers by HPLC provided diastereomer 1: MS(ES) 501 (M+H)$^+$ and diastereomer 2: MS(ES) 501 (M+H)$^+$.

Example 352

Preparation of Quinoxaline-2-carboxylic acid {(S)-1-[1-(2-fluoro-phenylcarbamoyl)-3-oxo-azepan-4-yl-carbamoyl]-3-methyl-butyl}-amide Following the general procedures of example 349c-d except substituting quinoxaline-2-carboxylic acid for benzo[b]thiophene-2-carboxylic acid the title compound was prepared.

Separation of the diastereomers by HPLC provided diastereomer 1: MS(ES) 535 (M+H)$^+$ and diastereomer 2: MS(ES) 535 (M+H)$^+$.

Example 353

Preparation of Thieno[3,2-b]thiophene-2-carboxylic acid {(S)-1-[1-(2-fluoro-phenylcarbamoyl)-3-oxo-azepan-4-ylcarbamoyl]-3-methyl-butyl}-amide Following the general procedures of example 349c-d except substituting thieno[3,2-b]thiophene-2-carboxylic acid for benzo[b]thiophene-2-carboxylic acid the title compound was prepared.

Separation of the diastereomers by HPLC provided diastereomer 1: MS(ES) 545 (M+H)$^+$ and diastereomer 2: MS(ES) 545 (M+H)$^+$.

Example 354

Preparation of Quinoline-2-carboxylic acid {(S)-1-[1-(2-fluoro-phenylcarbamoyl)-3-oxo-azepan-4-yl-carbamoyl]-3-methyl-butyl}-amide Following the general procedures of example 349c-d except substituting quinoline-2-carboxylic acid for benzo[b]thiophene-2-carboxylic acid the title compound was prepared.

Separation of the diastereomers by HPLC provided diastereomer 1: MS(ES) 534 (M+H)$^+$ and diastereomer 2: MS(ES) 534 (M+H)$^+$.

Example 355

Preparation of 4-Methyl-thiophene-2-carboxylic acid {(S)-1-[1-(2-fluoro-phenylcarbamoyl)-3-oxo-azepan-4-ylcarbamoyl]-3-methyl-butyl}-amide Following the general procedures of example 349c-d except substituting 4-methyl-thiophene-2-carboxylic acid for benzo[b]thiophene-2-carboxylic acid the title compound was prepared.

Separation of the diastereomers by HPLC provided diastereomer 1: MS(ES) 503 (M+H)$^+$ and diastereomer 2: MS(ES) 503 (M+H)$^+$.

Example 356

Preparation of 5-Methoxy-benzofuran-2-carboxylic acid {(S)-1-[1-(2-fluoro-phenylcarbamoyl)-3-oxo-azepan-4-ylcarbamoyl]-3-methyl-butyl}-amide Following the general procedures of example 349c-d except substituting 5-methoxy-benzofuran-2-carboxylic acid for benzo[b]thiophene-2-carboxylic acid the title compound was prepared.

Separation of the diastereomers by HPLC provided diastereomer 1: MS(ES) 553 (M+H)$^+$ and diastereomer 2: MS(ES) 553 (M+H)$^+$.

Example 357

Preparation of 4-Methyl-furan-2-carboxylic acid {(S)-1-[1-(2-fluoro-phenylcarbamoyl)-3-oxo-azepan-4-ylcarbamoyl]-3-methyl-butyl}-amide Following the general procedures of example 349c-d except substituting 4-methyl-furan-2-carboxylic acid for benzo[b]thiophene-2-carboxylic acid the title compound was prepared.

Separation of the diastereomers by HPLC provided diastereomer 1: MS(ES) 487 (M+H)$^+$ and diastereomer 2: MS(ES) 487 (M+H)$^+$.

Example 358

Preparation of Benzofuran-2-carboxylic acid [(S)-1-(1-butyl-3-oxo-azepan-4-ylcarbamoyl)-3-methyl-butyl]-amide Following the general procedure of Examples 331a-d except substituting butyraldehyde for α-quinoline carbaldehyde the title compound was prepared. Separation of the diastereomers by HPLC provided diastereomer 1: MS(ES) 441.9 (M+H)$^+$ and diastereomer 2: MS(ES) 441.9 (M+H)$^+$.

Example 359

Preparation of Benzofuran-2-carboxylic acid [(S)-1-(1-propyl-3-oxo-azepan-4-ylcarbamoyl)-3-methyl-butyl]-amide Following the general procedure of Examples 331a-d except substituting propionaldehyde for α-quinoline carbaldehyde the title compound was prepared. Separation of the diastereomers by HPLC provided diastereomer 1: MS(ES) 428 (M+H)$^+$ and diastereomer 2: MS(ES) 428 (M+H)$^+$.

Example 360

Preparation of Benzofuran-2-carboxylic acid {(S)-1-[1-(494.2)-3-oxo-azepan-4-ylcarbamoyl]-3-methyl-butyl}-amide Following the general procedure of Examples 331a-d except substituting 2-fluorobenzaldeyde for α-quinoline carbaldehyde the title compound was prepared. Separation of the diastereomers by HPLC provided diastereomer 1: MS(ES) (M+H)$^+$ and diastereomer 2: MS(ES) 494.2 (M+H)$^+$.

Example 361

Preparation of Benzofuran-2-carboxylic acid {(S)-3-methyl-1-[1-(2-morpholin-4-yl-thiazol-4-ylmethyl)-3-oxo-azepan-4-ylcarbamoyl]-butyl}-amide Following the general procedure of Examples 331a-d except substituting 2-morpholin-4-yl-thiazole-4-carbaldehyde for α-quinoline carbaldehyde the title compound was prepared. Separation of the diastereomers by HPLC provided diastereomer 1: MS(ES) 568.2 (M+H)$^+$ and diastereomer 2: MS(ES) 568.4 (M+H)$^+$.

Example 362

Preparation of Benzofuran-2-carboxylic acid {(S)-1-[1-(5-ethyl-furan-2-ylmethyl)-3-oxo-azepan-4-ylcarbamoyl]-3-methyl-butyl}-amide Following the general procedure of Examples 331a-d except substituting 5-ethyl-2-furaldehyde for α-quinoline carbaldehyde the title compound was prepared. Separation of the diastereomers by HPLC provided diastereomer 1: MS(ES) 549.4 (M+H)$^+$ and diastereomer 2: MS(ES) 549.4 (M+H)$^+$.

Example 363

Preparation of Benzofuran-2-carboxylic acid {(S)-1-[1-(3,4-dimethyl-thieno[3,2-b]thiophene-2-ylmethyl)-3-oxo-azepan-4-ylcarbamoyl]-3-methyl-butyl}-amide Following the general procedure of Examples 331a-d except substituting 3,4-diemethylthieno[b]thiophene-2-carboxaldehyde for α-quinoline carbaldehyde the title compound was prepared. Separation of the diastereomers by HPLC provided diastereomer 1: MS(ES) 566.2 (M+H)$^+$ and diastereomer 2: MS(ES) 566.2 (M+H)$^+$.

Example 364

Preparation of Benzofuran-2-carboxylic acid {(S)-3-methyl-1-[3-oxo-1-(3-phenyl-3H-[1,2,3]triazol-4-ylmethyl)-azepan-4-ylcarbamoyl]-butyl}-amide Following the general procedure of Examples 331a-d except substituting 2-phenyl-2H-pyrazole-3-carbaldehyde for α-quinoline carbaldehyde the title compound was prepared. Separation of the diastereomers by HPLC provided diastereomer 1: MS(ES) 543.2 (M+H)$^+$ and diastereomer 2: MS(ES) 543.4 (M+H)$^+$.

Example 365

Preparation of Benzofuran-2-carboxylic acid [(S)-1-[1-(isothiazol-3-ylmethyl-3-oxo-azepan-4-ylcarbamoyl)-3-methyl-butyl}-amide Following the general procedure of Examples 331a-d except substituting isothiazole-3-carbaldehyde for α-quinoline carbaldehyde the title compound was prepared. Separation of the diastereomers by HPLC provided diastereomer 1: MS(ES) 483.1 (M+H)$^+$ and diastereomer 2: MS(ES) 483.1 (M+H)$^+$.

Example 366

Preparation of Benzofuran-2-carboxylic acid [(S)-3-methyl-1-(3-oxo-1-thiophen-2-ylmethyl-azepan-4-ylcarbamoyl)-butyl]-amide Following the general procedure of Examples 331a-d except substituting thiophene-2-carbaldehyde for α-quinoline carbaldehyde the title compound was prepared. Separation of the diastereomers by HPLC provided diastereomer 1: MS(ES) 582 (M+H)$^+$ and diastereomer 2: MS(ES) 582 (M+H)$^+$.

Example 367

Preparation of Benzofuran-2-carboxylic acid [(S)-3-methyl-1-(3-oxo-1-thiophen-2-ylmethyl-azepan-4-ylcarbamoyl)-butyl]-amide Following the general procedure of Examples 331a-d except substituting benzo[b]thiophene-2-carbaldehyde for α-quinoline carbaldehyde the title compound was prepared. Separation of the diastereomers by HPLC provided diastereomer 1: MS(ES) 546 (M+H)$^+$ and diastereomer 2: MS(ES) 546 (M+H)$^+$.

Example 368

Preparation of Benzofuran-2-carboxylic acid [(S)-3-methyl-1-(3-oxo-1-pentyl-azepan-4-ylcarbamoyl)-butyl]-amide Following the general procedure of Examples 331a-d except substituting pentanal for α-quinoline carbaldehyde the title compound was prepared. Separation of the diastereomers by HPLC provided diastereomer 1: MS(ES) 556 (M+H)$^+$ and diastereomer 2: MS(ES) 556 (M+H)$^+$.

Example 369

Preparation of Benzofuran-2-carboxylic acid {(S)-3-methyl-1-[1-(1-methyl-1H-imidazol-2-ylmethyl)-3-oxo-azepan-4-ylcarbamoyl]-buty}-amide Following the general procedure of Examples 331a-d except substituting 3-methyl-3H-imidazole-4-carbaldehyde for α-quinoline carbaldehyde the title compound was prepared: MS(ES) 480.4 (M+H)$^+$.

Example 370

Preparation of 1-Oxy-pyridine-2-carboxylic acid {(S)-3-methyl-1-[3-oxo-1-(pyridine-2-sulfonyl)-azepan-4-ylcarbamoyl]-butyl}-amide Following the procedure of Example 280h-j except substituting 1-oxy-pyridine-2-carboxylic acid for 2-benzofuran-2-carboxylic acid and 2-pyridinesulfonyl chloride for 3-fluorobenzenesulfonyl chloride provided the title compound. Separation of the diastereomers by HPLC gave diastereomer 1 (ESMS: M+H$^+$=504.2) and diastereomer 2 (ESMS: M+H$^+$=504.2).

Example 371

Preparation of 2-Oxy-pyridine-3-carboxylic acid {(S)-3-methyl-1-[3-oxo-1-(pyridine-2-sulfonyl)-azepan-4-ylcarbamoyl]-butyl}-amide Following the procedure of Example 280h-j except substituting 2-oxy-pyridine-3-carboxylic acid for 2-benzofuran-2-carboxylic acid and 2-pyridinesulfonyl chloride for 3-fluorobenzenesulfonyl chloride provided the title compound. Separation of the diastereomers by HPLC gave diastereomer 1 (ESMS: M+H$^+$=504.2) and diastereomer 2 (ESMS: M+H$^+$=504.2).

Example 372

Preparation of 1H-Benzoimidazole-5-carboxylic acid {(S)-3-methyl-1-[3-oxo-1-(pyridine-2-sulfonyl)-azepan-4-ylcarbamoyl]-butyl}-amide Following the procedure of Example 280h-j except substituting 1H-benzoimidazole-5-carboxylic acid for 2-benzofuran-2-carboxylic acid and 2-pyridinesulfonyl chloride for 3-fluorobenzenesulfonyl chloride provided the title compound. Separation of the diastereomers by HPLC gave diastereomer 1 (ESMS: M+H$^+$=504.2) and diastereomer 2 (ESMS: M+H$^+$=504.2).

Example 373

Preparation of 4-{(S)-2-[(1-Benzofran-2-yl-methanoyl)-amino]-4-methyl-pentanoylamino}-1-methyl-3-oxo-1-pentyl-azepanium A solution of the compound of Example 368 in neat methyl iodide was heated at reflux for 48 hours whereupon the mixture was concentrated to provide the title compound: MS(ES) 471.6 (M+H)$^+$.

Example 374

Preparation of Benzofuran-2-carboxylic acid {(S)-1-[1-(1,2-dimethyl-1H-imidazole-4-sulfonyl)-3-oxo-azepan-4-ylcarbamoyl]-3-methyl-butyl}-amide Following the procedure of Example 280h-j except substituting 1,2-dimethyl-1H-imidazole-4-sulfonyl chloride for 3-fluorobenzenesulfonyl chloride provided the title compound: MS(ES) 544.4 (M+H)$^+$.

Example 375

Preparation of Benzofuran-2-carboxylic acid {(S)-1-[1-(1-methyl-1H-imidazole-4-sulfonyl)-3-oxo-azepan-4-ylcarbamoyl]-3-methyl-butyl}-amide Following the procedure of Example 280h-j except substituting 1-methyl-1H-imidazole-4-sulfonyl chloride for 3-fluorobenzenesulfonyl chloride provided the title compound: MS(ES) 530.2 (M+H)$^+$.

Example 376

Preparation of Benzofuran-2-carboxylic acid {(S)-1-[1-(1-methyl-1H-imidazole-4-sulfonyl)-3-oxo-azepan-4-ylcarbamoyl]-3-methyl-butyl}-amide Following the procedure of Example 280h-j except substituting 4-methanesulfonyl-benzenesulfonyl chloride for 3-fluorobenzenesulfonyl chloride provided the title compound. Separation of the diastereomers by HPLC gave diastereomer 1: MS(ES) 604.2 (M+H)$^+$ and diastereomer 2: MS(ES) 604.2 (M+H)$^+$.

Example 377

Preparation of Benzofuran-2-carboxylic acid {(S)-1-[1-(2-methanesulfonyl-benzenesulfonyl)-3-oxo-azepan-4-ylcarbamoyl]-3-methyl-butyl}-amide Following the procedure of Example 280h-j except substituting 2-methanesulfonyl-benzenesulfonyl chloride for 3-fluorobenzenesulfonyl chloride provided the title compound. Separation of the diastereomers by HPLC gave diastereomer 1: MS(ES) 604.2 (M+H)$^+$ and diastereomer 2: MS(ES) 604.2 (M+H)$^+$.

Example 378

Preparation of Benzofuran-2-carboxylic acid {(S)-1-[1-(3,5-dimethyl-isoxazole-4-sulfonyl)-3-oxo-azepan-4-ylcarbamoyl]-3-methyl-butyl}-amide Following the procedure of Example 280h-j except substituting 3,5-dimethyl-isoxazole-4-sulfonyl chloride for 3-fluorobenzenesulfonyl chloride provided the title compound. Separation of the diastereomers by HPLC gave diastereomer 1: MS(ES) 545.2 (M+H)$^+$ and diastereomer 2: MS(ES) 545.2 (M+H)$^+$.

Example 379

Preparation of 3-Methyl-benzofuran-2-carboxylic acid {(1S,2R)-2-methyl-1-[3-oxo-1-(pyridine-2-sulfonyl)-azepan-4-ylcarbamoyl]-butyl}-amide a.) 3-Methyl-benzofuran-2-carboxylic acid {(1S,2R)-2-methyl-1-[3-hydroxy-1-(pyridine-2-sulfonyl)-azepan-4-ylcarbamoyl]-butyl}-amide Following the general proceures of Example 280f-i except substituting N-Boc-allo-isoleucine for N-Boc-leucine and 2-pyridinesulfonyl chloride for 3-fluorobenzenesulfonyl chloride and 3-methyl-benzofuran-2-carboxylic acid for benzofuran-2-carboxylic acid the title compound was prepared.

b.) 3-Methyl-benzofuran-2-carboxylic acid {(1S,2R)-2-methyl-1-[3-oxo-1-(pyridine-2-sulfonyl)-azepan-4-ylcarbamoyl]-butyl}-amide Following the general procedure of Example 291d except substituting the compound of Example 105b the title compound was prepared. Separation of the diastereomers by HPLC provided diastereomer 1: MS(ES) 541 (M+H)$^+$ and diastereomer 2: MS(ES) 541 (M+H)$^+$.

Example 380

Preparation of 3-Methyl-benzofuran-2-carboxylic acid {1-[3-oxo-1-(pyridine-2-sulfonyl)-azepan-4-ylcarbamoyl]-cyclopentyl}-amide Following the general procedures of Examples 379a-b except substituting N-Boc-cycloleucine for N-Boc-allo-leucine the title compound was prepared: MS(ES) 539 (M+H)+.

Example 381

Preparation of Furo[3,2-b]-pyridine-2-carboxylic acid {(S)-3-methyl-1-[3-oxo-1-(1-oxy-pyridine-2-sulfonyl)-azepan-4-ylcarbamoyl]-butyl}-amide Following the general procedure of Examples 291c-d except substituting furo [3,2-b]-pyridine-2-carboxylic acid for 5-fluoro-benzofuran-2-carboxylic acid provided the title compound as a mixture of diastereomers: MS(ES) 587 (M+H)$^+$.

Separation of the diastereomers by HPLC provided diastereomer 1: MS(ES) 544.2 (M+H)$^+$ and diastereomer 2: MS(ES) 544.2 (M+H)$^+$.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

We claim:
1. A compound of Formula (I)

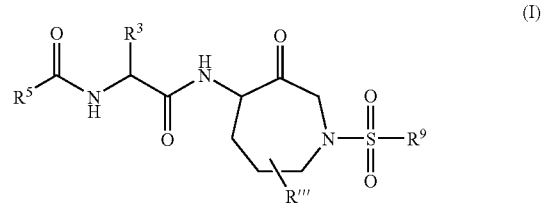

wherein:
$R^5$ is benzofuranyl, or thieno[3,2,b]thiophenyl, all of which may be substituted or unsubstituted by $C_{1-3}$alkyl;
$R'''$ is hydrogen or $C_{1-6}$alkyl;
$R^3$ is $C_{1-6}$alkyl, phenyl$C_{1-6}$alkyl, or naphthyl$C_{1-6}$alkyl;
$R^9$ is pyridinyl, 1-oxy-pyridinyl, phenyl, halogen substituted phenyl, $C_{1-6}$alkyl substituted phenyl, $C_{1-6}$alkoxy substituted phenyl, cyanophenyl, imidazolyl, or $C_{1-6}$alkyl substituted imidazolyl, or a pharmaceutically acceptable salt thereof.

2. A compound according to claim 1 wherein $R^3$ is selected from the group consisting of: methyl, ethyl, n-propyl, prop-2-yl, n-butyl, isobutyl, but-2-yl, and naphthalen-2-ylmethyl.

3. A compound according to claim 1 wherein $R^3$ is isobutyl.

4. A compound according to claim 1 wherein $R^5$ is thieno[3,2-b]thiophen-2-yl.

5. A compound according to claim 1 wherein $R'''$ is H.

6. A compound according to claim 1 wherein $R^9$ is selected from the group consisting of:
3,4-dichlorophenyl, 4-bromophenyl, 2-fluorophenyl, 4-fluorophenyl, 3-chlorophenyl, 4-chlorophenyl, 3-methoxyphenyl, 4-methoxyphenyl, 3,4-dimethoxyphenyl, 2-cyanophenyl;
pyridin-2-yl pyridin-3-yl, 1-oxy-pyridin-2-yl, 1-oxy-pyridin-3-yl;
1H-imidazol-2-yl, 1H-imidazol-4-yl, 1-methyl-1H-imidazol-2-yl, and 1-methyl-1H-imidazol-4-yl.

7. A compound according to claim 1 wherein:
$R^3$ is isobutyl;
$R^5$ is selected from the group consisting of: 3-methyl-benzofuran-2-yl or thieno[3,2-b]thiophen-2-yl; and
$R^9$ is selected from the group consisting of: pyridin-2-yl and 1-oxy-pyridin-2-yl.

8. A compound according to claim 1 wherein $R^5$ is benzofuran-2-yl.

9. A compound according to claim 1 wherein $R^9$ is pyridin-2-yl.

10. A compound of Formula II

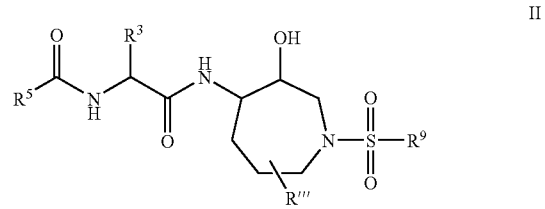

$R^5$ is benzofuranyl, benzo[b]thiophenyl, or thieno[3,2,b]thiophenyl;
$R'''$ is hydrogen or $C_{1-6}$alkyl;
$R^3$ is $C_{1-6}$alkyl, phenyl$C_{1-6}$alkyl, or naphthyl$C_{1-6}$alkyl;
$R^9$ is pyridinyl, 1-oxy-pyridinyl, phenyl, halogen substituted phenyl, $C_{1-6}$alkyl substituted phenyl, $C_{1-6}$alkoxy substituted phenyl, cyanophenyl, imidazolyl, or $C_{1-6}$alkyl substituted imidazolyl.

11. A pharmaceutical composition comprising a compound according to claim 1 and a pharmaceutically acceptable carrier, diluent or excipient.

12. A method of treating osteoporosis by administering to a patient in need thereof an effective amount of a compound according to claim 1.

13. A method of treating periodontitis by administering to a patient in need thereof an effective amount of a compound according to claim 1.

14. A method of treating gingivitis by administering to a patient in need thereof an effective amount of a compound according to claim 1.

15. A method of treating osteoarthritis by administering to a patient in need thereof an effective amount of a compound according to claim 1.

16. A method of treating rheumatoid arthritis by administering to a patient in need thereof an effective amount of a compound according to claim 1.

* * * * *